US012545723B2

(12) United States Patent
Emerling et al.

(10) Patent No.: US 12,545,723 B2
(45) **Date of Patent: *Feb. 10, 2026**

(54) ANTI-CSP ANTIBODIES

(71) Applicant: Atreca, Inc., San Carlos, CA (US)

(72) Inventors: Daniel Eric Emerling, San Carlos, CA (US); Randal R. Ketchem, Snohomish, WA (US); Shaun M. Lippow, San Carlos, CA (US); Wayne Volkmuth, San Carlos, CA (US); Katherine L. Williams, San Carlos, CA (US)

(73) Assignee: ATRECA, INC., San Carlos, CA (US)

( * ) Notice: Subject to any disclaimer, the term of this patent is extended or adjusted under 35 U.S.C. 154(b) by 578 days.

This patent is subject to a terminal disclaimer.

(21) Appl. No.: 18/101,933

(22) Filed: Jan. 26, 2023

(65) Prior Publication Data

US 2023/0167169 A1 Jun. 1, 2023

Related U.S. Application Data

(63) Continuation of application No. 17/842,351, filed on Jun. 16, 2022, now Pat. No. 11,655,290.

(60) Provisional application No. 63/211,820, filed on Jun. 17, 2021.

(51) Int. Cl.

| | |
|---|---|
| ***A61K 39/395*** | (2006.01) |
| ***A61P 33/06*** | (2006.01) |
| ***C07K 16/20*** | (2006.01) |
| *A61K 39/00* | (2006.01) |

(52) U.S. Cl.

CPC ............ *C07K 16/205* (2013.01); *A61P 33/06* (2018.01); *A61K 2039/505* (2013.01); *C07K 2317/33* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 6,602,684 B1 | 8/2003 | Umaña | |
| 8,088,376 B2 | 1/2012 | Chamberlain et al. | |
| 11,066,464 B2 * | 7/2021 | Liang | C07K 16/205 |

FOREIGN PATENT DOCUMENTS

| | | |
|---|---|---|
| WO | WO 1993/10152 A1 | 5/1993 |
| WO | WO 99/54342 A1 | 8/1999 |
| WO | WO 2010/054007 A1 | 5/2010 |
| WO | WO 2012/148497 A2 | 11/2012 |
| WO | WO 2017/015634 A2 | 1/2017 |
| WO | WO 2020/172220 A1 | 8/2020 |

OTHER PUBLICATIONS

U.S. Appl. No. 17/842,351 (US 2023/0002483), filed Jun. 16, 2022 (Jan. 5, 2023).

U.S. Appl. No. 17/842,351, Feb. 1, 2023 Notice of Allowance.

U.S. Appl. No. 17/842,351, Jan. 26, 2023 Issue Fee Payment.

U.S. Appl. No. 17/842,351, Oct. 28, 2022 Notice of Allowance.

"Efficacy and Safety of the RTS,S/AS01 Malaria Vaccine during 18 Months after Vaccination: A Phase 3 Randomized, Controlled Trial in Children and Young Infants at 11 African Sites," RTS,S Clinical Trials Partnership, PLoS Med.11(7): e1001685 (2014).

Abney et al., "Sequential Expression of Immunoglobulin On Developing Mouse B Lymphocytes: A Systematic Survey That Suggests A Model For The Generation Of Immunoglobulin Isotype Diversity," The Journal of Immunology, 120(6):2041-2049 (1978).

Achidi et al., "Lack of association between levels of transplacentally acquired Plasmodium falciparum-specific antibodies and age of onset of clinical malaria in infants in a malaria endemic area of Nigeria," Acta Tropica 61:315-326 (1996).

Agnandji et al., "Induction of Plasmodium falciparum-Specific CD4+ T Cells and Memory B Cells in Gabonese Children Vaccinated with RTS,S/AS01E and RTS,S/AS02D," PLos ONE 6(4):e18559 (2011) 9 pgs.

Ahuja et al., "Maintenance of the plasma cell pool is independent of memory B cells," PNAS 105(12):4802-4807 (2008).

Ajua et al., "The effect of immunization schedule with the malaria vaccine candidate RTS,S/AS01E on protective efficacy and anti-circumsporozoite protein antibody avidity in African infants," Malaria Journal 14:72 (2015) 6 pgs.

Aliprandini et al., "Cytotoxic anti-circumsporozoite antibodies target malaria sporozoites in the host skin," Nature Microbiology 3:1224-1233 (2018).

Al-Lazikani et al., "Standard Conformations for the Canonical Structures of Immunoglobulins," J. Mol. Biol, 273(4), 927-948 (1997).

Altschul et al., "Basic Local Alignment Search Tool," J. Mol. Biol. 215, 403-410 (1990).

Altschul et al., "Gapped BLAST and PSI-BLAST: a new generation of protein database search programs," Nuc. Acids Res., 25:3389-3402 (1977).

Anders, "Multiple cross-reactivities amongst antigens of Plasmodium fakiparum impair the development of protective immunity against malaria," Parasite Immunology 8:529-539 (1986).

Angal, et al., "A single amino acid substitution abolishes the heterogeneity of chimeric mouse/human (IgG4) antibody," Molecular Immunology, 30(1), 105-108 (1993).

Atcheson et al., "A VLP for validation of the Plasmodium falciparum circumsporozoite protein junctional epitope for vaccine development," NPJ Vaccines 6:46 (2021) 9 pgs.

Ausubel et al., "Current Protocols in Molecular Biology," John Wiley & Sons, Inc. (2003).

(Continued)

*Primary Examiner* — Meera Natarajan

(74) *Attorney, Agent, or Firm* — Kilpatrick Townsend & Stockton LLP

(57) ABSTRACT

The present disclosure provides anti-circumsporozoite (CSP) antibodies, compositions comprising such antibodies. Also disclosed are methods of producing the disclosed antibodies and methods of treating or preventing malaria using the same.

33 Claims, 86 Drawing Sheets

Specification includes a Sequence Listing.

(56) References Cited

OTHER PUBLICATIONS

Aye et al., "Malaria exposure drives both cognate and bystander human B cells to adopt an atypical phenotype," Eur. J. Immunol. 50:1187-1194 (2020).
Bailly et al., "Predicting Antibody Developability Profiles Through Early Stage Discovery Screening," mAbs, 12:1, 1743053 29 pgs. (2020).
Banach et al., "Highly protective antimalarial antibodies via precision library generation and yeast display screening," J. Exp. Med. 219(8):e20220323 (2022).
Bergmann-Leitner et al., "C3d binding to the circumsporozoite protein carboxy-terminus deviates immunity against malaria," International Immunology, 17(3):245-255 (2005).
Bernasconi et al., Maintenance of Serological Memory by Polyclonal Activation.
Beutler et al., "A novel CSP C-terminal epitope targeted by an antibody with protective activity against Plasmodium falciparum," PLoS Pathog 18(3): e1010409 (2022).
Beutler et al., "A novel CSP C-terminal epitope targeted by an antibody with protective activity against Plasmodium falciparum," PLoS Pathog 18(3):e1010409 (2022) 21 pgs.
Bowie et al., "Deciphering the message in protein sequences: tolerance to amino acid substitutions," Science 247:1306-1310 (1990).
Calvo-Calle et al., "A Linear Peptide Containing Minimal T- and B-Cell Epitopes of Plasmodium falciparum Circumsporozoite Protein Elicits Protection against Transgenic Sporozoite Challenge," Infection and Immunity, 74(12):6929-6939 (Dec. 2006).
Calvo-Calle et al., "Human CD4+ T Cells Induced by Synthetic Peptide Malaria Vaccine Are Comparable to Cells Elicited by Attenuated Plasmodium falciparum Sporozoites," The Journal of Immunology 175:7575-7585 (2005).
Calvo-Calle et al., "Identification of a neutralizing epitope within minor repeat region of Plasmodium falciparum CS protein," NPJ Vaccines 6:10 (2021) 8 pgs.
Casares et al., "The RTS,S malaria vaccine," Vaccine 28:4880-4894 (2010).
Chan et al., "Affinity-based selection and the germinal center response," Immunological Reviews 247:11-23 (2012).
Chappel et al., "Molecular dissection of the human antibody response to the structural repeat epitope of Plasmodium falciparum sporozoite from a protected donor," Malaria Journal 3:28 (2004) 12 pgs.
Chatterjee et al., "Avid binding by B cells to the Plasmodium circumsporozoite protein repeat suppresses responses to protective subdominant epitopes," Cell Reports 35:108996 (2021) 30 pgs.
Chatterjee et al., "The challenges of a circumsporozoite protein-based malaria vaccine," Expert Review of Vaccines, 20(2):113-125 (2021).
Chaudhury et al., "Breadth of humoral immune responses to the C-terminus of the circumsporozoite protein is associated with protective efficacy induced by the RTS,S malaria vaccine," Vaccine 39:968-975 (2021).
Chaudhury et al., "Delayed fractional dose regimen of the RTS,S/AS01 malaria vaccine candidate enhances an IgG4 response that inhibits serum opsonophagocytosis," Scientific Reports 7:7998 (2017) 10 pgs.
Chaudhury et al., "Simulation of B Cell Affinity Maturation Explains Enhanced Antibody Cross-Reactivity Induced by the Polyvalent Malaria Vaccine AMA1," The Journal of Immunology 193:2073-2086 (2014).
Chaudhury et al., "The biological function of antibodies induced by the RTS,S/AS01 malaria vaccine candidate is determined by their fine specificity," Malar J. 15:301 (2016) 12 pgs.
Chen et al., "Systematic analysis of human antibody response to ebolavirus glycoprotein reveals high prevalence of neutralizing public clonotypes," bioRxiv preprint doi: https://doi.org/10.1101/2022.01.12.476089 (Jan. 13, 2022).
Chothia et al., "Canonical Structures for the Hypervariable Regions of Immunoglobulins," J. Mol. Biol., 196, 901-917 (1987).
Chothia et al., "Conformations of immunoglobulin hypervariable regions," Nature 342, 877-883 (1989).
Chothia et al., "Structural repertoire of the human VH segments," J. Mol. Biol. 227(3), 799-817 (1992).
Cockburn et al., "Malaria prevention: from immunological concepts to effective vaccines and protective antibodies," Nature Immunology 19:1199-1211 (2018).
Coelho et al., "Unwanted Feedback: Malaria Antibodies Hinder Vaccine Boosting," Cell Host & Microbe 28:504-506 (2020).
Collins et al., "Ultra-low dose immunization and multi-component vaccination strategies enhance protection against malaria in mice," Scientific Reports 11:10792 (2021) 15 pgs.
Coppi et al., "The malaria circumsporozoite protein has two functional domains, each with distinct roles as sporozoites journey from mosquito to mammalian host," J. Exp. Med. 208(2):341-356 (2011).
Cox et al., "An early humoral immune response in peripheral blood following parenteral inactivated influenza vaccination," Vaccine 12(11):993-999 (1994).
Crompton et al., "A prospective analysis of the Ab response to Plasmodium falciparum before and after a malaria season by protein microarray," PNAS 107(15):6958-6963 (2010).
Crompton et al., "Advances and challenges in malaria vaccine development," The Journal of Clinical Investigation 120(12):4168-4178 (2010).
Daily, "Monoclonal Antibodies—A Different Approach to Combat Malaria," N Engl J Med 387(5):460-461 (2022).
Dame et al., "Structure of the Gene Encoding the Immunodominant Surface Antigen on the Sporozoite of the Human Malaria Parasite *Plasmodium falciparum*," Science 225:593-599 (1984).
Das et al., "Delayed fractional dosing with RTS,S/AS01 improves humoral immunity to malaria via a balance of polyfunctional NANP6- and Pf16-specific antibodies," Med 2:1269-1286 (2021).
Deal et al., "Vectored antibody gene delivery protects against Plasmodium falciparum sporozoite challenge in mice," PNAS 111(34):12528-12532 (2014).
Dekosky et al., "Large-scale sequence and structural comparisons of human naive and antigen-experienced antibody repertoires," PNAS e2636-e2645 (2016).
Dennison et al., "Qualified Biolayer Interferometry Avidity Measurements Distinguish the Heterogeneity of Antibody Interactions with Plasmodium falciparum Circumsporozoite Protein Antigens," J Immunol 201:1315-1326 (2018).
Dobano et al., "Concentration and avidity of antibodies to different circumsporozoite epitopes correlate with RTS,S/AS01E malaria vaccine efficacy," Nature Communications 10:2174, 13 pgs. (2019).
Dobano et al., "Differential Patterns of IgG Subclass Responses to plasmodium falciparum Antigens in Relation to Malaria Protection and RTS,S Vaccination," Frontiers in Immunology 10:439, 19 pgs. (2019).
Dobano et al., "RTS,S/AS01E immunization increases antibody responses to vaccine-unrelated Plasmodium falciparum antigens associated with protection against clinical malaria in African children: a case-control study," BMC Medicine 17:157, 19 pgs. (2019).
Du et al., "The Ratiometric Transcript Signature MX2/GPR183 Is Consistently Associated with RTS,S-Mediated Protection Against Controlled Human Malaria Infection," Frontiers in Immunology 11:669, 12 pgs. (2020).
Ellebedy et al., "Defining antigen-specific plasmablast and memory B cell subsets in human blood after viral infection or vaccination," Nature Immunology 17(10): 1226-1234 (2016).
Elliott et al., "Affinity Maturation Drives Epitope Spreading and Generation of Proinflammatory Anti-Citrullinated Protein Antibodies in Rheumatoid Arthritis," Arthritis & Rheumatology, 70(12):1946-1958 (2018).
Enea et al., "DNA Cloning of Plasmodium falciparum Circumsporozoite Gene: Amino Acid Sequence of Repetitive Epitope," Science 225:628-630 (1984).
Espinosa et al., "Development of a Chimeric Plasmodium berghei Strain Expressing the Repeat Region of the P. vivax Circumsporozoite Protein for In Vivo Evaluation of Vaccine Efficacy," Infect Immun., 81(8): 2882-2887 (2013).

(56) References Cited

OTHER PUBLICATIONS

Espinosa et al., "Proteolytic Cleavage of the Plasmodium falciparum Circumsporozoite Protein Is a Target of Protective Antibodies," JID 212:1111-1119 (2015).
Espinosa et al., "Robust antibody and CD8+ T-cell responses induced by P. falciparum CSP adsorbed to cationic liposomal adjuvant CAF09 confer sterilizing immunity against experimental rodent malaria infection," NJP Vaccines, 2, 10 (2017).
Fabra-García et al., "Human antibodies against noncircumsporozoite proteins block Plasmodium falciparum parasite development in hepatocytes," JCI Insight 7(6):e153524 (2022) 12 pgs.
Ferguson et al., "The Repeat Region of the Circumsporozoite Protein is Critical for Sporozoite Formation and Maturation in Plasmodium," PLoS One 9(12):e113923, 25 pgs. (2014).
Fernández-Quintero et al., "Antibody CDR loops as ensembles in solution vs. canonical clusters from X-ray structures," mAbs, 12:1744328 (2020) 12 pgs.
Fink et al., "Origin and function of circulating plasmablasts during acute viral infections," Frontiers in Immunology 3:78 (2012) 5 pgs.
Fisher et al., "T-dependent B cell responses to Plasmodium induce antibodies that form a high-avidity multivalent complex with the circumsporozoite protein," PLoS Pathog 13(7): e1006469 (2017).
Flores-Garcia et al., "Optimization of an in vivo model to study immunity to Plasmodium falciparum pre-erythrocytic stages," Malar J., 18(1):426, doi:10.1186/s12936-019-3055-9 (2019).
Flores-Garcia et al., "Optimization of an in vivo model to study immunity to Plasmodium falciparum pre-erythrocytic stages," Malar J. 18:426 (2019) 9 pgs.
Flores-Garcia et al., "The P. falciparum CSP repeat region contains three distinct epitopes required for protection by antibodies in vivo," PLoS Pathog 17(11):e1010042 (2021).
Foquet et al., "Vaccine-induced monoclonal antibodies targeting circumsporozoite protein prevent Plasmodium falciparum infection," J Clin Invest. 124(1):140-144 (2014).
Friedman-Klabanoff et al., "Epitope-Specific Antibody Responses to a Plasmodium falciparum Subunit Vaccine Target in a Malaria-Endemic Population," The Journal of Infectious Diseases XX:1-5 (2020) 5 pgs.
Gaudinski et al., "A Monoclonal Antibody for Malaria Prevention," N Engl. J Med (2021) 288 pgs.
Herrera et al., "Reversible Conformational Change in the Plasmodium falciparum Circumsporozoite Protein Masks Its Adhesion Domains," Infection and Immunity 83(10):3771-3780 (2015).
Hollingdale et al., "Activity of human volunteer sera to candidate Plasmodium falciparum circumsporozoite protein vaccines in the inhibition of sporozoite invasion assay of human hepatoma cells and hepatocytes," Transactions of the Royal Society of Tropical Medicine and Hygiene 84:325-329 (1990).
Honegger et al., "Yet Another Numbering Scheme for Immunoglobulin Variable Domains: An Automatic Modeling and Analysis Tool," J. Mol. Biol., 309:657-670 (2001).
Höfer et al., "Adaptation of humoral memory," Immunological Reviews 211:295-302 (2006).
Imkeller et al., "Antihomotypic affinity maturation improves human B cell responses against a repetitive epitope," Science 360:1358-1362 (2018).
International Search Report and Written Opinion mailed Oct. 28, 2022 in International Application No. PCT/US2022/033877.
Jacobi et al., "Correlation Between Circulating CD27high Plasma Cells and Disease Activity in Patients With Systemic Lupus Erythematosus," Arthritis & Rheumatism 48(5):1332-1342 (2003).
Jelínková et al., "A vaccine targeting the L9 epitope of the malaria circumsporozoite protein confers protection from blood-stage infection in a mouse challenge model," NPJ Vaccines 7(1):1-4 (2022).
Jelínková et al., "An epitope-based malaria vaccine targeting the junctional region of circumsporozoite protein," NPJ Vaccines 6:13 (2021) 10 pgs.
Julien et al., "Antibodies against Plasmodium falciparum malaria at the molecular level," Nature Reviews, Immunology 19:761-775 (2019).
Kabat et al., Sequences of Proteins of Immunological Interest, 5th Ed. Public Health Service, National Institute of Health, NIH Publication 91-3242, Bethesda, MD (1991).
Kazmin et al., "Systems analysis of protective immune responses to RTS,S malaria vaccination in humans," PNAS 114(9):2425-2430 (2017).
Keitany et al., "Blood Stage Malaria Disrupts Humoral Immunity to the Pre-erythrocytic Stage Circumsporozoite Protein," Cell Reports 17:3193-3205 (2016).
Kelley et al., "Process and operations strategies to enable global access to antibody therapies," Biotechnol Progress. 37:e3139 (2021) 15 pgs.
Kester et al., "A phase I/IIa safety, immunogenicity, and efficacy bridging randomized study of a two-dose regimen of liquid and lyophilized formulations of the candidate malaria vaccine RTS,S/AS02A in malaria-naive adults," Vaccine 25:5359-5366 (2007).
Kester et al., "Efficacy of Recombinant Circumsporozoite Protein Vaccine Regimens against Experimental Plasmodium falciparum Malaria," The Journal of Infectious Diseases 183:640-647 (2001).
Kester et al., "Randomized, Double-Blind, Phase 2a Trial of Falciparum Malaria Vaccines RTS,S/AS01B and RTS,S/AS02A in Malaria-Naive Adults: Safety, Efficacy, and Immunologic Associates of Protection," J Infect Dis 200: 337-346 (2009).
Kingston et al., "Hepatitis B virus-like particles expressing Plasmodium falciparum epitopes induce complement-fixing antibodies against the circumsporozoite protein," Vaccine 37:1674-1684 (2019).
Kisalu et al., "A human monoclonal antibody prevents malaria infection and defines a new site of vulnerability on Plasmodium falciparum circumsporozoite protein," Nat Med. 24(4):408-416 (2018).
Kisalu et al., "A human monoclonal antibody prevents malaria infection by targeting a new site of vulnerability on the parasite," Nature Medicine 24(4):408-416 (2018).
Kisalu et al., "Enhancing durability of CIS43 monoclonal antibody by Fc mutation or AAV delivery for malaria prevention," JCI Insight. 6(3):e143958 (2021).
Kratochvil et al., "Vaccination in a humanized mouse model elicits highly protective PfCSP-targeting anti-malarial antibodies," Immunity 54:2859-2876 (2021).
Krishnamurty et al., "Somatically Hypermutated Plasmodium-Specific IgM+ Memory B Cells Are Rapid, Plastic, Early Responders upon Malaria Rechallenge," Immunity 45:402-414 (2016).
Kucharska et al., "Structural basis of Plasmodium vivax inhibition by antibodies binding to the circumsporozoite protein repeats," eLife 11:e72908 (2022) 29 pgs.
Kucharska et al., "Structural ordering of the Plasmodium berghei circumsporozoite protein repeats by inhibitory antibody 3D11," eLife 9:e59018 (2020) 25 pgs.
Kurtovic et al., "Induction and decay of functional complement-fixing antibodies by the RTS,S malaria vaccine in children, and a negative impact of malaria exposure," BMC Medicine 17:45 (2019) 14 pgs.
Kurtovic et al., "Multifunctional Antibodies Are Induced by the RTS,S Malaria Vaccine and Associated With Protection in a Phase 1/2a Trial," JID (2020) 11 pgs.
Langowski et al., "Optimization of a Plasmodium falciparum circumsporozoite protein repeat vaccine using the tobacco mosaic virus platform," PNAS 117(6):3114-3122 (2020).
Langowski et al., "Restricted valency (NPNA)n repeats and junctional epitope-based circumsporozoite protein vaccines against Plasmodium falciparum," npj Vaccines 7:13 (2022) 11 pgs.
Laumont et al., "Noncoding regions are the main source of targetable tumor-specific antigens," Sci. Transl. Med. 10:eaau5516 (2018) 11 pgs.
Lefranc, "IMGT, the international ImMunoGeneTics database," Nucleic Acids Res., 29(1): 207-209 (2001).
Livingstone et al., "In vitro and in vivo inhibition of malaria parasite infection by monoclonal antibodies against Plasmodium falciparum circumsporozoite protein (CSP)," Scientific Reports 11:5318 (2021) 15 pgs.
MacCallum et al, "Antibody-antigen interactions: Contact analysis and binding site topography," J. Mol. Biol., 262 (5), 732-745 (1996).

(56) References Cited

OTHER PUBLICATIONS

Macia et al., "Strong off-target antibody reactivity to malarial antigens induced by RTS,S/AS01E vaccination is associated with protection," JCI Insight, 24 pgs. (2022).
Macià et al., "Strong off-target antibody reactivity to malarial antigens induced by RTS,S/AS01E vaccination is associated with protection," JCI Insight (2022) 24 pgs.
Macintyre et al., "Injectable anti-malarials revisited:discovery and development of new agents to protect against malaria," Malar J 17:402 (2018).
Martin et al., "Modeling antibody hypervariable loops: a combined algorithm," Proc. Natl Acad. Sci. USA, 86, 9268-9272 (1989).
Martin et al., "Molecular modeling of antibody combining sites," Methods Enzymol., 203, 121-153 (1991).
McNamara et al., "Antibody Feedback Limits the Expansion of B Cell Responses to Malaria Vaccination but Drives Diversification of the Humoral Response," Cell Host & Microbe 28:572-585 (2020).
McNamara et al., Splenic Dendritic Cells and Macrophages Drive B Cells to Adopt a Plasmablast Cell Fate, Frontiers in Immunology 13:825207 (2022) 15 pgs.
Mesin et al., "Germinal Center B Cell Dynamics," Immunity 45(3):471-482 (2016).
Mitchell et al., "Innate Immune Responses and P. falciparum CS Repeat-Specific Neutralizing Antibodies Following Vaccination by Skin Scarification," Frontiers in Immunology 13:801111 (2022) 14 pgs.
Moon et al., "A Phase IIa Controlled Human Malaria Infection and Immunogenicity Study of RTS,S/AS01E and RTS,S/AS01B Delayed Fractional Dose Regimens in Malaria-Naive Adults," JID 222:1681-1691 (2020).
Murugan et al., "Evolution of protective human antibodies against Plasmodium falciparum circumsporozoite protein repeat motifs," Nature Medicine 26:1135-1145 (2020).
Nadeem et al., "Mosquirix™ RTS, S/AS01 Vaccine Development, Immunogenicity, and Efficacy," Vaccines 10:713 (2022) 15 pgs.
Nardin et al., "Synthetic Malaria Peptide Vaccine Elicits High Levels of Antibodies in Vaccinees of Defined HLA Genotypes," The Journal of Infectious Diseases 182:1486-1496 (2000).
Nardin et al., "T Cell Responses To Repeat And Non-Repeat Regions Of The Circumsporozoite Protein Detected In Volunteers Immunized With Plasmodium Falciparum Sporozoites," Mem. Inst. Oswald Cruz, Rio de Janeiro, 87(Suppl. III):223-227 (1992).
Neafsey et al., "Genetic Diversity and Protective Efficacy of the RTS,S/AS01 Malaria Vaccine," N Engl J Med 373(21):2025-2037 (2015).
Nielsen et al., "RTS,S malaria vaccine efficacy and immunogenicity during Plasmodium falciparum challenge is associated with HLA genotype," Vaccine 36:1637-1642 (2018).
Ntoumi et al., "Vaccination with fractional doses: promise or illusion?," The Lancet 22:1258-1259 (2022).
Nutt et al., "The generation of antibody-secreting plasma cells," Nature Reviews Immunology 15:160-171 (2015).
O'Connor et al., "Short-lived and Long-lived Bone Marrow Plasma Cells Are Derived from a Novel Precursor Population," J. Exp. Med. 195(6):737-745 (2002).
Ochsenbein et al., "Protective long-term antibody memory by antigen-driven and T help-dependent differentiation of long-lived memory B cells to short-lived plasma cells independent of secondary lymphoid organs," PNAS 97(24):13263-13268 (2000).
Ockenhouse et al., "Ad35.CS.01-RTS,S/AS01 Heterologous Prime Boost Vaccine Efficacy against Sporozoite Challenge in Healthy Malaria-Naïve Adults," PLoS One 10(7):e0131571 (2015).
Of Human Memory B Cells, Science 298:2199-2202 (2002).
Olotu et al., "Avidity of Anti-Circumsporozoite Antibodies following Vaccination with RTS,S/AS01E in Young Children," PLoS One 9(12):e115126 (2014).
Oyen et al., "Cryo-EM structure of P. falciparum circumsporozoite protein with a vaccine-elicited antibody is stabilized by somatically mutated inter-Fab contacts," Sci. Adv. 4:eaau8529 (2018) 18 pgs.
Oyen et al., "Structural basis for antibody recognition of the NANP repeats in Plasmodium falciparum circumsporozoite protein," Proc. Natl. Acad Sci. USA, 114(48):E10438-E10445 (2017).
Oyen et al., "Structural basis for antibody recognition of the NANP repeats in Plasmodium falciparum circumsporozoite protein," PNAS E10438-E10445 (2017) 19 pgs.
Oyen et al., "Structure and mechanism of monoclonal antibody binding to the junctional epitope of Plasmodium falciparum circumsporozoite protein," PLoS Pathog 16(3):e1008373 (2020).
Pallikkuth et al., "A delayed fractionated dose Rts,S AS01 vaccine regimen mediates protection via improved T follicular helper and B cell responses," eLife 9:e51889 (2020) 25 pgs.
Patra et al., "Force Spectroscopy of the Plasmodium falciparum Vaccine Candidate Circumsporozoite Protein Suggests a Mechanically Pliable Repeat Region," The Journal Of Biological Chemistry 292(6):2110-2119 (2017).
Pedersen et al., "Antibody modeling: beyond homology," Immunomethods, 1, 126-136 (1992).
Pholcharee et al., "Diverse Antibody Responses to Conserved Structural Motifs in Plasmodium falciparum Circumsporozoite Protein," J. Mol. Bio., 432, 1048-1063 (2020).
Pholcharee et al., "Diverse Antibody Responses to Conserved Structural Motifs in Plasmodium falciparum Circumsporozoite Protein," Journal of Molecular Biology (2019) 28 pgs.
Pholcharee et al., "Structural and biophysical correlation of anti-NANP antibodies with in vivo protection against P. falciparum," Nature Communications 12:1063 (2021) 31 pgs.
Pieper et al., "Public antibodies to malaria antigens generated by two LAIR1 insertion modalities," Nature 548(7669):597-601 (2017).
Radbruch et al., "Competence and competition: the challenge of becoming a long-lived plasma cell," Nature Reviews, Immunology 6:741-750 (2006).
Radin et al., "A monoclonal antibody-based immunoassay to measure the antibody response against the repeat region of the circumsporozoite protein of Plasmodium falciparum," Malaria J. 15:543, 11 pgs. (2016).
Raghunandan et al., "Characterization of two in vivo challenge models to measure functional activity of monoclonal antibodies to Plasmodium falciparum circumsporozoite protein," Malaria J. 19:113 (2020) 15 pgs.
Ralph et al., "Using B cell receptor lineage structures to predict affinity," (Apr. 25, 2020) 46 pgs.
Reeder et al., "Strategic Variants of CSP Delivered as SynDNA Vaccines Demonstrate Heterogeneity of Immunogenicity and Protection from Plasmodium Infection in a Murine Model," Infect Immun 89:e00728-20 (2021).
Regules et al., "Fractional Third and Fourth Dose of RTS,S/AS01 Malaria Candidate Vaccine: A Phase 2a Controlled Human Malaria Parasite Infection and Immunogenicity Study," JID 214:762-771 (2016).
Renia et al., "Malaria Parasites: The Great Escape," Front. Immunol. 7:463, 14 pgs. (2016).
Robinson, "Sequencing the functional antibody repertoire-diagnostic and therapeutic discovery," Nat. Rev. Rheumatol. 11:171-182 (2015).
Ruiz et al., "IMGT, the international ImMunoGeneTics database," Nucleic Acids Res., 28, 219-221 (2000).
Sambrook & Russell, Molecular Cloning: A Laboratory Manual, Cold Spring Harbor Laboratory Press.
Sánchez et al., "Antibody responses to the RTS,S/AS01E vaccine and Plasmodium falciparum antigens after a booster dose within the phase 3 trial in Mozambique," NPJ Vaccines 5:46 (2020) 16 pgs.
Scally et al., "Peek-Peak-Pique: Repeating Motifs of Subtle Variance Are Targets for Potent Malaria Antibodies," Immunity 48:851-854 (2018).
Scally et al., "Rare PfCSP C-terminal antibodies induced by live sporozoite vaccination are ineffective against malaria infection," J. Exp. Med., 18 pgs. (2018).
Schofield et al., "Lack of Ir gene control in the immune response to malaria. I. A thymus-independent antibody response to the repetitive surface protein of sporozoites," J Immunol 144:2781-2788 (1990).

(56) References Cited

OTHER PUBLICATIONS

Schofield, "On the Function of Repetitive Domains in Protein Antigens of Plasmodium and Other Eukaryotic Parasites," Parasitology Today, 7(5):99-105 (1991).
Schofield, "The circumsporozoite protein of Plasmodium: a mechanism of immune evasion by the malaria parasite?" Bulletin of the World Health Organization, 68:66-73 (1990).
Schwenk et al., "IgG2 Antibodies against a Clinical Grade Plasmodium falciparum CSP Vaccine Antigen Associate with Protection against Transgenic Sporozoite Challenge in Mice," PLoS One 9(10):e111020 (2014) 16 pgs.
Seaton et al., "Subclass and avidity of circumsporozoite protein specific antibodies associate with protection status against malaria infection," NPJ Vaccines 6:110 (2021) 13 pgs.
Seder et al., "Protection Against Malaria by Intravenous Immunization with a Nonreplicating Sporozoite Vaccine," Science 341:1359-1365 (2013).
Sharma et al., "In silico selection of therapeutic antibodies for development: Viscosity, clearance, and chemical stability," Proc. Natl. Acad. Sci. USA, 111:18601-18606 (2014).
Singleton et al., Dictionary of Microbiology and Molecular Biology 2nd ed., J. Wiley & Sons (New York, N.Y) (1994).
Sinnis et al., "The RTS,S vaccine—a chance to regain the upper hand against malaria?" Cell 185:750-754 (2022).
Snapkov et al., "Progress and challenges in mass spectrometry-based analysis of antibody repertoires," Trends in Biotechnology, 40(4):463-481 (2022).
Soto et al., "High frequency of shared clonotypes in human B cell receptor repertoires," Nature, 18 pgs. (2019).
Stoute et al., "A Preliminary Evaluation of a Recombinant Circumsporozoite Protein Vaccine Against Plasmodium Falciparum Malaria," The New England Journal of Medicine 336(2):86-91 (2022).
Stoute et al., "A Preliminary Evaluation of a Recombinant Circumsporozoite Protein Vaccine against Plasmodium falciparum Malaria," N Engl J Med; 336:86-91(1997).
Suscovich et al., "Mapping functional humoral correlates of protection against malaria challenge following RTS,S/AS01 vaccination," Sci. Transl. Med. 12:eabb4757 (2020) 56 pgs.
Tan et al., "A public antibody lineage that potently inhibits malaria infection through dual binding to the circumsporozoite protein," Nature Medicine, 24(4):401-407 (2018).
Tan et al., "Functional human IgA targets a conserved site on malaria sporozoites," Sci Transl Med., 13(599):31 pgs. (2021).
Thai et al., "A high-affinity antibody against the CSP N-terminal domain lacks Plasmodium falciparum inhibitory activity," J. Exp. Med. 217(11):e20200061 (2020) 18 pgs.
Thompson et al., "Modelling the roles of antibody titre and avidity in protection from Plasmodium falciparum malaria infection following RTS,S/AS01 vaccination," Vaccine 38:7498-7507 (2020).
Triller et al., "Natural Parasite Exposure Induces Protective Human Anti-Malarial Antibodies," Immunity 47:1197-1209 (2017).
Ubillos et al., "Baseline exposure, antibody subclass, and hepatitis B response differentially affect malaria protective immunity following RTS,S/AS01E vaccination in African children," BMC Medicine 16:197 (2018) 18 pgs.
Urlaub et al., "Isolation of Chinese hamster cell mutants deficient in dihydrofolate reductase activity," Proc. Natl. Acad. Sci. USA, 77:4216-4220 (1980).
Vauquelin, "Effects of target binding kinetics on in vivo drug efficacy: koff, kon and rebinding," British Journal of Pharmacology 173:2319-2334 (2016).
Vauquelin, "Link between a high kon for drug binding and a fast clinical action: to be or not to be?" Med. Chem. Commun., 9:1426 (2018) 13 pgs.
Vijay et al., "Infection-induced plasmablasts are a nutrient sink that impairs humoral immunity to malaria," Nature Immunology 21:790-801 (2020).
Vijayan et al., "Antibody interference by a non-neutralizing antibody abrogates humoral protection against Plasmodium yoelii liver stage," Cell Reports 36:109489, 33 pgs. (2021).
Visweswaran et al., "Germinal center activity and B cell maturation are associated with protective antibody responses against Plasmodium pre-erythrocytic infection," PLoS Pathog 18(7):e1010671 (2022) 24 pgs.
Volpe et al., "SoDA: implementation of a 3D alignment algorithm for inference of antigen receptor recombinations," Bioinformatics 22(4):438-444 (2006).
Wahl et al., "Clonal evolution and TCR specificity of the human TFH cell response to Plasmodium falciparum CSP," Sci. Immunol. 7:eabm9644 (2022) 13 pgs.
Wahl et al., "How to induce protective humoral immunity against Plasmodium falciparum circumsporozoite protein," J. Exp. Med. 219(2):e20201313 (2022) 10 pgs.
Walker et al., "Passive immunotherapy of viral infections: 'super-antibodies' enter the fray," Nature Reviews, Immunology, 18:297-308 (2018).
Wang et al., "A Potent Anti-Malarial Human Monoclonal Antibody Targets Circumsporozoite Protein Minor Repeats and Neutralizes Sporozoites in the Liver," Immunity 53:733-744 (2020).
Wang et al., "Protective effects of combining monoclonal antibodies and vaccines against the Plasmodium falciparum circumsporozoite protein," PLoS Pathog 17(12):e1010133 (2021) 26 pgs.
Wang et al., "The light chain of the L9 antibody is critical for binding circumsporozoite protein minor repeats and preventing malaria," Cell Reports 38:110367 (2022) 24 pgs.
Wardemann et al., "From human antibody structure and function towards the design of a novel Plasmodium falciparum circumsporozoite protein malaria vaccine," Current Opinion in Immunology 53:119-123 (2018).
Wec et al., "Longitudinal dynamics of the human B cell response to the yellow fever 17D vaccine," PNAS 117(12):6675-6685 (2020).
Weiss et al., "The Plasmodium falciparum-Specific Human Memory B Cell Compartment Expands Gradually with Repeated Malaria Infections," 6(5):e1000912 (2010) 13 pgs.
White et al., "A combined analysis of immunogenicity, antibody kinetics and vaccine efficacy from phase 2 trials of the RTS,S malaria vaccine," BMC Medicine 12:117 (2014) 11 pgs.
White et al., "Immunogenicity of the RTS,S/AS01 malaria vaccine and implications for duration of vaccine efficacy: secondary analysis of data from a phase 3 randomised controlled trial," Lancet Infect Dis 15:1450-1458 (2015).
White et al., "The Relationship between RTS,S Vaccine-Induced Antibodies, CD4+ T Cell Responses and Protection against Plasmodium falciparum Infection," PLoS One 8(4):e61395 (2013) 10 pgs.
Woodruff et al., "B Cell Competition for Restricted T Cell Help Suppresses Rare-Epitope Responses," Cell Rep. 25(2):321-327 (2018) 19 pgs.
Wu et al., "Low-Dose Subcutaneous or Intravenous Monoclonal Antibody to Prevent Malaria," N Engl. J Med 387:397-407 (2022).
Xu et al., "Structure, heterogeneity and developability assessment of therapeutic antibodies," MABS 11(2):239-264 (2019).
Young et al., "Comprehensive Data Integration Approach to Assess Immune Responses and Correlates of RTS,S/AS01-Mediated Protection From Malaria Infection in Controlled Human Malaria Infection Trials," Frontiers in Big Data, 4:672460 (2021) 17 pgs.
Zapata et al., "Engineering linear F(ab')2 fragments for efficient production in *Escherichia coli* and enhanced antiproliferative activity," Protein Eng. 8(10): 1057-1062 (1995).
Zavala et al., "Circumsporozoite Proteins of Malaria Parasites Contain A Single Immunodominant Region With Two Or More Identical Epitopes," J. Exp. Med. 157:1947-1957 (1983).
Zavala et al., "Rationale for Development of a Synthetic Vaccine Against Plasmodium falciparum Malaria," 228:1436-1440 (1985).
Zavala, "RTS,S: the first malaria vaccine," J Clin Invest. 132(1):e156588 (2022) 3 pgs.
Zhang et al., "Monoclonal Antibodies against Plasmodium falciparum Circumsporozoite Protein," Antibodies 6:11 (2017) 10 pgs.

(56) References Cited

OTHER PUBLICATIONS

Zhao et al., "A Comprehensive Analysis of Plasmodium Circumsporozoite Protein Binding to Hepatocytes," PLoS One 11(8):e0161607 (2016).

* cited by examiner

| AB-000224_LS Light Chain | | | |
|---|---|---|---|
| | | | |
| **Residue** | **Linear #** | **Mat. Linear #** | **ASN #** |
| M | 1 | -19 | LmdLdr:-19 |
| A | 2 | -18 | LmdLdr:-18 |
| W | 3 | -17 | LmdLdr:-17 |
| A | 4 | -16 | LmdLdr:-16 |
| L | 5 | -15 | LmdLdr:-15 |
| L | 6 | -14 | LmdLdr:-14 |
| L | 7 | -13 | LmdLdr:-13 |
| L | 8 | -12 | LmdLdr:-12 |
| T | 9 | -11 | LmdLdr:-11 |
| L | 10 | -10 | LmdLdr:-10 |
| L | 11 | -9 | LmdLdr:-9 |
| T | 12 | -8 | LmdLdr:-8 |
| Q | 13 | -7 | LmdLdr:-7 |
| G | 14 | -6 | LmdLdr:-6 |
| T | 15 | -5 | LmdLdr:-5 |
| G | 16 | -4 | LmdLdr:-4 |
| S | 17 | -3 | LmdLdr:-3 |
| W | 18 | -2 | LmdLdr:-2 |
| A | 19 | -1 | LmdLdr:-1 |
| E | 20 | 1 | LmdV:1 |
| S | 21 | 2 | LmdV:2 |
| V | 22 | 3 | LmdV:3 |
| L | 23 | 4 | LmdV:4 |
| T | 24 | 5 | LmdV:5 |
| Q | 25 | 6 | LmdV:6 |
| P | 26 | 7 | LmdV:7 |
| - | 26.1 | 7.1 | LmdV:8 |
| P | 27 | 8 | LmdV:9 |
| S | 28 | 9 | LmdV:10 |
| V | 29 | 10 | LmdV:11 |
| S | 30 | 11 | LmdV:12 |
| G | 31 | 12 | LmdV:13 |
| A | 32 | 13 | LmdV:14 |
| P | 33 | 14 | LmdV:15 |
| G | 34 | 15 | LmdV:16 |
| Q | 35 | 16 | LmdV:17 |
| R | 36 | 17 | LmdV:18 |
| V | 37 | 18 | LmdV:19 |
| T | 38 | 19 | LmdV:20 |
| I | 39 | 20 | LmdV:21 |
| S | 40 | 21 | LmdV:22 |
| C | 41 | 22 | LmdV:23 |

FIG. 6

| AB-000224_LS Light Chain | | | |
|---|---|---|---|
| | | | |
| **Residue** | **Linear #** | **Mat. Linear #** | **ASN #** |
| T | 42 | 23 | LmdV:24 |
| G | 43 | 24 | LmdV:25 |
| M | 44 | 25 | LmdV:26 |
| N | 45 | 26 | LmdV:27 |
| - | 45.1 | 26.1 | LmdV:28 |
| S | 46 | 27 | LmdV:29 |
| N | 47 | 28 | LmdV:30 |
| I | 48 | 29 | LmdV:31 |
| G | 49 | 30 | LmdV:32 |
| A | 50 | 31 | LmdV:33 |
| G | 51 | 32 | LmdV:34 |
| - | 51.1 | 32.1 | LmdV:35 |
| - | 51.2 | 32.2 | LmdV:36 |
| - | 51.3 | 32.3 | LmdV:37 |
| - | 51.4 | 32.4 | LmdV:38 |
| Y | 52 | 33 | LmdV:39 |
| D | 53 | 34 | LmdV:40 |
| V | 54 | 35 | LmdV:41 |
| Y | 55 | 36 | LmdV:42 |
| W | 56 | 37 | LmdV:43 |
| Y | 57 | 38 | LmdV:44 |
| Q | 58 | 39 | LmdV:45 |
| Q | 59 | 40 | LmdV:46 |
| L | 60 | 41 | LmdV:47 |
| P | 61 | 42 | LmdV:48 |
| G | 62 | 43 | LmdV:49 |
| R | 63 | 44 | LmdV:50 |
| A | 64 | 45 | LmdV:51 |
| P | 65 | 46 | LmdV:52 |
| K | 66 | 47 | LmdV:53 |
| L | 67 | 48 | LmdV:54 |
| L | 68 | 49 | LmdV:55 |
| I | 69 | 50 | LmdV:56 |
| Y | 70 | 51 | LmdV:57 |
| G | 71 | 52 | LmdV:58 |
| - | 71.1 | 52.1 | LmdV:59 |
| - | 71.2 | 52.2 | LmdV:60 |
| - | 71.3 | 52.3 | LmdV:61 |
| - | 71.4 | 52.4 | LmdV:62 |
| - | 71.5 | 52.5 | LmdV:63 |
| - | 71.6 | 52.6 | LmdV:64 |
| - | 71.7 | 52.7 | LmdV:65 |

FIG. 6 Continued

| AB-000224_LS Light Chain | | | |
|---|---|---|---|
| | | | |
| **Residue** | **Linear #** | **Mat. Linear #** | **ASN #** |
| - | 71.8 | 52.8 | LmdV:66 |
| N | 72 | 53 | LmdV:67 |
| S | 73 | 54 | LmdV:68 |
| N | 74 | 55 | LmdV:69 |
| R | 75 | 56 | LmdV:70 |
| P | 76 | 57 | LmdV:71 |
| S | 77 | 58 | LmdV:72 |
| G | 78 | 59 | LmdV:73 |
| V | 79 | 60 | LmdV:74 |
| P | 80 | 61 | LmdV:75 |
| D | 81 | 62 | LmdV:76 |
| R | 82 | 63 | LmdV:77 |
| F | 83 | 64 | LmdV:78 |
| S | 84 | 65 | LmdV:79 |
| G | 85 | 66 | LmdV:80 |
| S | 86 | 67 | LmdV:81 |
| R | 87 | 68 | LmdV:82 |
| S | 88 | 69 | LmdV:83 |
| G | 89 | 70 | LmdV:84 |
| - | 89.1 | 70.1 | LmdV:85 |
| - | 89.2 | 70.2 | LmdV:86 |
| T | 90 | 71 | LmdV:87 |
| S | 91 | 72 | LmdV:88 |
| A | 92 | 73 | LmdV:89 |
| S | 93 | 74 | LmdV:90 |
| L | 94 | 75 | LmdV:91 |
| A | 95 | 76 | LmdV:92 |
| I | 96 | 77 | LmdV:93 |
| T | 97 | 78 | LmdV:94 |
| G | 98 | 79 | LmdV:95 |
| L | 99 | 80 | LmdV:96 |
| Q | 100 | 81 | LmdV:97 |
| A | 101 | 82 | LmdV:98 |
| E | 102 | 83 | LmdV:99 |
| D | 103 | 84 | LmdV:100 |
| E | 104 | 85 | LmdV:101 |
| A | 105 | 86 | LmdV:102 |
| D | 106 | 87 | LmdV:103 |
| Y | 107 | 88 | LmdV:104 |
| Y | 108 | 89 | LmdV:105 |
| C | 109 | 90 | LmdV:106 |
| Q | 110 | 91 | LmdV:107 |

FIG. 6 Continued

| AB-000224_LS Light Chain | | | |
|---|---|---|---|
| | | | |
| **Residue** | **Linear #** | **Mat. Linear #** | **ASN #** |
| S | 111 | 92 | LmdV:108 |
| Y | 112 | 93 | LmdV:109 |
| D | 113 | 94 | LmdV:110 |
| T | 114 | 95 | LmdV:111 |
| S | 115 | 96 | LmdV:112 |
| - | 115.1 | 96.1 | LmdV:113 |
| - | 115.2 | 96.2 | LmdV:114 |
| - | 115.3 | 96.3 | LmdV:115 |
| - | 115.4 | 96.4 | LmdV:116 |
| - | 115.5 | 96.5 | LmdV:117 |
| - | 115.6 | 96.6 | LmdV:118 |
| - | 115.7 | 96.7 | LmdV:119 |
| - | 115.8 | 96.8 | LmdV:120 |
| - | 115.9 | 96.9 | LmdV:121 |
| - | 115.10 | 96.10 | LmdV:122 |
| - | 115.11 | 96.11 | LmdV:123 |
| - | 115.12 | 96.12 | LmdV:124 |
| - | 115.13 | 96.13 | LmdV:125 |
| - | 115.14 | 96.14 | LmdV:126 |
| - | 115.15 | 96.15 | LmdV:127 |
| - | 115.16 | 96.16 | LmdV:128 |
| - | 115.17 | 96.17 | LmdV:129 |
| - | 115.18 | 96.18 | LmdV:130 |
| - | 115.19 | 96.19 | LmdV:131 |
| - | 115.20 | 96.20 | LmdV:132 |
| - | 115.21 | 96.21 | LmdV:133 |
| L | 116 | 97 | LmdV:134 |
| N | 117 | 98 | LmdV:135 |
| G | 118 | 99 | LmdV:136 |
| W | 119 | 100 | LmdV:137 |
| A | 120 | 101 | LmdV:138 |
| F | 121 | 102 | LmdV:139 |
| G | 122 | 103 | LmdV:140 |
| G | 123 | 104 | LmdV:141 |
| G | 124 | 105 | LmdV:142 |
| T | 125 | 106 | LmdV:143 |
| K | 126 | 107 | LmdV:144 |
| L | 127 | 108 | LmdV:145 |
| T | 128 | 109 | LmdV:146 |
| V | 129 | 110 | LmdV:147 |
| L | 130 | 111 | LmdV:148 |
| G | 131 | 112 | LmdV:149 |

FIG. 6 Continued

| AB-000224_LS Light Chain | | | |
|---|---|---|---|
| | | | |
| **Residue** | **Linear #** | **Mat. Linear #** | **ASN #** |
| Q | 132 | 113 | LmdCnst-Ig:1 |
| P | 133 | 114 | LmdCnst-Ig:2 |
| K | 134 | 115 | LmdCnst-Ig:3 |
| A | 135 | 116 | LmdCnst-Ig:4 |
| A | 136 | 117 | LmdCnst-Ig:5 |
| P | 137 | 118 | LmdCnst-Ig:6 |
| S | 138 | 119 | LmdCnst-Ig:7 |
| V | 139 | 120 | LmdCnst-Ig:8 |
| T | 140 | 121 | LmdCnst-Ig:9 |
| L | 141 | 122 | LmdCnst-Ig:10 |
| F | 142 | 123 | LmdCnst-Ig:11 |
| P | 143 | 124 | LmdCnst-Ig:12 |
| P | 144 | 125 | LmdCnst-Ig:13 |
| S | 145 | 126 | LmdCnst-Ig:14 |
| S | 146 | 127 | LmdCnst-Ig:15 |
| E | 147 | 128 | LmdCnst-Ig:16 |
| - | 147.1 | 128.1 | LmdCnst-Ig:17 |
| - | 147.2 | 128.2 | LmdCnst-Ig:18 |
| E | 148 | 129 | LmdCnst-Ig:19 |
| L | 149 | 130 | LmdCnst-Ig:20 |
| - | 149.1 | 130.1 | LmdCnst-Ig:21 |
| - | 149.2 | 130.2 | LmdCnst-Ig:22 |
| Q | 150 | 131 | LmdCnst-Ig:23 |
| A | 151 | 132 | LmdCnst-Ig:24 |
| N | 152 | 133 | LmdCnst-Ig:25 |
| K | 153 | 134 | LmdCnst-Ig:26 |
| A | 154 | 135 | LmdCnst-Ig:27 |
| T | 155 | 136 | LmdCnst-Ig:28 |
| L | 156 | 137 | LmdCnst-Ig:29 |
| V | 157 | 138 | LmdCnst-Ig:30 |
| C | 158 | 139 | LmdCnst-Ig:31 |
| L | 159 | 140 | LmdCnst-Ig:32 |
| V | 160 | 141 | LmdCnst-Ig:33 |
| S | 161 | 142 | LmdCnst-Ig:34 |
| D | 162 | 143 | LmdCnst-Ig:35 |
| F | 163 | 144 | LmdCnst-Ig:36 |
| Y | 164 | 145 | LmdCnst-Ig:37 |
| P | 165 | 146 | LmdCnst-Ig:38 |
| - | 165.1 | 146.1 | LmdCnst-Ig:39 |
| - | 165.2 | 146.2 | LmdCnst-Ig:40 |
| G | 166 | 147 | LmdCnst-Ig:41 |
| A | 167 | 148 | LmdCnst-Ig:42 |

FIG. 6 Continued

| AB-000224_LS Light Chain | | | |
|---|---|---|---|
| | | | |
| **Residue** | **Linear #** | **Mat. Linear #** | **ASN #** |
| V | 168 | 149 | LmdCnst-Ig:43 |
| T | 169 | 150 | LmdCnst-Ig:44 |
| V | 170 | 151 | LmdCnst-Ig:45 |
| A | 171 | 152 | LmdCnst-Ig:46 |
| W | 172 | 153 | LmdCnst-Ig:47 |
| - | 172.1 | 153.1 | LmdCnst-Ig:48 |
| K | 173 | 154 | LmdCnst-Ig:49 |
| A | 174 | 155 | LmdCnst-Ig:50 |
| D | 175 | 156 | LmdCnst-Ig:51 |
| G | 176 | 157 | LmdCnst-Ig:52 |
| S | 177 | 158 | LmdCnst-Ig:53 |
| P | 178 | 159 | LmdCnst-Ig:54 |
| V | 179 | 160 | LmdCnst-Ig:55 |
| K | 180 | 161 | LmdCnst-Ig:56 |
| V | 181 | 162 | LmdCnst-Ig:57 |
| G | 182 | 163 | LmdCnst-Ig:58 |
| V | 183 | 164 | LmdCnst-Ig:59 |
| E | 184 | 165 | LmdCnst-Ig:60 |
| T | 185 | 166 | LmdCnst-Ig:61 |
| T | 186 | 167 | LmdCnst-Ig:62 |
| K | 187 | 168 | LmdCnst-Ig:63 |
| P | 188 | 169 | LmdCnst-Ig:64 |
| S | 189 | 170 | LmdCnst-Ig:65 |
| K | 190 | 171 | LmdCnst-Ig:66 |
| Q | 191 | 172 | LmdCnst-Ig:67 |
| - | 191.1 | 172.1 | LmdCnst-Ig:68 |
| - | 191.2 | 172.2 | LmdCnst-Ig:69 |
| - | 191.3 | 172.3 | LmdCnst-Ig:70 |
| - | 191.4 | 172.4 | LmdCnst-Ig:71 |
| - | 191.5 | 172.5 | LmdCnst-Ig:72 |
| S | 192 | 173 | LmdCnst-Ig:73 |
| N | 193 | 174 | LmdCnst-Ig:74 |
| N | 194 | 175 | LmdCnst-Ig:75 |
| K | 195 | 176 | LmdCnst-Ig:76 |
| Y | 196 | 177 | LmdCnst-Ig:77 |
| A | 197 | 178 | LmdCnst-Ig:78 |
| A | 198 | 179 | LmdCnst-Ig:79 |
| S | 199 | 180 | LmdCnst-Ig:80 |
| S | 200 | 181 | LmdCnst-Ig:81 |
| Y | 201 | 182 | LmdCnst-Ig:82 |
| L | 202 | 183 | LmdCnst-Ig:83 |
| S | 203 | 184 | LmdCnst-Ig:84 |

FIG. 6 Continued

| AB-000224_LS Light Chain | | | |
|---|---|---|---|
| | | | |
| **Residue** | **Linear #** | **Mat. Linear #** | **ASN #** |
| L | 204 | 185 | LmdCnst-Ig:85 |
| T | 205 | 186 | LmdCnst-Ig:86 |
| P | 206 | 187 | LmdCnst-Ig:87 |
| E | 207 | 188 | LmdCnst-Ig:88 |
| Q | 208 | 189 | LmdCnst-Ig:89 |
| W | 209 | 190 | LmdCnst-Ig:90 |
| - | 209.1 | 190.1 | LmdCnst-Ig:91 |
| K | 210 | 191 | LmdCnst-Ig:92 |
| S | 211 | 192 | LmdCnst-Ig:93 |
| H | 212 | 193 | LmdCnst-Ig:94 |
| R | 213 | 194 | LmdCnst-Ig:95 |
| S | 214 | 195 | LmdCnst-Ig:96 |
| - | 214.1 | 195.1 | LmdCnst-Ig:97 |
| - | 214.2 | 195.2 | LmdCnst-Ig:98 |
| Y | 215 | 196 | LmdCnst-Ig:99 |
| S | 216 | 197 | LmdCnst-Ig:100 |
| C | 217 | 198 | LmdCnst-Ig:101 |
| R | 218 | 199 | LmdCnst-Ig:102 |
| V | 219 | 200 | LmdCnst-Ig:103 |
| T | 220 | 201 | LmdCnst-Ig:104 |
| H | 221 | 202 | LmdCnst-Ig:105 |
| E | 222 | 203 | LmdCnst-Ig:106 |
| G | 223 | 204 | LmdCnst-Ig:107 |
| S | 224 | 205 | LmdCnst-Ig:108 |
| T | 225 | 206 | LmdCnst-Ig:109 |
| - | 225.1 | 206.1 | LmdCnst-Ig:110 |
| - | 225.2 | 206.2 | LmdCnst-Ig:111 |
| V | 226 | 207 | LmdCnst-Ig:112 |
| E | 227 | 208 | LmdCnst-Ig:113 |
| K | 228 | 209 | LmdCnst-Ig:114 |
| T | 229 | 210 | LmdCnst-Ig:115 |
| V | 230 | 211 | LmdCnst-Ig:116 |
| - | 230.1 | 211.1 | LmdCnst-Ig:117 |
| A | 231 | 212 | LmdCnst-Ig:118 |
| P | 232 | 213 | LmdCnst-Ig:119 |
| A | 233 | 214 | LmdCnst-Ig:120 |
| E | 234 | 215 | LmdCnst-Ig:121 |
| C | 235 | 216 | LmdCnst-Ig:122 |
| S | 236 | 217 | LmdCnst-Ig:123 |

FIG. 6 Continued

| AB-000224_LS_Heavy Chain | | | |
|---|---|---|---|
| | | | |
| Residue | Linear # | Mat. Linear # | ASN # |
| M | 1 | -22 | KLdr:-22 |
| D | 2 | -21 | KLdr:-21 |
| M | 3 | -20 | KLdr:-20 |
| R | 4 | -19 | KLdr:-19 |
| V | 5 | -18 | KLdr:-18 |
| P | 6 | -17 | KLdr:-17 |
| A | 7 | -16 | KLdr:-16 |
| Q | 8 | -15 | KLdr:-15 |
| L | 9 | -14 | KLdr:-14 |
| L | 10 | -13 | KLdr:-13 |
| G | 11 | -12 | KLdr:-12 |
| L | 12 | -11 | KLdr:-11 |
| L | 13 | -10 | KLdr:-10 |
| L | 14 | -9 | KLdr:-9 |
| L | 15 | -8 | KLdr:-8 |
| W | 16 | -7 | KLdr:-7 |
| L | 17 | -6 | KLdr:-6 |
| R | 18 | -5 | KLdr:-5 |
| G | 19 | -4 | KLdr:-4 |
| A | 20 | -3 | KLdr:-3 |
| R | 21 | -2 | KLdr:-2 |
| C | 22 | -1 | KLdr:-1 |
| E | 23 | 1 | HV:1 |
| V | 24 | 2 | HV:2 |
| Q | 25 | 3 | HV:3 |
| L | 26 | 4 | HV:4 |
| V | 27 | 5 | HV:5 |
| E | 28 | 6 | HV:6 |
| S | 29 | 7 | HV:7 |
| - | 29.1 | 7.1 | HV:8 |
| G | 30 | 8 | HV:9 |
| G | 31 | 9 | HV:10 |
| G | 32 | 10 | HV:11 |
| L | 33 | 11 | HV:12 |
| V | 34 | 12 | HV:13 |
| Q | 35 | 13 | HV:14 |
| P | 36 | 14 | HV:15 |
| G | 37 | 15 | HV:16 |
| R | 38 | 16 | HV:17 |
| S | 39 | 17 | HV:18 |
| L | 40 | 18 | HV:19 |

FIG. 7

| AB-000224_LS_Heavy Chain | | | |
|---|---|---|---|
| | | | |
| Residue | Linear # | Mat. Linear # | ASN # |
| R | 41 | 19 | HV:20 |
| L | 42 | 20 | HV:21 |
| P | 43 | 21 | HV:22 |
| C | 44 | 22 | HV:23 |
| T | 45 | 23 | HV:24 |
| A | 46 | 24 | HV:25 |
| S | 47 | 25 | HV:26 |
| G | 48 | 26 | HV:27 |
| - | 48.1 | 26.1 | HV:28 |
| F | 49 | 27 | HV:29 |
| S | 50 | 28 | HV:30 |
| F | 51 | 29 | HV:31 |
| G | 52 | 30 | HV:32 |
| D | 53 | 31 | HV:33 |
| - | 53.1 | 31.1 | HV:34 |
| - | 53.2 | 31.2 | HV:35 |
| - | 53.3 | 31.3 | HV:36 |
| - | 53.4 | 31.4 | HV:37 |
| - | 53.5 | 31.5 | HV:38 |
| H | 54 | 32 | HV:39 |
| A | 55 | 33 | HV:40 |
| M | 56 | 34 | HV:41 |
| S | 57 | 35 | HV:42 |
| W | 58 | 36 | HV:43 |
| V | 59 | 37 | HV:44 |
| R | 60 | 38 | HV:45 |
| Q | 61 | 39 | HV:46 |
| A | 62 | 40 | HV:47 |
| P | 63 | 41 | HV:48 |
| G | 64 | 42 | HV:49 |
| K | 65 | 43 | HV:50 |
| G | 66 | 44 | HV:51 |
| L | 67 | 45 | HV:52 |
| E | 68 | 46 | HV:53 |
| W | 69 | 47 | HV:54 |
| V | 70 | 48 | HV:55 |
| G | 71 | 49 | HV:56 |
| F | 72 | 50 | HV:57 |
| I | 73 | 51 | HV:58 |
| R | 74 | 52 | HV:59 |
| K | 75 | 53 | HV:60 |
| T | 76 | 54 | HV:61 |
| - | 76.1 | 54.1 | HV:62 |

FIG. 7 Continued

| AB-000224_LS_Heavy Chain | | | |
|---|---|---|---|
| | | | |
| Residue | Linear # | Mat. Linear # | ASN # |
| T | 77 | 55 | HV:63 |
| Y | 78 | 56 | HV:64 |
| G | 79 | 57 | HV:65 |
| A | 80 | 58 | HV:66 |
| T | 81 | 59 | HV:67 |
| T | 82 | 60 | HV:68 |
| H | 83 | 61 | HV:69 |
| Y | 84 | 62 | HV:70 |
| A | 85 | 63 | HV:71 |
| A | 86 | 64 | HV:72 |
| A | 87 | 65 | HV:73 |
| V | 88 | 66 | HV:74 |
| R | 89 | 67 | HV:75 |
| G | 90 | 68 | HV:76 |
| R | 91 | 69 | HV:77 |
| F | 92 | 70 | HV:78 |
| T | 93 | 71 | HV:79 |
| I | 94 | 72 | HV:80 |
| S | 95 | 73 | HV:81 |
| R | 96 | 74 | HV:82 |
| D | 97 | 75 | HV:83 |
| D | 98 | 76 | HV:84 |
| S | 99 | 77 | HV:85 |
| K | 100 | 78 | HV:86 |
| S | 101 | 79 | HV:87 |
| I | 102 | 80 | HV:88 |
| V | 103 | 81 | HV:89 |
| Y | 104 | 82 | HV:90 |
| L | 105 | 83 | HV:91 |
| Q | 106 | 84 | HV:92 |
| M | 107 | 85 | HV:93 |
| N | 108 | 86 | HV:94 |
| S | 109 | 87 | HV:95 |
| L | 110 | 88 | HV:96 |
| K | 111 | 89 | HV:97 |
| T | 112 | 90 | HV:98 |
| E | 113 | 91 | HV:99 |
| D | 114 | 92 | HV:100 |
| T | 115 | 93 | HV:101 |
| A | 116 | 94 | HV:102 |
| V | 117 | 95 | HV:103 |
| Y | 118 | 96 | HV:104 |
| F | 119 | 97 | HV:105 |

FIG. 7 Continued

| AB-000224_LS_Heavy Chain | | | |
|---|---|---|---|
| | | | |
| Residue | Linear # | Mat. Linear # | ASN # |
| C | 120 | 98 | HV:106 |
| T | 121 | 99 | HV:107 |
| R | 122 | 100 | HV:108 |
| V | 123 | 101 | HV:109 |
| Q | 124 | 102 | HV:110 |
| L | 125 | 103 | HV:111 |
| D | 126 | 104 | HV:112 |
| Y | 127 | 105 | HV:113 |
| G | 128 | 106 | HV:114 |
| P | 129 | 107 | HV:115 |
| - | 129.1 | 107.1 | HV:116 |
| - | 129.2 | 107.2 | HV:117 |
| - | 129.3 | 107.3 | HV:118 |
| - | 129.4 | 107.4 | HV:119 |
| - | 129.5 | 107.5 | HV:120 |
| - | 129.6 | 107.6 | HV:121 |
| - | 129.7 | 107.7 | HV:122 |
| - | 129.8 | 107.8 | HV:123 |
| - | 129.9 | 107.9 | HV:124 |
| - | 129.10 | 107.10 | HV:125 |
| - | 129.11 | 107.11 | HV:126 |
| - | 129.12 | 107.12 | HV:127 |
| - | 129.13 | 107.13 | HV:128 |
| - | 129.14 | 107.14 | HV:129 |
| G | 130 | 108 | HV:130 |
| Y | 131 | 109 | HV:131 |
| Q | 132 | 110 | HV:132 |
| Y | 133 | 111 | HV:133 |
| Y | 134 | 112 | HV:134 |
| G | 135 | 113 | HV:135 |
| M | 136 | 114 | HV:136 |
| D | 137 | 115 | HV:137 |
| V | 138 | 116 | HV:138 |
| W | 139 | 117 | HV:139 |
| G | 140 | 118 | HV:140 |
| Q | 141 | 119 | HV:141 |
| G | 142 | 120 | HV:142 |
| T | 143 | 121 | HV:143 |
| T | 144 | 122 | HV:144 |
| V | 145 | 123 | HV:145 |
| T | 146 | 124 | HV:146 |
| V | 147 | 125 | HV:147 |
| S | 148 | 126 | HV:148 |

FIG. 7 Continued

| AB-000224_LS_Heavy Chain | | | |
|---|---|---|---|
| | | | |
| Residue | Linear # | Mat. Linear # | ASN # |
| S | 149 | 127 | HV:149 |
| - | 149.1 | 127.1 | HCnst-Ig:1 |
| - | 149.2 | 127.2 | HCnst-Ig:2 |
| A | 150 | 128 | HCnst-Ig:3 |
| S | 151 | 129 | HCnst-Ig:4 |
| T | 152 | 130 | HCnst-Ig:5 |
| K | 153 | 131 | HCnst-Ig:6 |
| G | 154 | 132 | HCnst-Ig:7 |
| P | 155 | 133 | HCnst-Ig:8 |
| S | 156 | 134 | HCnst-Ig:9 |
| V | 157 | 135 | HCnst-Ig:10 |
| F | 158 | 136 | HCnst-Ig:11 |
| P | 159 | 137 | HCnst-Ig:12 |
| L | 160 | 138 | HCnst-Ig:13 |
| A | 161 | 139 | HCnst-Ig:14 |
| P | 162 | 140 | HCnst-Ig:15 |
| - | 162.1 | 140.1 | HCnst-Ig:16 |
| S | 163 | 141 | HCnst-Ig:17 |
| - | 163.1 | 141.1 | HCnst-Ig:18 |
| S | 164 | 142 | HCnst-Ig:19 |
| K | 165 | 143 | HCnst-Ig:20 |
| S | 166 | 144 | HCnst-Ig:21 |
| T | 167 | 145 | HCnst-Ig:22 |
| S | 168 | 146 | HCnst-Ig:23 |
| G | 169 | 147 | HCnst-Ig:24 |
| G | 170 | 148 | HCnst-Ig:25 |
| T | 171 | 149 | HCnst-Ig:26 |
| A | 172 | 150 | HCnst-Ig:27 |
| A | 173 | 151 | HCnst-Ig:28 |
| L | 174 | 152 | HCnst-Ig:29 |
| G | 175 | 153 | HCnst-Ig:30 |
| C | 176 | 154 | HCnst-Ig:31 |
| L | 177 | 155 | HCnst-Ig:32 |
| V | 178 | 156 | HCnst-Ig:33 |
| K | 179 | 157 | HCnst-Ig:34 |
| D | 180 | 158 | HCnst-Ig:35 |
| Y | 181 | 159 | HCnst-Ig:36 |
| F | 182 | 160 | HCnst-Ig:37 |
| P | 183 | 161 | HCnst-Ig:38 |
| - | 183.1 | 161.1 | HCnst-Ig:39 |
| - | 183.2 | 161.2 | HCnst-Ig:40 |
| E | 184 | 162 | HCnst-Ig:41 |
| P | 185 | 163 | HCnst-Ig:42 |

FIG. 7 Continued

| AB-000224_LS_Heavy Chain | | | |
|---|---|---|---|
| | | | |
| **Residue** | **Linear #** | **Mat. Linear #** | **ASN #** |
| V | 186 | 164 | HCnst-Ig:43 |
| T | 187 | 165 | HCnst-Ig:44 |
| V | 188 | 166 | HCnst-Ig:45 |
| S | 189 | 167 | HCnst-Ig:46 |
| W | 190 | 168 | HCnst-Ig:47 |
| - | 190.1 | 168.1 | HCnst-Ig:48 |
| N | 191 | 169 | HCnst-Ig:49 |
| S | 192 | 170 | HCnst-Ig:50 |
| G | 193 | 171 | HCnst-Ig:51 |
| A | 194 | 172 | HCnst-Ig:52 |
| L | 195 | 173 | HCnst-Ig:53 |
| T | 196 | 174 | HCnst-Ig:54 |
| S | 197 | 175 | HCnst-Ig:55 |
| G | 198 | 176 | HCnst-Ig:56 |
| V | 199 | 177 | HCnst-Ig:57 |
| H | 200 | 178 | HCnst-Ig:58 |
| T | 201 | 179 | HCnst-Ig:59 |
| - | 201.1 | 179.1 | HCnst-Ig:60 |
| - | 201.2 | 179.2 | HCnst-Ig:61 |
| - | 201.3 | 179.3 | HCnst-Ig:62 |
| F | 202 | 180 | HCnst-Ig:63 |
| P | 203 | 181 | HCnst-Ig:64 |
| A | 204 | 182 | HCnst-Ig:65 |
| V | 205 | 183 | HCnst-Ig:66 |
| L | 206 | 184 | HCnst-Ig:67 |
| Q | 207 | 185 | HCnst-Ig:68 |
| - | 207.1 | 185.1 | HCnst-Ig:69 |
| - | 207.2 | 185.2 | HCnst-Ig:70 |
| - | 207.3 | 185.3 | HCnst-Ig:71 |
| - | 207.4 | 185.4 | HCnst-Ig:72 |
| S | 208 | 186 | HCnst-Ig:73 |
| S | 209 | 187 | HCnst-Ig:74 |
| G | 210 | 188 | HCnst-Ig:75 |
| L | 211 | 189 | HCnst-Ig:76 |
| Y | 212 | 190 | HCnst-Ig:77 |
| S | 213 | 191 | HCnst-Ig:78 |
| L | 214 | 192 | HCnst-Ig:79 |
| S | 215 | 193 | HCnst-Ig:80 |
| S | 216 | 194 | HCnst-Ig:81 |
| V | 217 | 195 | HCnst-Ig:82 |
| V | 218 | 196 | HCnst-Ig:83 |
| T | 219 | 197 | HCnst-Ig:84 |
| V | 220 | 198 | HCnst-Ig:85 |

FIG. 7 Continued$_2$

| AB-000224_LS_Heavy Chain | | | |
|---|---|---|---|
| | | | |
| Residue | Linear # | Mat. Linear # | ASN # |
| P | 221 | 199 | HCnst-Ig:86 |
| S | 222 | 200 | HCnst-Ig:87 |
| S | 223 | 201 | HCnst-Ig:88 |
| S | 224 | 202 | HCnst-Ig:89 |
| L | 225 | 203 | HCnst-Ig:90 |
| - | 225.1 | 203.1 | HCnst-Ig:91 |
| G | 226 | 204 | HCnst-Ig:92 |
| T | 227 | 205 | HCnst-Ig:93 |
| Q | 228 | 206 | HCnst-Ig:94 |
| T | 229 | 207 | HCnst-Ig:95 |
| - | 229.1 | 207.1 | HCnst-Ig:96 |
| - | 229.2 | 207.2 | HCnst-Ig:97 |
| - | 229.3 | 207.3 | HCnst-Ig:98 |
| Y | 230 | 208 | HCnst-Ig:99 |
| I | 231 | 209 | HCnst-Ig:100 |
| C | 232 | 210 | HCnst-Ig:101 |
| N | 233 | 211 | HCnst-Ig:102 |
| V | 234 | 212 | HCnst-Ig:103 |
| N | 235 | 213 | HCnst-Ig:104 |
| H | 236 | 214 | HCnst-Ig:105 |
| K | 237 | 215 | HCnst-Ig:106 |
| P | 238 | 216 | HCnst-Ig:107 |
| S | 239 | 217 | HCnst-Ig:108 |
| N | 240 | 218 | HCnst-Ig:109 |
| - | 240.1 | 218.1 | HCnst-Ig:110 |
| - | 240.2 | 218.2 | HCnst-Ig:111 |
| T | 241 | 219 | HCnst-Ig:112 |
| K | 242 | 220 | HCnst-Ig:113 |
| V | 243 | 221 | HCnst-Ig:114 |
| D | 244 | 222 | HCnst-Ig:115 |
| K | 245 | 223 | HCnst-Ig:116 |
| - | 245.1 | 223.1 | HCnst-Ig:117 |
| K | 246 | 224 | HCnst-Ig:118 |
| V | 247 | 225 | HCnst-Ig:119 |
| - | 247.1 | 225.1 | HCnst-Ig:120 |
| - | 247.2 | 225.2 | HCnst-Ig:121 |
| - | 247.3 | 225.3 | HCnst-Ig:122 |
| - | 247.4 | 225.4 | HCnst-Ig:123 |
| - | 247.5 | 225.1 | Hinge:1 |
| - | 247.6 | 225.2 | Hinge:2 |
| - | 247.7 | 225.3 | Hinge:3 |
| - | 247.8 | 225.4 | Hinge:4 |
| - | 247.9 | 225.5 | Hinge:5 |

FIG. 7 Continued

| AB-000224_LS_Heavy Chain | | | |
|---|---|---|---|
| | | | |
| Residue | Linear # | Mat. Linear # | ASN # |
| - | 247.10 | 225.6 | Hinge:6 |
| - | 247.11 | 225.7 | Hinge:7 |
| - | 247.12 | 225.8 | Hinge:8 |
| - | 247.13 | 225.9 | Hinge:9 |
| - | 247.14 | 225.10 | Hinge:10 |
| - | 247.15 | 225.11 | Hinge:11 |
| - | 247.16 | 225.12 | Hinge:12 |
| - | 247.17 | 225.13 | Hinge:13 |
| - | 247.18 | 225.14 | Hinge:14 |
| - | 247.19 | 225.15 | Hinge:15 |
| - | 247.20 | 225.16 | Hinge:16 |
| - | 247.21 | 225.17 | Hinge:17 |
| - | 247.22 | 225.18 | Hinge:18 |
| - | 247.23 | 225.19 | Hinge:19 |
| - | 247.24 | 225.20 | Hinge:20 |
| - | 247.25 | 225.21 | Hinge:21 |
| - | 247.26 | 225.22 | Hinge:22 |
| - | 247.27 | 225.23 | Hinge:23 |
| - | 247.28 | 225.24 | Hinge:24 |
| - | 247.29 | 225.25 | Hinge:25 |
| - | 247.30 | 225.26 | Hinge:26 |
| - | 247.31 | 225.27 | Hinge:27 |
| - | 247.32 | 225.28 | Hinge:28 |
| - | 247.33 | 225.29 | Hinge:29 |
| - | 247.34 | 225.30 | Hinge:30 |
| - | 247.35 | 225.31 | Hinge:31 |
| - | 247.36 | 225.32 | Hinge:32 |
| - | 247.37 | 225.33 | Hinge:33 |
| - | 247.38 | 225.34 | Hinge:34 |
| - | 247.39 | 225.35 | Hinge:35 |
| - | 247.40 | 225.36 | Hinge:36 |
| - | 247.41 | 225.37 | Hinge:37 |
| - | 247.42 | 225.38 | Hinge:38 |
| - | 247.43 | 225.39 | Hinge:39 |
| - | 247.44 | 225.40 | Hinge:40 |
| - | 247.45 | 225.41 | Hinge:41 |
| - | 247.46 | 225.42 | Hinge:42 |
| - | 247.47 | 225.43 | Hinge:43 |
| - | 247.48 | 225.44 | Hinge:44 |
| - | 247.49 | 225.45 | Hinge:45 |
| - | 247.50 | 225.46 | Hinge:46 |
| - | 247.51 | 225.47 | Hinge:47 |
| - | 247.52 | 225.48 | Hinge:48 |

FIG. 7 Continued

| AB-000224_LS_Heavy Chain | | | |
|---|---|---|---|
| | | | |
| Residue | Linear # | Mat. Linear # | ASN # |
| - | 247.53 | 225.49 | Hinge:49 |
| - | 247.54 | 225.50 | Hinge:50 |
| - | 247.55 | 225.51 | Hinge:51 |
| - | 247.56 | 225.52 | Hinge:52 |
| - | 247.57 | 225.53 | Hinge:53 |
| - | 247.58 | 225.54 | Hinge:54 |
| - | 247.59 | 225.55 | Hinge:55 |
| - | 247.60 | 225.56 | Hinge:56 |
| - | 247.61 | 225.57 | Hinge:57 |
| - | 247.62 | 225.58 | Hinge:58 |
| - | 247.63 | 225.59 | Hinge:59 |
| - | 247.64 | 225.60 | Hinge:60 |
| - | 247.65 | 225.61 | Hinge:61 |
| - | 247.66 | 225.62 | Hinge:62 |
| - | 247.67 | 225.63 | Hinge:63 |
| - | 247.68 | 225.64 | Hinge:64 |
| - | 247.69 | 225.65 | Hinge:65 |
| - | 247.70 | 225.66 | Hinge:66 |
| - | 247.71 | 225.67 | Hinge:67 |
| - | 247.72 | 225.68 | Hinge:68 |
| - | 247.73 | 225.69 | Hinge:69 |
| - | 247.74 | 225.70 | Hinge:70 |
| - | 247.75 | 225.71 | Hinge:71 |
| - | 247.76 | 225.72 | Hinge:72 |
| - | 247.77 | 225.73 | Hinge:73 |
| - | 247.78 | 225.74 | Hinge:74 |
| - | 247.79 | 225.75 | Hinge:75 |
| - | 247.80 | 225.76 | Hinge:76 |
| - | 247.81 | 225.77 | Hinge:77 |
| - | 247.82 | 225.78 | Hinge:78 |
| - | 247.83 | 225.79 | Hinge:79 |
| - | 247.84 | 225.80 | Hinge:80 |
| - | 247.85 | 225.81 | Hinge:81 |
| - | 247.86 | 225.82 | Hinge:82 |
| - | 247.87 | 225.83 | Hinge:83 |
| - | 247.88 | 225.84 | Hinge:84 |
| - | 247.89 | 225.85 | Hinge:85 |
| - | 247.90 | 225.86 | Hinge:86 |
| - | 247.91 | 225.87 | Hinge:87 |
| - | 247.92 | 225.88 | Hinge:88 |
| - | 247.93 | 225.89 | Hinge:89 |
| - | 247.94 | 225.90 | Hinge:90 |
| - | 247.95 | 225.91 | Hinge:91 |

FIG. 7 Continued

| AB-000224_LS_Heavy Chain | | | |
|---|---|---|---|
| | | | |
| Residue | Linear # | Mat. Linear # | ASN # |
| - | 247.96 | 225.92 | Hinge:92 |
| - | 247.97 | 225.93 | Hinge:93 |
| - | 247.98 | 225.94 | Hinge:94 |
| - | 247.99 | 225.95 | Hinge:95 |
| E | 248 | 226 | Hinge:96 |
| P | 249 | 227 | Hinge:97 |
| K | 250 | 228 | Hinge:98 |
| S | 251 | 229 | Hinge:99 |
| - | 251.1 | 229.1 | Hinge:100 |
| - | 251.2 | 229.2 | Hinge:101 |
| - | 251.3 | 229.3 | Hinge:102 |
| - | 251.4 | 229.4 | Hinge:103 |
| - | 251.5 | 229.5 | Hinge:104 |
| - | 251.6 | 229.6 | Hinge:105 |
| - | 251.7 | 229.7 | Hinge:106 |
| C | 252 | 230 | Hinge:107 |
| D | 253 | 231 | Hinge:108 |
| K | 254 | 232 | Hinge:109 |
| T | 255 | 233 | Hinge:110 |
| H | 256 | 234 | Hinge:111 |
| T | 257 | 235 | Hinge:112 |
| C | 258 | 236 | Hinge:113 |
| P | 259 | 237 | Hinge:114 |
| P | 260 | 238 | Hinge:115 |
| C | 261 | 239 | Hinge:116 |
| P | 262 | 240 | Hinge:117 |
| A | 263 | 241 | Hinge:118 |
| P | 264 | 242 | Hinge:119 |
| E | 265 | 243 | Hinge:120 |
| L | 266 | 244 | Hinge:121 |
| L | 267 | 245 | Hinge:122 |
| G | 268 | 246 | Hinge:123 |
| - | 268.1 | 246.1 | Fc-N:1 |
| - | 268.2 | 246.2 | Fc-N:2 |
| - | 268.3 | 246.3 | Fc-N:3 |
| - | 268.4 | 246.4 | Fc-N:4 |
| G | 269 | 247 | Fc-N:5 |
| P | 270 | 248 | Fc-N:6 |
| S | 271 | 249 | Fc-N:7 |
| V | 272 | 250 | Fc-N:8 |
| F | 273 | 251 | Fc-N:9 |
| L | 274 | 252 | Fc-N:10 |
| F | 275 | 253 | Fc-N:11 |

FIG. 7 Continued

| AB-000224_LS_Heavy Chain | | | |
|---|---|---|---|
| | | | |
| **Residue** | **Linear #** | **Mat. Linear #** | **ASN #** |
| P | 276 | 254 | Fc-N:12 |
| P | 277 | 255 | Fc-N:13 |
| - | 277.1 | 255.1 | Fc-N:14 |
| K | 278 | 256 | Fc-N:15 |
| P | 279 | 257 | Fc-N:16 |
| K | 280 | 258 | Fc-N:17 |
| - | 280.1 | 258.1 | Fc-N:18 |
| D | 281 | 259 | Fc-N:19 |
| T | 282 | 260 | Fc-N:20 |
| L | 283 | 261 | Fc-N:21 |
| M | 284 | 262 | Fc-N:22 |
| I | 285 | 263 | Fc-N:23 |
| S | 286 | 264 | Fc-N:24 |
| R | 287 | 265 | Fc-N:25 |
| T | 288 | 266 | Fc-N:26 |
| P | 289 | 267 | Fc-N:27 |
| E | 290 | 268 | Fc-N:28 |
| V | 291 | 269 | Fc-N:29 |
| T | 292 | 270 | Fc-N:30 |
| C | 293 | 271 | Fc-N:31 |
| V | 294 | 272 | Fc-N:32 |
| V | 295 | 273 | Fc-N:33 |
| V | 296 | 274 | Fc-N:34 |
| D | 297 | 275 | Fc-N:35 |
| V | 298 | 276 | Fc-N:36 |
| S | 299 | 277 | Fc-N:37 |
| H | 300 | 278 | Fc-N:38 |
| E | 301 | 279 | Fc-N:39 |
| D | 302 | 280 | Fc-N:40 |
| P | 303 | 281 | Fc-N:41 |
| E | 304 | 282 | Fc-N:42 |
| V | 305 | 283 | Fc-N:43 |
| K | 306 | 284 | Fc-N:44 |
| F | 307 | 285 | Fc-N:45 |
| N | 308 | 286 | Fc-N:46 |
| W | 309 | 287 | Fc-N:47 |
| - | 309.1 | 287.1 | Fc-N:48 |
| Y | 310 | 288 | Fc-N:49 |
| V | 311 | 289 | Fc-N:50 |
| D | 312 | 290 | Fc-N:51 |
| G | 313 | 291 | Fc-N:52 |
| V | 314 | 292 | Fc-N:53 |
| E | 315 | 293 | Fc-N:54 |

FIG. 7 Continued

| AB-000224_LS_Heavy Chain | | | |
|---|---|---|---|
| | | | |
| Residue | Linear # | Mat. Linear # | ASN # |
| - | 315.1 | 293.1 | Fc-N:55 |
| - | 315.2 | 293.2 | Fc-N:56 |
| V | 316 | 294 | Fc-N:57 |
| H | 317 | 295 | Fc-N:58 |
| N | 318 | 296 | Fc-N:59 |
| A | 319 | 297 | Fc-N:60 |
| K | 320 | 298 | Fc-N:61 |
| T | 321 | 299 | Fc-N:62 |
| K | 322 | 300 | Fc-N:63 |
| P | 323 | 301 | Fc-N:64 |
| R | 324 | 302 | Fc-N:65 |
| E | 325 | 303 | Fc-N:66 |
| E | 326 | 304 | Fc-N:67 |
| Q | 327 | 305 | Fc-N:68 |
| - | 327.1 | 305.1 | Fc-N:69 |
| - | 327.2 | 305.2 | Fc-N:70 |
| - | 327.3 | 305.3 | Fc-N:71 |
| - | 327.4 | 305.4 | Fc-N:72 |
| Y | 328 | 306 | Fc-N:73 |
| N | 329 | 307 | Fc-N:74 |
| S | 330 | 308 | Fc-N:75 |
| T | 331 | 309 | Fc-N:76 |
| Y | 332 | 310 | Fc-N:77 |
| R | 333 | 311 | Fc-N:78 |
| V | 334 | 312 | Fc-N:79 |
| V | 335 | 313 | Fc-N:80 |
| S | 336 | 314 | Fc-N:81 |
| V | 337 | 315 | Fc-N:82 |
| L | 338 | 316 | Fc-N:83 |
| T | 339 | 317 | Fc-N:84 |
| V | 340 | 318 | Fc-N:85 |
| L | 341 | 319 | Fc-N:86 |
| H | 342 | 320 | Fc-N:87 |
| Q | 343 | 321 | Fc-N:88 |
| D | 344 | 322 | Fc-N:89 |
| W | 345 | 323 | Fc-N:90 |
| - | 345.1 | 323.1 | Fc-N:91 |
| L | 346 | 324 | Fc-N:92 |
| N | 347 | 325 | Fc-N:93 |
| G | 348 | 326 | Fc-N:94 |
| K | 349 | 327 | Fc-N:95 |
| E | 350 | 328 | Fc-N:96 |
| - | 350.1 | 328.1 | Fc-N:97 |

FIG. 7 Continued

| AB-000224_LS_Heavy Chain | | | |
|---|---|---|---|
| | | | |
| **Residue** | **Linear #** | **Mat. Linear #** | **ASN #** |
| - | 350.2 | 328.2 | Fc-N:98 |
| Y | 351 | 329 | Fc-N:99 |
| K | 352 | 330 | Fc-N:100 |
| C | 353 | 331 | Fc-N:101 |
| K | 354 | 332 | Fc-N:102 |
| V | 355 | 333 | Fc-N:103 |
| S | 356 | 334 | Fc-N:104 |
| N | 357 | 335 | Fc-N:105 |
| K | 358 | 336 | Fc-N:106 |
| A | 359 | 337 | Fc-N:107 |
| L | 360 | 338 | Fc-N:108 |
| P | 361 | 339 | Fc-N:109 |
| - | 361.1 | 339.1 | Fc-N:110 |
| - | 361.2 | 339.2 | Fc-N:111 |
| A | 362 | 340 | Fc-N:112 |
| P | 363 | 341 | Fc-N:113 |
| I | 364 | 342 | Fc-N:114 |
| E | 365 | 343 | Fc-N:115 |
| K | 366 | 344 | Fc-N:116 |
| T | 367 | 345 | Fc-N:117 |
| I | 368 | 346 | Fc-N:118 |
| S | 369 | 347 | Fc-N:119 |
| K | 370 | 348 | Fc-N:120 |
| A | 371 | 349 | Fc-N:121 |
| K | 372 | 350 | Fc-N:122 |
| G | 373 | 351 | Fc-N:123 |
| - | 373.1 | 351.1 | Fc-C:1 |
| Q | 374 | 352 | Fc-C:2 |
| P | 375 | 353 | Fc-C:3 |
| R | 376 | 354 | Fc-C:4 |
| E | 377 | 355 | Fc-C:5 |
| P | 378 | 356 | Fc-C:6 |
| Q | 379 | 357 | Fc-C:7 |
| V | 380 | 358 | Fc-C:8 |
| Y | 381 | 359 | Fc-C:9 |
| T | 382 | 360 | Fc-C:10 |
| L | 383 | 361 | Fc-C:11 |
| P | 384 | 362 | Fc-C:12 |
| P | 385 | 363 | Fc-C:13 |
| - | 385.1 | 363.1 | Fc-C:14 |
| S | 386 | 364 | Fc-C:15 |
| R | 387 | 365 | Fc-C:16 |
| D | 388 | 366 | Fc-C:17 |

FIG. 7 Continued

| AB-000224_LS_Heavy Chain | | | |
|---|---|---|---|
| | | | |
| Residue | Linear # | Mat. Linear # | ASN # |
| - | 388.1 | 366.1 | Fc-C:18 |
| E | 389 | 367 | Fc-C:19 |
| L | 390 | 368 | Fc-C:20 |
| - | 390.1 | 368.1 | Fc-C:21 |
| - | 390.2 | 368.2 | Fc-C:22 |
| T | 391 | 369 | Fc-C:23 |
| K | 392 | 370 | Fc-C:24 |
| N | 393 | 371 | Fc-C:25 |
| Q | 394 | 372 | Fc-C:26 |
| V | 395 | 373 | Fc-C:27 |
| S | 396 | 374 | Fc-C:28 |
| L | 397 | 375 | Fc-C:29 |
| T | 398 | 376 | Fc-C:30 |
| C | 399 | 377 | Fc-C:31 |
| L | 400 | 378 | Fc-C:32 |
| V | 401 | 379 | Fc-C:33 |
| K | 402 | 380 | Fc-C:34 |
| G | 403 | 381 | Fc-C:35 |
| F | 404 | 382 | Fc-C:36 |
| Y | 405 | 383 | Fc-C:37 |
| P | 406 | 384 | Fc-C:38 |
| - | 406.1 | 384.1 | Fc-C:39 |
| - | 406.2 | 384.2 | Fc-C:40 |
| S | 407 | 385 | Fc-C:41 |
| D | 408 | 386 | Fc-C:42 |
| I | 409 | 387 | Fc-C:43 |
| A | 410 | 388 | Fc-C:44 |
| V | 411 | 389 | Fc-C:45 |
| E | 412 | 390 | Fc-C:46 |
| W | 413 | 391 | Fc-C:47 |
| - | 413.1 | 391.1 | Fc-C:48 |
| E | 414 | 392 | Fc-C:49 |
| S | 415 | 393 | Fc-C:50 |
| N | 416 | 394 | Fc-C:51 |
| G | 417 | 395 | Fc-C:52 |
| Q | 418 | 396 | Fc-C:53 |
| P | 419 | 397 | Fc-C:54 |
| - | 419.1 | 397.1 | Fc-C:55 |
| - | 419.2 | 397.2 | Fc-C:56 |
| E | 420 | 398 | Fc-C:57 |
| N | 421 | 399 | Fc-C:58 |
| N | 422 | 400 | Fc-C:59 |
| Y | 423 | 401 | Fc-C:60 |

FIG. 7 Continued

| AB-000224_LS_Heavy Chain | | | |
|---|---|---|---|
| | | | |
| Residue | Linear # | Mat. Linear # | ASN # |
| K | 424 | 402 | Fc-C:61 |
| T | 425 | 403 | Fc-C:62 |
| T | 426 | 404 | Fc-C:63 |
| P | 427 | 405 | Fc-C:64 |
| P | 428 | 406 | Fc-C:65 |
| V | 429 | 407 | Fc-C:66 |
| L | 430 | 408 | Fc-C:67 |
| D | 431 | 409 | Fc-C:68 |
| - | 431.1 | 409.1 | Fc-C:69 |
| - | 431.2 | 409.2 | Fc-C:70 |
| - | 431.3 | 409.3 | Fc-C:71 |
| - | 431.4 | 409.4 | Fc-C:72 |
| S | 432 | 410 | Fc-C:73 |
| D | 433 | 411 | Fc-C:74 |
| G | 434 | 412 | Fc-C:75 |
| S | 435 | 413 | Fc-C:76 |
| F | 436 | 414 | Fc-C:77 |
| F | 437 | 415 | Fc-C:78 |
| L | 438 | 416 | Fc-C:79 |
| Y | 439 | 417 | Fc-C:80 |
| S | 440 | 418 | Fc-C:81 |
| K | 441 | 419 | Fc-C:82 |
| L | 442 | 420 | Fc-C:83 |
| T | 443 | 421 | Fc-C:84 |
| V | 444 | 422 | Fc-C:85 |
| D | 445 | 423 | Fc-C:86 |
| K | 446 | 424 | Fc-C:87 |
| S | 447 | 425 | Fc-C:88 |
| R | 448 | 426 | Fc-C:89 |
| W | 449 | 427 | Fc-C:90 |
| - | 449.1 | 427.1 | Fc-C:91 |
| Q | 450 | 428 | Fc-C:92 |
| Q | 451 | 429 | Fc-C:93 |
| G | 452 | 430 | Fc-C:94 |
| N | 453 | 431 | Fc-C:95 |
| V | 454 | 432 | Fc-C:96 |
| - | 454.1 | 432.1 | Fc-C:97 |
| - | 454.2 | 432.2 | Fc-C:98 |
| F | 455 | 433 | Fc-C:99 |
| S | 456 | 434 | Fc-C:100 |
| C | 457 | 435 | Fc-C:101 |
| S | 458 | 436 | Fc-C:102 |
| V | 459 | 437 | Fc-C:103 |

FIG. 7 Continued

| AB-000224_LS_Heavy Chain | | | |
|---|---|---|---|
| | | | |
| Residue | Linear # | Mat. Linear # | ASN # |
| L | 460 | 438 | Fc-C:104 |
| H | 461 | 439 | Fc-C:105 |
| E | 462 | 440 | Fc-C:106 |
| A | 463 | 441 | Fc-C:107 |
| L | 464 | 442 | Fc-C:108 |
| H | 465 | 443 | Fc-C:109 |
| - | 465.1 | 443.1 | Fc-C:110 |
| - | 465.2 | 443.2 | Fc-C:111 |
| S | 466 | 444 | Fc-C:112 |
| H | 467 | 445 | Fc-C:113 |
| Y | 468 | 446 | Fc-C:114 |
| T | 469 | 447 | Fc-C:115 |
| - | 469.1 | 447.1 | Fc-C:116 |
| Q | 470 | 448 | Fc-C:117 |
| K | 471 | 449 | Fc-C:118 |
| S | 472 | 450 | Fc-C:119 |
| L | 473 | 451 | Fc-C:120 |
| S | 474 | 452 | Fc-C:121 |
| L | 475 | 453 | Fc-C:122 |
| S | 476 | 454 | Fc-C:123 |
| P | 477 | 455 | HCnst-Po:1 |
| G | 478 | 456 | HCnst-Po:2 |
| K | 479 | 457 | HCnst-Po:3 |
| - | 479.1 | 457.1 | HCnst-Po:4 |
| - | 479.2 | 457.2 | HCnst-Po:5 |
| - | 479.3 | 457.3 | HCnst-Po:6 |
| - | 479.4 | 457.4 | HCnst-Po:7 |
| - | 479.5 | 457.5 | HCnst-Po:8 |
| - | 479.6 | 457.6 | HCnst-Po:9 |
| - | 479.7 | 457.7 | HCnst-Po:10 |
| - | 479.8 | 457.8 | HCnst-Po:11 |
| - | 479.9 | 457.9 | HCnst-Po:12 |
| - | 479.10 | 457.10 | HCnst-Po:13 |
| - | 479.11 | 457.11 | HCnst-Po:14 |
| - | 479.12 | 457.12 | HCnst-Po:15 |
| - | 479.13 | 457.13 | HCnst-Po:16 |
| - | 479.14 | 457.14 | HCnst-Po:17 |
| - | 479.15 | 457.15 | HCnst-Po:18 |
| - | 479.16 | 457.16 | HCnst-Po:19 |
| - | 479.17 | 457.17 | HCnst-Po:20 |
| - | 479.18 | 457.18 | HCnst-Po:21 |
| - | 479.19 | 457.19 | HCnst-Po:22 |
| - | 479.20 | 457.20 | HCnst-Po:23 |

FIG. 7 Continued

| AB-000224_LS_Heavy Chain | | | |
|---|---|---|---|
| | | | |
| Residue | Linear # | Mat. Linear # | ASN # |
| - | 479.21 | 457.21 | HCnst-Po:24 |
| - | 479.22 | 457.22 | HCnst-Po:25 |
| - | 479.23 | 457.23 | HCnst-Po:26 |
| - | 479.24 | 457.24 | HCnst-Po:27 |
| - | 479.25 | 457.25 | HCnst-Po:28 |
| - | 479.26 | 457.26 | HCnst-Po:29 |
| - | 479.27 | 457.27 | HCnst-Po:30 |
| - | 479.28 | 457.28 | HCnst-Po:31 |
| - | 479.29 | 457.29 | HCnst-Po:32 |
| - | 479.30 | 457.30 | HCnst-Po:33 |
| - | 479.31 | 457.31 | HCnst-Po:34 |
| - | 479.32 | 457.32 | HCnst-Po:35 |
| - | 479.33 | 457.33 | HCnst-Po:36 |
| - | 479.34 | 457.34 | HCnst-Po:37 |
| - | 479.35 | 457.35 | HCnst-Po:38 |
| - | 479.36 | 457.36 | HCnst-Po:39 |
| - | 479.37 | 457.37 | HCnst-Po:40 |
| - | 479.38 | 457.38 | HCnst-Po:41 |
| - | 479.39 | 457.39 | HCnst-Po:42 |
| - | 479.40 | 457.40 | HCnst-Po:43 |
| - | 479.41 | 457.41 | HCnst-Po:44 |
| - | 479.42 | 457.42 | HCnst-Po:45 |
| - | 479.43 | 457.43 | HCnst-Po:46 |
| - | 479.44 | 457.44 | HCnst-Po:47 |
| - | 479.45 | 457.45 | HCnst-Po:48 |
| - | 479.46 | 457.46 | HCnst-Po:49 |
| - | 479.47 | 457.47 | HCnst-Po:50 |
| - | 479.48 | 457.48 | HCnst-Po:51 |
| - | 479.49 | 457.49 | HCnst-Po:52 |
| - | 479.50 | 457.50 | HCnst-Po:53 |
| - | 479.51 | 457.51 | HCnst-Po:54 |
| - | 479.52 | 457.52 | HCnst-Po:55 |
| - | 479.53 | 457.53 | HCnst-Po:56 |
| - | 479.54 | 457.54 | HCnst-Po:57 |
| - | 479.55 | 457.55 | HCnst-Po:58 |
| - | 479.56 | 457.56 | HCnst-Po:59 |
| - | 479.57 | 457.57 | HCnst-Po:60 |
| - | 479.58 | 457.58 | HCnst-Po:61 |
| - | 479.59 | 457.59 | HCnst-Po:62 |
| - | 479.60 | 457.60 | HCnst-Po:63 |
| - | 479.61 | 457.61 | HCnst-Po:64 |
| - | 479.62 | 457.62 | HCnst-Po:65 |
| - | 479.63 | 457.63 | HCnst-Po:66 |

FIG. 7 Continued

| AB-000224_LS_Heavy Chain | | | |
|---|---|---|---|
| | | | |
| Residue | Linear # | Mat. Linear # | ASN # |
| - | 479.64 | 457.64 | HCnst-Po:67 |
| - | 479.65 | 457.65 | HCnst-Po:68 |
| - | 479.66 | 457.66 | HCnst-Po:69 |
| - | 479.67 | 457.67 | HCnst-Po:70 |
| - | 479.68 | 457.68 | HCnst-Po:71 |
| - | 479.69 | 457.69 | HCnst-Po:72 |
| - | 479.70 | 457.70 | HCnst-Po:73 |
| - | 479.71 | 457.71 | HCnst-Po:74 |
| - | 479.72 | 457.72 | HCnst-Po:75 |
| - | 479.73 | 457.73 | HCnst-Po:76 |
| - | 479.74 | 457.74 | HCnst-Po:77 |
| - | 479.75 | 457.75 | HCnst-Po:78 |
| - | 479.76 | 457.76 | HCnst-Po:79 |
| - | 479.77 | 457.77 | HCnst-Po:80 |
| - | 479.78 | 457.78 | HCnst-Po:81 |
| - | 479.79 | 457.79 | HCnst-Po:82 |
| - | 479.80 | 457.80 | HCnst-Po:83 |
| - | 479.81 | 457.81 | HCnst-Po:84 |
| - | 479.82 | 457.82 | HCnst-Po:85 |
| - | 479.83 | 457.83 | HCnst-Po:86 |
| - | 479.84 | 457.84 | HCnst-Po:87 |
| - | 479.85 | 457.85 | HCnst-Po:88 |
| - | 479.86 | 457.86 | HCnst-Po:89 |
| - | 479.87 | 457.87 | HCnst-Po:90 |
| - | 479.88 | 457.88 | HCnst-Po:91 |
| - | 479.89 | 457.89 | HCnst-Po:92 |
| - | 479.90 | 457.90 | HCnst-Po:93 |
| - | 479.91 | 457.91 | HCnst-Po:94 |
| - | 479.92 | 457.92 | HCnst-Po:95 |
| - | 479.93 | 457.93 | HCnst-Po:96 |
| - | 479.94 | 457.94 | HCnst-Po:97 |
| - | 479.95 | 457.95 | HCnst-Po:98 |
| - | 479.96 | 457.96 | HCnst-Po:99 |
| - | 479.97 | 457.97 | HCnst-Po:100 |
| - | 479.98 | 457.98 | HCnst-Po:101 |
| - | 479.99 | 457.99 | HCnst-Po:102 |
| - | 479.100 | 457.100 | HCnst-Po:103 |
| - | 479.101 | 457.101 | HCnst-Po:104 |
| - | 479.102 | 457.102 | HCnst-Po:105 |
| - | 479.103 | 457.103 | HCnst-Po:106 |
| - | 479.104 | 457.104 | HCnst-Po:107 |
| - | 479.105 | 457.105 | HCnst-Po:108 |
| - | 479.106 | 457.106 | HCnst-Po:109 |

FIG. 7 Continued

| AB-000224_LS_Heavy Chain | | | |
|---|---|---|---|
| | | | |
| Residue | Linear # | Mat. Linear # | ASN # |
| - | 479.107 | 457.107 | HCnst-Po:110 |
| - | 479.108 | 457.108 | HCnst-Po:111 |
| - | 479.109 | 457.109 | HCnst-Po:112 |
| - | 479.110 | 457.110 | HCnst-Po:113 |
| - | 479.111 | 457.111 | HCnst-Po:114 |
| - | 479.112 | 457.112 | HCnst-Po:115 |
| - | 479.113 | 457.113 | HCnst-Po:116 |
| - | 479.114 | 457.114 | HCnst-Po:117 |
| - | 479.115 | 457.115 | HCnst-Po:118 |
| - | 479.116 | 457.116 | HCnst-Po:119 |
| - | 479.117 | 457.117 | HCnst-Po:120 |
| - | 479.118 | 457.118 | HCnst-Po:121 |
| - | 479.119 | 457.119 | HCnst-Po:122 |
| - | 479.120 | 457.120 | HCnst-Po:123 |

FIG. 7 Continued

| AB-007088_LS_Light Chain | | | |
|---|---|---|---|
| | | | |
| **Residue** | **Linear #** | **Mat. Linear #** | **ASN #** |
| M | 1 | -22 | KLdr:-22 |
| D | 2 | -21 | KLdr:-21 |
| M | 3 | -20 | KLdr:-20 |
| R | 4 | -19 | KLdr:-19 |
| V | 5 | -18 | KLdr:-18 |
| P | 6 | -17 | KLdr:-17 |
| A | 7 | -16 | KLdr:-16 |
| Q | 8 | -15 | KLdr:-15 |
| L | 9 | -14 | KLdr:-14 |
| L | 10 | -13 | KLdr:-13 |
| G | 11 | -12 | KLdr:-12 |
| L | 12 | -11 | KLdr:-11 |
| L | 13 | -10 | KLdr:-10 |
| L | 14 | -9 | KLdr:-9 |
| L | 15 | -8 | KLdr:-8 |
| W | 16 | -7 | KLdr:-7 |
| L | 17 | -6 | KLdr:-6 |
| R | 18 | -5 | KLdr:-5 |
| G | 19 | -4 | KLdr:-4 |
| A | 20 | -3 | KLdr:-3 |
| R | 21 | -2 | KLdr:-2 |
| C | 22 | -1 | KLdr:-1 |
| G | 23 | 1 | KV:1 |
| V | 24 | 2 | KV:2 |
| Q | 25 | 3 | KV:3 |
| M | 26 | 4 | KV:4 |
| T | 27 | 5 | KV:5 |
| Q | 28 | 6 | KV:6 |
| S | 29 | 7 | KV:7 |
| P | 30 | 8 | KV:8 |
| S | 31 | 9 | KV:9 |
| T | 32 | 10 | KV:10 |
| L | 33 | 11 | KV:11 |
| S | 34 | 12 | KV:12 |
| A | 35 | 13 | KV:13 |
| S | 36 | 14 | KV:14 |
| V | 37 | 15 | KV:15 |
| G | 38 | 16 | KV:16 |
| D | 39 | 17 | KV:17 |
| R | 40 | 18 | KV:18 |
| V | 41 | 19 | KV:19 |
| T | 42 | 20 | KV:20 |
| L | 43 | 21 | KV:21 |

FIG. 8

| | | | |
|---|---|---|---|
| T | 44 | 22 | KV:22 |
| C | 45 | 23 | KV:23 |
| R | 46 | 24 | KV:24 |
| A | 47 | 25 | KV:25 |
| S | 48 | 26 | KV:26 |
| - | 48.1 | 26.1 | KV:27 |
| - | 48.2 | 26.2 | KV:28 |
| Q | 49 | 27 | KV:29 |
| S | 50 | 28 | KV:30 |
| I | 51 | 29 | KV:31 |
| S | 52 | 30 | KV:32 |
| S | 53 | 31 | KV:33 |
| - | 53.1 | 31.1 | KV:34 |
| - | 53.2 | 31.2 | KV:35 |
| - | 53.3 | 31.3 | KV:36 |
| - | 53.4 | 31.4 | KV:37 |
| - | 53.5 | 31.5 | KV:38 |
| - | 53.6 | 31.6 | KV:39 |
| W | 54 | 32 | KV:40 |
| L | 55 | 33 | KV:41 |
| A | 56 | 34 | KV:42 |
| W | 57 | 35 | KV:43 |
| Y | 58 | 36 | KV:44 |
| Q | 59 | 37 | KV:45 |
| Q | 60 | 38 | KV:46 |
| K | 61 | 39 | KV:47 |
| P | 62 | 40 | KV:48 |
| G | 63 | 41 | KV:49 |
| K | 64 | 42 | KV:50 |
| A | 65 | 43 | KV:51 |
| P | 66 | 44 | KV:52 |
| K | 67 | 45 | KV:53 |
| L | 68 | 46 | KV:54 |
| L | 69 | 47 | KV:55 |
| I | 70 | 48 | KV:56 |
| Y | 71 | 49 | KV:57 |
| D | 72 | 50 | KV:58 |
| - | 72.1 | 50.1 | KV:59 |
| - | 72.2 | 50.2 | KV:60 |
| - | 72.3 | 50.3 | KV:61 |
| - | 72.4 | 50.4 | KV:62 |
| - | 72.5 | 50.5 | KV:63 |
| - | 72.6 | 50.6 | KV:64 |
| - | 72.7 | 50.7 | KV:65 |
| - | 72.8 | 50.8 | KV:66 |
| A | 73 | 51 | KV:67 |

FIG. 8 Continued

| | | | |
|---|---|---|---|
| S | 74 | 52 | KV:68 |
| S | 75 | 53 | KV:69 |
| L | 76 | 54 | KV:70 |
| E | 77 | 55 | KV:71 |
| S | 78 | 56 | KV:72 |
| G | 79 | 57 | KV:73 |
| V | 80 | 58 | KV:74 |
| P | 81 | 59 | KV:75 |
| S | 82 | 60 | KV:76 |
| R | 83 | 61 | KV:77 |
| F | 84 | 62 | KV:78 |
| S | 85 | 63 | KV:79 |
| G | 86 | 64 | KV:80 |
| S | 87 | 65 | KV:81 |
| G | 88 | 66 | KV:82 |
| S | 89 | 67 | KV:83 |
| G | 90 | 68 | KV:84 |
| - | 90.1 | 68.1 | KV:85 |
| - | 90.2 | 68.2 | KV:86 |
| T | 91 | 69 | KV:87 |
| E | 92 | 70 | KV:88 |
| F | 93 | 71 | KV:89 |
| T | 94 | 72 | KV:90 |
| L | 95 | 73 | KV:91 |
| T | 96 | 74 | KV:92 |
| I | 97 | 75 | KV:93 |
| S | 98 | 76 | KV:94 |
| S | 99 | 77 | KV:95 |
| L | 100 | 78 | KV:96 |
| Q | 101 | 79 | KV:97 |
| P | 102 | 80 | KV:98 |
| D | 103 | 81 | KV:99 |
| D | 104 | 82 | KV:100 |
| F | 105 | 83 | KV:101 |
| A | 106 | 84 | KV:102 |
| T | 107 | 85 | KV:103 |
| Y | 108 | 86 | KV:104 |
| Y | 109 | 87 | KV:105 |
| C | 110 | 88 | KV:106 |
| Q | 111 | 89 | KV:107 |
| Q | 112 | 90 | KV:108 |
| Y | 113 | 91 | KV:109 |
| N | 114 | 92 | KV:110 |
| S | 115 | 93 | KV:111 |
| - | 115.1 | 93.1 | KV:112 |
| - | 115.2 | 93.2 | KV:113 |

FIG. 8 Continued

| | | | |
|---|---|---|---|
| - | 115.3 | 93.3 | KV:114 |
| - | 115.4 | 93.4 | KV:115 |
| - | 115.5 | 93.5 | KV:116 |
| - | 115.6 | 93.6 | KV:117 |
| - | 115.7 | 93.7 | KV:118 |
| - | 115.8 | 93.8 | KV:119 |
| - | 115.9 | 93.9 | KV:120 |
| - | 115.10 | 93.10 | KV:121 |
| - | 115.11 | 93.11 | KV:122 |
| - | 115.12 | 93.12 | KV:123 |
| - | 115.13 | 93.13 | KV:124 |
| - | 115.14 | 93.14 | KV:125 |
| - | 115.15 | 93.15 | KV:126 |
| - | 115.16 | 93.16 | KV:127 |
| - | 115.17 | 93.17 | KV:128 |
| - | 115.18 | 93.18 | KV:129 |
| - | 115.19 | 93.19 | KV:130 |
| - | 115.20 | 93.20 | KV:131 |
| - | 115.21 | 93.21 | KV:132 |
| - | 115.22 | 93.22 | KV:133 |
| Y | 116 | 94 | KV:134 |
| S | 117 | 95 | KV:135 |
| F | 118 | 96 | KV:136 |
| W | 119 | 97 | KV:137 |
| T | 120 | 98 | KV:138 |
| F | 121 | 99 | KV:139 |
| G | 122 | 100 | KV:140 |
| Q | 123 | 101 | KV:141 |
| G | 124 | 102 | KV:142 |
| T | 125 | 103 | KV:143 |
| K | 126 | 104 | KV:144 |
| V | 127 | 105 | KV:145 |
| E | 128 | 106 | KV:146 |
| I | 129 | 107 | KV:147 |
| K | 130 | 108 | KV:148 |
| R | 131 | 109 | KV:149 |
| - | 131.1 | 109.1 | KCnst-Ig:1 |
| T | 132 | 110 | KCnst-Ig:2 |
| V | 133 | 111 | KCnst-Ig:3 |
| A | 134 | 112 | KCnst-Ig:4 |
| A | 135 | 113 | KCnst-Ig:5 |
| P | 136 | 114 | KCnst-Ig:6 |
| S | 137 | 115 | KCnst-Ig:7 |
| V | 138 | 116 | KCnst-Ig:8 |
| F | 139 | 117 | KCnst-Ig:9 |
| I | 140 | 118 | KCnst-Ig:10 |

FIG. 8 Continued

| | | | |
|---|---|---|---|
| F | 141 | 119 | KCnst-Ig:11 |
| P | 142 | 120 | KCnst-Ig:12 |
| P | 143 | 121 | KCnst-Ig:13 |
| S | 144 | 122 | KCnst-Ig:14 |
| D | 145 | 123 | KCnst-Ig:15 |
| E | 146 | 124 | KCnst-Ig:16 |
| - | 146.1 | 124.1 | KCnst-Ig:17 |
| - | 146.2 | 124.2 | KCnst-Ig:18 |
| Q | 147 | 125 | KCnst-Ig:19 |
| L | 148 | 126 | KCnst-Ig:20 |
| - | 148.1 | 126.1 | KCnst-Ig:21 |
| - | 148.2 | 126.2 | KCnst-Ig:22 |
| K | 149 | 127 | KCnst-Ig:23 |
| S | 150 | 128 | KCnst-Ig:24 |
| G | 151 | 129 | KCnst-Ig:25 |
| T | 152 | 130 | KCnst-Ig:26 |
| A | 153 | 131 | KCnst-Ig:27 |
| S | 154 | 132 | KCnst-Ig:28 |
| V | 155 | 133 | KCnst-Ig:29 |
| V | 156 | 134 | KCnst-Ig:30 |
| C | 157 | 135 | KCnst-Ig:31 |
| L | 158 | 136 | KCnst-Ig:32 |
| L | 159 | 137 | KCnst-Ig:33 |
| N | 160 | 138 | KCnst-Ig:34 |
| N | 161 | 139 | KCnst-Ig:35 |
| F | 162 | 140 | KCnst-Ig:36 |
| Y | 163 | 141 | KCnst-Ig:37 |
| P | 164 | 142 | KCnst-Ig:38 |
| - | 164.1 | 142.1 | KCnst-Ig:39 |
| - | 164.2 | 142.2 | KCnst-Ig:40 |
| R | 165 | 143 | KCnst-Ig:41 |
| E | 166 | 144 | KCnst-Ig:42 |
| A | 167 | 145 | KCnst-Ig:43 |
| K | 168 | 146 | KCnst-Ig:44 |
| V | 169 | 147 | KCnst-Ig:45 |
| Q | 170 | 148 | KCnst-Ig:46 |
| W | 171 | 149 | KCnst-Ig:47 |
| - | 171.1 | 149.1 | KCnst-Ig:48 |
| K | 172 | 150 | KCnst-Ig:49 |
| V | 173 | 151 | KCnst-Ig:50 |
| D | 174 | 152 | KCnst-Ig:51 |
| N | 175 | 153 | KCnst-Ig:52 |
| A | 176 | 154 | KCnst-Ig:53 |
| L | 177 | 155 | KCnst-Ig:54 |
| Q | 178 | 156 | KCnst-Ig:55 |
| S | 179 | 157 | KCnst-Ig:56 |

FIG. 8 Continued

| | | | |
|---|---|---|---|
| G | 180 | 158 | KCnst-Ig:57 |
| N | 181 | 159 | KCnst-Ig:58 |
| S | 182 | 160 | KCnst-Ig:59 |
| Q | 183 | 161 | KCnst-Ig:60 |
| E | 184 | 162 | KCnst-Ig:61 |
| S | 185 | 163 | KCnst-Ig:62 |
| V | 186 | 164 | KCnst-Ig:63 |
| T | 187 | 165 | KCnst-Ig:64 |
| E | 188 | 166 | KCnst-Ig:65 |
| Q | 189 | 167 | KCnst-Ig:66 |
| D | 190 | 168 | KCnst-Ig:67 |
| - | 190.1 | 168.1 | KCnst-Ig:68 |
| - | 190.2 | 168.2 | KCnst-Ig:69 |
| - | 190.3 | 168.3 | KCnst-Ig:70 |
| - | 190.4 | 168.4 | KCnst-Ig:71 |
| S | 191 | 169 | KCnst-Ig:72 |
| K | 192 | 170 | KCnst-Ig:73 |
| D | 193 | 171 | KCnst-Ig:74 |
| S | 194 | 172 | KCnst-Ig:75 |
| T | 195 | 173 | KCnst-Ig:76 |
| Y | 196 | 174 | KCnst-Ig:77 |
| S | 197 | 175 | KCnst-Ig:78 |
| L | 198 | 176 | KCnst-Ig:79 |
| S | 199 | 177 | KCnst-Ig:80 |
| S | 200 | 178 | KCnst-Ig:81 |
| T | 201 | 179 | KCnst-Ig:82 |
| L | 202 | 180 | KCnst-Ig:83 |
| T | 203 | 181 | KCnst-Ig:84 |
| L | 204 | 182 | KCnst-Ig:85 |
| S | 205 | 183 | KCnst-Ig:86 |
| K | 206 | 184 | KCnst-Ig:87 |
| A | 207 | 185 | KCnst-Ig:88 |
| D | 208 | 186 | KCnst-Ig:89 |
| Y | 209 | 187 | KCnst-Ig:90 |
| - | 209.1 | 187.1 | KCnst-Ig:91 |
| E | 210 | 188 | KCnst-Ig:92 |
| K | 211 | 189 | KCnst-Ig:93 |
| H | 212 | 190 | KCnst-Ig:94 |
| K | 213 | 191 | KCnst-Ig:95 |
| V | 214 | 192 | KCnst-Ig:96 |
| - | 214.1 | 192.1 | KCnst-Ig:97 |
| - | 214.2 | 192.2 | KCnst-Ig:98 |
| Y | 215 | 193 | KCnst-Ig:99 |
| A | 216 | 194 | KCnst-Ig:100 |
| C | 217 | 195 | KCnst-Ig:101 |
| E | 218 | 196 | KCnst-Ig:102 |

FIG. 8 Continued

| | | | |
|---|---|---|---|
| V | 219 | 197 | KCnst-Ig:103 |
| T | 220 | 198 | KCnst-Ig:104 |
| H | 221 | 199 | KCnst-Ig:105 |
| Q | 222 | 200 | KCnst-Ig:106 |
| G | 223 | 201 | KCnst-Ig:107 |
| L | 224 | 202 | KCnst-Ig:108 |
| S | 225 | 203 | KCnst-Ig:109 |
| - | 225.1 | 203.1 | KCnst-Ig:110 |
| S | 226 | 204 | KCnst-Ig:111 |
| P | 227 | 205 | KCnst-Ig:112 |
| V | 228 | 206 | KCnst-Ig:113 |
| T | 229 | 207 | KCnst-Ig:114 |
| K | 230 | 208 | KCnst-Ig:115 |
| S | 231 | 209 | KCnst-Ig:116 |
| F | 232 | 210 | KCnst-Ig:117 |
| N | 233 | 211 | KCnst-Ig:118 |
| R | 234 | 212 | KCnst-Ig:119 |
| G | 235 | 213 | KCnst-Ig:120 |
| E | 236 | 214 | KCnst-Ig:121 |
| C | 237 | 215 | KCnst-Ig:122 |
| - | 237.1 | 215.1 | KCnst-Ig:123 |

FIG. 8 Continued

| AB-007088_LS_Heavy Chain | | | |
|---|---|---|---|
| | | | |
| Residue | Linear # | Mat. Linear # | ASN # |
| M | 1 | -22 | KLdr:-22 |
| D | 2 | -21 | KLdr:-21 |
| M | 3 | -20 | KLdr:-20 |
| R | 4 | -19 | KLdr:-19 |
| V | 5 | -18 | KLdr:-18 |
| P | 6 | -17 | KLdr:-17 |
| A | 7 | -16 | KLdr:-16 |
| Q | 8 | -15 | KLdr:-15 |
| L | 9 | -14 | KLdr:-14 |
| L | 10 | -13 | KLdr:-13 |
| G | 11 | -12 | KLdr:-12 |
| L | 12 | -11 | KLdr:-11 |
| L | 13 | -10 | KLdr:-10 |
| L | 14 | -9 | KLdr:-9 |
| L | 15 | -8 | KLdr:-8 |
| W | 16 | -7 | KLdr:-7 |
| L | 17 | -6 | KLdr:-6 |
| R | 18 | -5 | KLdr:-5 |
| G | 19 | -4 | KLdr:-4 |
| A | 20 | -3 | KLdr:-3 |
| R | 21 | -2 | KLdr:-2 |
| C | 22 | -1 | KLdr:-1 |
| Q | 23 | 1 | HV:1 |
| V | 24 | 2 | HV:2 |
| Q | 25 | 3 | HV:3 |
| L | 26 | 4 | HV:4 |
| V | 27 | 5 | HV:5 |
| E | 28 | 6 | HV:6 |
| S | 29 | 7 | HV:7 |
| - | 29.1 | 7.1 | HV:8 |
| G | 30 | 8 | HV:9 |
| G | 31 | 9 | HV:10 |
| G | 32 | 10 | HV:11 |
| V | 33 | 11 | HV:12 |
| V | 34 | 12 | HV:13 |
| Q | 35 | 13 | HV:14 |
| P | 36 | 14 | HV:15 |
| G | 37 | 15 | HV:16 |
| R | 38 | 16 | HV:17 |

FIG. 9

| AB-007088_LS_Heavy Chain | | | |
|---|---|---|---|
| | | | |
| Residue | Linear # | Mat. Linear # | ASN # |
| S | 39 | 17 | HV:18 |
| L | 40 | 18 | HV:19 |
| R | 41 | 19 | HV:20 |
| L | 42 | 20 | HV:21 |
| S | 43 | 21 | HV:22 |
| C | 44 | 22 | HV:23 |
| A | 45 | 23 | HV:24 |
| A | 46 | 24 | HV:25 |
| S | 47 | 25 | HV:26 |
| G | 48 | 26 | HV:27 |
| - | 48.1 | 26.1 | HV:28 |
| F | 49 | 27 | HV:29 |
| A | 50 | 28 | HV:30 |
| F | 51 | 29 | HV:31 |
| N | 52 | 30 | HV:32 |
| T | 53 | 31 | HV:33 |
| - | 53.1 | 31.1 | HV:34 |
| - | 53.2 | 31.2 | HV:35 |
| - | 53.3 | 31.3 | HV:36 |
| - | 53.4 | 31.4 | HV:37 |
| - | 53.5 | 31.5 | HV:38 |
| Y | 54 | 32 | HV:39 |
| G | 55 | 33 | HV:40 |
| M | 56 | 34 | HV:41 |
| H | 57 | 35 | HV:42 |
| W | 58 | 36 | HV:43 |
| V | 59 | 37 | HV:44 |
| R | 60 | 38 | HV:45 |
| Q | 61 | 39 | HV:46 |
| T | 62 | 40 | HV:47 |
| P | 63 | 41 | HV:48 |
| G | 64 | 42 | HV:49 |
| K | 65 | 43 | HV:50 |
| G | 66 | 44 | HV:51 |
| L | 67 | 45 | HV:52 |
| E | 68 | 46 | HV:53 |
| W | 69 | 47 | HV:54 |
| V | 70 | 48 | HV:55 |
| A | 71 | 49 | HV:56 |
| I | 72 | 50 | HV:57 |
| I | 73 | 51 | HV:58 |
| W | 74 | 52 | HV:59 |
| Y | 75 | 53 | HV:60 |

FIG. 9 Continued

| AB-007088_LS_Heavy Chain | | | |
|---|---|---|---|
| | | | |
| **Residue** | **Linear #** | **Mat. Linear #** | **ASN #** |
| - | 75.1 | 53.1 | HV:61 |
| - | 75.2 | 53.2 | HV:62 |
| - | 75.3 | 53.3 | HV:63 |
| D | 76 | 54 | HV:64 |
| G | 77 | 55 | HV:65 |
| S | 78 | 56 | HV:66 |
| Q | 79 | 57 | HV:67 |
| K | 80 | 58 | HV:68 |
| Y | 81 | 59 | HV:69 |
| Y | 82 | 60 | HV:70 |
| A | 83 | 61 | HV:71 |
| D | 84 | 62 | HV:72 |
| S | 85 | 63 | HV:73 |
| V | 86 | 64 | HV:74 |
| Q | 87 | 65 | HV:75 |
| G | 88 | 66 | HV:76 |
| R | 89 | 67 | HV:77 |
| F | 90 | 68 | HV:78 |
| I | 91 | 69 | HV:79 |
| I | 92 | 70 | HV:80 |
| S | 93 | 71 | HV:81 |
| R | 94 | 72 | HV:82 |
| D | 95 | 73 | HV:83 |
| N | 96 | 74 | HV:84 |
| H | 97 | 75 | HV:85 |
| K | 98 | 76 | HV:86 |
| N | 99 | 77 | HV:87 |
| T | 100 | 78 | HV:88 |
| L | 101 | 79 | HV:89 |
| S | 102 | 80 | HV:90 |
| L | 103 | 81 | HV:91 |
| Q | 104 | 82 | HV:92 |
| M | 105 | 83 | HV:93 |
| N | 106 | 84 | HV:94 |
| G | 107 | 85 | HV:95 |
| L | 108 | 86 | HV:96 |
| R | 109 | 87 | HV:97 |
| A | 110 | 88 | HV:98 |
| E | 111 | 89 | HV:99 |
| D | 112 | 90 | HV:100 |
| T | 113 | 91 | HV:101 |
| A | 114 | 92 | HV:102 |
| V | 115 | 93 | HV:103 |

FIG. 9 Continued

| AB-007088_LS_Heavy Chain | | | |
|---|---|---|---|
| | | | |
| Residue | Linear # | Mat. Linear # | ASN # |
| Y | 116 | 94 | HV:104 |
| F | 117 | 95 | HV:105 |
| C | 118 | 96 | HV:106 |
| V | 119 | 97 | HV:107 |
| R | 120 | 98 | HV:108 |
| V | 121 | 99 | HV:109 |
| R | 122 | 100 | HV:110 |
| F | 123 | 101 | HV:111 |
| S | 124 | 102 | HV:112 |
| V | 125 | 103 | HV:113 |
| G | 126 | 104 | HV:114 |
| - | 126.1 | 104.1 | HV:115 |
| - | 126.2 | 104.2 | HV:116 |
| - | 126.3 | 104.3 | HV:117 |
| - | 126.4 | 104.4 | HV:118 |
| - | 126.5 | 104.5 | HV:119 |
| - | 126.6 | 104.6 | HV:120 |
| - | 126.7 | 104.7 | HV:121 |
| - | 126.8 | 104.8 | HV:122 |
| - | 126.9 | 104.9 | HV:123 |
| - | 126.10 | 104.10 | HV:124 |
| - | 126.11 | 104.11 | HV:125 |
| - | 126.12 | 104.12 | HV:126 |
| - | 126.13 | 104.13 | HV:127 |
| - | 126.14 | 104.14 | HV:128 |
| - | 126.15 | 104.15 | HV:129 |
| - | 126.16 | 104.16 | HV:130 |
| P | 127 | 105 | HV:131 |
| H | 128 | 106 | HV:132 |
| G | 129 | 107 | HV:133 |
| S | 130 | 108 | HV:134 |
| A | 131 | 109 | HV:135 |
| F | 132 | 110 | HV:136 |
| D | 133 | 111 | HV:137 |
| L | 134 | 112 | HV:138 |
| W | 135 | 113 | HV:139 |
| G | 136 | 114 | HV:140 |
| Q | 137 | 115 | HV:141 |
| G | 138 | 116 | HV:142 |
| T | 139 | 117 | HV:143 |
| M | 140 | 118 | HV:144 |
| V | 141 | 119 | HV:145 |
| I | 142 | 120 | HV:146 |

FIG. 9 Continued

| AB-007088_LS_Heavy Chain | | | |
|---|---|---|---|
| | | | |
| Residue | Linear # | Mat. Linear # | ASN # |
| V | 143 | 121 | HV:147 |
| S | 144 | 122 | HV:148 |
| S | 145 | 123 | HV:149 |
| - | 145.1 | 123.1 | HCnst-Ig:1 |
| - | 145.2 | 123.2 | HCnst-Ig:2 |
| A | 146 | 124 | HCnst-Ig:3 |
| S | 147 | 125 | HCnst-Ig:4 |
| T | 148 | 126 | HCnst-Ig:5 |
| K | 149 | 127 | HCnst-Ig:6 |
| G | 150 | 128 | HCnst-Ig:7 |
| P | 151 | 129 | HCnst-Ig:8 |
| S | 152 | 130 | HCnst-Ig:9 |
| V | 153 | 131 | HCnst-Ig:10 |
| F | 154 | 132 | HCnst-Ig:11 |
| P | 155 | 133 | HCnst-Ig:12 |
| L | 156 | 134 | HCnst-Ig:13 |
| A | 157 | 135 | HCnst-Ig:14 |
| P | 158 | 136 | HCnst-Ig:15 |
| - | 158.1 | 136.1 | HCnst-Ig:16 |
| S | 159 | 137 | HCnst-Ig:17 |
| - | 159.1 | 137.1 | HCnst-Ig:18 |
| S | 160 | 138 | HCnst-Ig:19 |
| K | 161 | 139 | HCnst-Ig:20 |
| S | 162 | 140 | HCnst-Ig:21 |
| T | 163 | 141 | HCnst-Ig:22 |
| S | 164 | 142 | HCnst-Ig:23 |
| G | 165 | 143 | HCnst-Ig:24 |
| G | 166 | 144 | HCnst-Ig:25 |
| T | 167 | 145 | HCnst-Ig:26 |
| A | 168 | 146 | HCnst-Ig:27 |
| A | 169 | 147 | HCnst-Ig:28 |
| L | 170 | 148 | HCnst-Ig:29 |
| G | 171 | 149 | HCnst-Ig:30 |
| C | 172 | 150 | HCnst-Ig:31 |
| L | 173 | 151 | HCnst-Ig:32 |
| V | 174 | 152 | HCnst-Ig:33 |
| K | 175 | 153 | HCnst-Ig:34 |
| D | 176 | 154 | HCnst-Ig:35 |
| Y | 177 | 155 | HCnst-Ig:36 |
| F | 178 | 156 | HCnst-Ig:37 |
| P | 179 | 157 | HCnst-Ig:38 |
| - | 179.1 | 157.1 | HCnst-Ig:39 |
| - | 179.2 | 157.2 | HCnst-Ig:40 |

FIG. 9 Continued

| AB-007088_LS_Heavy Chain | | | |
|---|---|---|---|
| | | | |
| Residue | Linear # | Mat. Linear # | ASN # |
| E | 180 | 158 | HCnst-Ig:41 |
| P | 181 | 159 | HCnst-Ig:42 |
| V | 182 | 160 | HCnst-Ig:43 |
| T | 183 | 161 | HCnst-Ig:44 |
| V | 184 | 162 | HCnst-Ig:45 |
| S | 185 | 163 | HCnst-Ig:46 |
| W | 186 | 164 | HCnst-Ig:47 |
| - | 186.1 | 164.1 | HCnst-Ig:48 |
| N | 187 | 165 | HCnst-Ig:49 |
| S | 188 | 166 | HCnst-Ig:50 |
| G | 189 | 167 | HCnst-Ig:51 |
| A | 190 | 168 | HCnst-Ig:52 |
| L | 191 | 169 | HCnst-Ig:53 |
| T | 192 | 170 | HCnst-Ig:54 |
| S | 193 | 171 | HCnst-Ig:55 |
| G | 194 | 172 | HCnst-Ig:56 |
| V | 195 | 173 | HCnst-Ig:57 |
| H | 196 | 174 | HCnst-Ig:58 |
| T | 197 | 175 | HCnst-Ig:59 |
| - | 197.1 | 175.1 | HCnst-Ig:60 |
| - | 197.2 | 175.2 | HCnst-Ig:61 |
| - | 197.3 | 175.3 | HCnst-Ig:62 |
| F | 198 | 176 | HCnst-Ig:63 |
| P | 199 | 177 | HCnst-Ig:64 |
| A | 200 | 178 | HCnst-Ig:65 |
| V | 201 | 179 | HCnst-Ig:66 |
| L | 202 | 180 | HCnst-Ig:67 |
| Q | 203 | 181 | HCnst-Ig:68 |
| - | 203.1 | 181.1 | HCnst-Ig:69 |
| - | 203.2 | 181.2 | HCnst-Ig:70 |
| - | 203.3 | 181.3 | HCnst-Ig:71 |
| - | 203.4 | 181.4 | HCnst-Ig:72 |
| S | 204 | 182 | HCnst-Ig:73 |
| S | 205 | 183 | HCnst-Ig:74 |
| G | 206 | 184 | HCnst-Ig:75 |
| L | 207 | 185 | HCnst-Ig:76 |
| Y | 208 | 186 | HCnst-Ig:77 |
| S | 209 | 187 | HCnst-Ig:78 |
| L | 210 | 188 | HCnst-Ig:79 |
| S | 211 | 189 | HCnst-Ig:80 |
| S | 212 | 190 | HCnst-Ig:81 |
| V | 213 | 191 | HCnst-Ig:82 |
| V | 214 | 192 | HCnst-Ig:83 |

FIG. 9 Continued

| AB-007088_LS_Heavy Chain | | | |
|---|---|---|---|
| | | | |
| **Residue** | **Linear #** | **Mat. Linear #** | **ASN #** |
| T | 215 | 193 | HCnst-Ig:84 |
| V | 216 | 194 | HCnst-Ig:85 |
| P | 217 | 195 | HCnst-Ig:86 |
| S | 218 | 196 | HCnst-Ig:87 |
| S | 219 | 197 | HCnst-Ig:88 |
| S | 220 | 198 | HCnst-Ig:89 |
| L | 221 | 199 | HCnst-Ig:90 |
| - | 221.1 | 199.1 | HCnst-Ig:91 |
| G | 222 | 200 | HCnst-Ig:92 |
| T | 223 | 201 | HCnst-Ig:93 |
| Q | 224 | 202 | HCnst-Ig:94 |
| T | 225 | 203 | HCnst-Ig:95 |
| - | 225.1 | 203.1 | HCnst-Ig:96 |
| - | 225.2 | 203.2 | HCnst-Ig:97 |
| - | 225.3 | 203.3 | HCnst-Ig:98 |
| Y | 226 | 204 | HCnst-Ig:99 |
| I | 227 | 205 | HCnst-Ig:100 |
| C | 228 | 206 | HCnst-Ig:101 |
| N | 229 | 207 | HCnst-Ig:102 |
| V | 230 | 208 | HCnst-Ig:103 |
| N | 231 | 209 | HCnst-Ig:104 |
| H | 232 | 210 | HCnst-Ig:105 |
| K | 233 | 211 | HCnst-Ig:106 |
| P | 234 | 212 | HCnst-Ig:107 |
| S | 235 | 213 | HCnst-Ig:108 |
| N | 236 | 214 | HCnst-Ig:109 |
| - | 236.1 | 214.1 | HCnst-Ig:110 |
| - | 236.2 | 214.2 | HCnst-Ig:111 |
| T | 237 | 215 | HCnst-Ig:112 |
| K | 238 | 216 | HCnst-Ig:113 |
| V | 239 | 217 | HCnst-Ig:114 |
| D | 240 | 218 | HCnst-Ig:115 |
| K | 241 | 219 | HCnst-Ig:116 |
| - | 241.1 | 219.1 | HCnst-Ig:117 |
| K | 242 | 220 | HCnst-Ig:118 |
| V | 243 | 221 | HCnst-Ig:119 |
| - | 243.1 | 221.1 | HCnst-Ig:120 |
| - | 243.2 | 221.2 | HCnst-Ig:121 |
| - | 243.3 | 221.3 | HCnst-Ig:122 |
| - | 243.4 | 221.4 | HCnst-Ig:123 |
| - | 243.5 | 221.1 | Hinge:1 |
| - | 243.6 | 221.2 | Hinge:2 |
| - | 243.7 | 221.3 | Hinge:3 |

FIG. 9 Continued

| AB-007088_LS_Heavy Chain | | | |
|---|---|---|---|
| | | | |
| Residue | Linear # | Mat. Linear # | ASN # |
| - | 243.8 | 221.4 | Hinge:4 |
| - | 243.9 | 221.5 | Hinge:5 |
| - | 243.10 | 221.6 | Hinge:6 |
| - | 243.11 | 221.7 | Hinge:7 |
| - | 243.12 | 221.8 | Hinge:8 |
| - | 243.13 | 221.9 | Hinge:9 |
| - | 243.14 | 221.10 | Hinge:10 |
| - | 243.15 | 221.11 | Hinge:11 |
| - | 243.16 | 221.12 | Hinge:12 |
| - | 243.17 | 221.13 | Hinge:13 |
| - | 243.18 | 221.14 | Hinge:14 |
| - | 243.19 | 221.15 | Hinge:15 |
| - | 243.20 | 221.16 | Hinge:16 |
| - | 243.21 | 221.17 | Hinge:17 |
| - | 243.22 | 221.18 | Hinge:18 |
| - | 243.23 | 221.19 | Hinge:19 |
| - | 243.24 | 221.20 | Hinge:20 |
| - | 243.25 | 221.21 | Hinge:21 |
| - | 243.26 | 221.22 | Hinge:22 |
| - | 243.27 | 221.23 | Hinge:23 |
| - | 243.28 | 221.24 | Hinge:24 |
| - | 243.29 | 221.25 | Hinge:25 |
| - | 243.30 | 221.26 | Hinge:26 |
| - | 243.31 | 221.27 | Hinge:27 |
| - | 243.32 | 221.28 | Hinge:28 |
| - | 243.33 | 221.29 | Hinge:29 |
| - | 243.34 | 221.30 | Hinge:30 |
| - | 243.35 | 221.31 | Hinge:31 |
| - | 243.36 | 221.32 | Hinge:32 |
| - | 243.37 | 221.33 | Hinge:33 |
| - | 243.38 | 221.34 | Hinge:34 |
| - | 243.39 | 221.35 | Hinge:35 |
| - | 243.40 | 221.36 | Hinge:36 |
| - | 243.41 | 221.37 | Hinge:37 |
| - | 243.42 | 221.38 | Hinge:38 |
| - | 243.43 | 221.39 | Hinge:39 |
| - | 243.44 | 221.40 | Hinge:40 |
| - | 243.45 | 221.41 | Hinge:41 |
| - | 243.46 | 221.42 | Hinge:42 |
| - | 243.47 | 221.43 | Hinge:43 |
| - | 243.48 | 221.44 | Hinge:44 |
| - | 243.49 | 221.45 | Hinge:45 |
| - | 243.50 | 221.46 | Hinge:46 |

FIG. 9 Continued

| AB-007088_LS_Heavy Chain | | | |
|---|---|---|---|
| | | | |
| Residue | Linear # | Mat. Linear # | ASN # |
| - | 243.51 | 221.47 | Hinge:47 |
| - | 243.52 | 221.48 | Hinge:48 |
| - | 243.53 | 221.49 | Hinge:49 |
| - | 243.54 | 221.50 | Hinge:50 |
| - | 243.55 | 221.51 | Hinge:51 |
| - | 243.56 | 221.52 | Hinge:52 |
| - | 243.57 | 221.53 | Hinge:53 |
| - | 243.58 | 221.54 | Hinge:54 |
| - | 243.59 | 221.55 | Hinge:55 |
| - | 243.60 | 221.56 | Hinge:56 |
| - | 243.61 | 221.57 | Hinge:57 |
| - | 243.62 | 221.58 | Hinge:58 |
| - | 243.63 | 221.59 | Hinge:59 |
| - | 243.64 | 221.60 | Hinge:60 |
| - | 243.65 | 221.61 | Hinge:61 |
| - | 243.66 | 221.62 | Hinge:62 |
| - | 243.67 | 221.63 | Hinge:63 |
| - | 243.68 | 221.64 | Hinge:64 |
| - | 243.69 | 221.65 | Hinge:65 |
| - | 243.70 | 221.66 | Hinge:66 |
| - | 243.71 | 221.67 | Hinge:67 |
| - | 243.72 | 221.68 | Hinge:68 |
| - | 243.73 | 221.69 | Hinge:69 |
| - | 243.74 | 221.70 | Hinge:70 |
| - | 243.75 | 221.71 | Hinge:71 |
| - | 243.76 | 221.72 | Hinge:72 |
| - | 243.77 | 221.73 | Hinge:73 |
| - | 243.78 | 221.74 | Hinge:74 |
| - | 243.79 | 221.75 | Hinge:75 |
| - | 243.80 | 221.76 | Hinge:76 |
| - | 243.81 | 221.77 | Hinge:77 |
| - | 243.82 | 221.78 | Hinge:78 |
| - | 243.83 | 221.79 | Hinge:79 |
| - | 243.84 | 221.80 | Hinge:80 |
| - | 243.85 | 221.81 | Hinge:81 |
| - | 243.86 | 221.82 | Hinge:82 |
| - | 243.87 | 221.83 | Hinge:83 |
| - | 243.88 | 221.84 | Hinge:84 |
| - | 243.89 | 221.85 | Hinge:85 |
| - | 243.90 | 221.86 | Hinge:86 |
| - | 243.91 | 221.87 | Hinge:87 |
| - | 243.92 | 221.88 | Hinge:88 |
| - | 243.93 | 221.89 | Hinge:89 |

FIG. 9 Continued

| AB-007088_LS_Heavy Chain | | | |
|---|---|---|---|
| | | | |
| Residue | Linear # | Mat. Linear # | ASN # |
| - | 243.94 | 221.90 | Hinge:90 |
| - | 243.95 | 221.91 | Hinge:91 |
| - | 243.96 | 221.92 | Hinge:92 |
| - | 243.97 | 221.93 | Hinge:93 |
| - | 243.98 | 221.94 | Hinge:94 |
| - | 243.99 | 221.95 | Hinge:95 |
| E | 244 | 222 | Hinge:96 |
| P | 245 | 223 | Hinge:97 |
| K | 246 | 224 | Hinge:98 |
| S | 247 | 225 | Hinge:99 |
| - | 247.1 | 225.1 | Hinge:100 |
| - | 247.2 | 225.2 | Hinge:101 |
| - | 247.3 | 225.3 | Hinge:102 |
| - | 247.4 | 225.4 | Hinge:103 |
| - | 247.5 | 225.5 | Hinge:104 |
| - | 247.6 | 225.6 | Hinge:105 |
| - | 247.7 | 225.7 | Hinge:106 |
| C | 248 | 226 | Hinge:107 |
| D | 249 | 227 | Hinge:108 |
| K | 250 | 228 | Hinge:109 |
| T | 251 | 229 | Hinge:110 |
| H | 252 | 230 | Hinge:111 |
| T | 253 | 231 | Hinge:112 |
| C | 254 | 232 | Hinge:113 |
| P | 255 | 233 | Hinge:114 |
| P | 256 | 234 | Hinge:115 |
| C | 257 | 235 | Hinge:116 |
| P | 258 | 236 | Hinge:117 |
| A | 259 | 237 | Hinge:118 |
| P | 260 | 238 | Hinge:119 |
| E | 261 | 239 | Hinge:120 |
| L | 262 | 240 | Hinge:121 |
| L | 263 | 241 | Hinge:122 |
| G | 264 | 242 | Hinge:123 |
| - | 264.1 | 242.1 | Fc-N:1 |
| - | 264.2 | 242.2 | Fc-N:2 |
| - | 264.3 | 242.3 | Fc-N:3 |
| - | 264.4 | 242.4 | Fc-N:4 |
| G | 265 | 243 | Fc-N:5 |
| P | 266 | 244 | Fc-N:6 |
| S | 267 | 245 | Fc-N:7 |
| V | 268 | 246 | Fc-N:8 |
| F | 269 | 247 | Fc-N:9 |

FIG. 9 Continued

| AB-007088_LS_Heavy Chain | | | |
|---|---|---|---|
| | | | |
| Residue | Linear # | Mat. Linear # | ASN # |
| L | 270 | 248 | Fc-N:10 |
| F | 271 | 249 | Fc-N:11 |
| P | 272 | 250 | Fc-N:12 |
| P | 273 | 251 | Fc-N:13 |
| - | 273.1 | 251.1 | Fc-N:14 |
| K | 274 | 252 | Fc-N:15 |
| P | 275 | 253 | Fc-N:16 |
| K | 276 | 254 | Fc-N:17 |
| - | 276.1 | 254.1 | Fc-N:18 |
| D | 277 | 255 | Fc-N:19 |
| T | 278 | 256 | Fc-N:20 |
| L | 279 | 257 | Fc-N:21 |
| M | 280 | 258 | Fc-N:22 |
| I | 281 | 259 | Fc-N:23 |
| S | 282 | 260 | Fc-N:24 |
| R | 283 | 261 | Fc-N:25 |
| T | 284 | 262 | Fc-N:26 |
| P | 285 | 263 | Fc-N:27 |
| E | 286 | 264 | Fc-N:28 |
| V | 287 | 265 | Fc-N:29 |
| T | 288 | 266 | Fc-N:30 |
| C | 289 | 267 | Fc-N:31 |
| V | 290 | 268 | Fc-N:32 |
| V | 291 | 269 | Fc-N:33 |
| V | 292 | 270 | Fc-N:34 |
| D | 293 | 271 | Fc-N:35 |
| V | 294 | 272 | Fc-N:36 |
| S | 295 | 273 | Fc-N:37 |
| H | 296 | 274 | Fc-N:38 |
| E | 297 | 275 | Fc-N:39 |
| D | 298 | 276 | Fc-N:40 |
| P | 299 | 277 | Fc-N:41 |
| E | 300 | 278 | Fc-N:42 |
| V | 301 | 279 | Fc-N:43 |
| K | 302 | 280 | Fc-N:44 |
| F | 303 | 281 | Fc-N:45 |
| N | 304 | 282 | Fc-N:46 |
| W | 305 | 283 | Fc-N:47 |
| - | 305.1 | 283.1 | Fc-N:48 |
| Y | 306 | 284 | Fc-N:49 |
| V | 307 | 285 | Fc-N:50 |
| D | 308 | 286 | Fc-N:51 |
| G | 309 | 287 | Fc-N:52 |

FIG. 9 Continued

| AB-007088_LS_Heavy Chain | | | |
|---|---|---|---|
| | | | |
| Residue | Linear # | Mat. Linear # | ASN # |
| V | 310 | 288 | Fc-N:53 |
| E | 311 | 289 | Fc-N:54 |
| - | 311.1 | 289.1 | Fc-N:55 |
| - | 311.2 | 289.2 | Fc-N:56 |
| V | 312 | 290 | Fc-N:57 |
| H | 313 | 291 | Fc-N:58 |
| N | 314 | 292 | Fc-N:59 |
| A | 315 | 293 | Fc-N:60 |
| K | 316 | 294 | Fc-N:61 |
| T | 317 | 295 | Fc-N:62 |
| K | 318 | 296 | Fc-N:63 |
| P | 319 | 297 | Fc-N:64 |
| R | 320 | 298 | Fc-N:65 |
| E | 321 | 299 | Fc-N:66 |
| E | 322 | 300 | Fc-N:67 |
| Q | 323 | 301 | Fc-N:68 |
| - | 323.1 | 301.1 | Fc-N:69 |
| - | 323.2 | 301.2 | Fc-N:70 |
| - | 323.3 | 301.3 | Fc-N:71 |
| - | 323.4 | 301.4 | Fc-N:72 |
| Y | 324 | 302 | Fc-N:73 |
| N | 325 | 303 | Fc-N:74 |
| S | 326 | 304 | Fc-N:75 |
| T | 327 | 305 | Fc-N:76 |
| Y | 328 | 306 | Fc-N:77 |
| R | 329 | 307 | Fc-N:78 |
| V | 330 | 308 | Fc-N:79 |
| V | 331 | 309 | Fc-N:80 |
| S | 332 | 310 | Fc-N:81 |
| V | 333 | 311 | Fc-N:82 |
| L | 334 | 312 | Fc-N:83 |
| T | 335 | 313 | Fc-N:84 |
| V | 336 | 314 | Fc-N:85 |
| L | 337 | 315 | Fc-N:86 |
| H | 338 | 316 | Fc-N:87 |
| Q | 339 | 317 | Fc-N:88 |
| D | 340 | 318 | Fc-N:89 |
| W | 341 | 319 | Fc-N:90 |
| - | 341.1 | 319.1 | Fc-N:91 |
| L | 342 | 320 | Fc-N:92 |
| N | 343 | 321 | Fc-N:93 |
| G | 344 | 322 | Fc-N:94 |
| K | 345 | 323 | Fc-N:95 |

FIG. 9 Continued

| AB-007088_LS_Heavy Chain | | | |
|---|---|---|---|
| | | | |
| Residue | Linear # | Mat. Linear # | ASN # |
| E | 346 | 324 | Fc-N:96 |
| - | 346.1 | 324.1 | Fc-N:97 |
| - | 346.2 | 324.2 | Fc-N:98 |
| Y | 347 | 325 | Fc-N:99 |
| K | 348 | 326 | Fc-N:100 |
| C | 349 | 327 | Fc-N:101 |
| K | 350 | 328 | Fc-N:102 |
| V | 351 | 329 | Fc-N:103 |
| S | 352 | 330 | Fc-N:104 |
| N | 353 | 331 | Fc-N:105 |
| K | 354 | 332 | Fc-N:106 |
| A | 355 | 333 | Fc-N:107 |
| L | 356 | 334 | Fc-N:108 |
| P | 357 | 335 | Fc-N:109 |
| - | 357.1 | 335.1 | Fc-N:110 |
| - | 357.2 | 335.2 | Fc-N:111 |
| A | 358 | 336 | Fc-N:112 |
| P | 359 | 337 | Fc-N:113 |
| I | 360 | 338 | Fc-N:114 |
| E | 361 | 339 | Fc-N:115 |
| K | 362 | 340 | Fc-N:116 |
| T | 363 | 341 | Fc-N:117 |
| I | 364 | 342 | Fc-N:118 |
| S | 365 | 343 | Fc-N:119 |
| K | 366 | 344 | Fc-N:120 |
| A | 367 | 345 | Fc-N:121 |
| K | 368 | 346 | Fc-N:122 |
| G | 369 | 347 | Fc-N:123 |
| - | 369.1 | 347.1 | Fc-C:1 |
| Q | 370 | 348 | Fc-C:2 |
| P | 371 | 349 | Fc-C:3 |
| R | 372 | 350 | Fc-C:4 |
| E | 373 | 351 | Fc-C:5 |
| P | 374 | 352 | Fc-C:6 |
| Q | 375 | 353 | Fc-C:7 |
| V | 376 | 354 | Fc-C:8 |
| Y | 377 | 355 | Fc-C:9 |
| T | 378 | 356 | Fc-C:10 |
| L | 379 | 357 | Fc-C:11 |
| P | 380 | 358 | Fc-C:12 |
| P | 381 | 359 | Fc-C:13 |
| - | 381.1 | 359.1 | Fc-C:14 |
| S | 382 | 360 | Fc-C:15 |

FIG. 9 Continued

| AB-007088_LS_Heavy Chain | | | |
|---|---|---|---|
| | | | |
| Residue | Linear # | Mat. Linear # | ASN # |
| R | 383 | 361 | Fc-C:16 |
| D | 384 | 362 | Fc-C:17 |
| - | 384.1 | 362.1 | Fc-C:18 |
| E | 385 | 363 | Fc-C:19 |
| L | 386 | 364 | Fc-C:20 |
| - | 386.1 | 364.1 | Fc-C:21 |
| - | 386.2 | 364.2 | Fc-C:22 |
| T | 387 | 365 | Fc-C:23 |
| K | 388 | 366 | Fc-C:24 |
| N | 389 | 367 | Fc-C:25 |
| Q | 390 | 368 | Fc-C:26 |
| V | 391 | 369 | Fc-C:27 |
| S | 392 | 370 | Fc-C:28 |
| L | 393 | 371 | Fc-C:29 |
| T | 394 | 372 | Fc-C:30 |
| C | 395 | 373 | Fc-C:31 |
| L | 396 | 374 | Fc-C:32 |
| V | 397 | 375 | Fc-C:33 |
| K | 398 | 376 | Fc-C:34 |
| G | 399 | 377 | Fc-C:35 |
| F | 400 | 378 | Fc-C:36 |
| Y | 401 | 379 | Fc-C:37 |
| P | 402 | 380 | Fc-C:38 |
| - | 402.1 | 380.1 | Fc-C:39 |
| - | 402.2 | 380.2 | Fc-C:40 |
| S | 403 | 381 | Fc-C:41 |
| D | 404 | 382 | Fc-C:42 |
| I | 405 | 383 | Fc-C:43 |
| A | 406 | 384 | Fc-C:44 |
| V | 407 | 385 | Fc-C:45 |
| E | 408 | 386 | Fc-C:46 |
| W | 409 | 387 | Fc-C:47 |
| - | 409.1 | 387.1 | Fc-C:48 |
| E | 410 | 388 | Fc-C:49 |
| S | 411 | 389 | Fc-C:50 |
| N | 412 | 390 | Fc-C:51 |
| G | 413 | 391 | Fc-C:52 |
| Q | 414 | 392 | Fc-C:53 |
| P | 415 | 393 | Fc-C:54 |
| - | 415.1 | 393.1 | Fc-C:55 |
| - | 415.2 | 393.2 | Fc-C:56 |
| E | 416 | 394 | Fc-C:57 |
| N | 417 | 395 | Fc-C:58 |

FIG. 9 Continued

| AB-007088_LS_Heavy Chain | | | |
|---|---|---|---|
| | | | |
| Residue | Linear # | Mat. Linear # | ASN # |
| N | 418 | 396 | Fc-C:59 |
| Y | 419 | 397 | Fc-C:60 |
| K | 420 | 398 | Fc-C:61 |
| T | 421 | 399 | Fc-C:62 |
| T | 422 | 400 | Fc-C:63 |
| P | 423 | 401 | Fc-C:64 |
| P | 424 | 402 | Fc-C:65 |
| V | 425 | 403 | Fc-C:66 |
| L | 426 | 404 | Fc-C:67 |
| D | 427 | 405 | Fc-C:68 |
| - | 427.1 | 405.1 | Fc-C:69 |
| - | 427.2 | 405.2 | Fc-C:70 |
| - | 427.3 | 405.3 | Fc-C:71 |
| - | 427.4 | 405.4 | Fc-C:72 |
| S | 428 | 406 | Fc-C:73 |
| D | 429 | 407 | Fc-C:74 |
| G | 430 | 408 | Fc-C:75 |
| S | 431 | 409 | Fc-C:76 |
| F | 432 | 410 | Fc-C:77 |
| F | 433 | 411 | Fc-C:78 |
| L | 434 | 412 | Fc-C:79 |
| Y | 435 | 413 | Fc-C:80 |
| S | 436 | 414 | Fc-C:81 |
| K | 437 | 415 | Fc-C:82 |
| L | 438 | 416 | Fc-C:83 |
| T | 439 | 417 | Fc-C:84 |
| V | 440 | 418 | Fc-C:85 |
| D | 441 | 419 | Fc-C:86 |
| K | 442 | 420 | Fc-C:87 |
| S | 443 | 421 | Fc-C:88 |
| R | 444 | 422 | Fc-C:89 |
| W | 445 | 423 | Fc-C:90 |
| - | 445.1 | 423.1 | Fc-C:91 |
| Q | 446 | 424 | Fc-C:92 |
| Q | 447 | 425 | Fc-C:93 |
| G | 448 | 426 | Fc-C:94 |
| N | 449 | 427 | Fc-C:95 |
| V | 450 | 428 | Fc-C:96 |
| - | 450.1 | 428.1 | Fc-C:97 |
| - | 450.2 | 428.2 | Fc-C:98 |
| F | 451 | 429 | Fc-C:99 |
| S | 452 | 430 | Fc-C:100 |
| C | 453 | 431 | Fc-C:101 |

FIG. 9 Continued

| AB-007088_LS_Heavy Chain | | | |
|---|---|---|---|
| | | | |
| **Residue** | **Linear #** | **Mat. Linear #** | **ASN #** |
| S | 454 | 432 | Fc-C:102 |
| V | 455 | 433 | Fc-C:103 |
| L | 456 | 434 | Fc-C:104 |
| H | 457 | 435 | Fc-C:105 |
| E | 458 | 436 | Fc-C:106 |
| A | 459 | 437 | Fc-C:107 |
| L | 460 | 438 | Fc-C:108 |
| H | 461 | 439 | Fc-C:109 |
| - | 461.1 | 439.1 | Fc-C:110 |
| - | 461.2 | 439.2 | Fc-C:111 |
| S | 462 | 440 | Fc-C:112 |
| H | 463 | 441 | Fc-C:113 |
| Y | 464 | 442 | Fc-C:114 |
| T | 465 | 443 | Fc-C:115 |
| - | 465.1 | 443.1 | Fc-C:116 |
| Q | 466 | 444 | Fc-C:117 |
| K | 467 | 445 | Fc-C:118 |
| S | 468 | 446 | Fc-C:119 |
| L | 469 | 447 | Fc-C:120 |
| S | 470 | 448 | Fc-C:121 |
| L | 471 | 449 | Fc-C:122 |
| S | 472 | 450 | Fc-C:123 |
| P | 473 | 451 | HCnst-Po:1 |
| G | 474 | 452 | HCnst-Po:2 |
| K | 475 | 453 | HCnst-Po:3 |
| - | 475.1 | 453.1 | HCnst-Po:4 |
| - | 475.2 | 453.2 | HCnst-Po:5 |
| - | 475.3 | 453.3 | HCnst-Po:6 |
| - | 475.4 | 453.4 | HCnst-Po:7 |
| - | 475.5 | 453.5 | HCnst-Po:8 |
| - | 475.6 | 453.6 | HCnst-Po:9 |
| - | 475.7 | 453.7 | HCnst-Po:10 |
| - | 475.8 | 453.8 | HCnst-Po:11 |
| - | 475.9 | 453.9 | HCnst-Po:12 |
| - | 475.10 | 453.10 | HCnst-Po:13 |
| - | 475.11 | 453.11 | HCnst-Po:14 |
| - | 475.12 | 453.12 | HCnst-Po:15 |
| - | 475.13 | 453.13 | HCnst-Po:16 |
| - | 475.14 | 453.14 | HCnst-Po:17 |
| - | 475.15 | 453.15 | HCnst-Po:18 |
| - | 475.16 | 453.16 | HCnst-Po:19 |
| - | 475.17 | 453.17 | HCnst-Po:20 |
| - | 475.18 | 453.18 | HCnst-Po:21 |

FIG. 9 Continued

| AB-007088_LS_Heavy Chain | | | |
|---|---|---|---|
| | | | |
| Residue | Linear # | Mat. Linear # | ASN # |
| - | 475.19 | 453.19 | HCnst-Po:22 |
| - | 475.20 | 453.20 | HCnst-Po:23 |
| - | 475.21 | 453.21 | HCnst-Po:24 |
| - | 475.22 | 453.22 | HCnst-Po:25 |
| - | 475.23 | 453.23 | HCnst-Po:26 |
| - | 475.24 | 453.24 | HCnst-Po:27 |
| - | 475.25 | 453.25 | HCnst-Po:28 |
| - | 475.26 | 453.26 | HCnst-Po:29 |
| - | 475.27 | 453.27 | HCnst-Po:30 |
| - | 475.28 | 453.28 | HCnst-Po:31 |
| - | 475.29 | 453.29 | HCnst-Po:32 |
| - | 475.30 | 453.30 | HCnst-Po:33 |
| - | 475.31 | 453.31 | HCnst-Po:34 |
| - | 475.32 | 453.32 | HCnst-Po:35 |
| - | 475.33 | 453.33 | HCnst-Po:36 |
| - | 475.34 | 453.34 | HCnst-Po:37 |
| - | 475.35 | 453.35 | HCnst-Po:38 |
| - | 475.36 | 453.36 | HCnst-Po:39 |
| - | 475.37 | 453.37 | HCnst-Po:40 |
| - | 475.38 | 453.38 | HCnst-Po:41 |
| - | 475.39 | 453.39 | HCnst-Po:42 |
| - | 475.40 | 453.40 | HCnst-Po:43 |
| - | 475.41 | 453.41 | HCnst-Po:44 |
| - | 475.42 | 453.42 | HCnst-Po:45 |
| - | 475.43 | 453.43 | HCnst-Po:46 |
| - | 475.44 | 453.44 | HCnst-Po:47 |
| - | 475.45 | 453.45 | HCnst-Po:48 |
| - | 475.46 | 453.46 | HCnst-Po:49 |
| - | 475.47 | 453.47 | HCnst-Po:50 |
| - | 475.48 | 453.48 | HCnst-Po:51 |
| - | 475.49 | 453.49 | HCnst-Po:52 |
| - | 475.50 | 453.50 | HCnst-Po:53 |
| - | 475.51 | 453.51 | HCnst-Po:54 |
| - | 475.52 | 453.52 | HCnst-Po:55 |
| - | 475.53 | 453.53 | HCnst-Po:56 |
| - | 475.54 | 453.54 | HCnst-Po:57 |
| - | 475.55 | 453.55 | HCnst-Po:58 |
| - | 475.56 | 453.56 | HCnst-Po:59 |
| - | 475.57 | 453.57 | HCnst-Po:60 |
| - | 475.58 | 453.58 | HCnst-Po:61 |
| - | 475.59 | 453.59 | HCnst-Po:62 |
| - | 475.60 | 453.60 | HCnst-Po:63 |
| - | 475.61 | 453.61 | HCnst-Po:64 |

FIG. 9 Continued

| AB-007088_LS_Heavy Chain | | | |
|---|---|---|---|
| | | | |
| Residue | Linear # | Mat. Linear # | ASN # |
| - | 475.62 | 453.62 | HCnst-Po:65 |
| - | 475.63 | 453.63 | HCnst-Po:66 |
| - | 475.64 | 453.64 | HCnst-Po:67 |
| - | 475.65 | 453.65 | HCnst-Po:68 |
| - | 475.66 | 453.66 | HCnst-Po:69 |
| - | 475.67 | 453.67 | HCnst-Po:70 |
| - | 475.68 | 453.68 | HCnst-Po:71 |
| - | 475.69 | 453.69 | HCnst-Po:72 |
| - | 475.70 | 453.70 | HCnst-Po:73 |
| - | 475.71 | 453.71 | HCnst-Po:74 |
| - | 475.72 | 453.72 | HCnst-Po:75 |
| - | 475.73 | 453.73 | HCnst-Po:76 |
| - | 475.74 | 453.74 | HCnst-Po:77 |
| - | 475.75 | 453.75 | HCnst-Po:78 |
| - | 475.76 | 453.76 | HCnst-Po:79 |
| - | 475.77 | 453.77 | HCnst-Po:80 |
| - | 475.78 | 453.78 | HCnst-Po:81 |
| - | 475.79 | 453.79 | HCnst-Po:82 |
| - | 475.80 | 453.80 | HCnst-Po:83 |
| - | 475.81 | 453.81 | HCnst-Po:84 |
| - | 475.82 | 453.82 | HCnst-Po:85 |
| - | 475.83 | 453.83 | HCnst-Po:86 |
| - | 475.84 | 453.84 | HCnst-Po:87 |
| - | 475.85 | 453.85 | HCnst-Po:88 |
| - | 475.86 | 453.86 | HCnst-Po:89 |
| - | 475.87 | 453.87 | HCnst-Po:90 |
| - | 475.88 | 453.88 | HCnst-Po:91 |
| - | 475.89 | 453.89 | HCnst-Po:92 |
| - | 475.90 | 453.90 | HCnst-Po:93 |
| - | 475.91 | 453.91 | HCnst-Po:94 |
| - | 475.92 | 453.92 | HCnst-Po:95 |
| - | 475.93 | 453.93 | HCnst-Po:96 |
| - | 475.94 | 453.94 | HCnst-Po:97 |
| - | 475.95 | 453.95 | HCnst-Po:98 |
| - | 475.96 | 453.96 | HCnst-Po:99 |
| - | 475.97 | 453.97 | HCnst-Po:100 |
| - | 475.98 | 453.98 | HCnst-Po:101 |
| - | 475.99 | 453.99 | HCnst-Po:102 |
| - | 475.100 | 453.100 | HCnst-Po:103 |
| - | 475.101 | 453.101 | HCnst-Po:104 |
| - | 475.102 | 453.102 | HCnst-Po:105 |
| - | 475.103 | 453.103 | HCnst-Po:106 |
| - | 475.104 | 453.104 | HCnst-Po:107 |

FIG. 9 Continued

| AB-007088_LS_Heavy Chain | | | |
|---|---|---|---|
| | | | |
| **Residue** | **Linear #** | **Mat. Linear #** | **ASN #** |
| - | 475.105 | 453.105 | HCnst-Po:108 |
| - | 475.106 | 453.106 | HCnst-Po:109 |
| - | 475.107 | 453.107 | HCnst-Po:110 |
| - | 475.108 | 453.108 | HCnst-Po:111 |
| - | 475.109 | 453.109 | HCnst-Po:112 |
| - | 475.110 | 453.110 | HCnst-Po:113 |
| - | 475.111 | 453.111 | HCnst-Po:114 |
| - | 475.112 | 453.112 | HCnst-Po:115 |
| - | 475.113 | 453.113 | HCnst-Po:116 |
| - | 475.114 | 453.114 | HCnst-Po:117 |
| - | 475.115 | 453.115 | HCnst-Po:118 |
| - | 475.116 | 453.116 | HCnst-Po:119 |
| - | 475.117 | 453.117 | HCnst-Po:120 |
| - | 475.118 | 453.118 | HCnst-Po:121 |
| - | 475.119 | 453.119 | HCnst-Po:122 |
| - | 475.120 | 453.120 | HCnst-Po:123 |

FIG. 9 Continued

SEQUENCE LISTING

```
Sequence total quantity: 289
SEQ ID NO: 1            moltype = AA  length = 14
FEATURE                 Location/Qualifiers
REGION                  1..14
                        note = Synthetic
source                  1..14
                        mol_type = protein
                        organism = synthetic construct
SEQUENCE: 1
TGMNSNIGAG YDVY                                                 14

SEQ ID NO: 2            moltype = AA  length = 7
FEATURE                 Location/Qualifiers
REGION                  1..7
                        note = Synthetic
source                  1..7
                        mol_type = protein
                        organism = synthetic construct
SEQUENCE: 2
GNSNRPS                                                         7

SEQ ID NO: 3            moltype = AA  length = 11
FEATURE                 Location/Qualifiers
REGION                  1..11
                        note = Synthetic
source                  1..11
                        mol_type = protein
                        organism = synthetic construct
SEQUENCE: 3
QSYDTSLNGW A                                                    11

SEQ ID NO: 4            moltype = AA  length = 5
FEATURE                 Location/Qualifiers
REGION                  1..5
                        note = Synthetic
source                  1..5
                        mol_type = protein
                        organism = synthetic construct
SEQUENCE: 4
DHAMS                                                           5

SEQ ID NO: 5            moltype = AA  length = 19
FEATURE                 Location/Qualifiers
REGION                  1..19
                        note = Synthetic
source                  1..19
                        mol_type = protein
                        organism = synthetic construct
SEQUENCE: 5
FIRKTTYGAT THYAAAVRG                                            19

SEQ ID NO: 6            moltype = AA  length = 16
FEATURE                 Location/Qualifiers
REGION                  1..16
                        note = Synthetic
source                  1..16
                        mol_type = protein
                        organism = synthetic construct
SEQUENCE: 6
VQLDYGPGYQ YYGMDV                                               16

SEQ ID NO: 7            moltype = AA  length = 14
FEATURE                 Location/Qualifiers
REGION                  1..14
                        note = Synthetic
source                  1..14
                        mol_type = protein
                        organism = synthetic construct
```

```
SEQUENCE: 7
TGMNSNIGAG YDVY                                                   14

SEQ ID NO: 8            moltype = AA  length = 7
FEATURE                 Location/Qualifiers
REGION                  1..7
                        note = Synthetic
source                  1..7
                        mol_type = protein
                        organism = synthetic construct
SEQUENCE: 8
GNSNRPS                                                           7

SEQ ID NO: 9            moltype = AA  length = 11
FEATURE                 Location/Qualifiers
REGION                  1..11
                        note = Synthetic
source                  1..11
                        mol_type = protein
                        organism = synthetic construct
SEQUENCE: 9
QSYDTSLNGW A                                                      11

SEQ ID NO: 10           moltype = AA  length = 5
FEATURE                 Location/Qualifiers
REGION                  1..5
                        note = Synthetic
source                  1..5
                        mol_type = protein
                        organism = synthetic construct
SEQUENCE: 10
DHAMS                                                             5

SEQ ID NO: 11           moltype = AA  length = 19
FEATURE                 Location/Qualifiers
REGION                  1..19
                        note = Synthetic
source                  1..19
                        mol_type = protein
                        organism = synthetic construct
SEQUENCE: 11
FIRKTTYGAT THYAAAVRG                                              19

SEQ ID NO: 12           moltype = AA  length = 16
FEATURE                 Location/Qualifiers
REGION                  1..16
                        note = Synthetic
source                  1..16
                        mol_type = protein
                        organism = synthetic construct
SEQUENCE: 12
VQLDYGPGYQ YYGMDV                                                 16

SEQ ID NO: 13           moltype = AA  length = 112
FEATURE                 Location/Qualifiers
REGION                  1..112
                        note = Synthetic
source                  1..112
                        mol_type = protein
                        organism = synthetic construct
SEQUENCE: 13
ESVLTQPPSV SGAPGQRVTI SCTGMNSNIG AGYDVYWYQQ LPGRAPKLLI YGNSNRPSGV  60
PDRFSGSRSG TSASLAITGL QAEDEADYYC QSYDTSLNGW AFGGGTKLTV LG          112

SEQ ID NO: 14           moltype = AA  length = 127
FEATURE                 Location/Qualifiers
REGION                  1..127
                        note = Synthetic
source                  1..127
                        mol_type = protein
                        organism = synthetic construct
SEQUENCE: 14
EVQLVESGGG LVQPGRSLRL PCTASGFSFG DHAMSWVRQA PGKGLEWVGF IRKTTYGATT  60
HYAAAVRGRF TISRDDSKSI VYLQMNSLKT EDTAVYFCTR VQLDYGPGYQ YYGMDVWGQG  120
TTVTVSS                                                           127

SEQ ID NO: 15           moltype = DNA  length = 336
FEATURE                 Location/Qualifiers
misc_feature            1..336
```

```
                        note = Synthetic
source                  1..336
                        mol_type = other DNA
                        organism = synthetic construct
SEQUENCE: 15
gagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa gagcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 16           moltype = DNA  length = 381
FEATURE                 Location/Qualifiers
misc_feature            1..381
                        note = Synthetic
source                  1..381
                        mol_type = other DNA
                        organism = synthetic construct
SEQUENCE: 16
gaggtgcagc tggtggagtc tgggggaggc ttggtacagc cagggcggtc cctgagactc  60
ccctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc a                                            381

SEQ ID NO: 17           moltype = AA  length = 217
FEATURE                 Location/Qualifiers
REGION                  1..217
                        note = Synthetic
source                  1..217
                        mol_type = protein
                        organism = synthetic construct
SEQUENCE: 17
ESVLTQPPSV SGAPGQRVTI SCTGMNSNIG AGYDVYWYQQ LPGRAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                           217

SEQ ID NO: 18           moltype = AA  length = 457
FEATURE                 Location/Qualifiers
REGION                  1..457
                        note = Synthetic
source                  1..457
                        mol_type = protein
                        organism = synthetic construct
SEQUENCE: 18
EVQLVESGGG LVQPGRSLRL PCTASGFSFG DHAMSWVRQA PGKGLEWVGF IRKTTYGATT  60
HYAAAVRGRF TISRDDSKSI VYLQMNSLKT EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                           457

SEQ ID NO: 19           moltype = AA  length = 457
FEATURE                 Location/Qualifiers
REGION                  1..457
                        note = Synthetic
source                  1..457
                        mol_type = protein
                        organism = synthetic construct
SEQUENCE: 19
EVQLVESGGG LVQPGRSLRL PCTASGFSFG DHAMSWVRQA PGKGLEWVGF IRKTTYGATT  60
HYAAAVRGRF TISRDDSKSI VYLQMNSLKT EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                           457

SEQ ID NO: 20           moltype = DNA  length = 651
FEATURE                 Location/Qualifiers
misc_feature            1..651
                        note = Synthetic
```

```
source                  1..651
                        mol_type = other DNA
                        organism = synthetic construct
SEQUENCE: 20
gagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa gagcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagcccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t           651

SEQ ID NO: 21           moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 21
gaggtgcagc tggtggagtc tgggggaggc ttggtacagc cagggcggtc cctgagactc  60
ccctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 22           moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 22
gaggtgcagc tggtggagtc tgggggaggc ttggtacagc cagggcggtc cctgagactc  60
ccctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371
```

```
SEQ ID NO: 23          moltype = AA  length = 112
FEATURE                Location/Qualifiers
REGION                 1..112
                       note = Synthetic
source                 1..112
                       mol_type = protein
                       organism = synthetic construct
SEQUENCE: 23
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 24          moltype = AA  length = 127
FEATURE                Location/Qualifiers
REGION                 1..127
                       note = Synthetic
source                 1..127
                       mol_type = protein
                       organism = synthetic construct
SEQUENCE: 24
EVQLVESGGG LVQPGRSLRL SCTASGFSFG DHAMSWVRQA PGKGLEWVGF IRKTTYGATT  60
HYAAAVRGRF TISRDDSKSI VYLQMNSLKT EDTAVYFCTR VQLDYGPGYQ YYGMDVWGQG  120
TTVTVSS                                                            127

SEQ ID NO: 25          moltype = DNA  length = 336
FEATURE                Location/Qualifiers
misc_feature           1..336
                       note = Synthetic
source                 1..336
                       mol_type = other DNA
                       organism = synthetic construct
SEQUENCE: 25
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 26          moltype = DNA  length = 381
FEATURE                Location/Qualifiers
misc_feature           1..381
                       note = Synthetic
source                 1..381
                       mol_type = other DNA
                       organism = synthetic construct
SEQUENCE: 26
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc a                                            381

SEQ ID NO: 27          moltype = AA  length = 217
FEATURE                Location/Qualifiers
REGION                 1..217
                       note = Synthetic
source                 1..217
                       mol_type = protein
                       organism = synthetic construct
SEQUENCE: 27
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                           217

SEQ ID NO: 28          moltype = AA  length = 457
FEATURE                Location/Qualifiers
REGION                 1..457
                       note = Synthetic
source                 1..457
                       mol_type = protein
                       organism = synthetic construct
SEQUENCE: 28
EVQLVESGGG LVQPGRSLRL SCTASGFSFG DHAMSWVRQA PGKGLEWVGF IRKTTYGATT  60
HYAAAVRGRF TISRDDSKSI VYLQMNSLKT EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
```

```
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                          457

SEQ ID NO: 29          moltype = AA  length = 457
FEATURE                Location/Qualifiers
REGION                 1..457
                       note = Synthetic
source                 1..457
                       mol_type = protein
                       organism = synthetic construct
SEQUENCE: 29
EVQLVESGGG LVQPGRSLRL SCTASGFSFG DHAMSWVRQA PGKGLEWVGF IRKTTYGATT  60
HYAAAVRGRF TISRDDSKSI VYLQMNSLKT EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                          457

SEQ ID NO: 30          moltype = DNA  length = 651
FEATURE                Location/Qualifiers
misc_feature           1..651
                       note = Synthetic
source                 1..651
                       mol_type = other DNA
                       organism = synthetic construct
SEQUENCE: 30
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t           651

SEQ ID NO: 31          moltype = DNA  length = 1371
FEATURE                Location/Qualifiers
misc_feature           1..1371
                       note = Synthetic
source                 1..1371
                       mol_type = other DNA
                       organism = synthetic construct
SEQUENCE: 31
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 32          moltype = DNA  length = 1371
FEATURE                Location/Qualifiers
misc_feature           1..1371
                       note = Synthetic
```

```
source                  1..1371
                        mol_type = other DNA
                        organism = synthetic construct
SEQUENCE: 32
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 33           moltype = AA  length = 112
FEATURE                 Location/Qualifiers
REGION                  1..112
                        note = Synthetic
source                  1..112
                        mol_type = protein
                        organism = synthetic construct
SEQUENCE: 33
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 34           moltype = AA  length = 127
FEATURE                 Location/Qualifiers
REGION                  1..127
                        note = Synthetic
source                  1..127
                        mol_type = protein
                        organism = synthetic construct
SEQUENCE: 34
EVQLVESGGG LVQPGRSLRL SCAASGFSFG DHAMSWVRQA PGKGLEWVGF IRKTTYGATT  60
HYAAAVRGRF TISRDDSKSI VYLQMNSLKT EDTAVYFCTR VQLDYGPGYQ YYGMDVWGQG  120
TTVTVSS                                                            127

SEQ ID NO: 35           moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 35
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 36           moltype = DNA  length = 381
FEATURE                 Location/Qualifiers
misc_feature            1..381
                        note = Synthetic
source                  1..381
                        mol_type = other DNA
                        organism = synthetic construct
SEQUENCE: 36
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaaacc gaggacacag ccgtgtattt ctgtactaga  300
```

```
gtgcagcttg actatggccc gggataccag tactacggta tggacgtctg gggccaaggg  360
accacggtca ccgtctcctc a                                           381

SEQ ID NO: 37          moltype = AA  length = 217
FEATURE                Location/Qualifiers
REGION                 1..217
                       note = Synthetic
source                 1..217
                       mol_type = protein
                       organism = synthetic construct
SEQUENCE: 37
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                          217

SEQ ID NO: 38          moltype = AA  length = 457
FEATURE                Location/Qualifiers
REGION                 1..457
                       note = Synthetic
source                 1..457
                       mol_type = protein
                       organism = synthetic construct
SEQUENCE: 38
EVQLVESGGG LVQPGRSLRL SCAASGFSFG DHAMSWVRQA PGKGLEWVGF IRKTTYGATT  60
HYAAAVRGRF TISRDDSKSI VYLQMNSLKT EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                          457

SEQ ID NO: 39          moltype = AA  length = 457
FEATURE                Location/Qualifiers
REGION                 1..457
                       note = Synthetic
source                 1..457
                       mol_type = protein
                       organism = synthetic construct
SEQUENCE: 39
EVQLVESGGG LVQPGRSLRL SCAASGFSFG DHAMSWVRQA PGKGLEWVGF IRKTTYGATT  60
HYAAAVRGRF TISRDDSKSI VYLQMNSLKT EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                          457

SEQ ID NO: 40          moltype = DNA  length = 651
FEATURE                Location/Qualifiers
misc_feature           1..651
                       note = Synthetic
source                 1..651
                       mol_type = other DNA
                       organism = synthetic construct
SEQUENCE: 40
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t          651

SEQ ID NO: 41          moltype = DNA  length = 1371
FEATURE                Location/Qualifiers
misc_feature           1..1371
                       note = Synthetic
source                 1..1371
                       mol_type = other DNA
                       organism = synthetic construct
SEQUENCE: 41
gaggtgcagc tggtggagtc tgggggaggc ttggtacagc cagggcggtc cctgagactc  60
```

```
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 42          moltype = DNA  length = 1371
FEATURE                Location/Qualifiers
misc_feature           1..1371
                       note = Synthetic
source                 1..1371
                       mol_type = other DNA
                       organism = synthetic construct
SEQUENCE: 42
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 43          moltype = AA  length = 112
FEATURE                Location/Qualifiers
REGION                 1..112
                       note = Synthetic
source                 1..112
                       mol_type = protein
                       organism = synthetic construct
SEQUENCE: 43
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 44          moltype = AA  length = 127
FEATURE                Location/Qualifiers
REGION                 1..127
                       note = Synthetic
source                 1..127
                       mol_type = protein
                       organism = synthetic construct
SEQUENCE: 44
EVQLVESGGG LVQPGRSLRL SCTASGFSFG DHAMSWVRQA PGKGLEWVGF IRKTTYGATT  60
HYAAAVRGRF TISRDDSKST VYLQMNSLKT EDTAVYFCTR VQLDYGPGYQ YYGMDVWGQG  120
TTVTVSS                                                            127

SEQ ID NO: 45          moltype = DNA  length = 336
```

```
FEATURE               Location/Qualifiers
misc_feature          1..336
                      note = Synthetic
source                1..336
                      mol_type = other DNA
                      organism = synthetic construct
SEQUENCE: 45
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 46         moltype = DNA  length = 381
FEATURE               Location/Qualifiers
misc_feature          1..381
                      note = Synthetic
source                1..381
                      mol_type = other DNA
                      organism = synthetic construct
SEQUENCE: 46
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc a                                            381

SEQ ID NO: 47         moltype = AA  length = 217
FEATURE               Location/Qualifiers
REGION                1..217
                      note = Synthetic
source                1..217
                      mol_type = protein
                      organism = synthetic construct
SEQUENCE: 47
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                           217

SEQ ID NO: 48         moltype = AA  length = 457
FEATURE               Location/Qualifiers
REGION                1..457
                      note = Synthetic
source                1..457
                      mol_type = protein
                      organism = synthetic construct
SEQUENCE: 48
EVQLVESGGG LVQPGRSLRL SCTASGFSFG DHAMSWVRQA PGKGLEWVGF IRKTTYGATT  60
HYAAAVRGRF TISRDDSKST VYLQMNSLKT EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                           457

SEQ ID NO: 49         moltype = AA  length = 457
FEATURE               Location/Qualifiers
REGION                1..457
                      note = Synthetic
source                1..457
                      mol_type = protein
                      organism = synthetic construct
SEQUENCE: 49
EVQLVESGGG LVQPGRSLRL SCTASGFSFG DHAMSWVRQA PGKGLEWVGF IRKTTYGATT  60
HYAAAVRGRF TISRDDSKST VYLQMNSLKT EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                           457

SEQ ID NO: 50         moltype = DNA  length = 651
FEATURE               Location/Qualifiers
```

```
misc_feature            1..651
                        note = Synthetic
source                  1..651
                        mol_type = other DNA
                        organism = synthetic construct
SEQUENCE: 50
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t           651

SEQ ID NO: 51           moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 51
gaggtgcagc tggtggagtc tggggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 52           moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 52
gaggtgcagc tggtggagtc tggggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
```

```
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 53          moltype = AA  length = 112
FEATURE                Location/Qualifiers
REGION                 1..112
                       note = Synthetic
source                 1..112
                       mol_type = protein
                       organism = synthetic construct
SEQUENCE: 53
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 54          moltype = AA  length = 127
FEATURE                Location/Qualifiers
REGION                 1..127
                       note = Synthetic
source                 1..127
                       mol_type = protein
                       organism = synthetic construct
SEQUENCE: 54
EVQLVESGGG LVQPGRSLRL SCTASGFSFG DHAMSWVRQA PGKGLEWVGF IRKTTYGATT  60
HYAAAVRGRF TISRDDSKSI VYLQMNSLKA EDTAVYFCTR VQLDYGPGYQ YYGMDVWGQG  120
TTVTVSS                                                            127

SEQ ID NO: 55          moltype = DNA  length = 336
FEATURE                Location/Qualifiers
misc_feature           1..336
                       note = Synthetic
source                 1..336
                       mol_type = other DNA
                       organism = synthetic construct
SEQUENCE: 55
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 56          moltype = DNA  length = 381
FEATURE                Location/Qualifiers
misc_feature           1..381
                       note = Synthetic
source                 1..381
                       mol_type = other DNA
                       organism = synthetic construct
SEQUENCE: 56
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaagca gaggacacag ccgtgtattt ctgtactaga  300
gtgcagcttg actatggccc gggataccag tactacggta tggacgtctg gggccaaggg  360
accacggtca ccgtctcctc a                                            381

SEQ ID NO: 57          moltype = AA  length = 217
FEATURE                Location/Qualifiers
REGION                 1..217
                       note = Synthetic
source                 1..217
                       mol_type = protein
                       organism = synthetic construct
SEQUENCE: 57
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                           217

SEQ ID NO: 58          moltype = AA  length = 457
FEATURE                Location/Qualifiers
REGION                 1..457
                       note = Synthetic
source                 1..457
                       mol_type = protein
                       organism = synthetic construct
SEQUENCE: 58
EVQLVESGGG LVQPGRSLRL SCTASGFSFG DHAMSWVRQA PGKGLEWVGF IRKTTYGATT  60
```

```
HYAAAVRGRF TISRDDSKSI VYLQMNSLKA EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                           457

SEQ ID NO: 59          moltype = AA  length = 457
FEATURE                Location/Qualifiers
REGION                 1..457
                       note = Synthetic
source                 1..457
                       mol_type = protein
                       organism = synthetic construct
SEQUENCE: 59
EVQLVESGGG LVQPGRSLRL SCTASGFSFG DHAMSWVRQA PGKGLEWVGF IRKTTYGATT  60
HYAAAVRGRF TISRDDSKSI VYLQMNSLKA EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                           457

SEQ ID NO: 60          moltype = DNA  length = 651
FEATURE                Location/Qualifiers
misc_feature           1..651
                       note = Synthetic
source                 1..651
                       mol_type = other DNA
                       organism = synthetic construct
SEQUENCE: 60
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagcccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t           651

SEQ ID NO: 61          moltype = DNA  length = 1371
FEATURE                Location/Qualifiers
misc_feature           1..1371
                       note = Synthetic
source                 1..1371
                       mol_type = other DNA
                       organism = synthetic construct
SEQUENCE: 61
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaagca gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 62          moltype = DNA  length = 1371
FEATURE                Location/Qualifiers
```

```
misc_feature          1..1371
                      note = Synthetic
source                1..1371
                      mol_type = other DNA
                      organism = synthetic construct
SEQUENCE: 62
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaagca gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 63         moltype = AA  length = 112
FEATURE               Location/Qualifiers
REGION                1..112
                      note = Synthetic
source                1..112
                      mol_type = protein
                      organism = synthetic construct
SEQUENCE: 63
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 64         moltype = AA  length = 127
FEATURE               Location/Qualifiers
REGION                1..127
                      note = Synthetic
source                1..127
                      mol_type = protein
                      organism = synthetic construct
SEQUENCE: 64
EVQLVESGGG LVQPGRSLRL SCTASGFSFG DHAMSWVRQA PGKGLEWVGF IRKTTYGATT  60
HYAAAVRGRF TISRDDSKSI VYLQMNSLKT EDTAVYFCAR VQLDYGPGYQ YYGMDVWGQG  120
TTVTVSS                                                            127

SEQ ID NO: 65         moltype = DNA  length = 336
FEATURE               Location/Qualifiers
misc_feature          1..336
                      note = Synthetic
source                1..336
                      mol_type = other DNA
                      organism = synthetic construct
SEQUENCE: 65
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 66         moltype = DNA  length = 381
FEATURE               Location/Qualifiers
misc_feature          1..381
                      note = Synthetic
source                1..381
                      mol_type = other DNA
                      organism = synthetic construct
SEQUENCE: 66
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
```

```
cactacgccg cggctgtgag aggcagattc accatctcgc gagatgattc taaaagcatt  240
gtctatctgc aaatgaacag cctgaaaacc gaggacacag ccgtgtattt ctgtgctaga  300
gtgcagcttg actatggccc gggataccag tactacggta tggacgtctg ggccaaggg   360
accacggtca ccgtctcctc a                                            381

SEQ ID NO: 67          moltype = AA  length = 217
FEATURE                Location/Qualifiers
REGION                 1..217
                       note = Synthetic
source                 1..217
                       mol_type = protein
                       organism = synthetic construct
SEQUENCE: 67
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                          217

SEQ ID NO: 68          moltype = AA  length = 457
FEATURE                Location/Qualifiers
REGION                 1..457
                       note = Synthetic
source                 1..457
                       mol_type = protein
                       organism = synthetic construct
SEQUENCE: 68
EVQLVESGGG LVQPGRSLRL SCTASGFSFG DHAMSWVRQA PGKGLEWVGF IRKTTYGATT  60
HYAAAVRGRF TISRDDSKSI VYLQMNSLKT EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                          457

SEQ ID NO: 69          moltype = AA  length = 457
FEATURE                Location/Qualifiers
REGION                 1..457
                       note = Synthetic
source                 1..457
                       mol_type = protein
                       organism = synthetic construct
SEQUENCE: 69
EVQLVESGGG LVQPGRSLRL SCTASGFSFG DHAMSWVRQA PGKGLEWVGF IRKTTYGATT  60
HYAAAVRGRF TISRDDSKSI VYLQMNSLKT EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                          457

SEQ ID NO: 70          moltype = DNA  length = 651
FEATURE                Location/Qualifiers
misc_feature           1..651
                       note = Synthetic
source                 1..651
                       mol_type = other DNA
                       organism = synthetic construct
SEQUENCE: 70
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t            651

SEQ ID NO: 71          moltype = DNA  length = 1371
FEATURE                Location/Qualifiers
misc_feature           1..1371
                       note = Synthetic
source                 1..1371
                       mol_type = other DNA
                       organism = synthetic construct
```

SEQUENCE: 71
gaggtgcagc tggtggagtc tgggggaggc ttggtacagc cagggcggtc cctgagactc 60
agctgtacag cctctgggtt tagttttggt gatcatgcta tgagctgggt ccgccaggct 120
ccagggaagg ggctggagtg ggtaggtttc attagaaaga caacttatgg tgcgacaaca 180
cactacgccg cggctgtgag aggcagattc accatctcgc gagatgattc taaaagcatt 240
gtctatctgc aaatgaacag cctgaaaacc gaggacacag ccgtgtattt ctgtgctaga 300
gtgcagcttg actatggccc gggataccag tactacggta tggacgtctg gggccaaggg 360
accacggtca ccgtctcctc agcctccacc aagggcccat cggtcttccc cctggcaccc 420
tcctccaaga gcacctctgg gggcacagca gccctgggct gcctggtcaa ggactacttc 480
cccgaaccgg tgacggtgtc gtggaactca ggcgccctga ccagcggcgt gcacaccttc 540
ccggctgtcc tacagtcctc aggactctac tccctcagca gcgtggtgac cgtgccctcc 600
agcagcttgg gcacccagac ctacatctgc aacgtgaatc acaagcccag caacaccaag 660
gtggacaaga aagttgagcc caaatcttgt gacaaaactc acacatgccc accgtgccca 720
gcacctgaac tcctgggggg accgtcagtc ttcctcttcc ccccaaaacc caaggacacc 780
ctcatgatct cccggacccc tgaggtcaca tgcgtggtgg tggacgtgag ccacgaagac 840
cctgaggtca agttcaactg gtacgtggac ggcgtggagg tgcataatgc caagacaaag 900
ccgcgggagg agcagtacaa cagcacgtac cgtgtggtca gcgtcctcac cgtcctgcac 960
caggactggc tgaatggcaa ggagtacaag tgcaaggtct ccaacaaagc cctcccagcc 1020
cccatcgaga aaaccatctc caaagccaaa gggcagcccc gagaaccaca ggtgtacacc 1080
ctgcccccat cccgggatga gctgaccaag aaccaggtca gcctgacctg cctggtcaaa 1140
ggcttctatc ccagcgacat cgccgtggag tgggagagca atgggcagcc ggagaacaac 1200
tacaagacca cgcctcccgt gctggactcc gacggctcct tcttcctcta cagcaagctc 1260
accgtggaca agagcaggtg gcagcagggg aacgtcttct catgctccgt gatgcatgag 1320
gctctgcaca accactacac acagaagagc ctctccctgt ctccgggtaa a 1371

SEQ ID NO: 72 moltype = DNA length = 1371
FEATURE Location/Qualifiers
misc_feature 1..1371
note = Synthetic
source 1..1371
mol_type = other DNA
organism = synthetic construct
SEQUENCE: 72
gaggtgcagc tggtggagtc tgggggaggc ttggtacagc cagggcggtc cctgagactc 60
agctgtacag cctctgggtt tagttttggt gatcatgcta tgagctgggt ccgccaggct 120
ccagggaagg ggctggagtg ggtaggtttc attagaaaga caacttatgg tgcgacaaca 180
cactacgccg cggctgtgag aggcagattc accatctcgc gagatgattc taaaagcatt 240
gtctatctgc aaatgaacag cctgaaaacc gaggacacag ccgtgtattt ctgtgctaga 300
gtgcagcttg actatggccc gggataccag tactacggta tggacgtctg gggccaaggg 360
accacggtca ccgtctcctc agcctccacc aagggcccat cggtcttccc cctggcaccc 420
tcctccaaga gcacctctgg gggcacagca gccctgggct gcctggtcaa ggactacttc 480
cccgaaccgg tgacggtgtc gtggaactca ggcgccctga ccagcggcgt gcacaccttc 540
ccggctgtcc tacagtcctc aggactctac tccctcagca gcgtggtgac cgtgccctcc 600
agcagcttgg gcacccagac ctacatctgc aacgtgaatc acaagcccag caacaccaag 660
gtggacaaga aagttgagcc caaatcttgt gacaaaactc acacatgccc accgtgccca 720
gcacctgaac tcctgggggg accgtcagtc ttcctcttcc ccccaaaacc caaggacacc 780
ctcatgatct cccggacccc tgaggtcaca tgcgtggtgg tggacgtgag ccacgaagac 840
cctgaggtca agttcaactg gtacgtggac ggcgtggagg tgcataatgc caagacaaag 900
ccgcgggagg agcagtacaa cagcacgtac cgtgtggtca gcgtcctcac cgtcctgcac 960
caggactggc tgaatggcaa ggagtacaag tgcaaggtct ccaacaaagc cctcccagcc 1020
cccatcgaga aaaccatctc caaagccaaa gggcagcccc gagaaccaca ggtgtacacc 1080
ctgcccccat cccgggatga gctgaccaag aaccaggtca gcctgacctg cctggtcaaa 1140
ggcttctatc ccagcgacat cgccgtggag tgggagagca atgggcagcc ggagaacaac 1200
tacaagacca cgcctcccgt gctggactcc gacggctcct tcttcctcta cagcaagctc 1260
accgtggaca agagcaggtg gcagcagggg aacgtcttct catgctccgt gctgcatgag 1320
gctctgcact cccactacac acagaagagc ctctccctgt ctccgggtaa a 1371

SEQ ID NO: 73 moltype = AA length = 112
FEATURE Location/Qualifiers
REGION 1..112
note = Synthetic
source 1..112
mol_type = protein
organism = synthetic construct
SEQUENCE: 73
QSVLTQPPSV SGAPGQRVTI SCTGMNSNIG AGYDVYWYQQ LPGTAPKLLI YGNSNRPSGV 60
PDRFSGSRSG TSASLAITGL QAEDEADYYC QSYDTSLNGW AFGGGTKLTV LG 112

SEQ ID NO: 74 moltype = AA length = 127
FEATURE Location/Qualifiers
REGION 1..127
note = Synthetic
source 1..127
mol_type = protein
organism = synthetic construct
SEQUENCE: 74
EVQLVESGGG LVQPGRSLRL SCAASGFSFG DHAMSWVRQA PGKGLEWVGF IRKTTYGATT 60
HYAAAVRGRF TISRDDSKST VYLQMNSLKT EDTAVYFCTR VQLDYGPGYQ YYGMDVWGQG 120
TTVTVSS 127

```
SEQ ID NO: 75          moltype = DNA  length = 336
FEATURE                Location/Qualifiers
misc_feature           1..336
                       note = Synthetic
source                 1..336
                       mol_type = other DNA
                       organism = synthetic construct
SEQUENCE: 75
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 76          moltype = DNA  length = 381
FEATURE                Location/Qualifiers
misc_feature           1..381
                       note = Synthetic
source                 1..381
                       mol_type = other DNA
                       organism = synthetic construct
SEQUENCE: 76
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc a                                            381

SEQ ID NO: 77          moltype = AA  length = 217
FEATURE                Location/Qualifiers
REGION                 1..217
                       note = Synthetic
source                 1..217
                       mol_type = protein
                       organism = synthetic construct
SEQUENCE: 77
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                           217

SEQ ID NO: 78          moltype = AA  length = 457
FEATURE                Location/Qualifiers
REGION                 1..457
                       note = Synthetic
source                 1..457
                       mol_type = protein
                       organism = synthetic construct
SEQUENCE: 78
EVQLVESGGG LVQPGRSLRL SCAASGFSFG DHAMSWVRQA PGKGLEWVGF IRKTTYGATT  60
HYAAAVRGRF TISRDDSKST VYLQMNSLKT EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                           457

SEQ ID NO: 79          moltype = AA  length = 457
FEATURE                Location/Qualifiers
REGION                 1..457
                       note = Synthetic
source                 1..457
                       mol_type = protein
                       organism = synthetic construct
SEQUENCE: 79
EVQLVESGGG LVQPGRSLRL SCAASGFSFG DHAMSWVRQA PGKGLEWVGF IRKTTYGATT  60
HYAAAVRGRF TISRDDSKST VYLQMNSLKT EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                           457
```

```
SEQ ID NO: 80           moltype = DNA  length = 651
FEATURE                 Location/Qualifiers
misc_feature            1..651
                        note = Synthetic
source                  1..651
                        mol_type = other DNA
                        organism = synthetic construct
SEQUENCE: 80
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t           651

SEQ ID NO: 81           moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 81
gaggtgcagc tggtggagtc tggggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 82           moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 82
gaggtgcagc tggtggagtc tggggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
```

```
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 83          moltype = AA  length = 112
FEATURE                Location/Qualifiers
REGION                 1..112
                       note = Synthetic
source                 1..112
                       mol_type = protein
                       organism = synthetic construct
SEQUENCE: 83
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 84          moltype = AA  length = 127
FEATURE                Location/Qualifiers
REGION                 1..127
                       note = Synthetic
source                 1..127
                       mol_type = protein
                       organism = synthetic construct
SEQUENCE: 84
EVQLVESGGG LVQPGRSLRL SCAASGFSFG DHAMSWVRQA PGKGLEWVGF IRKTTYGATT  60
HYAAAVRGRF TISRDDSKSI VYLQMNSLKA EDTAVYFCTR VQLDYGPGYQ YYGMDVWGQG  120
TTVTVSS                                                            127

SEQ ID NO: 85          moltype = DNA  length = 336
FEATURE                Location/Qualifiers
misc_feature           1..336
                       note = Synthetic
source                 1..336
                       mol_type = other DNA
                       organism = synthetic construct
SEQUENCE: 85
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 86          moltype = DNA  length = 381
FEATURE                Location/Qualifiers
misc_feature           1..381
                       note = Synthetic
source                 1..381
                       mol_type = other DNA
                       organism = synthetic construct
SEQUENCE: 86
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaagca gaggacacag ccgtgtattt ctgtactaga  300
gtgcagcttg actatggccc gggataccag tactacggta tggacgtctg gggccaaggg  360
accacggtca ccgtctcctc a                                            381

SEQ ID NO: 87          moltype = AA  length = 217
FEATURE                Location/Qualifiers
REGION                 1..217
                       note = Synthetic
source                 1..217
                       mol_type = protein
                       organism = synthetic construct
SEQUENCE: 87
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                           217

SEQ ID NO: 88          moltype = AA  length = 457
FEATURE                Location/Qualifiers
REGION                 1..457
                       note = Synthetic
source                 1..457
                       mol_type = protein
                       organism = synthetic construct
```

SEQUENCE: 88
EVQLVESGGG LVQPGRSLRL SCAASGFSFG DHAMSWVRQA PGKGLEWVGF IRKTTYGATT 60
HYAAAVRGRF TISRDDSKSI VYLQMNSLKA EDTAVYFCTR VQLDYGPGYQ YYGMDVWGQG 120
TTVTVSSAST KGPSVFPLAP SSKSTSGGTA ALGCLVKDYF PEPVTVSWNS GALTSGVHTF 180
PAVLQSSGLY SLSSVVTVPS SSLGTQTYIC NVNHKPSNTK VDKKVEPKSC DKTHTCPPCP 240
APELLGGPSV FLFPPKPKDT LMISRTPEVT CVVVDVSHED PEVKFNWYVD GVEVHNAKTK 300
PREEQYNSTY RVVSVLTVLH QDWLNGKEYK CKVSNKALPA PIEKTISKAK GQPREPQVYT 360
LPPSRDELTK NQVSLTCLVK GFYPSDIAVE WESNGQPENN YKTTPPVLDS DGSFFLYSKL 420
TVDKSRWQQG NVFSCSVMHE ALHNHYTQKS LSLSPGK 457

SEQ ID NO: 89 moltype = AA length = 457
FEATURE Location/Qualifiers
REGION 1..457
note = Synthetic
source 1..457
mol_type = protein
organism = synthetic construct
SEQUENCE: 89
EVQLVESGGG LVQPGRSLRL SCAASGFSFG DHAMSWVRQA PGKGLEWVGF IRKTTYGATT 60
HYAAAVRGRF TISRDDSKSI VYLQMNSLKA EDTAVYFCTR VQLDYGPGYQ YYGMDVWGQG 120
TTVTVSSAST KGPSVFPLAP SSKSTSGGTA ALGCLVKDYF PEPVTVSWNS GALTSGVHTF 180
PAVLQSSGLY SLSSVVTVPS SSLGTQTYIC NVNHKPSNTK VDKKVEPKSC DKTHTCPPCP 240
APELLGGPSV FLFPPKPKDT LMISRTPEVT CVVVDVSHED PEVKFNWYVD GVEVHNAKTK 300
PREEQYNSTY RVVSVLTVLH QDWLNGKEYK CKVSNKALPA PIEKTISKAK GQPREPQVYT 360
LPPSRDELTK NQVSLTCLVK GFYPSDIAVE WESNGQPENN YKTTPPVLDS DGSFFLYSKL 420
TVDKSRWQQG NVFSCSVLHE ALHSHYTQKS LSLSPGK 457

SEQ ID NO: 90 moltype = DNA length = 651
FEATURE Location/Qualifiers
misc_feature 1..651
note = Synthetic
source 1..651
mol_type = other DNA
organism = synthetic construct
SEQUENCE: 90
cagtctgtgc tgacgcagcc gccctcagtg tctggggccc cagggcagag ggtcaccatc 60
tcctgcactg ggatgaactc caacatcggg gcaggttatg atgtatactg gtaccaacaa 120
cttccaggaa ctgcccccaa actcctcatc tatggtaaca gcaatcggcc ctcaggggtc 180
cctgaccgat tctctggctc caggtctggc acctcagcct ccctggccat cactgggctc 240
caggctgagg atgaggctga ttattactgc cagtcctatg acaccagcct gaatggttgg 300
gctttcggcg gagggaccaa gttgaccgtc ctaggccagc ccaaggctgc cccctcggtc 360
actctgttcc caccctcctc tgaggagctt caagccaaca aggccacact ggtgtgtctc 420
gtaagtgact tctacccggg agccgtgaca gtggcctgga aggcagatgg cagccccgtc 480
aaggtgggag tggagaccac caaaccctcc aaacaaagca acaacaagta tgcggccagc 540
agctacctga gcctgacgcc cgagcagtgg aagtcccaca gaagctacag ctgccgggtc 600
acgcatgaag ggagcaccgt ggagaagaca gtggcccctg cagaatgctc t 651

SEQ ID NO: 91 moltype = DNA length = 1371
FEATURE Location/Qualifiers
misc_feature 1..1371
note = Synthetic
source 1..1371
mol_type = other DNA
organism = synthetic construct
SEQUENCE: 91
gaggtgcagc tggtggagtc tgggggaggc ttggtacagc cagggcggtc cctgagactc 60
agctgtgcgg cctctgggtt tagttttggt gatcatgcta tgagctgggt ccgccaggct 120
ccagggaagg ggctggagtg ggtaggtttc attagaaaga caacttatgg tgcgacaaca 180
cactacgccg cggctgtgag aggcagattc accatctcgc gagatgattc taaaagcatt 240
gtctatctgc aaatgaacag cctgaaagca gaggacacag ccgtgtattt ctgtactaga 300
gtgcagcttg actatggccc gggataccag tactacggta tggacgtctg gggccaaggg 360
accacggtca ccgtctcctc agcctccacc aagggcccat cggtcttccc cctggcaccc 420
tcctccaaga gcacctctgg gggcacagca gccctgggct gcctggtcaa ggactacttc 480
cccgaaccgg tgacggtgtc gtggaactca ggcgccctga ccagcggcgt gcacaccttc 540
ccggctgtcc tacagtcctc aggactctac tccctcagca gcgtggtgac cgtgccctcc 600
agcagcttgg gcacccagac ctacatctgc aacgtgaatc acaagcccag caacaccaag 660
gtggacaaga aagttgagcc caaatcttgt gacaaaactc acacatgccc accgtgccca 720
gcacctgaac tcctgggggg accgtcagtc ttcctcttcc ccccaaaacc caaggacacc 780
ctcatgatct cccggacccc tgaggtcaca tgcgtggtgg tggacgtgag ccacgaagac 840
cctgaggtca agttcaactg gtacgtggac ggcgtggagg tgcataatgc caagacaaag 900
ccgcgggagg agcagtacaa cagcacgtac cgtgtggtca gcgtcctcac cgtcctgcac 960
caggactggc tgaatggcaa ggagtacaag tgcaaggtct ccaacaaagc cctcccagcc 1020
cccatcgaga aaaccatctc caaagccaaa gggcagcccc gagaaccaca ggtgtacacc 1080
ctgcccccat cccgggatga gctgaccaag aaccaggtca gcctgacctg cctggtcaaa 1140
ggcttctatc ccagcgacat cgccgtggag tgggagagca atgggcagcc ggagaacaac 1200
tacaagacca cgcctcccgt gctggactcc gacggctcct tcttcctcta cagcaagctc 1260
accgtggaca agagcaggtg gcagcagggg aacgtcttct catgctccgt gatgcatgag 1320
gctctgcaca accactacac acagaagagc ctctccctgt ctccgggtaa a 1371

```
SEQ ID NO: 92           moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 92
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaagca gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 93           moltype = AA  length = 112
FEATURE                 Location/Qualifiers
REGION                  1..112
                        note = Synthetic
source                  1..112
                        mol_type = protein
                        organism = synthetic construct
SEQUENCE: 93
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 94           moltype = AA  length = 127
FEATURE                 Location/Qualifiers
REGION                  1..127
                        note = Synthetic
source                  1..127
                        mol_type = protein
                        organism = synthetic construct
SEQUENCE: 94
EVQLVESGGG LVQPGRSLRL SCAASGFSFG DHAMSWVRQA PGKGLEWVGF IRKTTYGATT  60
HYAAAVRGRF TISRDDSKSI VYLQMNSLKT EDTAVYFCAR VQLDYGPGYQ YYGMDVWGQG  120
TTVTVSS                                                            127

SEQ ID NO: 95           moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 95
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 96           moltype = DNA  length = 381
FEATURE                 Location/Qualifiers
misc_feature            1..381
                        note = Synthetic
source                  1..381
                        mol_type = other DNA
                        organism = synthetic construct
SEQUENCE: 96
gaggtgcagc tggtggagtc tgggggaggc ttggtacagc cagggcggtc cctgagactc  60
```

```
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaaacc gaggacacag ccgtgtattt ctgtgctaga  300
gtgcagcttg actatggccc gggataccag tactacggta tggacgtctg gggccaaggg  360
accacggtca ccgtctcctc a                                              381

SEQ ID NO: 97          moltype = AA  length = 217
FEATURE                Location/Qualifiers
REGION                 1..217
                       note = Synthetic
source                 1..217
                       mol_type = protein
                       organism = synthetic construct
SEQUENCE: 97
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                          217

SEQ ID NO: 98          moltype = AA  length = 457
FEATURE                Location/Qualifiers
REGION                 1..457
                       note = Synthetic
source                 1..457
                       mol_type = protein
                       organism = synthetic construct
SEQUENCE: 98
EVQLVESGGG LVQPGRSLRL SCAASGFSFG DHAMSWVRQA PGKGLEWVGF IRKTTYGATT  60
HYAAAVRGRF TISRDDSKSI VYLQMNSLKT EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                          457

SEQ ID NO: 99          moltype = AA  length = 457
FEATURE                Location/Qualifiers
REGION                 1..457
                       note = Synthetic
source                 1..457
                       mol_type = protein
                       organism = synthetic construct
SEQUENCE: 99
EVQLVESGGG LVQPGRSLRL SCAASGFSFG DHAMSWVRQA PGKGLEWVGF IRKTTYGATT  60
HYAAAVRGRF TISRDDSKSI VYLQMNSLKT EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                          457

SEQ ID NO: 100         moltype = DNA  length = 651
FEATURE                Location/Qualifiers
misc_feature           1..651
                       note = Synthetic
source                 1..651
                       mol_type = other DNA
                       organism = synthetic construct
SEQUENCE: 100
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t          651

SEQ ID NO: 101         moltype = DNA  length = 1371
FEATURE                Location/Qualifiers
misc_feature           1..1371
                       note = Synthetic
source                 1..1371
```

```
                        mol_type = other DNA
                        organism = synthetic construct
SEQUENCE: 101
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaaacc gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 102          moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 102
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaaacc gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 103          moltype = AA  length = 112
FEATURE                 Location/Qualifiers
REGION                  1..112
                        note = Synthetic
source                  1..112
                        mol_type = protein
                        organism = synthetic construct
SEQUENCE: 103
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 104          moltype = AA  length = 127
FEATURE                 Location/Qualifiers
REGION                  1..127
                        note = Synthetic
source                  1..127
                        mol_type = protein
                        organism = synthetic construct
SEQUENCE: 104
EVQLVESGGG LVQPGRSLRL SCTASGFSFG DHAMSWVRQA PGKGLEWVGF IRKTTYGATT  60
```

```
HYAAAVRGRF TISRDDSKST VYLQMNSLKA EDTAVYFCTR VQLDYGPGYQ YYGMDVWGQG  120
TTVTVSS                                                           127

SEQ ID NO: 105         moltype = DNA  length = 336
FEATURE                Location/Qualifiers
misc_feature           1..336
                       note = Synthetic
source                 1..336
                       mol_type = other DNA
                       organism = synthetic construct
SEQUENCE: 105
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                           336

SEQ ID NO: 106         moltype = DNA  length = 381
FEATURE                Location/Qualifiers
misc_feature           1..381
                       note = Synthetic
source                 1..381
                       mol_type = other DNA
                       organism = synthetic construct
SEQUENCE: 106
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaagca gaggacacag ccgtgtattt ctgtactaga  300
gtgcagcttg actatggccc gggataccag tactacggta tggacgtctg gggccaaggg  360
accacggtca ccgtctcctc a                                           381

SEQ ID NO: 107         moltype = AA  length = 217
FEATURE                Location/Qualifiers
REGION                 1..217
                       note = Synthetic
source                 1..217
                       mol_type = protein
                       organism = synthetic construct
SEQUENCE: 107
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                          217

SEQ ID NO: 108         moltype = AA  length = 457
FEATURE                Location/Qualifiers
REGION                 1..457
                       note = Synthetic
source                 1..457
                       mol_type = protein
                       organism = synthetic construct
SEQUENCE: 108
EVQLVESGGG LVQPGRSLRL SCTASGFSFG DHAMSWVRQA PGKGLEWVGF IRKTTYGATT  60
HYAAAVRGRF TISRDDSKST VYLQMNSLKA EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                          457

SEQ ID NO: 109         moltype = AA  length = 457
FEATURE                Location/Qualifiers
REGION                 1..457
                       note = Synthetic
source                 1..457
                       mol_type = protein
                       organism = synthetic construct
SEQUENCE: 109
EVQLVESGGG LVQPGRSLRL SCTASGFSFG DHAMSWVRQA PGKGLEWVGF IRKTTYGATT  60
HYAAAVRGRF TISRDDSKST VYLQMNSLKA EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
```

TVDKSRWQQG NVFSCSVLHE ALHSHYTQKS LSLSPGK 457

SEQ ID NO: 110 moltype = DNA length = 651
FEATURE Location/Qualifiers
misc_feature 1..651
note = Synthetic
source 1..651
mol_type = other DNA
organism = synthetic construct
SEQUENCE: 110
cagtctgtgc tgacgcagcc gccctcagtg tctggggccc cagggcagag ggtcaccatc 60
tcctgcactg ggatgaactc caacatcggg gcaggttatg atgtatactg gtaccaacaa 120
cttccaggaa ctgcccccaa actcctcatc tatggtaaca gcaatcggcc ctcaggggtc 180
cctgaccgat tctctggctc caggtctggc acctcagcct ccctggccat cactgggctc 240
caggctgagg atgaggctga ttattactgc cagtcctatg acaccagcct gaatggttgg 300
gctttcggcg gagggaccaa gttgaccgtc ctaggccagc ccaaggctgc cccctcggtc 360
actctgttcc caccctcctc tgaggagctt caagccaaca aggccacact ggtgtgtctc 420
gtaagtgact tctacccggg agccgtgaca gtggcctgga aggcagatgg cagccccgtc 480
aaggtgggag tggagaccac caaaccctcc aaacaaagca acaacaagta tgcggccagc 540
agctacctga gcctgacgcc cgagcagtgg aagtcccaca gaagctacag ctgccgggtc 600
acgcatgaag ggagcaccgt ggagaagaca gtggcccctg cagaatgctc t 651

SEQ ID NO: 111 moltype = DNA length = 1371
FEATURE Location/Qualifiers
misc_feature 1..1371
note = Synthetic
source 1..1371
mol_type = other DNA
organism = synthetic construct
SEQUENCE: 111
gaggtgcagc tggtggagtc tgggggaggc ttggtacagc cagggcggtc cctgagactc 60
agctgtacag cctctgggtt tagttttggt gatcatgcta tgagctgggt ccgccaggct 120
ccagggaagg ggctggagtg ggtaggtttc attagaaaga caacttatgg tgcgacaaca 180
cactacgccg cggctgtgag aggcagattc accatctcgc gagatgattc taaaagcact 240
gtctatctgc aaatgaacag cctgaaagca gaggacacag ccgtgtattt ctgtactaga 300
gtgcagcttg actatggccc gggataccag tactacggta tggacgtctg gggccaaggg 360
accacggtca ccgtctcctc agcctccacc aagggcccat cggtcttccc cctggcaccc 420
tcctccaaga gcacctctgg gggcacagca gccctgggct gcctggtcaa ggactacttc 480
cccgaaccgg tgacggtgtc gtggaactca ggcgccctga ccagcggcgt gcacaccttc 540
ccggctgtcc tacagtcctc aggactctac tccctcagca gcgtggtgac cgtgccctcc 600
agcagcttgg gcacccagac ctacatctgc aacgtgaatc acaagcccag caacaccaag 660
gtggacaaga aagttgagcc caaatcttgt gacaaaactc acacatgccc accgtgccca 720
gcacctgaac tcctgggggg accgtcagtc ttcctcttcc ccccaaaacc caaggacacc 780
ctcatgatct cccggacccc tgaggtcaca tgcgtggtgg tggacgtgag ccacgaagac 840
cctgaggtca agttcaactg gtacgtggac ggcgtggagg tgcataatgc caagacaaag 900
ccgcgggagg agcagtacaa cagcacgtac cgtgtggtca gcgtcctcac cgtcctgcac 960
caggactggc tgaatggcaa ggagtacaag tgcaaggtct ccaacaaagc cctcccagcc 1020
cccatcgaga aaaccatctc caaagccaaa gggcagcccc gagaaccaca ggtgtacacc 1080
ctgcccccat cccgggatga gctgaccaag aaccaggtca gcctgacctg cctggtcaaa 1140
ggcttctatc ccagcgacat cgccgtggag tgggagagca atgggcagcc ggagaacaac 1200
tacaagacca cgcctcccgt gctggactcc gacggctcct tcttcctcta cagcaagctc 1260
accgtggaca agagcaggtg gcagcagggg aacgtcttct catgctccgt gatgcatgag 1320
gctctgcaca accactacac acagaagagc ctctccctgt ctccgggtaa a 1371

SEQ ID NO: 112 moltype = DNA length = 1371
FEATURE Location/Qualifiers
misc_feature 1..1371
note = Synthetic
source 1..1371
mol_type = other DNA
organism = synthetic construct
SEQUENCE: 112
gaggtgcagc tggtggagtc tgggggaggc ttggtacagc cagggcggtc cctgagactc 60
agctgtacag cctctgggtt tagttttggt gatcatgcta tgagctgggt ccgccaggct 120
ccagggaagg ggctggagtg ggtaggtttc attagaaaga caacttatgg tgcgacaaca 180
cactacgccg cggctgtgag aggcagattc accatctcgc gagatgattc taaaagcact 240
gtctatctgc aaatgaacag cctgaaagca gaggacacag ccgtgtattt ctgtactaga 300
gtgcagcttg actatggccc gggataccag tactacggta tggacgtctg gggccaaggg 360
accacggtca ccgtctcctc agcctccacc aagggcccat cggtcttccc cctggcaccc 420
tcctccaaga gcacctctgg gggcacagca gccctgggct gcctggtcaa ggactacttc 480
cccgaaccgg tgacggtgtc gtggaactca ggcgccctga ccagcggcgt gcacaccttc 540
ccggctgtcc tacagtcctc aggactctac tccctcagca gcgtggtgac cgtgccctcc 600
agcagcttgg gcacccagac ctacatctgc aacgtgaatc acaagcccag caacaccaag 660
gtggacaaga aagttgagcc caaatcttgt gacaaaactc acacatgccc accgtgccca 720
gcacctgaac tcctgggggg accgtcagtc ttcctcttcc ccccaaaacc caaggacacc 780
ctcatgatct cccggacccc tgaggtcaca tgcgtggtgg tggacgtgag ccacgaagac 840
cctgaggtca agttcaactg gtacgtggac ggcgtggagg tgcataatgc caagacaaag 900
ccgcgggagg agcagtacaa cagcacgtac cgtgtggtca gcgtcctcac cgtcctgcac 960
caggactggc tgaatggcaa ggagtacaag tgcaaggtct ccaacaaagc cctcccagcc 1020

```
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 113          moltype = AA  length = 112
FEATURE                 Location/Qualifiers
REGION                  1..112
                        note = Synthetic
source                  1..112
                        mol_type = protein
                        organism = synthetic construct
SEQUENCE: 113
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 114          moltype = AA  length = 127
FEATURE                 Location/Qualifiers
REGION                  1..127
                        note = Synthetic
source                  1..127
                        mol_type = protein
                        organism = synthetic construct
SEQUENCE: 114
EVQLVESGGG LVQPGRSLRL SCTASGFSFG DHAMSWVRQA PGKGLEWVGF IRKTTYGATT  60
HYAAAVRGRF TISRDDSKST VYLQMNSLKT EDTAVYFCAR VQLDYGPGYQ YYGMDVWGQG  120
TTVTVSS                                                            127

SEQ ID NO: 115          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 115
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 116          moltype = DNA  length = 381
FEATURE                 Location/Qualifiers
misc_feature            1..381
                        note = Synthetic
source                  1..381
                        mol_type = other DNA
                        organism = synthetic construct
SEQUENCE: 116
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaaacc gaggacacag ccgtgtattt ctgtgctaga  300
gtgcagcttg actatggccc gggataccag tactacggta tggacgtctg gggccaaggg  360
accacggtca ccgtctcctc a                                            381

SEQ ID NO: 117          moltype = AA  length = 217
FEATURE                 Location/Qualifiers
REGION                  1..217
                        note = Synthetic
source                  1..217
                        mol_type = protein
                        organism = synthetic construct
SEQUENCE: 117
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                           217

SEQ ID NO: 118          moltype = AA  length = 457
FEATURE                 Location/Qualifiers
REGION                  1..457
                        note = Synthetic
source                  1..457
```

```
                        mol_type = protein
                        organism = synthetic construct
SEQUENCE: 118
EVQLVESGGG LVQPGRSLRL SCTASGFSFG DHAMSWVRQA PGKGLEWVGF IRKTTYGATT  60
HYAAAVRGRF TISRDDSKST VYLQMNSLKT EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                          457

SEQ ID NO: 119          moltype = AA  length = 457
FEATURE                 Location/Qualifiers
REGION                  1..457
                        note = Synthetic
source                  1..457
                        mol_type = protein
                        organism = synthetic construct
SEQUENCE: 119
EVQLVESGGG LVQPGRSLRL SCTASGFSFG DHAMSWVRQA PGKGLEWVGF IRKTTYGATT  60
HYAAAVRGRF TISRDDSKST VYLQMNSLKT EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                          457

SEQ ID NO: 120          moltype = DNA  length = 651
FEATURE                 Location/Qualifiers
misc_feature            1..651
                        note = Synthetic
source                  1..651
                        mol_type = other DNA
                        organism = synthetic construct
SEQUENCE: 120
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t          651

SEQ ID NO: 121          moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 121
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaaacc gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
```

```
gctctgcaca accactacac acagaagagc ctctccctgt ctccgggtaa a          1371

SEQ ID NO: 122         moltype = DNA  length = 1371
FEATURE                Location/Qualifiers
misc_feature           1..1371
                       note = Synthetic
source                 1..1371
                       mol_type = other DNA
                       organism = synthetic construct
SEQUENCE: 122
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaaacc gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a          1371

SEQ ID NO: 123         moltype = AA  length = 112
FEATURE                Location/Qualifiers
REGION                 1..112
                       note = Synthetic
source                 1..112
                       mol_type = protein
                       organism = synthetic construct
SEQUENCE: 123
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 124         moltype = AA  length = 127
FEATURE                Location/Qualifiers
REGION                 1..127
                       note = Synthetic
source                 1..127
                       mol_type = protein
                       organism = synthetic construct
SEQUENCE: 124
EVQLVESGGG LVQPGRSLRL SCTASGFSFG DHAMSWVRQA PGKGLEWVGF IRKTTYGATT  60
HYAAAVRGRF TISRDDSKSI VYLQMNSLKA EDTAVYFCAR VQLDYGPGYQ YYGMDVWGQG  120
TTVTVSS                                                            127

SEQ ID NO: 125         moltype = DNA  length = 336
FEATURE                Location/Qualifiers
misc_feature           1..336
                       note = Synthetic
source                 1..336
                       mol_type = other DNA
                       organism = synthetic construct
SEQUENCE: 125
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 126         moltype = DNA  length = 381
FEATURE                Location/Qualifiers
misc_feature           1..381
                       note = Synthetic
source                 1..381
                       mol_type = other DNA
                       organism = synthetic construct
```

```
SEQUENCE: 126
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaagca gaggacacag ccgtgtattt ctgtgctaga  300
gtgcagcttg actatggccc gggataccag tactacggta tggacgtctg gggccaaggg  360
accacggtca ccgtctcctc a                                            381

SEQ ID NO: 127         moltype = AA  length = 217
FEATURE                Location/Qualifiers
REGION                 1..217
                       note = Synthetic
source                 1..217
                       mol_type = protein
                       organism = synthetic construct
SEQUENCE: 127
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                        217

SEQ ID NO: 128         moltype = AA  length = 457
FEATURE                Location/Qualifiers
REGION                 1..457
                       note = Synthetic
source                 1..457
                       mol_type = protein
                       organism = synthetic construct
SEQUENCE: 128
EVQLVESGGG LVQPGRSLRL SCTASGFSFG DHAMSWVRQA PGKGLEWVGF IRKTTYGATT  60
HYAAAVRGRF TISRDDSKSI VYLQMNSLKA EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                        457

SEQ ID NO: 129         moltype = AA  length = 457
FEATURE                Location/Qualifiers
REGION                 1..457
                       note = Synthetic
source                 1..457
                       mol_type = protein
                       organism = synthetic construct
SEQUENCE: 129
EVQLVESGGG LVQPGRSLRL SCTASGFSFG DHAMSWVRQA PGKGLEWVGF IRKTTYGATT  60
HYAAAVRGRF TISRDDSKSI VYLQMNSLKA EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                        457

SEQ ID NO: 130         moltype = DNA  length = 651
FEATURE                Location/Qualifiers
misc_feature           1..651
                       note = Synthetic
source                 1..651
                       mol_type = other DNA
                       organism = synthetic construct
SEQUENCE: 130
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t            651

SEQ ID NO: 131         moltype = DNA  length = 1371
FEATURE                Location/Qualifiers
misc_feature           1..1371
```

```
                        note = Synthetic
source                  1..1371
                        mol_type = other DNA
                        organism = synthetic construct
SEQUENCE: 131
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaagca gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 132          moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 132
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaagca gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 133          moltype = AA  length = 112
FEATURE                 Location/Qualifiers
REGION                  1..112
                        note = Synthetic
source                  1..112
                        mol_type = protein
                        organism = synthetic construct
SEQUENCE: 133
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 134          moltype = AA  length = 127
FEATURE                 Location/Qualifiers
REGION                  1..127
                        note = Synthetic
source                  1..127
                        mol_type = protein
                        organism = synthetic construct
```

```
SEQUENCE: 134
EVQLVESGGG LVQPGRSLRL SCAASGFSFG DHAMSWVRQA PGKGLEWVGF IRKTTYGATT  60
HYAAAVRGRF TISRDDSKST VYLQMNSLKA EDTAVYFCTR VQLDYGPGYQ YYGMDVWGQG  120
TTVTVSS                                                           127

SEQ ID NO: 135          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 135
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                           336

SEQ ID NO: 136          moltype = DNA  length = 381
FEATURE                 Location/Qualifiers
misc_feature            1..381
                        note = Synthetic
source                  1..381
                        mol_type = other DNA
                        organism = synthetic construct
SEQUENCE: 136
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaagca gaggacacag ccgtgtattt ctgtactaga  300
gtgcagcttg actatggccc gggataccag tactacggta tggacgtctg gggccaaggg  360
accacggtca ccgtctcctc a                                           381

SEQ ID NO: 137          moltype = AA  length = 217
FEATURE                 Location/Qualifiers
REGION                  1..217
                        note = Synthetic
source                  1..217
                        mol_type = protein
                        organism = synthetic construct
SEQUENCE: 137
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                          217

SEQ ID NO: 138          moltype = AA  length = 457
FEATURE                 Location/Qualifiers
REGION                  1..457
                        note = Synthetic
source                  1..457
                        mol_type = protein
                        organism = synthetic construct
SEQUENCE: 138
EVQLVESGGG LVQPGRSLRL SCAASGFSFG DHAMSWVRQA PGKGLEWVGF IRKTTYGATT  60
HYAAAVRGRF TISRDDSKST VYLQMNSLKA EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                          457

SEQ ID NO: 139          moltype = AA  length = 457
FEATURE                 Location/Qualifiers
REGION                  1..457
                        note = Synthetic
source                  1..457
                        mol_type = protein
                        organism = synthetic construct
SEQUENCE: 139
EVQLVESGGG LVQPGRSLRL SCAASGFSFG DHAMSWVRQA PGKGLEWVGF IRKTTYGATT  60
HYAAAVRGRF TISRDDSKST VYLQMNSLKA EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
```

```
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                           457

SEQ ID NO: 140          moltype = DNA  length = 651
FEATURE                 Location/Qualifiers
misc_feature            1..651
                        note = Synthetic
source                  1..651
                        mol_type = other DNA
                        organism = synthetic construct
SEQUENCE: 140
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t           651

SEQ ID NO: 141          moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 141
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaagca gaggacacag ccgtgtattt ctgtactaga  300
gtgcagcttg actatggccc gggataccag tactacggta tggacgtctg ggccaagggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 142          moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 142
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaagca gaggacacag ccgtgtattt ctgtactaga  300
gtgcagcttg actatggccc gggataccag tactacggta tggacgtctg ggccaagggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
```

```
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 143         moltype = AA  length = 112
FEATURE                Location/Qualifiers
REGION                 1..112
                       note = Synthetic
source                 1..112
                       mol_type = protein
                       organism = synthetic construct
SEQUENCE: 143
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 144         moltype = AA  length = 127
FEATURE                Location/Qualifiers
REGION                 1..127
                       note = Synthetic
source                 1..127
                       mol_type = protein
                       organism = synthetic construct
SEQUENCE: 144
EVQLVESGGG LVQPGRSLRL SCAASGFSFG DHAMSWVRQA PGKGLEWVGF IRKTTYGATT  60
HYAAAVRGRF TISRDDSKST VYLQMNSLKT EDTAVYFCAR VQLDYGPGYQ YYGMDVWGQG  120
TTVTVSS                                                            127

SEQ ID NO: 145         moltype = DNA  length = 336
FEATURE                Location/Qualifiers
misc_feature           1..336
                       note = Synthetic
source                 1..336
                       mol_type = other DNA
                       organism = synthetic construct
SEQUENCE: 145
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 146         moltype = DNA  length = 381
FEATURE                Location/Qualifiers
misc_feature           1..381
                       note = Synthetic
source                 1..381
                       mol_type = other DNA
                       organism = synthetic construct
SEQUENCE: 146
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaaacc gaggacacag ccgtgtattt ctgtgctaga  300
gtgcagcttg actatggccc gggataccag tactacggta tggacgtctg gggccaaggg  360
accacggtca ccgtctcctc a                                            381

SEQ ID NO: 147         moltype = AA  length = 217
FEATURE                Location/Qualifiers
REGION                 1..217
                       note = Synthetic
source                 1..217
                       mol_type = protein
                       organism = synthetic construct
SEQUENCE: 147
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                           217

SEQ ID NO: 148         moltype = AA  length = 457
FEATURE                Location/Qualifiers
REGION                 1..457
```

```
                         note = Synthetic
source                   1..457
                         mol_type = protein
                         organism = synthetic construct
SEQUENCE: 148
EVQLVESGGG LVQPGRSLRL SCAASGFSFG DHAMSWVRQA PGKGLEWVGF IRKTTYGATT  60
HYAAAVRGRF TISRDDSKST VYLQMNSLKT EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                          457

SEQ ID NO: 149           moltype = AA  length = 457
FEATURE                  Location/Qualifiers
REGION                   1..457
                         note = Synthetic
source                   1..457
                         mol_type = protein
                         organism = synthetic construct
SEQUENCE: 149
EVQLVESGGG LVQPGRSLRL SCAASGFSFG DHAMSWVRQA PGKGLEWVGF IRKTTYGATT  60
HYAAAVRGRF TISRDDSKST VYLQMNSLKT EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                          457

SEQ ID NO: 150           moltype = DNA  length = 651
FEATURE                  Location/Qualifiers
misc_feature             1..651
                         note = Synthetic
source                   1..651
                         mol_type = other DNA
                         organism = synthetic construct
SEQUENCE: 150
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t          651

SEQ ID NO: 151           moltype = DNA  length = 1371
FEATURE                  Location/Qualifiers
misc_feature             1..1371
                         note = Synthetic
source                   1..1371
                         mol_type = other DNA
                         organism = synthetic construct
SEQUENCE: 151
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaaacc gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
```

```
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 152          moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 152
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaaacc gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 153          moltype = AA  length = 112
FEATURE                 Location/Qualifiers
REGION                  1..112
                        note = Synthetic
source                  1..112
                        mol_type = protein
                        organism = synthetic construct
SEQUENCE: 153
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 154          moltype = AA  length = 127
FEATURE                 Location/Qualifiers
REGION                  1..127
                        note = Synthetic
source                  1..127
                        mol_type = protein
                        organism = synthetic construct
SEQUENCE: 154
EVQLVESGGG LVQPGRSLRL SCAASGFSFG DHAMSWVRQA PGKGLEWVGF IRKTTYGATT  60
HYAAAVRGRF TISRDDSKSI VYLQMNSLKA EDTAVYFCAR VQLDYGPGYQ YYGMDVWGQG  120
TTVTVSS                                                            127

SEQ ID NO: 155          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 155
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 156          moltype = DNA  length = 381
FEATURE                 Location/Qualifiers
misc_feature            1..381
                        note = Synthetic
source                  1..381
```

```
                       mol_type = other DNA
                       organism = synthetic construct
SEQUENCE: 156
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaagca gaggacacag ccgtgtattt ctgtgctaga  300
gtgcagcttg actatggccc gggataccag tactacggta tggacgtctg gggccaaggg  360
accacggtca ccgtctcctc a                                            381

SEQ ID NO: 157         moltype = AA  length = 217
FEATURE                Location/Qualifiers
REGION                 1..217
                       note = Synthetic
source                 1..217
                       mol_type = protein
                       organism = synthetic construct
SEQUENCE: 157
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                           217

SEQ ID NO: 158         moltype = AA  length = 457
FEATURE                Location/Qualifiers
REGION                 1..457
                       note = Synthetic
source                 1..457
                       mol_type = protein
                       organism = synthetic construct
SEQUENCE: 158
EVQLVESGGG LVQPGRSLRL SCAASGFSFG DHAMSWVRQA PGKGLEWVGF IRKTTYGATT  60
HYAAAVRGRF TISRDDSKSI VYLQMNSLKA EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                           457

SEQ ID NO: 159         moltype = AA  length = 457
FEATURE                Location/Qualifiers
REGION                 1..457
                       note = Synthetic
source                 1..457
                       mol_type = protein
                       organism = synthetic construct
SEQUENCE: 159
EVQLVESGGG LVQPGRSLRL SCAASGFSFG DHAMSWVRQA PGKGLEWVGF IRKTTYGATT  60
HYAAAVRGRF TISRDDSKSI VYLQMNSLKA EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                           457

SEQ ID NO: 160         moltype = DNA  length = 651
FEATURE                Location/Qualifiers
misc_feature           1..651
                       note = Synthetic
source                 1..651
                       mol_type = other DNA
                       organism = synthetic construct
SEQUENCE: 160
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t            651

SEQ ID NO: 161         moltype = DNA  length = 1371
```

```
FEATURE                Location/Qualifiers
misc_feature           1..1371
                       note = Synthetic
source                 1..1371
                       mol_type = other DNA
                       organism = synthetic construct
SEQUENCE: 161
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaagca gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 162         moltype = DNA  length = 1371
FEATURE                Location/Qualifiers
misc_feature           1..1371
                       note = Synthetic
source                 1..1371
                       mol_type = other DNA
                       organism = synthetic construct
SEQUENCE: 162
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcatt  240
gtctatctgc aaatgaacag cctgaaagca gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 163         moltype = AA  length = 112
FEATURE                Location/Qualifiers
REGION                 1..112
                       note = Synthetic
source                 1..112
                       mol_type = protein
                       organism = synthetic construct
SEQUENCE: 163
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 164         moltype = AA  length = 127
FEATURE                Location/Qualifiers
REGION                 1..127
                       note = Synthetic
source                 1..127
```

```
                         mol_type = protein
                         organism = synthetic construct
SEQUENCE: 164
EVQLVESGGG LVQPGRSLRL SCTASGFSFG DHAMSWVRQA PGKGLEWVGF IRKTTYGATT  60
HYAAAVRGRF TISRDDSKST VYLQMNSLKA EDTAVYFCAR VQLDYGPGYQ YYGMDVWGQG  120
TTVTVSS                                                            127

SEQ ID NO: 165           moltype = DNA  length = 336
FEATURE                  Location/Qualifiers
misc_feature             1..336
                         note = Synthetic
source                   1..336
                         mol_type = other DNA
                         organism = synthetic construct
SEQUENCE: 165
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 166           moltype = DNA  length = 381
FEATURE                  Location/Qualifiers
misc_feature             1..381
                         note = Synthetic
source                   1..381
                         mol_type = other DNA
                         organism = synthetic construct
SEQUENCE: 166
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaagca gaggacacag ccgtgtattt ctgtgctaga  300
gtgcagcttg actatggccc gggataccag tactacggta tggacgtctg ggccaaggg  360
accacggtca ccgtctcctc a                                            381

SEQ ID NO: 167           moltype = AA  length = 217
FEATURE                  Location/Qualifiers
REGION                   1..217
                         note = Synthetic
source                   1..217
                         mol_type = protein
                         organism = synthetic construct
SEQUENCE: 167
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                           217

SEQ ID NO: 168           moltype = AA  length = 457
FEATURE                  Location/Qualifiers
REGION                   1..457
                         note = Synthetic
source                   1..457
                         mol_type = protein
                         organism = synthetic construct
SEQUENCE: 168
EVQLVESGGG LVQPGRSLRL SCTASGFSFG DHAMSWVRQA PGKGLEWVGF IRKTTYGATT  60
HYAAAVRGRF TISRDDSKST VYLQMNSLKA EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                           457

SEQ ID NO: 169           moltype = AA  length = 457
FEATURE                  Location/Qualifiers
REGION                   1..457
                         note = Synthetic
source                   1..457
                         mol_type = protein
                         organism = synthetic construct
SEQUENCE: 169
EVQLVESGGG LVQPGRSLRL SCTASGFSFG DHAMSWVRQA PGKGLEWVGF IRKTTYGATT  60
HYAAAVRGRF TISRDDSKST VYLQMNSLKA EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
```

```
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                          457

SEQ ID NO: 170          moltype = DNA  length = 651
FEATURE                 Location/Qualifiers
misc_feature            1..651
                        note = Synthetic
source                  1..651
                        mol_type = other DNA
                        organism = synthetic construct
SEQUENCE: 170
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t           651

SEQ ID NO: 171          moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 171
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaagca gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 172          moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 172
gaggtgcagc tggtggagtc tgggggaggc ttggtacagc cagggcggtc cctgagactc  60
agctgtacag cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaagca gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
```

```
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 173         moltype = AA  length = 112
FEATURE                Location/Qualifiers
REGION                 1..112
                       note = Synthetic
source                 1..112
                       mol_type = protein
                       organism = synthetic construct
SEQUENCE: 173
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LG          112

SEQ ID NO: 174         moltype = AA  length = 127
FEATURE                Location/Qualifiers
REGION                 1..127
                       note = Synthetic
source                 1..127
                       mol_type = protein
                       organism = synthetic construct
SEQUENCE: 174
EVQLVESGGG LVQPGRSLRL SCAASGFSFG DHAMSWVRQA PGKGLEWVGF IRKTTYGATT  60
HYAAAVRGRF TISRDDSKST VYLQMNSLKA EDTAVYFCAR VQLDYGPGYQ YYGMDVWGQG  120
TTVTVSS                                                            127

SEQ ID NO: 175         moltype = DNA  length = 336
FEATURE                Location/Qualifiers
misc_feature           1..336
                       note = Synthetic
source                 1..336
                       mol_type = other DNA
                       organism = synthetic construct
SEQUENCE: 175
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggc                            336

SEQ ID NO: 176         moltype = DNA  length = 381
FEATURE                Location/Qualifiers
misc_feature           1..381
                       note = Synthetic
source                 1..381
                       mol_type = other DNA
                       organism = synthetic construct
SEQUENCE: 176
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaagca gaggacacag ccgtgtattt ctgtgctaga  300
gtgcagcttg actatggccc gggataccag tactacggta tggacgtctg gggccaaggg  360
accacggtca ccgtctcctc a                                            381

SEQ ID NO: 177         moltype = AA  length = 217
FEATURE                Location/Qualifiers
REGION                 1..217
                       note = Synthetic
source                 1..217
                       mol_type = protein
                       organism = synthetic construct
SEQUENCE: 177
QSVLTQPPSV SGAPGQRVTI SCTGMNSNIG AGYDVYWYQQ LPGTAPKLLI YGNSNRPSGV  60
PDRFSGSRSG TSASLAITGL QAEDEADYYC QSYDTSLNGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                           217

SEQ ID NO: 178         moltype = AA  length = 457
```

```
FEATURE                 Location/Qualifiers
REGION                  1..457
                        note = Synthetic
source                  1..457
                        mol_type = protein
                        organism = synthetic construct
SEQUENCE: 178
EVQLVESGGG LVQPGRSLRL SCAASGFSFG DHAMSWVRQA PGKGLEWVGF IRKTTYGATT  60
HYAAAVRGRF TISRDDSKST VYLQMNSLKA EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                          457

SEQ ID NO: 179          moltype = AA  length = 457
FEATURE                 Location/Qualifiers
REGION                  1..457
                        note = Synthetic
source                  1..457
                        mol_type = protein
                        organism = synthetic construct
SEQUENCE: 179
EVQLVESGGG LVQPGRSLRL SCAASGFSFG DHAMSWVRQA PGKGLEWVGF IRKTTYGATT  60
HYAAAVRGRF TISRDDSKST VYLQMNSLKA EDTAVYFCAR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                          457

SEQ ID NO: 180          moltype = DNA  length = 651
FEATURE                 Location/Qualifiers
misc_feature            1..651
                        note = Synthetic
source                  1..651
                        mol_type = other DNA
                        organism = synthetic construct
SEQUENCE: 180
cagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa ctgcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct gaatggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t          651

SEQ ID NO: 181          moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 181
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaagca gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
```

```
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 182          moltype = DNA  length = 1371
FEATURE                 Location/Qualifiers
misc_feature            1..1371
                        note = Synthetic
source                  1..1371
                        mol_type = other DNA
                        organism = synthetic construct
SEQUENCE: 182
gaggtgcagc tggtggagtc tgggggaggc ttggtacagc cagggcggtc cctgagactc  60
agctgtgcgg cctctgggtt tagttttggt gatcatgcta tgagctgggt ccgccaggct  120
ccagggaagg ggctggagtg ggtaggtttc attagaaaga caacttatgg tgcgacaaca  180
cactacgccg cggctgtgag aggcagattc accatctcgc gagatgattc taaaagcact  240
gtctatctgc aaatgaacag cctgaaagca gaggacacag ccgtgtattt ctgtgctaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 183          moltype = AA  length = 14
FEATURE                 Location/Qualifiers
REGION                  1..14
                        note = Synthetic
source                  1..14
                        mol_type = protein
                        organism = synthetic construct
SEQUENCE: 183
TGMNSNIGAG YDVY                                                    14

SEQ ID NO: 184          moltype = AA  length = 7
FEATURE                 Location/Qualifiers
REGION                  1..7
                        note = Synthetic
source                  1..7
                        mol_type = protein
                        organism = synthetic construct
SEQUENCE: 184
GNSNRPS                                                            7

SEQ ID NO: 185          moltype = AA  length = 11
FEATURE                 Location/Qualifiers
REGION                  1..11
                        note = Synthetic
source                  1..11
                        mol_type = protein
                        organism = synthetic construct
SEQUENCE: 185
QSYDTSLDGW A                                                       11

SEQ ID NO: 186          moltype = AA  length = 5
FEATURE                 Location/Qualifiers
REGION                  1..5
                        note = Synthetic
source                  1..5
                        mol_type = protein
                        organism = synthetic construct
SEQUENCE: 186
DHAMS                                                              5

SEQ ID NO: 187          moltype = AA  length = 19
```

```
FEATURE               Location/Qualifiers
REGION                1..19
                      note = Synthetic
source                1..19
                      mol_type = protein
                      organism = synthetic construct
SEQUENCE: 187
FIRKTTYGAT TKYAAAVKG                                                19

SEQ ID NO: 188        moltype = AA  length = 16
FEATURE               Location/Qualifiers
REGION                1..16
                      note = Synthetic
source                1..16
                      mol_type = protein
                      organism = synthetic construct
SEQUENCE: 188
VQLDYGPGYQ YYGMDV                                                   16

SEQ ID NO: 189        moltype = AA  length = 14
FEATURE               Location/Qualifiers
REGION                1..14
                      note = Synthetic
source                1..14
                      mol_type = protein
                      organism = synthetic construct
SEQUENCE: 189
TGMNSNIGAG YDVY                                                     14

SEQ ID NO: 190        moltype = AA  length = 7
FEATURE               Location/Qualifiers
REGION                1..7
                      note = Synthetic
source                1..7
                      mol_type = protein
                      organism = synthetic construct
SEQUENCE: 190
GNSNRPS                                                             7

SEQ ID NO: 191        moltype = AA  length = 11
FEATURE               Location/Qualifiers
REGION                1..11
                      note = Synthetic
source                1..11
                      mol_type = protein
                      organism = synthetic construct
SEQUENCE: 191
QSYDTSLDGW A                                                        11

SEQ ID NO: 192        moltype = AA  length = 5
FEATURE               Location/Qualifiers
REGION                1..5
                      note = Synthetic
source                1..5
                      mol_type = protein
                      organism = synthetic construct
SEQUENCE: 192
DHAMS                                                               5

SEQ ID NO: 193        moltype = AA  length = 19
FEATURE               Location/Qualifiers
REGION                1..19
                      note = Synthetic
source                1..19
                      mol_type = protein
                      organism = synthetic construct
SEQUENCE: 193
FIRKTTYGAT TKYAAAVKG                                                19

SEQ ID NO: 194        moltype = AA  length = 16
FEATURE               Location/Qualifiers
REGION                1..16
                      note = Synthetic
source                1..16
                      mol_type = protein
                      organism = synthetic construct
SEQUENCE: 194
VQLDYGPGYQ YYGMDV                                                   16
```

```
SEQ ID NO: 195          moltype = AA  length = 112
FEATURE                 Location/Qualifiers
REGION                  1..112
                        note = Synthetic
source                  1..112
                        mol_type = protein
                        organism = synthetic construct
SEQUENCE: 195
ESVLTQPPSV SGAPGQRVTI SCTGMNSNIG AGYDVYWYQQ LPGRAPKLLI YGNSNRPSGV  60
PDRFSGSRSG TSASLAITGL QAEDEADYYC QSYDTSLDGW AFGGGTKLTV LG          112

SEQ ID NO: 196          moltype = AA  length = 127
FEATURE                 Location/Qualifiers
REGION                  1..127
                        note = Synthetic
source                  1..127
                        mol_type = protein
                        organism = synthetic construct
SEQUENCE: 196
EVQLVESGGG LVQPGRSLRL PCTASGFSFG DHAMSWVRQA PGKGLEWVGF IRKTTYGATT  60
KYAAAVKGRF TISRDDSKSI VYLQMNSLKT EDTAVYFCTR VQLDYGPGYQ YYGMDVWGQG  120
TTVTVSS                                                            127

SEQ ID NO: 197          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 197
gagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa gagcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct ggacggttgg  300
gctttcggcg gagggaccaa gttgaccgtc ctaggc                            336

SEQ ID NO: 198          moltype = DNA  length = 381
FEATURE                 Location/Qualifiers
misc_feature            1..381
                        note = Synthetic
source                  1..381
                        mol_type = other DNA
                        organism = synthetic construct
SEQUENCE: 198
gaggtgcagc tggtggagtc tgggggaggc ttggtacagc cagggcggtc cctgagactc  60
ccctgtacag cctctgggtt tagttttggt gatcatgcta tgagctgggt ccgccaggct  120
ccagggaagg ggctggagtg ggtaggtttc attagaaaga caacttatgg tgcgacaaca  180
aagtacgccg cggctgtgaa gggcagattc accatctcgc gagatgattc taaaagcatt  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc a                                            381

SEQ ID NO: 199          moltype = AA  length = 217
FEATURE                 Location/Qualifiers
REGION                  1..217
                        note = Synthetic
source                  1..217
                        mol_type = protein
                        organism = synthetic construct
SEQUENCE: 199
ESVLTQPPSV SGAPGQRVTI SCTGMNSNIG AGYDVYWYQQ LPGRAPKLLI YGNSNRPSGV  60
PDRFSGSRSG TSASLAITGL QAEDEADYYC QSYDTSLDGW AFGGGTKLTV LGQPKAAPSV  120
TLFPPSSEEL QANKATLVCL VSDFYPGAVT VAWKADGSPV KVGVETTKPS KQSNNKYAAS  180
SYLSLTPEQW KSHRSYSCRV THEGSTVEKT VAPAECS                           217

SEQ ID NO: 200          moltype = AA  length = 457
FEATURE                 Location/Qualifiers
REGION                  1..457
                        note = Synthetic
source                  1..457
                        mol_type = protein
                        organism = synthetic construct
SEQUENCE: 200
EVQLVESGGG LVQPGRSLRL PCTASGFSFG DHAMSWVRQA PGKGLEWVGF IRKTTYGATT  60
KYAAAVKGRF TISRDDSKSI VYLQMNSLKT EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
```

```
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                          457

SEQ ID NO: 201         moltype = AA  length = 457
FEATURE                Location/Qualifiers
REGION                 1..457
                       note = Synthetic
source                 1..457
                       mol_type = protein
                       organism = synthetic construct
SEQUENCE: 201
EVQLVESGGG LVQPGRSLRL PCTASGFSFG DHAMSWVRQA PGKGLEWVGF IRKTTYGATT  60
KYAAAVKGRF TISRDDSKSI VYLQMNSLKT EDTAVYFCTR VQLDYGPGYQ YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVLHE ALHSHYTQKS LSLSPGK                          457

SEQ ID NO: 202         moltype = DNA  length = 651
FEATURE                Location/Qualifiers
misc_feature           1..651
                       note = Synthetic
source                 1..651
                       mol_type = other DNA
                       organism = synthetic construct
SEQUENCE: 202
gagtctgtgc tgacgcagcc gccctcagtg tctggggccc cagggcagag ggtcaccatc  60
tcctgcactg ggatgaactc caacatcggg gcaggttatg atgtatactg gtaccaacaa  120
cttccaggaa gagcccccaa actcctcatc tatggtaaca gcaatcggcc ctcaggggtc  180
cctgaccgat tctctggctc caggtctggc acctcagcct ccctggccat cactgggctc  240
caggctgagg atgaggctga ttattactgc cagtcctatg acaccagcct ggacggttgg  300
gctttcggcg gagggaccaa gttgaccgtc ctaggccagc ccaaggctgc cccctcggtc  360
actctgttcc caccctcctc tgaggagctt caagccaaca aggccacact ggtgtgtctc  420
gtaagtgact tctacccggg agccgtgaca gtggcctgga aggcagatgg cagccccgtc  480
aaggtgggag tggagaccac caaaccctcc aaacaaagca acaacaagta tgcggccagc  540
agctacctga gcctgacgcc cgagcagtgg aagtcccaca gaagctacag ctgccgggtc  600
acgcatgaag ggagcaccgt ggagaagaca gtggcccctg cagaatgctc t           651

SEQ ID NO: 203         moltype = DNA  length = 1371
FEATURE                Location/Qualifiers
misc_feature           1..1371
                       note = Synthetic
source                 1..1371
                       mol_type = other DNA
                       organism = synthetic construct
SEQUENCE: 203
gaggtgcagc tggtggagtc tgggggaggc ttggtacagc cagggcggtc cctgagactc  60
ccctgtacag cctctgggtt tagttttggt gatcatgcta tgagctgggt ccgccaggct  120
ccagggaagg ggctggagtg ggtaggtttc attagaaaga caacttatgg tgcgacaaca  180
aagtacgccg cggctgtgaa gggcagattc accatctcgc gagatgattc taaaagcatt  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac acagaagagc ctctccctgt ctccgggtaa a           1371

SEQ ID NO: 204         moltype = DNA  length = 1371
FEATURE                Location/Qualifiers
misc_feature           1..1371
                       note = Synthetic
source                 1..1371
```

```
                        mol_type = other DNA
                        organism = synthetic construct
SEQUENCE: 204
gaggtgcagc tggtggagtc tgggggaggc ttggtacagc cagggcggtc cctgagactc  60
ccctgtacag cctctgggtt tagttttggt gatcatgcta tgagctgggt ccgccaggct  120
ccagggaagg ggctggagtg ggtaggtttc attagaaaga caacttatgg tgcgacaaca  180
aagtacgccg cggctgtgaa gggcagattc accatctcgc gagatgattc taaaagcatt  240
gtctatctgc aaatgaacag cctgaaaacc gaggacacag ccgtgtattt ctgtactaga  300
gtgcagcttg actatggccc gggataccag tactacggta tggacgtctg gggccaaggg  360
accacggtca ccgtctcctc agcctccacc aagggcccat cggtcttccc cctggcaccc  420
tcctccaaga gcacctctgg gggcacagca gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gctgcatgag  1320
gctctgcact cccactacac acagaagagc ctctccctgt ctccgggtaa a           1371

SEQ ID NO: 205          moltype = AA  length = 11
FEATURE                 Location/Qualifiers
REGION                  1..11
                        note = Synthetic
source                  1..11
                        mol_type = protein
                        organism = synthetic construct
SEQUENCE: 205
RASQSISSWL A                                                       11

SEQ ID NO: 206          moltype = AA  length = 7
FEATURE                 Location/Qualifiers
REGION                  1..7
                        note = Synthetic
source                  1..7
                        mol_type = protein
                        organism = synthetic construct
SEQUENCE: 206
DASSLES                                                            7

SEQ ID NO: 207          moltype = AA  length = 10
FEATURE                 Location/Qualifiers
REGION                  1..10
                        note = Synthetic
source                  1..10
                        mol_type = protein
                        organism = synthetic construct
SEQUENCE: 207
QQYNSYSFWT                                                         10

SEQ ID NO: 208          moltype = AA  length = 5
FEATURE                 Location/Qualifiers
REGION                  1..5
                        note = Synthetic
source                  1..5
                        mol_type = protein
                        organism = synthetic construct
SEQUENCE: 208
TYGMH                                                              5

SEQ ID NO: 209          moltype = AA  length = 17
FEATURE                 Location/Qualifiers
REGION                  1..17
                        note = Synthetic
source                  1..17
                        mol_type = protein
                        organism = synthetic construct
SEQUENCE: 209
IIWYDGSQKY YADSVQG                                                 17

SEQ ID NO: 210          moltype = AA  length = 14
FEATURE                 Location/Qualifiers
```

```
REGION              1..14
                    note = Synthetic
source              1..14
                    mol_type = protein
                    organism = synthetic construct
SEQUENCE: 210
VRFSVGPHGS AFDL                                              14

SEQ ID NO: 211      moltype = AA  length = 11
FEATURE             Location/Qualifiers
REGION              1..11
                    note = Synthetic
source              1..11
                    mol_type = protein
                    organism = synthetic construct
SEQUENCE: 211
RASQSISSWL A                                                 11

SEQ ID NO: 212      moltype = AA  length = 7
FEATURE             Location/Qualifiers
REGION              1..7
                    note = Synthetic
source              1..7
                    mol_type = protein
                    organism = synthetic construct
SEQUENCE: 212
DASSLES                                                      7

SEQ ID NO: 213      moltype = AA  length = 11
FEATURE             Location/Qualifiers
REGION              1..11
                    note = Synthetic
source              1..11
                    mol_type = protein
                    organism = synthetic construct
SEQUENCE: 213
QQYNSYSFWT F                                                 11

SEQ ID NO: 214      moltype = AA  length = 5
FEATURE             Location/Qualifiers
REGION              1..5
                    note = Synthetic
source              1..5
                    mol_type = protein
                    organism = synthetic construct
SEQUENCE: 214
TYGMH                                                        5

SEQ ID NO: 215      moltype = AA  length = 17
FEATURE             Location/Qualifiers
REGION              1..17
                    note = Synthetic
source              1..17
                    mol_type = protein
                    organism = synthetic construct
SEQUENCE: 215
IIWYDGSQKY YADSVQG                                           17

SEQ ID NO: 216      moltype = AA  length = 5
FEATURE             Location/Qualifiers
REGION              1..5
                    note = Synthetic
source              1..5
                    mol_type = protein
                    organism = synthetic construct
SEQUENCE: 216
SAFDL                                                        5

SEQ ID NO: 217      moltype = AA  length = 109
FEATURE             Location/Qualifiers
REGION              1..109
                    note = Synthetic
source              1..109
                    mol_type = protein
                    organism = synthetic construct
SEQUENCE: 217
GVQMTQSPST LSASVGDRVT LTCRASQSIS SWLAWYQQKP GKAPKLLIYD ASSLESGVPS  60
RFSGSGSGTE FTLTISSLQP DDFATYYCQQ YNSYSFWTFG QGTKVEIKR             109
```

```
SEQ ID NO: 218         moltype = AA  length = 123
FEATURE                Location/Qualifiers
REGION                 1..123
                       note = Synthetic
source                 1..123
                       mol_type = protein
                       organism = synthetic construct
SEQUENCE: 218
QVQLVESGGG VVQPGRSLRL SCAASGFAFN TYGMHWVRQT PGKGLEWVAI IWYDGSQKYY  60
ADSVQGRFII SRDNHKNTLS LQMNGLRAED TAVYFCVRVR FSVGPHGSAF DLWGQGTMVI  120
VSS                                                                123

SEQ ID NO: 219         moltype = DNA  length = 327
FEATURE                Location/Qualifiers
misc_feature           1..327
                       note = Synthetic
source                 1..327
                       mol_type = other DNA
                       organism = synthetic construct
SEQUENCE: 219
ggcgtccaga tgacccagtc tccttccacc ctgtctgcat ctgtgggaga cagagtcacc  60
ctcacttgcc gggccagtca gagtattagt agttggttgg cctggtatca gcagaaacca  120
gggaaagccc ctaaactcct gatctatgat gcctccagtt tggaaagtgg ggtcccatca  180
aggttcagcg gcagtggatc tgggacagaa ttcactctca ccatcagcag cctgcaacct  240
gatgattttg caacttatta ctgccaacag tataatagtt attctttttg gacgttcggc  300
caagggacca aggtggaaat caaacgc                                      327

SEQ ID NO: 220         moltype = DNA  length = 369
FEATURE                Location/Qualifiers
misc_feature           1..369
                       note = Synthetic
source                 1..369
                       mol_type = other DNA
                       organism = synthetic construct
SEQUENCE: 220
caggtgcaac tggtggagtc tgggggaggc gtggtccagc ctgggaggtc cctgagactc  60
tcctgtgcag cgtctgggtt cgctttcaat acctatggca tgcactgggt ccgccagact  120
ccaggcaagg ggctggagtg ggtggcaatt atctggtatg atgggagcca gaaatactat  180
gcagactccg tgcagggccg attcatcatc tccagagaca atcacaagaa cacgttgtct  240
ctgcaaatga acggcctgag agccgaggac acggctgtgt atttctgtgt gagagtccgc  300
tttagcgttg gcccccacgg gagtgctttt gatctctggg gccaggggac aatggtcatc  360
gtctcttca                                                          369

SEQ ID NO: 221         moltype = AA  length = 215
FEATURE                Location/Qualifiers
REGION                 1..215
                       note = Synthetic
source                 1..215
                       mol_type = protein
                       organism = synthetic construct
SEQUENCE: 221
GVQMTQSPST LSASVGDRVT LTCRASQSIS SWLAWYQQKP GKAPKLLIYD ASSLESGVPS  60
RFSGSGSGTE FTLTISSLQP DDFATYYCQQ YNSYSFWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 222         moltype = AA  length = 453
FEATURE                Location/Qualifiers
REGION                 1..453
                       note = Synthetic
source                 1..453
                       mol_type = protein
                       organism = synthetic construct
SEQUENCE: 222
QVQLVESGGG VVQPGRSLRL SCAASGFAFN TYGMHWVRQT PGKGLEWVAI IWYDGSQKYY  60
ADSVQGRFII SRDNHKNTLS LQMNGLRAED TAVYFCVRVR FSVGPHGSAF DLWGQGTMVI  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 223         moltype = AA  length = 453
FEATURE                Location/Qualifiers
REGION                 1..453
                       note = Synthetic
source                 1..453
                       mol_type = protein
```

```
                         organism = synthetic construct
SEQUENCE: 223
QVQLVESGGG VVQPGRSLRL SCAASGFAFN TYGMHWVRQT PGKGLEWVAI IWYDGSQKYY  60
ADSVQGRFII SRDNHKNTLS LQMNGLRAED TAVYFCVRVR FSVGPHGSAF DLWGQGTMVI  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVLHEALHS HYTQKSLSLS PGK                              453

SEQ ID NO: 224           moltype = DNA  length = 645
FEATURE                  Location/Qualifiers
misc_feature             1..645
                         note = Synthetic
source                   1..645
                         mol_type = other DNA
                         organism = synthetic construct
SEQUENCE: 224
ggcgtccaga tgacccagtc tccttccacc ctgtctgcat ctgtgggaga cagagtcacc  60
ctcacttgcc gggccagtca gagtattagt agttggttgg cctggtatca gcagaaacca  120
gggaaagccc ctaaactcct gatctatgat gcctccagtt tggaaagtgg ggtcccatca  180
aggttcagcg gcagtggatc tgggacagaa ttcactctca ccatcagcag cctgcaacct  240
gatgattttg caacttatta ctgccaacag tataatagtt attctttttg gacgttcggc  300
caagggacca aggtggaaat caaacgcact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgt                 645

SEQ ID NO: 225           moltype = DNA  length = 1359
FEATURE                  Location/Qualifiers
misc_feature             1..1359
                         note = Synthetic
source                   1..1359
                         mol_type = other DNA
                         organism = synthetic construct
SEQUENCE: 225
caggtgcaac tggtggagtc tgggggaggc gtggtccagc ctgggaggtc cctgagactc  60
tcctgtgcag cgtctgggtt cgctttcaat acctatggca tgcactgggt ccgccagact  120
ccaggcaagg ggctggagtg ggtggcaatt atctggtatg atgggagcca gaaatactat  180
gcagactccg tgcagggccg attcatcatc tccagagaca atcacaagaa cacgttgtct  240
ctgcaaatga acggcctgag agccgaggac acggctgtgt atttctgtgt gagagtccgc  300
tttagcgttg gcccccacgg gagtgctttt gatctctggg gccaggggac aatggtcatc  360
gtctcttcag cctccaccaa gggcccatcg gtcttccccc tggcaccctc ctccaagagc  420
acctctgggg gcacagcagc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtga tgcatgaggc tctgcacaac  1320
cactacacac agaagagcct ctccctgtct ccgggtaaa                        1359

SEQ ID NO: 226           moltype = DNA  length = 1359
FEATURE                  Location/Qualifiers
misc_feature             1..1359
                         note = Synthetic
source                   1..1359
                         mol_type = other DNA
                         organism = synthetic construct
SEQUENCE: 226
caggtgcaac tggtggagtc tgggggaggc gtggtccagc ctgggaggtc cctgagactc  60
tcctgtgcag cgtctgggtt cgctttcaat acctatggca tgcactgggt ccgccagact  120
ccaggcaagg ggctggagtg ggtggcaatt atctggtatg atgggagcca gaaatactat  180
gcagactccg tgcagggccg attcatcatc tccagagaca atcacaagaa cacgttgtct  240
ctgcaaatga acggcctgag agccgaggac acggctgtgt atttctgtgt gagagtccgc  300
tttagcgttg gcccccacgg gagtgctttt gatctctggg gccaggggac aatggtcatc  360
gtctcttcag cctccaccaa gggcccatcg gtcttccccc tggcaccctc ctccaagagc  420
acctctgggg gcacagcagc cctgggctgc ctggtcaagg actacttccc cgaaccggtg  480
```

```
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtgc tgcatgaggc tctgcactcc  1320
cactacacac agaagagcct ctccctgtct ccgggtaaa                         1359

SEQ ID NO: 227          moltype = AA  length = 109
FEATURE                 Location/Qualifiers
REGION                  1..109
                        note = Synthetic
source                  1..109
                        mol_type = protein
                        organism = synthetic construct
SEQUENCE: 227
GVQMTQSPST LSASVGDRVT LTCRASQSIS SWLAWYQQKP GKAPKLLIYD ASSLESGVPS  60
RFSGSGSGTE FTLTISSLQP DDFATYYCQQ YNSYSFWTFG QGTKVEIKR              109

SEQ ID NO: 228          moltype = AA  length = 123
FEATURE                 Location/Qualifiers
REGION                  1..123
                        note = Synthetic
source                  1..123
                        mol_type = protein
                        organism = synthetic construct
SEQUENCE: 228
QVQLVESGGG VVQPGRSLRL SCAASGFAFN TYGMHWVRQA PGKGLEWVAI IWYDGSQKYY  60
ADSVQGRFII SRDNHKNTLS LQMNSLRAED TAVYFCVRVR FSVGPHGSAF DLWGQGTMVT  120
VSS                                                                123

SEQ ID NO: 229          moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 229
ggcgtccaga tgacccagtc tccttccacc ctgtctgcat ctgtgggaga cagagtcacc  60
ctcacttgcc gggccagtca gagtattagt agttggttgg cctggtatca gcagaaacca  120
gggaaagccc ctaaactcct gatctatgat gcctccagtt tggaaagtgg ggtcccatca  180
aggttcagcg gcagtggatc tgggacagaa ttcactctca ccatcagcag cctgcaacct  240
gatgattttg caacttatta ctgccaacag tataatagtt attctttttg gacgttcggc  300
caagggacca aggtggaaat caaacgc                                      327

SEQ ID NO: 230          moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 230
caggtgcaac tggtggagtc tgggggaggc gtggtccagc ctgggaggtc cctgagactc  60
tcctgtgcag cgtctgggtt cgctttcaat acctatggca tgcactgggt ccgccaggca  120
ccaggcaagg ggctggagtg ggtggcaatt atctggtatg atgggagcca gaaatactat  180
gcagactccg tgcagggccg attcatcatc tccagagaca atcacaagaa cacgttgtct  240
ctgcaaatga actccctgag agccgaggac acggctgtgt atttctgtgt gagagtccgc  300
tttagcgttg gcccccacgg gagtgctttt gatctctggg gccaggggac aatggtcaca  360
gtctcttca                                                          369

SEQ ID NO: 231          moltype = AA  length = 215
FEATURE                 Location/Qualifiers
REGION                  1..215
                        note = Synthetic
source                  1..215
                        mol_type = protein
                        organism = synthetic construct
SEQUENCE: 231
GVQMTQSPST LSASVGDRVT LTCRASQSIS SWLAWYQQKP GKAPKLLIYD ASSLESGVPS  60
```

```
RFSGSGSGTE FTLTISSLQP DDFATYYCQQ YNSYSFWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 232          moltype = AA  length = 453
FEATURE                 Location/Qualifiers
REGION                  1..453
                        note = Synthetic
source                  1..453
                        mol_type = protein
                        organism = synthetic construct
SEQUENCE: 232
QVQLVESGGG VVQPGRSLRL SCAASGFAFN TYGMHWVRQA PGKGLEWVAI IWYDGSQKYY  60
ADSVQGRFII SRDNHKNTLS LQMNSLRAED TAVYFCVRVR FSVGPHGSAF DLWGQGTMVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 233          moltype = AA  length = 453
FEATURE                 Location/Qualifiers
REGION                  1..453
                        note = Synthetic
source                  1..453
                        mol_type = protein
                        organism = synthetic construct
SEQUENCE: 233
QVQLVESGGG VVQPGRSLRL SCAASGFAFN TYGMHWVRQA PGKGLEWVAI IWYDGSQKYY  60
ADSVQGRFII SRDNHKNTLS LQMNSLRAED TAVYFCVRVR FSVGPHGSAF DLWGQGTMVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVLHEALHS HYTQKSLSLS PGK                              453

SEQ ID NO: 234          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 234
ggcgtccaga tgacccagtc tccttccacc ctgtctgcat ctgtgggaga cagagtcacc  60
ctcacttgcc gggccagtca gagtattagt agttggttgg cctggtatca gcagaaacca  120
gggaaagccc ctaaactcct gatctatgat gcctccagtt tggaaagtgg ggtcccatca  180
aggttcagcg gcagtggatc tgggacagaa ttcactctca ccatcagcag cctgcaacct  240
gatgattttg caacttatta ctgccaacag tataatagtt attctttttg gacgttcggc  300
caagggacca aggtggaaat caaacgcact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgt                 645

SEQ ID NO: 235          moltype = DNA  length = 1359
FEATURE                 Location/Qualifiers
misc_feature            1..1359
                        note = Synthetic
source                  1..1359
                        mol_type = other DNA
                        organism = synthetic construct
SEQUENCE: 235
caggtgcaac tggtggagtc tgggggaggc gtggtccagc ctgggaggtc cctgagactc  60
tcctgtgcag cgtctgggtt cgctttcaat acctatggca tgcactgggt ccgccaggca  120
ccaggcaagg ggctggagtg ggtggcaatt atctggtatg atgggagcca gaaatactat  180
gcagactccg tgcagggccg attcatcatc tccagagaca atcacaagaa cacgttgtct  240
ctgcaaatga actccctgag agccgaggac acggctgtgt atttctgtgt gagagtccgc  300
tttagcgttg gcccccacgg gagtgctttt gatctctggg gccaggggac aatggtcaca  360
gtctcttcag cctccaccaa gggcccatcg gtcttccccc tggcaccctc ctccaagagc  420
acctctgggg gcacagcagc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
```

```
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtga tgcatgaggc tctgcacaac  1320
cactacacac agaagagcct ctccctgtct ccgggtaaa                        1359

SEQ ID NO: 236          moltype = DNA  length = 1359
FEATURE                 Location/Qualifiers
misc_feature            1..1359
                        note = Synthetic
source                  1..1359
                        mol_type = other DNA
                        organism = synthetic construct
SEQUENCE: 236
caggtgcaac tggtggagtc tgggggaggc gtggtccagc ctgggaggtc cctgagactc  60
tcctgtgcag cgtctgggtt cgctttcaat acctatggca tgcactgggt ccgccaggca  120
ccaggcaagg ggctggagtg ggtggcaatt atctggtatg atgggagcca gaaatactat  180
gcagactccg tgcagggccg attcatcatc tccagagaca atcacaagaa cacgttgtct  240
ctgcaaatga actccctgag agccgaggac acggctgtgt atttctgtgt gagagtccgc  300
tttagcgttg gcccccacgg gagtgctttt gatctctggg gccaggggac aatggtcaca  360
gtctcttcag cctccaccaa gggcccatcg gtcttccccc tggcaccctc ctccaagagc  420
acctctgggg gcacagcagc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtgc tgcatgaggc tctgcactcc  1320
cactacacac agaagagcct ctccctgtct ccgggtaaa                        1359

SEQ ID NO: 237          moltype = AA  length = 109
FEATURE                 Location/Qualifiers
REGION                  1..109
                        note = Synthetic
source                  1..109
                        mol_type = protein
                        organism = synthetic construct
SEQUENCE: 237
GVQMTQSPST LSASVGDRVT LTCRASQSIS SWLAWYQQKP GKAPKLLIYD ASSLESGVPS  60
RFSGSGSGTE FTLTISSLQP DDFATYYCQQ YNSYSFWTFG QGTKVEIKR             109

SEQ ID NO: 238          moltype = AA  length = 123
FEATURE                 Location/Qualifiers
REGION                  1..123
                        note = Synthetic
source                  1..123
                        mol_type = protein
                        organism = synthetic construct
SEQUENCE: 238
QVQLVESGGG VVQPGRSLRL SCAASGFTFN TYGMHWVRQA PGKGLEWVAI IWYDGSQKYY  60
ADSVQGRFII SRDNHKNTLS LQMNSLRAED TAVYFCVRVR FSVGPHGSAF DLWGQGTMVT  120
VSS                                                               123

SEQ ID NO: 239          moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 239
ggcgtccaga tgacccagtc tccttccacc ctgtctgcat ctgtgggaga cagagtcacc  60
ctcacttgcc gggccagtca gagtattagt agttggttgg cctggtatca gcagaaacca  120
gggaaagccc ctaaactcct gatctatgat gcctccagtt tggaaagtgg ggtcccatca  180
aggttcagcg gcagtggatc tgggacagaa ttcactctca ccatcagcag cctgcaacct  240
gatgattttg caacttatta ctgccaacag tataatagtt attctttttg gacgttcggc  300
```

```
caagggacca aggtggaaat caaacgc                                    327

SEQ ID NO: 240         moltype = DNA  length = 369
FEATURE                Location/Qualifiers
misc_feature           1..369
                       note = Synthetic
source                 1..369
                       mol_type = other DNA
                       organism = synthetic construct
SEQUENCE: 240
caggtgcaac tggtggagtc tgggggaggc gtggtccagc ctgggaggtc cctgagactc  60
tcctgtgcag cgtctgggtt cactttcaat acctatggca tgcactgggt ccgccaggca  120
ccaggcaagg ggctggagtg ggtggcaatt atctggtatg atgggagcca gaaatactat  180
gcagactccg tgcagggccg attcatcatc tccagagaca atcacaagaa cacgttgtct  240
ctgcaaatga actccctgag agccgaggac acggctgtgt atttctgtgt gagagtccgc  300
tttagcgttg gcccccacgg gagtgctttt gatctctggg gccaggggac aatggtcaca  360
gtctcttca                                                        369

SEQ ID NO: 241         moltype = AA  length = 215
FEATURE                Location/Qualifiers
REGION                 1..215
                       note = Synthetic
source                 1..215
                       mol_type = protein
                       organism = synthetic construct
SEQUENCE: 241
GVQMTQSPST LSASVGDRVT LTCRASQSIS SWLAWYQQKP GKAPKLLIYD ASSLESGVPS  60
RFSGSGSGTE FTLTISSLQP DDFATYYCQQ YNSYSFWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                           215

SEQ ID NO: 242         moltype = AA  length = 453
FEATURE                Location/Qualifiers
REGION                 1..453
                       note = Synthetic
source                 1..453
                       mol_type = protein
                       organism = synthetic construct
SEQUENCE: 242
QVQLVESGGG VVQPGRSLRL SCAASGFTFN TYGMHWVRQA PGKGLEWVAI IWYDGSQKYY  60
ADSVQGRFII SRDNHKNTLS LQMNSLRAED TAVYFCVRVR FSVGPHGSAF DLWGQGTMVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                             453

SEQ ID NO: 243         moltype = AA  length = 453
FEATURE                Location/Qualifiers
REGION                 1..453
                       note = Synthetic
source                 1..453
                       mol_type = protein
                       organism = synthetic construct
SEQUENCE: 243
QVQLVESGGG VVQPGRSLRL SCAASGFTFN TYGMHWVRQA PGKGLEWVAI IWYDGSQKYY  60
ADSVQGRFII SRDNHKNTLS LQMNSLRAED TAVYFCVRVR FSVGPHGSAF DLWGQGTMVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVLHEALHS HYTQKSLSLS PGK                             453

SEQ ID NO: 244         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 244
ggcgtccaga tgacccagtc tccttccacc ctgtctgcat ctgtgggaga cagagtcacc  60
ctcacttgcc gggccagtca gagtattagt agttggttgg cctggtatca gcagaaacca  120
gggaaagccc ctaaactcct gatctatgat gcctccagtt tggaaagtgg ggtcccatca  180
aggttcagcg gcagtggatc tgggacagaa ttcactctca ccatcagcag cctgcaacct  240
gatgattttg caacttatta ctgccaacag tataatagtt attctttttg gacgttcggc  300
caagggacca aggtggaaat caaacgcact gtggctgcac catctgtctt catcttcccg  360
```

```
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgt                  645

SEQ ID NO: 245         moltype = DNA  length = 1359
FEATURE                Location/Qualifiers
misc_feature           1..1359
                       note = Synthetic
source                 1..1359
                       mol_type = other DNA
                       organism = synthetic construct
SEQUENCE: 245
caggtgcaac tggtggagtc tgggggaggc gtggtccagc ctgggaggtc cctgagactc  60
tcctgtgcag cgtctgggtt cactttcaat acctatggca tgcactgggt ccgccaggca  120
ccaggcaagg ggctggagtg ggtggcaatt atctggtatg atgggagcca gaaatactat  180
gcagactccg tgcagggccg attcatcatc tccagagaca atcacaagaa cacgttgtct  240
ctgcaaatga actccctgag agccgaggac acggctgtgt atttctgtgt gagagtccgc  300
tttagcgttg gcccccacgg gagtgctttt gatctctggg gccaggggac aatggtcaca  360
gtctcttcag cctccaccaa gggcccatcg gtcttccccc tggcaccctc ctccaagagc  420
acctctgggg gcacagcagc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtga tgcatgaggc tctgcacaac  1320
cactacacac agaagagcct ctccctgtct ccgggtaaa                         1359

SEQ ID NO: 246         moltype = DNA  length = 1359
FEATURE                Location/Qualifiers
misc_feature           1..1359
                       note = Synthetic
source                 1..1359
                       mol_type = other DNA
                       organism = synthetic construct
SEQUENCE: 246
caggtgcaac tggtggagtc tgggggaggc gtggtccagc ctgggaggtc cctgagactc  60
tcctgtgcag cgtctgggtt cactttcaat acctatggca tgcactgggt ccgccaggca  120
ccaggcaagg ggctggagtg ggtggcaatt atctggtatg atgggagcca gaaatactat  180
gcagactccg tgcagggccg attcatcatc tccagagaca atcacaagaa cacgttgtct  240
ctgcaaatga actccctgag agccgaggac acggctgtgt atttctgtgt gagagtccgc  300
tttagcgttg gcccccacgg gagtgctttt gatctctggg gccaggggac aatggtcaca  360
gtctcttcag cctccaccaa gggcccatcg gtcttccccc tggcaccctc ctccaagagc  420
acctctgggg gcacagcagc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtgc tgcatgaggc tctgcactcc  1320
cactacacac agaagagcct ctccctgtct ccgggtaaa                         1359

SEQ ID NO: 247         moltype = AA  length = 109
FEATURE                Location/Qualifiers
REGION                 1..109
                       note = Synthetic
source                 1..109
                       mol_type = protein
                       organism = synthetic construct
SEQUENCE: 247
GVQMTQSPST LSASVGDRVT LTCRASQSIS SWLAWYQQKP GKAPKLLIYD ASSLESGVPS  60
```

```
RFSGSGSGTE FTLTISSLQP DDFATYYCQQ YNSYSFWTFG QGTKVEIKR              109

SEQ ID NO: 248          moltype = AA  length = 123
FEATURE                 Location/Qualifiers
REGION                  1..123
                        note = Synthetic
source                  1..123
                        mol_type = protein
                        organism = synthetic construct
SEQUENCE: 248
QVQLVESGGG VVQPGRSLRL SCAASGFAFN TYGMHWVRQA PGKGLEWVAI IWYDGSQKYY  60
ADSVQGRFTI SRDNHKNTLS LQMNSLRAED TAVYFCVRVR FSVGPHGSAF DLWGQGTMVT  120
VSS                                                                123

SEQ ID NO: 249          moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 249
ggcgtccaga tgacccagtc tccttccacc ctgtctgcat ctgtgggaga cagagtcacc  60
ctcacttgcc gggccagtca gagtattagt agttggttgg cctggtatca gcagaaacca  120
gggaaagccc ctaaactcct gatctatgat gcctccagtt tggaaagtgg ggtcccatca  180
aggttcagcg gcagtggatc tgggacagaa ttcactctca ccatcagcag cctgcaacct  240
gatgattttg caacttatta ctgccaacag tataatagtt attctttttg gacgttcggc  300
caagggacca aggtggaaat caaacgc                                      327

SEQ ID NO: 250          moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 250
caggtgcaac tggtggagtc tgggggaggc gtggtccagc ctgggaggtc cctgagactc  60
tcctgtgcag cgtctgggtt cgctttcaat acctatggca tgcactgggt ccgccaggca  120
ccaggcaagg ggctggagtg ggtggcaatt atctggtatg atgggagcca gaaatactat  180
gcagactccg tgcagggccg attcactatc tccagagaca atcacaagaa cacgttgtct  240
ctgcaaatga actccctgag agccgaggac acggctgtgt atttctgtgt gagagtccgc  300
tttagcgttg gcccccacgg gagtgctttt gatctctggg gccaggggac aatggtcaca  360
gtctcttca                                                          369

SEQ ID NO: 251          moltype = AA  length = 215
FEATURE                 Location/Qualifiers
REGION                  1..215
                        note = Synthetic
source                  1..215
                        mol_type = protein
                        organism = synthetic construct
SEQUENCE: 251
GVQMTQSPST LSASVGDRVT LTCRASQSIS SWLAWYQQKP GKAPKLLIYD ASSLESGVPS  60
RFSGSGSGTE FTLTISSLQP DDFATYYCQQ YNSYSFWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 252          moltype = AA  length = 453
FEATURE                 Location/Qualifiers
REGION                  1..453
                        note = Synthetic
source                  1..453
                        mol_type = protein
                        organism = synthetic construct
SEQUENCE: 252
QVQLVESGGG VVQPGRSLRL SCAASGFAFN TYGMHWVRQA PGKGLEWVAI IWYDGSQKYY  60
ADSVQGRFTI SRDNHKNTLS LQMNSLRAED TAVYFCVRVR FSVGPHGSAF DLWGQGTMVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 253          moltype = AA  length = 453
FEATURE                 Location/Qualifiers
REGION                  1..453
                        note = Synthetic
```

```
source                  1..453
                        mol_type = protein
                        organism = synthetic construct
SEQUENCE: 253
QVQLVESGGG VVQPGRSLRL SCAASGFAFN TYGMHWVRQA PGKGLEWVAI IWYDGSQKYY  60
ADSVQGRFTI SRDNHKNTLS LQMNSLRAED TAVYFCVRVR FSVGPHGSAF DLWGQGTMVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVLHEALHS HYTQKSLSLS PGK                              453

SEQ ID NO: 254          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 254
ggcgtccaga tgacccagtc tccttccacc ctgtctgcat ctgtgggaga cagagtcacc  60
ctcacttgcc gggccagtca gagtattagt agttggttgg cctggtatca gcagaaacca  120
gggaaagccc ctaaactcct gatctatgat gcctccagtt tggaaagtgg ggtcccatca  180
aggttcagcg gcagtggatc tgggacagaa ttcactctca ccatcagcag cctgcaacct  240
gatgattttg caacttatta ctgccaacag tataatagtt attctttttg gacgttcggc  300
caagggacca aggtggaaat caaacgcact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgt                 645

SEQ ID NO: 255          moltype = DNA  length = 1359
FEATURE                 Location/Qualifiers
misc_feature            1..1359
                        note = Synthetic
source                  1..1359
                        mol_type = other DNA
                        organism = synthetic construct
SEQUENCE: 255
caggtgcaac tggtggagtc tgggggaggc gtggtccagc ctgggaggtc cctgagactc  60
tcctgtgcag cgtctgggtt cgctttcaat acctatggca tgcactgggt ccgccaggca  120
ccaggcaagg ggctggagtg ggtggcaatt atctggtatg atgggagcca gaaatactat  180
gcagactccg tgcagggccg attcactatc tccagagaca atcacaagaa cacgttgtct  240
ctgcaaatga actccctgag agccgaggac acggctgtgt atttctgtgt gagagtccgc  300
tttagcgttg gcccccacgg gagtgctttt gatctctggg gccaggggac aatggtcaca  360
gtctcttcag cctccaccaa gggcccatcg gtcttccccc tggcaccctc ctccaagagc  420
acctctgggg gcacagcagc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtga tgcatgaggc tctgcacaac  1320
cactacacac agaagagcct ctccctgtct ccgggtaaa                         1359

SEQ ID NO: 256          moltype = DNA  length = 1359
FEATURE                 Location/Qualifiers
misc_feature            1..1359
                        note = Synthetic
source                  1..1359
                        mol_type = other DNA
                        organism = synthetic construct
SEQUENCE: 256
caggtgcaac tggtggagtc tgggggaggc gtggtccagc ctgggaggtc cctgagactc  60
tcctgtgcag cgtctgggtt cgctttcaat acctatggca tgcactgggt ccgccaggca  120
ccaggcaagg ggctggagtg ggtggcaatt atctggtatg atgggagcca gaaatactat  180
gcagactccg tgcagggccg attcactatc tccagagaca atcacaagaa cacgttgtct  240
ctgcaaatga actccctgag agccgaggac acggctgtgt atttctgtgt gagagtccgc  300
tttagcgttg gcccccacgg gagtgctttt gatctctggg gccaggggac aatggtcaca  360
```

```
gtctcttcag cctccaccaa gggcccatcg gtcttccccc tggcaccctc ctccaagagc  420
acctctgggg gcacagcagc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtgc tgcatgaggc tctgcactcc  1320
cactacacac agaagagcct ctccctgtct ccgggtaaa                         1359

SEQ ID NO: 257         moltype = AA  length = 109
FEATURE                Location/Qualifiers
REGION                 1..109
                       note = Synthetic
source                 1..109
                       mol_type = protein
                       organism = synthetic construct
SEQUENCE: 257
GVQMTQSPST LSASVGDRVT LTCRASQSIS SWLAWYQQKP GKAPKLLIYD ASSLESGVPS  60
RFSGSGSGTE FTLTISSLQP DDFATYYCQQ YNSYSFWTFG QGTKVEIKR              109

SEQ ID NO: 258         moltype = AA  length = 123
FEATURE                Location/Qualifiers
REGION                 1..123
                       note = Synthetic
source                 1..123
                       mol_type = protein
                       organism = synthetic construct
SEQUENCE: 258
QVQLVESGGG VVQPGRSLRL SCAASGFTFN TYGMHWVRQA PGKGLEWVAI IWYDGSQKYY  60
ADSVQGRFTI SRDNHKNTLS LQMNSLRAED TAVYFCVRVR FSVGPHGSAF DLWGQGTMVT  120
VSS                                                                123

SEQ ID NO: 259         moltype = DNA  length = 327
FEATURE                Location/Qualifiers
misc_feature           1..327
                       note = Synthetic
source                 1..327
                       mol_type = other DNA
                       organism = synthetic construct
SEQUENCE: 259
ggcgtccaga tgacccagtc tccttccacc ctgtctgcat ctgtgggaga cagagtcacc  60
ctcacttgcc gggccagtca gagtattagt agttggttgg cctggtatca gcagaaacca  120
gggaaagccc ctaaactcct gatctatgat gcctccagtt tggaaagtgg ggtcccatca  180
aggttcagcg gcagtggatc tgggacagaa ttcactctca ccatcagcag cctgcaacct  240
gatgattttg caacttatta ctgccaacag tataatagtt attctttttg gacgttcggc  300
caagggacca aggtggaaat caaacgc                                      327

SEQ ID NO: 260         moltype = DNA  length = 369
FEATURE                Location/Qualifiers
misc_feature           1..369
                       note = Synthetic
source                 1..369
                       mol_type = other DNA
                       organism = synthetic construct
SEQUENCE: 260
caggtgcaac tggtggagtc tgggggaggc gtggtccagc ctgggaggtc cctgagactc  60
tcctgtgcag cgtctgggtt cactttcaat acctatggca tgcactgggt ccgccaggca  120
ccaggcaagg ggctggagtg ggtggcaatt atctggtatg atgggagcca gaaatactat  180
gcagactccg tgcagggccg attcactatc tccagagaca atcacaagaa cacgttgtct  240
ctgcaaatga actccctgag agccgaggac acggctgtgt atttctgtgt gagagtccgc  300
tttagcgttg gcccccacgg gagtgctttt gatctctggg gccaggggac aatggtcaca  360
gtctcttca                                                          369

SEQ ID NO: 261         moltype = AA  length = 215
FEATURE                Location/Qualifiers
REGION                 1..215
                       note = Synthetic
source                 1..215
                       mol_type = protein
                       organism = synthetic construct
```

SEQUENCE: 261
GVQMTQSPST LSASVGDRVT LTCRASQSIS SWLAWYQQKP GKAPKLLIYD ASSLESGVPS 60
RFSGSGSGTE FTLTISSLQP DDFATYYCQQ YNSYSFWTFG QGTKVEIKRT VAAPSVFIFP 120
PSDEQLKSGT ASVVCLLNNF YPREAKVQWK VDNALQSGNS QESVTEQDSK DSTYSLSSTL 180
TLSKADYEKH KVYACEVTHQ GLSSPVTKSF NRGEC 215

SEQ ID NO: 262 moltype = AA length = 453
FEATURE Location/Qualifiers
REGION 1..453
note = Synthetic
source 1..453
mol_type = protein
organism = synthetic construct
SEQUENCE: 262
QVQLVESGGG VVQPGRSLRL SCAASGFTFN TYGMHWVRQA PGKGLEWVAI IWYDGSQKYY 60
ADSVQGRFTI SRDNHKNTLS LQMNSLRAED TAVYFCVRVR FSVGPHGSAF DLWGQGTMVT 120
VSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEL 240
LGGPSVFLFP PKPKDTLMIS RTPEVTCVVV DVSHEDPEVK FNWYVDGVEV HNAKTKPREE 300
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVMHEALHN HYTQKSLSLS PGK 453

SEQ ID NO: 263 moltype = AA length = 453
FEATURE Location/Qualifiers
REGION 1..453
note = Synthetic
source 1..453
mol_type = protein
organism = synthetic construct
SEQUENCE: 263
QVQLVESGGG VVQPGRSLRL SCAASGFTFN TYGMHWVRQA PGKGLEWVAI IWYDGSQKYY 60
ADSVQGRFTI SRDNHKNTLS LQMNSLRAED TAVYFCVRVR FSVGPHGSAF DLWGQGTMVT 120
VSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEL 240
LGGPSVFLFP PKPKDTLMIS RTPEVTCVVV DVSHEDPEVK FNWYVDGVEV HNAKTKPREE 300
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVLHEALHS HYTQKSLSLS PGK 453

SEQ ID NO: 264 moltype = DNA length = 645
FEATURE Location/Qualifiers
misc_feature 1..645
note = Synthetic
source 1..645
mol_type = other DNA
organism = synthetic construct
SEQUENCE: 264
ggcgtccaga tgacccagtc tccttccacc ctgtctgcat ctgtgggaga cagagtcacc 60
ctcacttgcc gggccagtca gagtattagt agttggttgg cctggtatca gcagaaacca 120
gggaaagccc ctaaactcct gatctatgat gcctccagtt tggaaagtgg ggtcccatca 180
aggttcagcg gcagtggatc tgggacagaa ttcactctca ccatcagcag cctgcaacct 240
gatgattttg caacttatta ctgccaacag tataatagtt attctttttg gacgttcggc 300
caagggacca aggtggaaat caaacgcact gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgt 645

SEQ ID NO: 265 moltype = DNA length = 1359
FEATURE Location/Qualifiers
misc_feature 1..1359
note = Synthetic
source 1..1359
mol_type = other DNA
organism = synthetic construct
SEQUENCE: 265
caggtgcaac tggtggagtc tgggggaggc gtggtccagc ctgggaggtc cctgagactc 60
tcctgtgcag cgtctgggtt cactttcaat acctatggca tgcactgggt ccgccaggca 120
ccaggcaagg ggctggagtg ggtggcaatt atctggtatg atgggagcca gaaatactat 180
gcagactccg tgcagggccg attcactatc tccagagaca atcacaagaa cacgttgtct 240
ctgcaaatga actccctgag agccgaggac acggctgtgt atttctgtgt gagagtccgc 300
tttagcgttg gcccccacgg gagtgctttt gatctctggg gccaggggac aatggtcaca 360
gtctcttcag cctccaccaa gggcccatcg gtcttccccc tggcaccctc ctccaagagc 420
acctctgggg gcacagcagc cctgggctgc ctggtcaagg actacttccc cgaaccggtg 480
acggtgtcgt ggaactcagg cgccctgacc agcggcgtgc acaccttccc ggctgtccta 540
cagtcctcag gactctactc cctcagcagc gtggtgaccg tgccctccag cagcttgggc 600
acccagacct acatctgcaa cgtgaatcac aagcccagca acaccaaggt ggacaagaaa 660

```
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtga tgcatgaggc tctgcacaac  1320
cactacacac agaagagcct ctccctgtct ccgggtaaa                        1359

SEQ ID NO: 266          moltype = DNA  length = 1359
FEATURE                 Location/Qualifiers
misc_feature            1..1359
                        note = Synthetic
source                  1..1359
                        mol_type = other DNA
                        organism = synthetic construct
SEQUENCE: 266
caggtgcaac tggtggagtc tggggggaggc gtggtccagc ctgggaggtc cctgagactc  60
tcctgtgcag cgtctgggtt cactttcaat acctatggca tgcactgggt ccgccaggca  120
ccaggcaagg ggctggagtg ggtggcaatt atctggtatg atgggagcca gaaatactat  180
gcagactccg tgcagggccg attcactatc tccagagaca atcacaagaa cacgttgtct  240
ctgcaaatga actccctgag agccgaggac acggctgtgt atttctgtgt gagagtccgc  300
tttagcgttg gcccccacgg gagtgctttt gatctctggg gccaggggac aatggtcaca  360
gtctcttcag cctccaccaa gggcccatcg gtcttccccc tggcaccctc ctccaagagc  420
acctctgggg gcacagcagc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtgc tgcatgaggc tctgcactcc  1320
cactacacac agaagagcct ctccctgtct ccgggtaaa                        1359

SEQ ID NO: 267          moltype = AA  length = 109
FEATURE                 Location/Qualifiers
REGION                  1..109
                        note = Synthetic
source                  1..109
                        mol_type = protein
                        organism = synthetic construct
SEQUENCE: 267
GVQMTQSPST LSASVGDRVT LTCRASQSIS SWLAWYQQKP GKAPKLLIYD ASSLESGVPS  60
RFSGSGSGTE FTLTISSLQP DDFATYYCQQ YNSYSFWTFG QGTKVEIKR             109

SEQ ID NO: 268          moltype = AA  length = 123
FEATURE                 Location/Qualifiers
REGION                  1..123
                        note = Synthetic
source                  1..123
                        mol_type = protein
                        organism = synthetic construct
SEQUENCE: 268
QVQLVESGGG VVQPGRSLRL SCAASGFTFN TYGMHWVRQA PGKGLEWVAI IWYDGSQKYY  60
ADSVQGRFTI SRDNHKNTLY LQMNSLRAED TAVYFCVRVR FSVGPHGSAF DLWGQGTMVT  120
VSS                                                               123

SEQ ID NO: 269          moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 269
ggcgtccaga tgacccagtc tccttccacc ctgtctgcat ctgtgggaga cagagtcacc  60
ctcacttgcc gggccagtca gagtattagt agttggttgg cctggtatca gcagaaacca  120
gggaaagccc ctaaactcct gatctatgat gcctccagtt tggaaagtgg ggtcccatca  180
```

```
aggttcagcg gcagtggatc tgggacagaa ttcactctca ccatcagcag cctgcaacct  240
gatgattttg caacttatta ctgccaacag tataatagtt attctttttg gacgttcggc  300
caagggacca aggtggaaat caaacgc                                      327

SEQ ID NO: 270         moltype = DNA  length = 369
FEATURE                Location/Qualifiers
misc_feature           1..369
                       note = Synthetic
source                 1..369
                       mol_type = other DNA
                       organism = synthetic construct
SEQUENCE: 270
caggtgcaac tggtggagtc tgggggaggc gtggtccagc ctgggaggtc cctgagactc  60
tcctgtgcag cgtctgggtt cactttcaat acctatggca tgcactgggt ccgccaggca  120
ccaggcaagg ggctggagtg ggtggcaatt atctggtatg atgggagcca gaaatactat  180
gcagactccg tgcagggccg attcactatc tccagagaca atcacaagaa cacgttgtac  240
ctgcaaatga actccctgag agccgaggac acggctgtgt atttctgtgt gagagtccgc  300
tttagcgttg gcccccacgg gagtgctttt gatctctggg gccaggggac aatggtcaca  360
gtctcttca                                                          369

SEQ ID NO: 271         moltype = AA  length = 215
FEATURE                Location/Qualifiers
REGION                 1..215
                       note = Synthetic
source                 1..215
                       mol_type = protein
                       organism = synthetic construct
SEQUENCE: 271
GVQMTQSPST LSASVGDRVT LTCRASQSIS SWLAWYQQKP GKAPKLLIYD ASSLESGVPS  60
RFSGSGSGTE FTLTISSLQP DDFATYYCQQ YNSYSFWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 272         moltype = AA  length = 453
FEATURE                Location/Qualifiers
REGION                 1..453
                       note = Synthetic
source                 1..453
                       mol_type = protein
                       organism = synthetic construct
SEQUENCE: 272
QVQLVESGGG VVQPGRSLRL SCAASGFTFN TYGMHWVRQA PGKGLEWVAI IWYDGSQKYY  60
ADSVQGRFTI SRDNHKNTLY LQMNSLRAED TAVYFCVRVR FSVGPHGSAF DLWGQGTMVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 273         moltype = AA  length = 453
FEATURE                Location/Qualifiers
REGION                 1..453
                       note = Synthetic
source                 1..453
                       mol_type = protein
                       organism = synthetic construct
SEQUENCE: 273
QVQLVESGGG VVQPGRSLRL SCAASGFTFN TYGMHWVRQA PGKGLEWVAI IWYDGSQKYY  60
ADSVQGRFTI SRDNHKNTLY LQMNSLRAED TAVYFCVRVR FSVGPHGSAF DLWGQGTMVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVLHEALHS HYTQKSLSLS PGK                               453

SEQ ID NO: 274         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 274
ggcgtccaga tgacccagtc tccttccacc ctgtctgcat ctgtgggaga cagagtcacc  60
ctcacttgcc gggccagtca gagtattagt agttggttgg cctggtatca gcagaaacca  120
gggaaagccc ctaaactcct gatctatgat gcctccagtt tggaaagtgg ggtcccatca  180
aggttcagcg gcagtggatc tgggacagaa ttcactctca ccatcagcag cctgcaacct  240
```

```
gatgattttg caacttatta ctgccaacag tataatagtt attctttttg gacgttcggc  300
caagggacca aggtggaaat caaacgcact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgt                 645

SEQ ID NO: 275          moltype = DNA  length = 1359
FEATURE                 Location/Qualifiers
misc_feature            1..1359
                        note = Synthetic
source                  1..1359
                        mol_type = other DNA
                        organism = synthetic construct
SEQUENCE: 275
caggtgcaac tggtggagtc tgggggaggc gtggtccagc ctgggaggtc cctgagactc  60
tcctgtgcag cgtctgggtt cactttcaat acctatggca tgcactgggt ccgccaggca  120
ccaggcaagg ggctggagtg ggtggcaatt atctggtatg atgggagcca gaaatactat  180
gcagactccg tgcagggccg attcactatc tccagagaca atcacaagaa cacgttgtac  240
ctgcaaatga actccctgag agccgaggac acggctgtgt atttctgtgt gagagtccgc  300
tttagcgttg gcccccacgg gagtgctttt gatctctggg gccaggggac aatggtcaca  360
gtctcttcag cctccaccaa gggcccatcg gtcttccccc tggcaccctc ctccaagagc  420
acctctgggg gcacagcagc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtga tgcatgaggc tctgcacaac  1320
cactacacac agaagagcct ctccctgtct ccgggtaaa                        1359

SEQ ID NO: 276          moltype = DNA  length = 1359
FEATURE                 Location/Qualifiers
misc_feature            1..1359
                        note = Synthetic
source                  1..1359
                        mol_type = other DNA
                        organism = synthetic construct
SEQUENCE: 276
caggtgcaac tggtggagtc tgggggaggc gtggtccagc ctgggaggtc cctgagactc  60
tcctgtgcag cgtctgggtt cactttcaat acctatggca tgcactgggt ccgccaggca  120
ccaggcaagg ggctggagtg ggtggcaatt atctggtatg atgggagcca gaaatactat  180
gcagactccg tgcagggccg attcactatc tccagagaca atcacaagaa cacgttgtac  240
ctgcaaatga actccctgag agccgaggac acggctgtgt atttctgtgt gagagtccgc  300
tttagcgttg gcccccacgg gagtgctttt gatctctggg gccaggggac aatggtcaca  360
gtctcttcag cctccaccaa gggcccatcg gtcttccccc tggcaccctc ctccaagagc  420
acctctgggg gcacagcagc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtgc tgcatgaggc tctgcactcc  1320
cactacacac agaagagcct ctccctgtct ccgggtaaa                        1359

SEQ ID NO: 277          moltype = AA  length = 19
FEATURE                 Location/Qualifiers
REGION                  1..19
                        note = Synthetic
source                  1..19
                        mol_type = protein
                        organism = synthetic construct
```

SEQUENCE: 277
MAWALLLLTL LTQGTGSWA 19

SEQ ID NO: 278 moltype = AA length = 22
FEATURE Location/Qualifiers
REGION 1..22
note = Synthetic
source 1..22
mol_type = protein
organism = synthetic construct
SEQUENCE: 278
MDMRVPAQLL GLLLLWLRGA RC 22

SEQ ID NO: 279 moltype = AA length = 24
FEATURE Location/Qualifiers
REGION 1..24
note = Synthetic
source 1..24
mol_type = protein
organism = synthetic construct
SEQUENCE: 279
NANPNANPNA NPNANPNANP NANP 24

SEQ ID NO: 280 moltype = AA length = 12
FEATURE Location/Qualifiers
REGION 1..12
note = Synthetic
source 1..12
mol_type = protein
organism = synthetic construct
SEQUENCE: 280
NPNANPNANP NA 12

SEQ ID NO: 281 moltype = AA length = 20
FEATURE Location/Qualifiers
REGION 1..20
note = Synthetic
source 1..20
mol_type = protein
organism = synthetic construct
SEQUENCE: 281
NVDPNANPNV DPNANPNVDP 20

SEQ ID NO: 282 moltype = AA length = 16
FEATURE Location/Qualifiers
REGION 1..16
note = Synthetic
source 1..16
mol_type = protein
organism = synthetic construct
SEQUENCE: 282
NPDPNANPNV DPNANP 16

SEQ ID NO: 283 moltype = AA length = 12
FEATURE Location/Qualifiers
REGION 1..12
note = Synthetic
source 1..12
mol_type = protein
organism = synthetic construct
SEQUENCE: 283
DPNANPNVDP NA 12

SEQ ID NO: 284 moltype = AA length = 15
FEATURE Location/Qualifiers
REGION 1..15
note = Synthetic
source 1..15
mol_type = protein
organism = synthetic construct
SEQUENCE: 284
KQPADGNPDP NANPN 15

SEQ ID NO: 285 moltype = AA length = 424
FEATURE Location/Qualifiers
REGION 1..424
note = Synthetic
source 1..424
mol_type = protein

```
                         organism = synthetic construct
SEQUENCE: 285
MMRKLAILSV SSFLFVEALF QEYQCYGSSS NTRVLNELNY DNAGINLYNE LEMNYYGKQE  60
NWYSLKKNSR SLGENDDGNN NNGDNGREGK DEDKRDGNNE DNEKLRKPKH KKLKQPGDGN  120
PDPNANPNVD PNANPNVDPN ANPNVDPNAN PNANPNANPN ANPNANPNAN PNANPNANPN  180
ANPNANPNAN PNANPNANPN ANPNANPNAN PNANPNANPN ANPNANPNAN PNANPNANPN  240
ANPNANPNAN PNANPNANPN ANPNANPNAN PNANPNANPN ANPNANPNAN PNANPNANPN  300
KNNQGNGQGH NMPNDPNRNV DENANANNAV KNNNNEEPSD KHIEQYLKKI QNSLSTEWSP  360
CSVTCGNGIQ VRIKPGSANK PKDELDYEND IEKKICKMEK CSSVFNVVNS SIGLIMVLSF  420
LFLN                                                              424

SEQ ID NO: 286          moltype = AA  length = 236
FEATURE                 Location/Qualifiers
REGION                  1..236
                        note = Synthetic
source                  1..236
                        mol_type = protein
                        organism = synthetic construct
SEQUENCE: 286
MAWALLLLTL LTQGTGSWAE SVLTQPPSVS GAPGQRVTIS CTGMNSNIGA GYDVYWYQQL  60
PGRAPKLLIY GNSNRPSGVP DRFSGSRSGT SASLAITGLQ AEDEADYYCQ SYDTSLNGWA  120
FGGGTKLTVL GQPKAAPSVT LFPPSSEELQ ANKATLVCLV SDFYPGAVTV AWKADGSPVK  180
VGVETTKPSK QSNNKYAASS YLSLTPEQWK SHRSYSCRVT HEGSTVEKTV APAECS      236

SEQ ID NO: 287          moltype = AA  length = 479
FEATURE                 Location/Qualifiers
REGION                  1..479
                        note = Synthetic
source                  1..479
                        mol_type = protein
                        organism = synthetic construct
SEQUENCE: 287
MDMRVPAQLL GLLLLWLRGA RCEVQLVESG GGLVQPGRSL RLPCTASGFS FGDHAMSWVR  60
QAPGKGLEWV GFIRKTTYGA TTHYAAAVRG RFTISRDDSK SIVYLQMNSL KTEDTAVYFC  120
TRVQLDYGPG YQYYGMDVWG QGTTVTVSSA STKGPSVFPL APSSKSTSGG TAALGCLVKD  180
YFPEPVTVSW NSGALTSGVH TFPAVLQSSG LYSLSSVVTV PSSSLGTQTY ICNVNHKPSN  240
TKVDKKVEPK SCDKTHTCPP CPAPELLGGP SVFLFPPKPK DTLMISRTPE VTCVVVDVSH  300
EDPEVKFNWY VDGVEVHNAK TKPREEQYNS TYRVVSVLTV LHQDWLNGKE YKCKVSNKAL  360
PAPIEKTISK AKGQPREPQV YTLPPSRDEL TKNQVSLTCL VKGFYPSDIA VEWESNGQPE  420
NNYKTTPPVL DSDGSFFLYS KLTVDKSRWQ QGNVFSCSVL HEALHSHYTQ KSLSLSPGK   479

SEQ ID NO: 288          moltype = AA  length = 237
FEATURE                 Location/Qualifiers
REGION                  1..237
                        note = Synthetic
source                  1..237
                        mol_type = protein
                        organism = synthetic construct
SEQUENCE: 288
MDMRVPAQLL GLLLLWLRGA RCGVQMTQSP STLSASVGDR VTLTCRASQS ISSWLAWYQQ  60
KPGKAPKLLI YDASSLESGV PSRFSGSGSG TEFTLTISSL QPDDFATYYC QQYNSYSFWT  120
FGQGTKVEIK RTVAAPSVFI FPPSDEQLKS GTASVVCLLN NFYPREAKVQ WKVDNALQSG  180
NSQESVTEQD SKDSTYSLSS TLTLSKADYE KHKVYACEVT HQGLSSPVTK SFNRGEC     237

SEQ ID NO: 289          moltype = AA  length = 475
FEATURE                 Location/Qualifiers
REGION                  1..475
                        note = Synthetic
source                  1..475
                        mol_type = protein
                        organism = synthetic construct
SEQUENCE: 289
MDMRVPAQLL GLLLLWLRGA RCQVQLVESG GGVVQPGRSL RLSCAASGFA FNTYGMHWVR  60
QTPGKGLEWV AIIWYDGSQK YYADSVQGRF IISRDNHKNT LSLQMNGLRA EDTAVYFCVR  120
VRFSVGPHGS AFDLWGQGTM VIVSSASTKG PSVFPLAPSS KSTSGGTAAL GCLVKDYFPE  180
PVTVSWNSGA LTSGVHTFPA VLQSSGLYSL SSVVTVPSSS LGTQTYICNV NHKPSNTKVD  240
KKVEPKSCDK THTCPPCPAP ELLGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPQVYTLP PSRDELTKNQ VSLTCLVKGF YPSDIAVEWE SNGQPENNYK  420
TTPPVLDSDG SFFLYSKLTV DKSRWQQGNV FSCSVLHEAL HSHYTQKSLS LSPGK       475
```

ANTI-CSP ANTIBODIES

CROSS-REFERENCE TO RELATED APPLICATIONS

This application is a continuation of U.S. patent application Ser. No. 17/842,351, filed Jun. 16, 2022, which claims priority to U.S. Provisional Application No. 63/211,820, filed Jun. 17, 2021, the content of each of which is incorporated by reference in its entirety, and to each of which priority is claimed.

SEQUENCE LISTING

This application contains a Sequence Listing which has been submitted in XML format and is hereby incorporated by reference in its entirety. Said XML copy, created on Jan. 25, 2023, is named 087996.0108.xml and is 490,821 bytes in size.

FIELD

The present disclosure relates to compositions for treating or preventing malaria, and to antibodies conferring protection against infection by malarial parasites such as *Plasmodium falciparum* by insect vector transmission. The present disclosure also relates to methods for treating, preventing, or diagnosing *Plasmodium* infection in a mammal.

BACKGROUND

Malaria causes a large burden of morbidity and mortality, especially in the developing world. The causative agent of malaria is a protozoal parasite, which is transmitted by mosquitoes. Several infectious *Plasmodium* species cause malaria, the deadliest of which is *Plasmodium falciparum*. Others include *P. vivax, P. ovale*, and *P. malariae*. A first-generation vaccine (RTS,S) has been developed using portions of the malaria protein CSP, including part of the NANP repeats. CSP-based vaccines have consistently shown 30-50% efficacy in the prevention of erythrocytic-stage infection. This level of efficacy is not sufficient for eradication and new pre-erythrocytic treatments will need superior efficacy. Despite the existence of other anti-malarial products such as mefloquinine, doxycycline, and atovaquone/proguanil, there is a need for new antimalarials options for cases that are resistant to existing antimalarial drugs.

SUMMARY

The present disclosure provides to antibodies targeting *Plasmodium falciparum*. In certain non-limiting embodiments, the antibody is a recombinant anti-circumsporozoite (CSP) antibody. In certain embodiments, the recombinant antibody comprises a light chain variable region (VL) and a heavy chain variable region (VH), wherein the light chain variable region comprises a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3; and the heavy chain variable region comprises a CDR1 comprising the amino acid sequence set forth in SEQ ID NO: 4, a CDR2 comprising the amino acid sequence set forth in SEQ ID NO: 5, and a CDR3 comprising the amino acid sequence set forth in SEQ ID NO: 6.

In certain embodiments, the VL comprises the amino acid sequence set forth in SEQ ID NO: 163; the amino acid sequence set forth in SEQ ID NO: 23; the amino acid sequence set forth in SEQ ID NO: 33; the amino acid sequence set forth in SEQ ID NO: 43; the amino acid sequence set forth in SEQ ID NO: 53; the amino acid sequence set forth in SEQ ID NO: 63; the amino acid sequence set forth in SEQ ID NO: 73; the amino acid sequence set forth in SEQ ID NO: 83; the amino acid sequence set forth in SEQ ID NO: 93; the amino acid sequence set forth in SEQ ID NO: 103; the amino acid sequence set forth in SEQ ID NO: 113; the amino acid sequence set forth in SEQ ID NO: 123; the amino acid sequence set forth in SEQ ID NO: 133; the amino acid sequence set forth in SEQ ID NO: 143; the amino acid sequence set forth in SEQ ID NO: 153; or the amino acid sequence set forth in SEQ ID NO: 173. In certain embodiments, the VH comprises the amino acid sequence set forth in SEQ ID NO: 164; the amino acid sequence set forth in SEQ ID NO: 24; the amino acid sequence set forth in SEQ ID NO: 34; the amino acid sequence set forth in SEQ ID NO: 44; the amino acid sequence set forth in SEQ ID NO: 54; the amino acid sequence set forth in SEQ ID NO: 64; the amino acid sequence set forth in SEQ ID NO: 74; the amino acid sequence set forth in SEQ ID NO: 84; the amino acid sequence set forth in SEQ ID NO: 94; the amino acid sequence set forth in SEQ ID NO: 104; the amino acid sequence set forth in SEQ ID NO: 114; the amino acid sequence set forth in SEQ ID NO: 124; the amino acid sequence set forth in SEQ ID NO: 134; the amino acid sequence set forth in SEQ ID NO: 144; the amino acid sequence set forth in SEQ ID NO: 154; or the amino acid sequence set forth in SEQ ID NO: 174.

In certain embodiments, the VL comprises the amino acid sequence set forth in SEQ ID NO: 163, and the VH comprises the amino acid sequence set forth in SEQ ID NO: 164; the VL comprises the amino acid sequence set forth in SEQ ID NO: 33, and the VH comprises the amino acid sequence set forth in SEQ ID NO: 34; the VL comprises the amino acid sequence set forth in SEQ ID NO: 43, and the VH comprises the amino acid sequence set forth in SEQ ID NO: 44; the VL comprises the amino acid sequence set forth in SEQ ID NO: 53, and the VH comprises the amino acid sequence set forth in SEQ ID NO: 54; the VL comprises the amino acid sequence set forth in SEQ ID NO: 63, and the VH comprises the amino acid sequence set forth in SEQ ID NO: 64; the VL comprises the amino acid sequence set forth in SEQ ID NO: 73, and the VH comprises the amino acid sequence set forth in SEQ ID NO: 74; the VL comprises the amino acid sequence set forth in SEQ ID NO: 83, and the VH comprises the amino acid sequence set forth in SEQ ID NO: 84; the VL comprises the amino acid sequence set forth in SEQ ID NO: 93, and the VH comprises the amino acid sequence set forth in SEQ ID NO: 94; the VL comprises the amino acid sequence set forth in SEQ ID NO: 103, and the VH comprises the amino acid sequence set forth in SEQ ID NO: 104; the VL comprises the amino acid sequence set forth in SEQ ID NO: 113, and the VH comprises the amino acid sequence set forth in SEQ ID NO: 114; the VL comprises the amino acid sequence set forth in SEQ ID NO: 123, and the VH comprises the amino acid sequence set forth in SEQ ID NO: 124; the VL comprises the amino acid sequence set forth in SEQ ID NO: 133, and the VH comprises the amino acid sequence set forth in SEQ ID NO: 134; the VL comprises the amino acid sequence set forth in SEQ ID NO: 143, and the VH comprises the amino acid sequence set forth in SEQ ID NO: 144; the VL comprises the amino acid sequence set forth in SEQ ID NO: 153, and the VH comprises the amino acid sequence set forth in SEQ ID NO:

154; or the VL comprises the amino acid sequence set forth in SEQ ID NO: 173, and the VH comprises the amino acid sequence set forth in SEQ ID NO: 174.

In certain embodiments, the VL comprises the amino acid sequence set forth in SEQ ID NO: 63, and the VH comprises the amino acid sequence set forth in SEQ ID NO: 64. In certain embodiments, the VL comprises the amino acid sequence set forth in SEQ ID NO: 133, and the VH comprises the amino acid sequence set forth in SEQ ID NO: 134. In certain embodiments, the VL comprises the amino acid sequence set forth in SEQ ID NO: 163, and the VH comprises the amino acid sequence set forth in SEQ ID NO: 164.

In certain embodiments, the recombinant antibody comprises a light chain (LC) and a heavy chain (HC). In certain embodiments, the LC comprises the amino acid sequence set forth in SEQ ID NO: 27; the amino acid sequence set forth in SEQ ID NO: 37; the amino acid sequence set forth in SEQ ID NO: 47; the amino acid sequence set forth in SEQ ID NO: 57; the amino acid sequence set forth in SEQ ID NO: 67; the amino acid sequence set forth in SEQ ID NO: 77; the amino acid sequence set forth in SEQ ID NO: 87; the amino acid sequence set forth in SEQ ID NO: 97; the amino acid sequence set forth in SEQ ID NO: 107; the amino acid sequence set forth in SEQ ID NO: 117; the amino acid sequence set forth in SEQ ID NO: 127; the amino acid sequence set forth in SEQ ID NO: 137; the amino acid sequence set forth in SEQ ID NO: 147; the amino acid sequence set forth in SEQ ID NO: 157; the amino acid sequence set forth in SEQ ID NO: 167; or the amino acid sequence set forth in SEQ ID NO: 177. In certain embodiments, the HC comprises the amino acid sequence set forth in SEQ ID NO: 28 or SEQ ID NO: 29; the amino acid sequence set forth in SEQ ID NO: 38 or SEQ ID NO: 39; the amino acid sequence set forth in SEQ ID NO: 48 or SEQ ID NO: 49; the amino acid sequence set forth in SEQ ID NO: 58 or SEQ ID NO: 59; the amino acid sequence set forth in SEQ ID NO: 68 or SEQ ID NO: 69; the amino acid sequence set forth in SEQ ID NO: 78 or SEQ ID NO: 79; the amino acid sequence set forth in SEQ ID NO: 88 or SEQ ID NO: 89; the amino acid sequence set forth in SEQ ID NO: 98 or SEQ ID NO: 99; the amino acid sequence set forth in SEQ ID NO: 108 or SEQ ID NO: 109; the amino acid sequence set forth in SEQ ID NO: 118 or SEQ ID NO: 119; the amino acid sequence set forth in SEQ ID NO: 128 or SEQ ID NO: 129; the amino acid sequence set forth in SEQ ID NO: 138 or SEQ ID NO: 139; the amino acid sequence set forth in SEQ ID NO: 148 or SEQ ID NO: 149; the amino acid sequence set forth in SEQ ID NO: 158 or SEQ ID NO: 159; the amino acid sequence set forth in SEQ ID NO: 168 or SEQ ID NO: 169; or the amino acid sequence set forth in SEQ ID NO: 178 or SEQ ID NO: 179.

In certain embodiments, the LC comprises the amino acid sequence set forth in SEQ ID NO: 27, and the HC comprises the amino acid sequence set forth in SEQ ID NO: 28 or SEQ ID NO: 29; the LC comprises the amino acid sequence set forth in SEQ ID NO: 37, and the HC comprises the amino acid sequence set forth in SEQ ID NO: 38 or SEQ ID NO: 39; the LC comprises the amino acid sequence set forth in SEQ ID NO: 47, and the HC comprises the amino acid sequence set forth in SEQ ID NO: 48 or SEQ ID NO: 49; the LC comprises the amino acid sequence set forth in SEQ ID NO: 57, and the HC comprises the amino acid sequence set forth in SEQ ID NO: 58 or SEQ ID NO: 59; the LC comprises the amino acid sequence set forth in SEQ ID NO: 67, and the HC comprises the amino acid sequence set forth in SEQ ID NO: 68 or SEQ ID NO: 69; the LC comprises the amino acid sequence set forth in SEQ ID NO: 77, and the HC comprises the amino acid sequence set forth in SEQ ID NO: 78 or SEQ ID NO: 79; the LC comprises the amino acid sequence set forth in SEQ ID NO: 87, and the HC comprises the amino acid sequence set forth in SEQ ID NO: 88 or SEQ ID NO: 89; the LC comprises the amino acid sequence set forth in SEQ ID NO: 97, and the HC comprises the amino acid sequence set forth in SEQ ID NO: 98 or SEQ ID NO: 99; the LC comprises the amino acid sequence set forth in SEQ ID NO: 107, and the HC comprises the amino acid sequence set forth in SEQ ID NO: 108 or SEQ ID NO: 109; the LC comprises the amino acid sequence set forth in SEQ ID NO: 117, and the HC comprises the amino acid sequence set forth in SEQ ID NO: 118 or SEQ ID NO: 119; the LC comprises the amino acid sequence set forth in SEQ ID NO: 127, and the HC comprises the amino acid sequence set forth in SEQ ID NO: 128 or SEQ ID NO: 129; the LC comprises the amino acid sequence set forth in SEQ ID NO: 137, and the HC comprises the amino acid sequence set forth in SEQ ID NO: 138 or SEQ ID NO: 139; the LC comprises the amino acid sequence set forth in SEQ ID NO: 147, and the HC comprises the amino acid sequence set forth in SEQ ID NO: 148 or SEQ ID NO: 149; the LC comprises the amino acid sequence set forth in SEQ ID NO: 157, and the HC comprises the amino acid sequence set forth in SEQ ID NO: 158 or SEQ ID NO: 159; the LC comprises the amino acid sequence set forth in SEQ ID NO: 167, and the HC comprises the amino acid sequence set forth in SEQ ID NO: 168 or SEQ ID NO: 169; or the LC comprises the amino acid sequence set forth in SEQ ID NO: 177, and the HC comprises the amino acid sequence set forth in SEQ ID NO: 178 or SEQ ID NO: 179.

In certain embodiments, the LC comprises the amino acid sequence set forth in SEQ ID NO: 67, and the HC comprises the amino acid sequence set forth in SEQ ID NO: 69. In certain embodiments, the LC comprises the amino acid sequence set forth in SEQ ID NO: 137, and the HC comprises the amino acid sequence set forth in SEQ ID NO: 139. In certain embodiments, the LC comprises the amino acid sequence set forth in SEQ ID NO: 167, and the HC comprises the amino acid sequence set forth in SEQ ID NO: 169.

In certain embodiments, the recombinant antibody comprises a light chain variable region (VL) and a heavy chain variable region (VH), wherein the VL comprises the amino acid sequence set forth in SEQ ID NO: 13. In certain embodiments, the VL comprises at least one amino acid substitution. In certain embodiments, the at least one amino acid substitution is at position 1 and/or at position 44. In certain embodiments, the amino acid substitution at position 1 is E1Q. In certain embodiments, the amino acid substitution at position 44 is R44T. In certain embodiments, the VH comprises the amino acid sequence set forth in SEQ ID NO: 14. In certain embodiments, the VH comprises at least one amino acid substitution. In certain embodiments, the at least one amino acid substitution is at position 21, position 23, position 88, position 98, or a combination thereof. In certain embodiments, the amino acid substitution at position 1 is E1Q. In certain embodiments, the amino acid substitution at position 44 is R44T. In certain embodiments, the amino acid substitution at position 21 is P21S. In certain embodiments, the amino acid substitution at position 23 is T23A. In certain embodiments, the amino acid substitution at position 80 is I80T. In certain embodiments, the amino acid substitution at position 90 is T90A.

In certain embodiments, the recombinant antibody comprises a heavy chain (HC) comprising the amino acid sequence set forth in SEQ ID NO: 18. In certain embodiments, the HC comprises at least one amino acid substitution. In certain embodiments, the at least one amino acid substitution is at position 438 and/or or at position 444. In certain embodiments, the amino acid substitution at position 438 is M438L. In certain embodiments, the amino acid substitution at position 444 is N444S.

In certain non-limiting embodiments, the present disclosure also provides a recombinant anti-circumsporozoite (CSP) antibody comprising a light chain variable region (VL) and a heavy chain variable region (VH), wherein the VL comprises the amino acid sequence set forth in SEQ ID NO: 163 and the VH comprises the amino acid sequence set forth in SEQ ID NO: 164. In certain embodiments, the recombinant antibody comprises a light chain (LC) and a heavy chain (HC), wherein the LC comprises the amino acid sequence set forth in SEQ ID NO: 167 and the HC comprises the amino acid sequence set forth in SEQ ID NO: 169.

In certain non-limiting embodiments, the present disclosure provides a recombinant anti-circumsporozoite (CSP) antibody comprising a light chain variable region (VL) and a heavy chain variable region (VH), wherein the VL comprises the amino acid sequence set forth in SEQ ID NO: 63 and the VH comprises the amino acid sequence set forth in SEQ ID NO: 64. In certain embodiments, the recombinant antibody comprises a light chain (LC) and a heavy chain (HC), wherein the LC comprises the amino acid sequence set forth in SEQ ID NO: 67 and the HC comprises the amino acid sequence set forth in SEQ ID NO: 69.

In certain non-limiting embodiments, the present disclosure further provides a recombinant anti-circumsporozoite (CSP) antibody comprising a light chain variable region (VL) and a heavy chain variable region (VH), wherein the VL comprises the amino acid sequence set forth in SEQ ID NO: 133 and the VH comprises the amino acid sequence set forth in SEQ ID NO: 134. In certain embodiments, the recombinant antibody comprises a light chain (LC) and a heavy chain (HC), wherein the LC comprises the amino acid sequence set forth in SEQ ID NO: 137 and the HC comprises the amino acid sequence set forth in SEQ ID NO: 139.

In certain non-limiting embodiments, the present disclosure provides a recombinant anti-circumsporozoite (CSP) antibody comprising a light chain variable region (VL) and a heavy chain variable region (VH), wherein the light chain variable region comprises a CDR1 comprising the amino acid sequence set forth in SEQ ID NO: 183, a CDR2 comprising the amino acid sequence set forth in SEQ ID NO: 184, and a CDR3 comprising the amino acid sequence set forth in SEQ ID NO: 185; and the heavy chain variable region comprises a CDR1 comprising the amino acid sequence set forth in SEQ ID NO: 186, a CDR2 comprising the amino acid sequence set forth in SEQ ID NO: 187, and a CDR3 comprising the amino acid sequence set forth in SEQ ID NO: 188. In certain embodiments, the VL comprises the amino acid sequence set forth in SEQ ID NO: 195, and the VH comprises the amino acid sequence set forth in SEQ ID NO: 196. In certain embodiments, the antibody comprises comprising a LC and a HC. In certain embodiments, the LC comprises the amino acid sequence set forth in SEQ ID NO: 199, and the HC comprises the amino acid sequence set forth in SEQ ID NO: 200 or SEQ ID NO: 201.

In certain non-limiting embodiments, the present disclosure provides a recombinant anti-circumsporozoite (CSP) antibody comprising a light chain variable region (VL) and a heavy chain variable region (VH), wherein the light chain variable region comprises a CDR1 comprising the amino acid sequence set forth in SEQ ID NO: 205, a CDR2 comprising the amino acid sequence set forth in SEQ ID NO: 206, and a CDR3 comprising the amino acid sequence set forth in SEQ ID NO: 207; and the heavy chain variable region comprises a CDR1 comprising the amino acid sequence set forth in SEQ ID NO: 208, a CDR2 comprising the amino acid sequence set forth in SEQ ID NO: 209, and a CDR3 comprising the amino acid sequence set forth in SEQ ID NO: 210.

In certain embodiments, the amino acid sequence set forth in SEQ ID NO: 227; the amino acid sequence set forth in SEQ ID NO: 237; the amino acid sequence set forth in SEQ ID NO: 247; the amino acid sequence set forth in SEQ ID NO: 257; or the amino acid sequence set forth in SEQ ID NO: 267. In certain embodiments, the VH comprises the amino acid sequence set forth in SEQ ID NO: 228; the amino acid sequence set forth in SEQ ID NO: 238; the amino acid sequence set forth in SEQ ID NO: 248; the amino acid sequence set forth in SEQ ID NO: 258; or the amino acid sequence set forth in SEQ ID NO: 268.

In certain embodiments, the VL comprises the amino acid sequence set forth in SEQ ID NO: 227, and the VH comprises the amino acid sequence set forth in SEQ ID NO: 228; the VL comprises the amino acid sequence set forth in SEQ ID NO: 237, and the VH comprises the amino acid sequence set forth in SEQ ID NO: 238; the VL comprises the amino acid sequence set forth in SEQ ID NO: 247, and the VH comprises the amino acid sequence set forth in SEQ ID NO: 248; the VL comprises the amino acid sequence set forth in SEQ ID NO: 257, and the VH comprises the amino acid sequence set forth in SEQ ID NO: 258; or the VL comprises the amino acid sequence set forth in SEQ ID NO: 267, and the VH comprises the amino acid sequence set forth in SEQ ID NO: 268.

In certain embodiments, the recombinant antibody comprises a LC and a HC. In certain embodiments, the LC comprises the amino acid sequence set forth in SEQ ID NO: 231; the amino acid sequence set forth in SEQ ID NO: 241; the amino acid sequence set forth in SEQ ID NO: 251; the amino acid sequence set forth in SEQ ID NO: 261; or the amino acid sequence set forth in SEQ ID NO: 271. In certain embodiments, the HC comprises the amino acid sequence set forth in SEQ ID NO: 232 or SEQ ID NO: 233; the amino acid sequence set forth in SEQ ID NO: 242 or SEQ ID NO: 243; the amino acid sequence set forth in SEQ ID NO: 252 or SEQ ID NO: 253; the amino acid sequence set forth in SEQ ID NO: 262 or SEQ ID NO: 263; or the amino acid sequence set forth in SEQ ID NO: 272 or SEQ ID NO: 273.

In certain embodiments, the LC comprises the amino acid sequence set forth in SEQ ID NO: 231, and the HC comprises the amino acid sequence set forth in SEQ ID NO: 232 or SEQ ID NO: 233; the LC comprises the amino acid sequence set forth in SEQ ID NO: 241, and the HC comprises the amino acid sequence set forth in SEQ ID NO: 242 or SEQ ID NO: 243; the LC comprises the amino acid sequence set forth in SEQ ID NO: 251, and the HC comprises the amino acid sequence set forth in SEQ ID NO: 252 or SEQ ID NO: 253; the LC comprises the amino acid sequence set forth in SEQ ID NO: 261, and the HC comprises the amino acid sequence set forth in SEQ ID NO: 262 or SEQ ID NO: 263; or the LC comprises the amino acid sequence set forth in SEQ ID NO: 271, and the HC comprises the amino acid sequence set forth in SEQ ID NO: 272 or SEQ ID NO: 273.

In certain embodiments, the VH comprises the amino acid sequence set forth in SEQ ID NO: 218. In certain embodiments, the VH comprises at least one amino acid substitution. In certain embodiments, the at least one amino acid substitution is at position 40, position 69, position 80, position 85, position 120, or a combination thereof. In certain embodiments, the amino acid substitution at position 40 is T40A. In certain embodiments, the amino acid substitution at position 69 is I69T. In certain embodiments, the amino acid substitution at position 80 is S80Y. In certain embodiments, the amino acid substitution at position 85 is G85S. In certain embodiments, the amino acid substitution at position 120 is I120T. In certain embodiments, the HC comprises the amino acid sequence set forth in SEQ ID NO: 222. In certain embodiments, the HC comprises at least one amino acid substitution. In certain embodiments, the at least one amino acid substitution is at position 434 and/or at position 440. In certain embodiments, the amino acid substitution at position 434 is M434L. In certain embodiments, the amino acid substitution at position 440 is N440S.

In certain embodiments, the recombinant antibody exhibits at least 20% reduction in parasite liver load as compared to a reference antibody. In certain embodiments, the recombinant antibody exhibits at least 20% increase in survival rate as compared to a reference antibody. In certain embodiments, the recombinant antibody exhibits increased conformational stability as compared to a reference antibody. In certain embodiments, the recombinant antibody exhibits increased colloidal stability as compared to a reference antibody. In certain embodiments, the reference antibody is AB-000317. In certain embodiments, the reference antibody is AB-000224. In certain embodiments, the reference antibody is AB-007088.

In certain embodiments, the recombinant antibody binds to a NANP repeat region. In certain embodiments, the recombinant antibody binds to a polypeptide comprising or consisting of the amino acid sequence set forth in SEQ ID NO: 280.

In certain embodiments, the recombinant antibody comprises at least one modification relative to the native AB-000224 variable heavy chain amino acid sequence set forth in SEQ ID NO: 14. In certain embodiments, the recombinant antibody comprises at least one modification relative to the native AB-000224 variable light chain amino acid sequence set forth in SEQ ID NO: 13. In certain embodiments, the recombinant antibody comprises at least one modification relative to the native AB-000224 variable heavy chain amino acid sequence set forth in SEQ ID NO: 14 and at least one modification relative to the native AB-000224 variable light chain amino acid sequence set forth in SEQ ID NO: 13.

In certain embodiments, the recombinant antibody comprises at least one modification relative to the native AB-007088 variable heavy chain amino acid sequence set forth in SEQ ID NO: 218. In certain embodiments, the recombinant antibody comprises at least one modification relative to the native AB-007088 variable light chain amino acid sequence set forth in SEQ ID NO: 217. In certain embodiments, the recombinant antibody comprises at least one modification relative to the native AB-007088 variable heavy chain amino acid sequence set forth in SEQ ID NO: 218 and at least one modification relative to the native AB-000224 variable light chain amino acid sequence set forth in SEQ ID NO: 217.

In certain non-limiting embodiments, the present disclosure provides a polynucleotide encoding an antibody disclosed herein. In certain non-limiting embodiments, the present disclosure provides an expression vector comprising the polynucleotide disclosed herein. In certain non-limiting embodiments, the present disclosure provides a host cell comprising the expression vector or the polynucleotide disclosed herein.

In certain non-limiting embodiments, the present disclosure provides a composition comprising the antibody disclosed herein. In certain embodiments, the composition further comprises a pharmaceutically acceptable carrier.

In certain non-limiting embodiments, the present disclosure provides a method of preventing and/or treating malaria in a subject in need thereof, comprising administering an effective amount of the antibody disclosed herein or of the composition disclosed herein. In certain embodiments, the subject is a pediatric patient.

In certain non-limiting embodiments, the present disclosure provides the antibodies or compositions disclosed herein for use in the prevention and/or treatment of malaria in a subject in need thereof. Additionally, in certain non-limiting embodiments, the present disclosure provides the antibodies or compositions disclosed herein for the manufacture of a medicament for the prevention and/or treatment of malaria in a subject in need thereof. Furthermore, the present disclosure provides use of the antibodies or compositions disclosed herein for the prevention and/or treatment and/or prevention of malaria in a subject in need thereof. In certain embodiments, the subject is a pediatric patient.

BRIEF DESCRIPTION OF THE DRAWINGS

FIG. 4A shows the AB-000224 Lambda Light Chain sequence (SEQ ID NO: 286). FIG. 4B shows the AB-000224 IgG1 Heavy Chain sequence (SEQ ID NO: 287). Framework and CDR regions are designated using the ASN system.

FIG. 5A shows the AB-007088 Lambda Light Chain sequence (SEQ ID NO: 288). FIG. 5B shows the AB-007088 IgG1 Heavy Chain sequence (SEQ ID NO: 289). Framework and CDR regions are designated using the ASN system.

FIG. 6 shows the ASN numbering system for the light chain of AB-000224.

FIG. 7 shows the ASN numbering system for the heavy chain of AB-000224.

FIG. 8 shows the ASN numbering system for the light chain of AB-007088.

FIG. 9 shows the ASN numbering system for the heavy chain of AB-007088.

DETAILED DESCRIPTION

Figure 1A:
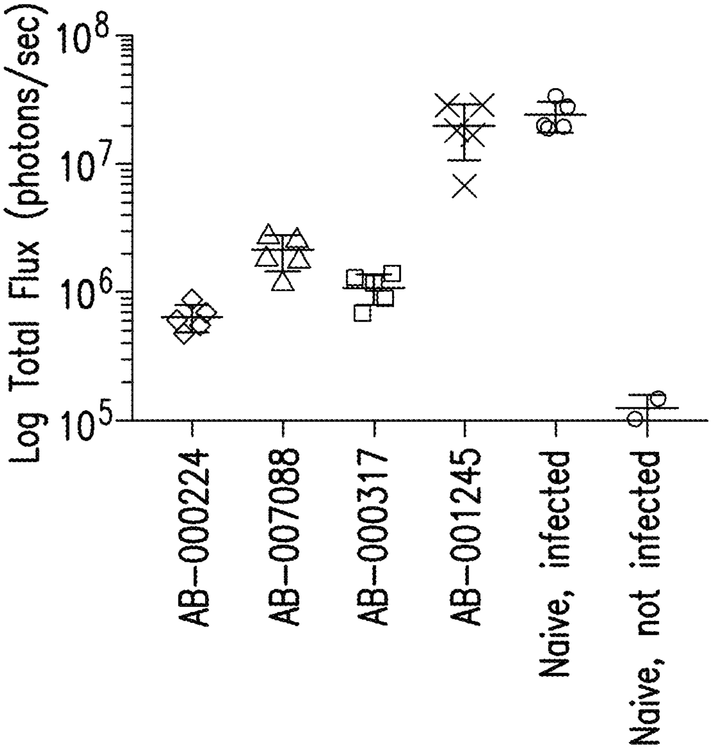
FIG. 1A illustrates parasite liver load following administration of experimental anti-CSP antibodies, AB-000224 and AB-007088. Parasite liver burden load was measured by bioluminescence (photons/sec) generated from the fluorescent sporozoites (y-axis). The individual points indicate the total amount of bioluminescence measured in a single mouse and by extension, the sporozoite liver burden. AB-001245 is a non-malaria-specific antibody that was used as a negative control. AB-000317 is a positive control.

The present disclosure is based, at least in part, on the finding of several anti-CSP antibody variants. The present disclosure surprisingly shows that the disclosed anti-CSP antibodies and variants thereof have superior properties as compared to previously disclosed antibodies.

Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

As used in this specification and the appended claims, the singular forms "a," "an" and "the" include plural referents unless the context dictates otherwise. Thus, for example, reference to "a protein" or an "antibody" includes a plurality of proteins or antibodies, respectively; reference to "a cell" includes mixtures of cells and the like.

As used herein, the term "about" or "approximately" refers to the usual error range for the respective value readily known to the skilled person in this technical field, for example, ±20%, ±10%, or ±5%, are within the intended meaning of the recited value.

As used herein, the term "antibody" means an isolated or recombinant binding agent that comprises the necessary variable region sequences to specifically bind an antigenic epitope. Therefore, an "antibody" as used herein is any form of antibody or fragment thereof that exhibits the desired biological activity, e.g., binding the specific target antigen. Thus, it is used in the broadest sense and specifically covers a monoclonal antibody (including full-length monoclonal antibodies), human antibodies, chimeric antibodies, nanobodies, diabodies, multispecific antibodies (e.g., bispecific antibodies), and antibody fragments including but not limited to scFv, Fab, and the like so long as they exhibit the desired biological activity.

"Antibody fragments" comprise a portion of an intact antibody, for example, the antigen-binding or variable region of the intact antibody. Examples of antibody fragments include Fab, Fab', F(ab')2, and Fv fragments; diabodies; linear antibodies (e.g., Zapata et al., Protein Eng. 8(10): 1057-1062 (1995)); single-chain antibody molecules (e.g., scFv); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

As used herein, "recombinant antibody" refers to an antibody wherein the exact amino acid sequence of the antibody is not naturally found in a given organism (e.g., an antibody from a mammal). In certain embodiments, this term can refer to an antibody including one or more amino acid residues that are not found in a naturally occurring antibody. In certain embodiments, a recombinant antibody can have a CDR including an amino acid residue that is not found in a naturally occurring antibody (e.g., an antibody from a mammal). In another exemplary embodiment, a recombinant antibody can have a framework (FR) including an amino acid residue that is not found in a naturally occurring antibody (e.g., an antibody from a mammal). In certain embodiments, a recombinant antibody can have a constant region including an amino acid residue that is not found in a naturally occurring antibody (e.g., an antibody from a mammal). In certain embodiments, a recombinant antibody is variant of a naturally occurring antibody (e.g., AB-000224) including at least one modification, e.g., substitution, relative to the native variable heavy chain amino acid sequence or variable light chain amino acid sequence.

For example, but without any limitation, a recombinant antibody can be an anti-CSP antibody AB-000224 disclosed herein comprising at least one modification, e.g., substitution, relative to the native AB-000224 variable heavy chain amino acid sequence (SEQ ID NO: 14) or variable light chain amino acid sequence (SEQ ID NO: 13) described herein. A recombinant antibody has improved developability, e.g., decreased heterogeneity, increased yield, increased stability, improved net charges to improve pharmacokinetics, and/or reduced immunogenicity.

As used herein, the terms, "anti-CSP antibody" and "CSP antibody" are used synonymously and refer to an antibody that binds to *Plasmodium falciparum* circumsporozoite (CSP) antigen.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

As used herein, "V-region" refers to an antibody variable region domain comprising the segments of Framework 1, CDR1, Framework 2, CDR2, Framework 3, CDR3, and Framework 4. The heavy chain V-region, VH, is a consequence of rearrangement of a V-gene (HV), a D-gene (HD), and a J-gene (HJ), in what is known as V(D)J recombination during B-cell differentiation. The light chain V-region, VL, is a consequence of the rearrangement of a V-gene (LV) and a J-gene. In certain embodiments, the terms "VH" and "heavy chain variable" refer to the heavy chain V-region of an antibody. In certain embodiments, the terms "VL" and "light chain variable" refer to the light chain V-region of an antibody.

As used herein, "complementarity-determining region (CDR)" refers to the three hypervariable regions (HVRs) in each chain that interrupt the four "framework" regions established by the light and heavy chain variable regions. The CDRs are the primary contributors to binding to an epitope of an antigen. The CDRs of each chain are referred to as CDR1, CDR2, and CDR3 numbered sequentially starting from the N-terminus, and are also identified by the chain in which the particular CDR is located. Thus, a VH CDR3 (HCDR3) is located in the variable domain of the heavy chain of the antibody in which it is found, whereas a VL CDR3 (LCDR3) is the CDR3 from the variable domain of the light chain of the antibody in which it is found. The term "CDR" is used interchangeably with "HVR" when referring to CDR sequences.

The amino acid sequences of the CDRs and framework regions can be determined using various definitions in the art, e.g., Kabat, Chothia, international ImMunoGeneTics database (IMGT), and AbM (see, e.g., Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, Structural repertoire of the human VH segments J. Mol. Biol. 227, 799,817; Al-Lazikani et al., J. Mol. Biol 1997, 273(4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29(1):207-9 (2001); MacCallum et al, Antibody-antigen interactions: Contact analysis and binding site topography, J. Mol. Biol., 262 (5), 732-745 (1996); and Martin et al, Proc. Natl Acad. Sci. USA, 86, 9268-9272 (1989); Martin, et al, Methods Enzymol., 203, 121-153, (1991); Pedersen et al, Immunomethods, 1, 126, (1992); and Rees et al, In Sternberg M. J. E. (ed.), Protein Structure Prediction. Oxford University Press, Oxford, 141-172 1996). Reference to CDRs as determined by Kabat numbering is based, for example, on Kabat et al., Sequences of Proteins of Immunological Interest, 5th Ed. Public Health Service, National Institute of Health, Bethesda, MD (1991)). Chothia CDRs are determined as defined by Chothia (see, e.g., Chothia and Lesk J. Mol. Biol. 196:901-917 (1987)). In certain embodiments, the amino acid sequences of the CDRs and framework regions are numbered using the Antibody Structural Numbering (ASN) system. Antibody Structural Numbering (ASN) is a numbering system developed based on the AHo numbering system (Honegger & Pluckthun, J. Mol. Biol. 309:657-670 (2001)) defined by Annemarie Honegger for the variable region, but extended to include constant domains. FIGS. 6-7 illustrates ASN numbering for AB-000224-LS light and heavy chain, respectively. FIGS. 8-9 illustrates ASN numbering for AB-007088-LS light and heavy chain, respectively.

An "Fc region" refers to the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ. It is understood in the art that the boundaries of the Fc region may vary, however, the human IgG heavy chain Fc region is usually defined to comprise residues C226 or P230 to its carboxyl-terminus, using the numbering according to the EU index as in Kabat et al. (1991, NIH Publication 91-3242, National Technical Information Service, Springfield, Va.). The term "Fc region" may refer to this region in isolation or this region in the context of an antibody or antibody fragment. "Fc region" includes naturally occurring allelic variants of the Fc region as well as modifications that modulate effector function. Fc regions also include variants that don't result in alterations to biological function. For example, one or more amino acids can be deleted from the N-terminus or C-terminus of the Fc region of an immunoglobulin without substantial loss of biological function. Such variants can be selected according to general rules known in the art to have minimal effect on activity (see, e.g., Bowie, et al., Science 247:306-1310, 1990). For example, for IgG4 antibodies, a single amino acid substitution (S228P according to Kabat numbering; designated IgG4Pro) may be introduced to abolish the heterogeneity observed in recombinant IgG4 antibodies (see, e.g., Angal, et al., Mol Immunol 30:105-108, 1993). In certain embodiments, the Fc region includes substitutions that improve pharmacokinetics properties of an antibody, e.g., increased serum half-life. Non-limiting examples of substitutions of the Fc region can be found in U.S. Pat. No. 8,088,376, the content of which is incorporated by reference in its entirety.

The term "equilibrium dissociation constant" abbreviated (KD), refers to the dissociation rate constant (kd, $time^{-1}$) divided by the association rate constant (ka, $time^{-1}$ $M^{-1}$). Equilibrium dissociation constants can be measured using any method. Thus, in certain embodiments, the antibodies of the present disclosure have a KD of less than about 50 nM, typically less than about 25 nM, or less than 10 nM, e.g., less than about 5 nM, or than about 1 nM and often less than about 10 nM as determined by surface plasmon resonance analysis using a biosensor system such as a Biacore® system performed at 37° C. In certain embodiments, an antibody of the present disclosure has a KD of less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$ M, less than $5\times10^{-9}$M, less than $10^{-9}$M, less than $5\times10^{-10}$M, less than $10^{-10}$M, less than $5\times10^{-11}$M, less than $10^{-11}$M, less than $5\times10^{-12}$M, less than $10^{-12}$M, less than $5\times10^{-13}$M, less than $10^{-13}$M, less than $5\times10^{-14}$M, less than $10^{-14}$M, less than $5\times10^{-15}$M, or less than $10^{-15}$M or lower as measured as a bivalent antibody. As used herein, an "improved" KD refers to a lower KD. In certain embodiments, an antibody of the present disclosure has a KD of less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$M, less than $5\times10^{-9}$M, less than $10^{-9}$M, less than $5\times10^{-10}$M, less than $10^{-10}$M, less than $5\times10^{-11}$M, less than $10^{-11}$M, less than $5\times10^{-12}$M, less than $10^{-12}$M, less than $5\times10^{-13}$M, less than $10^{-13}$M, less than $5\times10^{-14}$M, less than $10^{-14}$M, less than $5\times10^{-15}$M, or less than $10^{-15}$M or lower as measured as a monovalent antibody, such as a monovalent Fab. In certain embodiments, an anti-CSP antibody of the present disclosure has KD less than 100 pM, e.g., or less than 75 pM, e.g., in the range of 1 to 100 pM, when measured by surface plasmon resonance analysis using a biosensor system such as a Biacore® system performed at 37° C. In certain embodiments, an anti-CSP antibody of the present disclosure has KD of greater than 100 pM, e.g., in the range of 100-1000 pM or 500-1000 pM when measured by surface plasmon resonance analysis using a biosensor system such as a Biacore® system performed at 37° C.

The term "monovalent molecule" as used herein refers to a molecule that has one antigen-binding site, e.g., a Fab or scFv.

The term "bivalent molecule" as used herein refers to a molecule that has two antigen-binding sites. In certain embodiments, a bivalent molecule of the present invention is a bivalent antibody or a bivalent fragment thereof. In certain embodiments, a bivalent molecule of the present invention is a bivalent antibody. In certain embodiments, a bivalent molecule of the present invention is an IgG. In certain embodiments, monoclonal antibodies have a bivalent basic structure. IgG and IgE have only one bivalent unit, while IgA and IgM consist of multiple bivalent units (2 and 5, respectively) and thus have higher valencies. This bivalency increases the avidity of antibodies for antigens.

The terms "monovalent binding" or "monovalently binds to" as used herein refer to the binding of one antigen-binding site to its antigen.

The terms "bivalent binding" or "bivalently binds to" as used herein refer to the binding of both antigen-binding sites of a bivalent molecule to its antigen. In certain embodiments, both antigen-binding sites of a bivalent molecule share the same antigen specificity.

The term "valency" as used herein refers to the number of different binding sites of an antibody for an antigen. A monovalent antibody includes one binding site for an antigen. A bivalent antibody (e.g., a bivalent IgG antibody) includes two binding sites for the same antigen.

The term "affinity" as used herein refers to either the single or combined strength of one or both arms of an antibody (e.g., an IgG antibody) binding to either a simple or complex antigen-expressing one or more epitopes. As defined here, the term "affinity" does not imply a specific number of valencies between the two binding partners.

The phrase "specifically (or selectively) binds" to an antigen or target or "specifically (or selectively) immunoreactive with," when referring to a protein or peptide, refers to a binding reaction whereby the antibody binds to the antigen or target of interest with an affinity that can be distinguished from non-specific interactions occurring between two proteins.

The terms "identical" or percent "identity," in the context of two or more polypeptide sequences, refer to two or more sequences or subsequences that are the same or have a specified percentage of amino acid residues that are the same (e.g., at least 70%, at least 75%, at least 80%, 85%, 90%, 91%, 92%, 93%, 94%, 95%, 96%, 97%, 98%, 99%, or higher) identity over a specified region, e.g., the length of the two sequences, when compared and aligned for maximum correspondence over a comparison window or designated region. Alignment for purposes of determining percent amino acid sequence identity can be performed in various methods, including, without any limitation, BLAST, BLAST-2, ALIGN, or Megalign (DNASTAR) software. Examples of algorithms that are suitable for determining percent sequence identity and sequence similarity the BLAST 2.0 algorithms, which are described in Altschul et al., Nuc. Acids Res. 25:3389-3402 (1977) and Altschul et al., J. Mol. Biol. 215:403-410 (1990). In certain embodiments, BLAST 2.0 can be used with the default parameters to determine percent sequence identity.

A "substitution," as used herein, denotes the replacement of one or more amino acids or nucleotides by different amino acids or nucleotides, respectively.

A "conservative" substitution as used herein refers to a substitution of an amino acid such that charge, polarity, hydropathy (hydrophobic, neutral, or hydrophilic), and/or size of the side group chain is maintained. Illustrative sets of amino acids that may be substituted for one another include (i) positively-charged amino acids Lys and Arg; and His at pH of about 6; (ii) negatively charged amino acids Glu and Asp; (iii) aromatic amino acids Phe, Tyr and Trp; (iv) nitrogen ring amino acids His and Trp; (v) aliphatic hydrophobic amino acids Ala, Val, Leu and Ile, (vi) hydrophobic sulfur-containing amino acids Met and Cys, which are not as hydrophobic as Val, Leu, and Ile, (vii) small polar uncharged amino acids Ser, Thr, Asp, and Asn (viii) small hydrophobic or neutral amino acids Gly, Ala, and Pro; (ix) amide-comprising amino acids Asn and Gln; and (xi) beta-branched amino acids Thr, Val, and Ile. Reference to the charge of an amino acid refers to the charge at pH 6-7.

As used herein, the terms "nucleic acid" and "polynucleotide" are used interchangeably and as used herein refer to both sense and anti-sense strands of RNA, cDNA, genomic DNA, and synthetic forms and mixed polymers of the above. In certain embodiments, a polynucleotide refers to a polyribonucleotide, polydeoxynucleotide or a modified form of either type of nucleotide, and combinations thereof. The terms also include, but are not limited to, single- and double-stranded forms of DNA. In addition, a polynucleotide, e.g., a cDNA or mRNA, may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitutions of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular, and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-optimized nucleic acids that encode the same polypeptide sequence.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody or fragment thereof" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. A "vector," as used herein, refers to a recombinant construct in which a nucleic acid sequence of interest is inserted into the vector. Certain vectors can direct the expression of nucleic acids to which they are operatively linked. Such vectors are referred to herein as "expression vectors".

The terms "host cell," "host cell line," and "host cell culture" are used interchangeably and refer to cells into which exogenous nucleic acid has been introduced, including the progeny of such cells. A host cell can be a recombinant host cell and includes the primary transformed cell and progeny derived therefrom without regard to the number of passages.

A polypeptide "variant," as the term is used herein, is a polypeptide that typically differs from a polypeptide specifically disclosed herein in one or more substitutions, deletions, additions, and/or insertions. In the present invention, a "variant" with reference to the sequences described in the "Anti-CSP Antibody Variants" section refers to an engineered sequence, rather than a naturally occurring sequence.

The term "comparable," in the context of describing the strength of binding of two antibodies to the same target, refers to two dissociation constant (KD) values calculated from two binding reactions that are within three (3) fold from each other. In certain embodiments, the ratio between the first KD (the KD of the binding reaction between the first antibody and the target) and the second KD (the KD of the binding reaction between the second antibody and the target) is within the range of 1:3 or 3:1, endpoints exclusive. A lower KD value denotes stronger binding. For example, without any limitation, an antibody variant that has stronger binding as compared to AB-000224 binds to the target with a KD that is at least ⅓ of the KD measured against the same target for AB-000224.

Anti-CSP Antibodies

The present disclosure provides anti-CSP antibodies AB-000224 and AB-007088 and variants thereof. AB-000224 and AB-007088 were discovered in antibody repertoires generated by Immune Repertoire Capture® (IRC®) technology from plasmablast B cells isolated from two donors enrolled in a Phase 2a study evaluating the efficacy of the RTS,S vaccine in preventing malaria infection. The IRC® technology and its use in antibody discovery is well known and disclosed in, e.g., WO 2012148497A2, the entire content of which is herein incorporated by reference. The RTS,S vaccine is a pseudo-viral particle vaccine that combines the hepatitis B surface antigen and the central repeat and C-terminal regions of the *Plasmodium falciparum* (*P. falciparum*) circumsporozoite protein (CSP). RTS,S consists of two polypeptides; RTS is a single polypeptide chain corresponding to amino acids 207 to 395 of *P. falciparum* (3D7) that is fused to HBsAg and S is a polypeptide of 226 amino acids that corresponds to HBsAg. Stoute, et. al., N Engl J Med; 336:86-91(1997); RTS,S Clinical Trials Partnership, PLoS Med.11(7):e1001685, (2014), WO1993/10152.

CSP is composed of an N-terminal domain containing a heparan sulfate binding site for hepatocyte adhesion, a central repeat region, and a structured C-terminal α-thrombospondin repeat (aTSR) that is followed by a GPI anchor, which attaches CSP to the sporozoite membrane. The central repeat region of CSP is highly immunogenic, and in all *P. falciparum* strains with a CSP sequence available, the repeat region is composed of 1 NPDP repeat, 3-5 NVDP repeats, and 35-41 NANP repeats (e.g., a total of 1/4/38 of NPDP/NVDP/NANP motifs are present in the *P. falciparum* 3D7 strain). The repeat region begins with the junctional NPDP sequence, typically followed by three alternations of NANP and NVDP sequences, and continues with the remaining NANP repeats, with most *P. falciparum* strains having one NVDP interspersed in the middle of the long NANP repeat region. Pholcharee, T. et al., J. Mol. Bio. 432: 1048-1063 (2020).

In certain embodiments, the anti-CSP antibodies disclosed herein bind to the central repeat region of *P. falciparum* CSP. In certain embodiments, the antibodies disclosed herein bind to *P. falciparum* CSP protein in the repeat and/or junctional regions that contain NPNA, NPDP, and/or NVDP motifs. In certain embodiments, the anti-CSP antibodies disclosed herein bind to the NANP repeat region of *P. falciparum* CSP. In certain embodiments, the anti-CSP antibodies disclosed herein bind to a polypeptide comprising the amino acid sequence of (NPNA)3 (SEQ ID NO: 280).

In certain embodiments, the present disclosure provides anti-CSP antibody variants of AB-000224. In certain embodiments, the present disclosure provides anti-CSP antibody variants of AB-007088. In certain embodiments, the variants exhibit protective effects in vivo, e.g., as shown by a reduction in parasite number in a mouse model of malaria infection.

In certain embodiments, the anti-CSP variants disclosed herein maintain the binding specificity, activity and stability and/or manufacturing properties of the parental antibody. In certain embodiments, the anti-CSP variants disclosed herein generated have improved developability, e.g., as identified through various in vitro assays, such as aggregation assessment by HPLC or UPLC, hydrophobic interaction chromatography (HIC), polyspecificity assays (e.g., baculovirus particle binding), self-interaction nanoparticle spectroscopy (SINS), or mass spec analysis after incubation in an accelerated degradation condition such as high temperature, low pH, high pH, or oxidative $H_2O_2$. Mutations are successful if the activity is maintained (or enhanced) while removing or reducing the severity of the liability.

Antibody liabilities are further described in Table 1 below:

TABLE 1

| Description of potential development liabilities | | | |
|---|---|---|---|
| Free cysteine[1] | Yield, heterogeneity, stability, activity | sequence comprises an odd number of cysteines | High |
| N-linked glycosylation | Yield, heterogeneity, activity | N(—P)(S, T)[2] | High |
| Abnormal net charge | Platform fit, PK | Sharma 2014[3] | High |
| Patches of hydrophobicity | Stability, PK | Sharma 2014 | High |
| Patches of same charge | Stability, PK | N/A (based on structure) | Medium |
| Proteolysis | Stability, PK | (K, R)(K, R)[4] | Medium |
| Proteolysis | Stability, PK | DP | Medium |
| Asparagine deamidation | Heterogeneity, stability, activity | NG;<br>N(A, N, S, T)[5] | Medium;<br>Low |
| Aspartate isomerization | Heterogeneity, stability, activity | DG;<br>D(A, D, S, T)[6] | Medium;<br>Low |
| Lysine glycation | Heterogeneity, stability, activity | K | Low |
| Methionine oxidation | Heterogeneity, stability, activity | M | Low |
| Tryptophan oxidation | Heterogeneity, stability, activity | W | Low |

[1]"Free cysteine" refers to a cysteine that does not form a disulfide bond with another cysteine and thus is left "free" as thiols. The presence of free cysteines in the antibody can be a potential development liability. Typically, an odd net number of cysteines in the protein shows a likelihood there is a free cysteine.
[2]The N-linked glycosylation site is N-X-S/T, where X is any residue other than proline.
[3]Sharma et al., Proc. Natl. Acad. Sci. USA 111: 18601-18606, 2014.
[4]This motif consists of a K or R, followed by a K or R. Stated differently, the motif can be KK, KR, RK, or RR.
[5]The dipeptide NG poses a medium risk of development liability. The dipeptides NA, NN, NS, and NT pose a low risk of development liability. N may also exhibit low risk of liability for other successor residues, e.g., D, H, or P. Stated differently, dipeptide ND, NH, or NP poses a low risk of development liability.
[6]Similarly to the above, the dipeptide DG poses a medium risk of development liability. The dipeptides DA, DD, DS, and DT pose a low risk of development liability. D may also exhibit low risk of development liability for other successor residues, e.g., N, H, or P.

Another goal for engineering variants is to reduce the risk of clinical immunogenicity. For example, reducing the generation of anti-drug antibodies against the therapeutic antibody. In certain embodiments, the anti-CSP antibody variants have reduced immunogenicity as compared to the parental antibody.

The factors that drive clinical immunogenicity can be classified into two groups. First are factors that are intrinsic to the drug, such as sequence, post-translational modifications, aggregates, degradation products, and contaminants. Second are factors related to how the drug is used, such as dose level, dose frequency, route of administration, patient immune status, and patient HLA type.

One approach to engineering a variant to be as much like self as possible is to identify a close germline sequence and mutate as many mismatched positions (also known as "germline deviations") to the germline residue type as possible. This approach applies for germline genes IGHV, IGHJ, IGKV, IGKJ, IGLV, and IGLJ, and accounts for all of the variable heavy (V11) and variable light (VL) regions except for part of H-CDR3. Germline gene IGHD codes for part of the H-CDR3 region but typically exhibits too much variation in how it is recombined with IGHV and IGHJ (e.g., forward or reverse orientation, any of three translation frames, and 5' and 3' modifications and non-templated additions) to present a "self" sequence template from a population perspective.

Each germline gene can present as different alleles in the population. The least immunogenic drug candidate, in terms of minimizing the percent of patients with an immunogenic response, would likely be one that matches an allele commonly found in the patient population. Single nucleotide polymorphism (SNP) data from the human genome can be used to approximate the frequency of alleles in the population.

Another approach to engineering a lead for reduced immunogenicity risk is to use in silico predictions of immunogenicity, such as the prediction of T cell epitopes, or use in vitro assays of immunogenicity, such as ex vivo human T cell activation. For example, services such as those offered by Lonza, United Kingdom, are available that employ platforms for prediction of HLA binding and in vitro assessment to further identify potential epitopes.

In certain embodiments, antibody variants are additionally designed to enhance the efficacy of the antibody. Design parameters for this aspect focused on CDRs, e.g., CDR3. Positions to be mutated were identified based on structural analysis of antibody-antigen co-crystals (Oyen et al., Proc. Natl. Acad Sci. USA 114:E10438-E10445, 2017) and based on sequence information of other antibodies from the same lineage as AB-000224 or AB-007088.

1. Approaches to Mutation Design

Development liabilities can be removed or reduced by one or more mutations. Mutations are designed to preserve antibody structure and function while removing or reducing development liabilities and to improve function. In certain embodiments, mutations to chemically similar residues were identified to maintain size, shape, charge, and/or polarity. Non-limiting examples of mutations are described in Table 2 below:

TABLE 2

| | | | |
|---|---|---|---|
| Free cysteine | Odd #C | High | C(A, S) |
| N-linked glycosylation | N(—P)(S, T) | High | N-*(Q, D, S, A);<br>(S, T)-*(A, N) |
| Proteolytic cleavage | (K, R)(K, R) | Medium | K, R-*(Q, S, A) |
| Proteolytic cleavage | DP | Medium | D(E, S, A) |
| Asparagine deamidation | NG;<br>N(A, N, S, T)* | Medium;<br>Low | N-*(Q, S, A);<br>G-*(A, S) |

TABLE 2-continued

| | | | |
|---|---|---|---|
| Aspartate isomerization | DG;<br>D(A, D, S, T)* | Medium;<br>Low | D-*(E, S, A);<br>G-*(A, S) |
| Lysine glycation | K | Low | K(R, Q, S, A) |
| Methionine oxidation | M | Low | M-*(Q, L, S, A) |
| Tryptophan oxidation | W | Low | W-*(Y, F) |
| Proteolytic cleavage | (K, R)(K, R) | Medium | K, R-*(Q, S, A) |

2. Anti-CSP Antibody Variants of AB-000224

In certain embodiments, a variant of an anti-CSP antibody AB-000224 disclosed herein comprises modifications compared to AB-000224 that provide improved pharmacokinetic properties, increased serum stability, stronger binding, and/or improved in vivo protective effects compared to AB-000224. In certain embodiments, a variant of an anti-CSP antibody AB-000224 disclosed herein exhibits reduced immunogenicity and/or increased manufacturability as compared to AB-000224. In certain embodiments, a variant of an anti-CSP antibody AB-000224 disclosed herein has at least one modification, e.g., substitution, relative to the native AB-000224 variable heavy chain amino acid sequence (SEQ ID NO: 14) or variable light chain amino acid sequence (SEQ ID NO: 13) described herein, and has improved developability, e.g., decreased heterogeneity, increased yield, increased stability, improved net charges to improve pharmacokinetics, and/or reduced immunogenicity. In certain embodiments, a VH region or a VL region of such a variant of an anti-CSP antibody AB-000224 disclosed herein has at least two, three, four, five, or six, or more modifications, e.g., substitutions. In certain embodiments, a variant of the an anti-CSP antibody AB-000224 disclosed herein has a total of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 modifications, e.g. substitutions, including both variable regions, compared to AB-000224.

In certain embodiments, a variant of an anti-CSP antibody AB-000224 disclosed herein exhibits increased serum half-life as compared to AB-000224. In certain embodiments, a variant of an anti-CSP antibody AB-000224 disclosed herein has at least one modification, e.g., substitution, relative to the native AB-000224 Fc region of the heavy chain sequence described herein, and has improved pharmacokinetics properties, e.g., half-life. In certain embodiments, an Fc region of the heavy chain of such a variant of an anti-CSP antibody AB-000224 disclosed herein has at least two, three, four, five, or six, or more modifications, e.g., substitutions. In certain embodiments, a variant of an anti-CSP antibody AB-000224 disclosed herein has a total of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 modifications, e.g. substitutions, including both heavy and light chains, compared to AB-000224. In certain non-limiting embodiments, an Fc region of the heavy chain of a variant of an anti-CSP antibody AB-000224 disclosed herein can include an isoleucine at position 250, a tyrosine at position 252, an isoleucine at position 259, a glutamine at position 307, a phenylalanine at position 308, a leucine at position 319, a leucine at position 428, a histidine at position 434, a phenylalanine at position 434, an alanine at position 434, a serine at position 434, a methionine at position 434, or a combination thereof, wherein the numbering is defined by EU index as in Kabat. In certain embodiments, an Fc region of the heavy chain of a variant of an anti-CSP antibody AB-000224 disclosed herein includes a leucine at position 428 and a serine at position 434, wherein the numbering is defined by EU index as in Kabat.

The light and heavy chain CDRs of AB-000224 as defined by Kabat numbering system are shown in Table 3 below:

TABLE 3

| AB-000224 CDR sequences (Kabat) | | | |
|---|---|---|---|
| | CDR1 | CDR2 | CDR3 |
| VL region | TGMNSNIGAGYDVY<br>(SEQ ID NO: 1) | GNSNRPS<br>(SEQ ID NO: 2) | QSYDTSLNGWA<br>(SEQ ID NO: 3) |
| VH region | DHAMS<br>(SEQ ID NO: 4) | FIRKTTYGATTHYAAAVRG<br>(SEQ ID NO: 5) | VQLDYGPGYQYYGMDV<br>(SEQ ID NO: 6) |

The light and heavy chain CDRs of AB-000224 as defined by ASN numbering system are shown in Table 4 below:

TABLE 4

| AB-000224 CDR sequences (ASN) | | | |
|---|---|---|---|
| | CDR1 | CDR2 | CDR3 |
| VL region | TGMNSNIGAGYDVY<br>(SEQ ID NO: 7) | GNSNRPS<br>(SEQ ID NO: 8) | QSYDTSLNGWA<br>(SEQ ID NO: 9) |
| VH region | DHAMS<br>(SEQ ID NO: 10) | FIRKTTYGATTHYAAAVRG<br>(SEQ ID NO: 11) | VQLDYGPGYQYYGMDV<br>(SEQ ID NO: 12) |

The heavy chain variable region (VH) and light chain variable region (VL) sequences and heavy and light chain sequences of AB-000224 are shown in Table 5 below:

TABLE 5

| AB-000224 variable region and full chain sequences | |
|---|---|
| VL region | ESVLTQPPSVSGAPGQRVTISCTGMNSNIGAGYDVYWYQQLPGRAPKLLIYGNSNRP SGVPDRFSGSRSGTSASLAITGLQAEDEADYYCQSYDTSLNGWAFGGGTKLTVLG (SEQ ID NO: 13) |
| VH region | EVQLVESGGGLVQPGRSLRLPCTASGFSFGDHAMSWVRQAPGKGLEWVGFIRKTTYG ATTHYAAAVRGRFTISRDDSKSIVYLQMNSLKTEDTAVYFCTRVQLDYGPGYQYYGM DVWGQGTTVTVSS (SEQ ID NO: 14) |
| DNA for VL region | GAGTCTGTGCTGACGCAGCCGCCCTCAGTGTCTGGGGCCCCAGGGCAGAGGGTCACC ATCTCCTGCACTGGGATGAACTCCAACATCGGGGCAGGTTATGATGTATACTGGTAC CAACAACTTCCAGGAAGAGCCCCCAAACTCCTCATCTATGGTAACAGCAATCGGCCC TCAGGGGTCCCTGACCGATTCTCTGGCTCCAGGTCTGGCACCTCAGCCTCCCTGGCC ATCACTGGGCTCCAGGCTGAGGATGAGGCTGATTATTACTGCCAGTCCTATGACACC AGCCTGAATGGTTGGGCTTTCGGCGGAGGGACCAAGTTGACCGTCCTAGGC [SEQ ID NO: 15] |
| DNA for VH region | GAGGTGCAGCTGGTGGAGTCTGGGGGAGGCTTGGTACAGCCAGGGCGGTCCCTGAGA CTCCCCTGTACAGCCTCTGGGTTTAGTTTTGGTGATCATGCTATGAGCTGGGTCCGC CAGGCTCCAGGGAAGGGGCTGGAGTGGGTAGGTTTCATTAGAAAGACAACTTATGGT GCGACAACACACTACGCCGCGGCTGTGAGAGGCAGATTCACCATCTCGCGAGATGAT TCTAAAAGCATTGTCTATCTGCAAATGAACAGCCTGAAAACCGAGGACACAGCCGTG TATTTCTGTACTAGAGTGCAGCTTGACTATGGCCCGGGATACCAGTACTACGGTATG GACGTCTGGGGCCAAGGGACCACGGTCACCGTCTCCTCA [SEQ ID NO: 16] |
| Light Chain | ESVLTQPPSVSGAPGQRVTISCTGMNSNIGAGYDVYWYQQLPGRAPKLLIYGNSNRP SGVPDRFSGSRSGTSASLAITGLQAEDEADYYCQSYDTSLNGWAFGGGTKLTVLGQP KAAPSVTLFPPSSEELQANKATLVCLVSDFYPGAVTVAWKADGSPVKVGVETTKPSK QSNNKYAASSYLSLTPEQWKSHRSYSCRVTHEGSTVEKTVAPAECS [SEQ ID NO: 17] |
| Heavy Chain version 1 | EVQLVESGGGLVQPGRSLRLPCTASGFSFGDHAMSWVRQAPGKGLEWVGFIRKTTYG ATTHYAAAVRGRFTISRDDSKSIVYLQMNSLKTEDTAVYFCTRVQLDYGPGYQYYGM DVWGQGTTVTVSSASTKGPSVFPLAPSSKSTSGGTAALGCLVKDYFPEPVTVSWNSG ALTSGVHTFPAVLQSSGLYSLSSWTVPSSSLGTQTYICNVNHKPSNTKVDKKVEPK SCDKTHTCPPCPAPELLGGPSVFLFPPKPKDTLMISRTPEVTCVVVDVSHEDPEVKF NWYVDGVEVHNAKTKPREEQYNSTYRWSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 18] |
| Heavy Chain version 2 | EVQLVESGGGLVQPGRSLRLPCTASGFSFGDHAMSWVRQAPGKGLEWVGFIRKTTYG ATTHYAAAVRGRFTISRDDSKSIVYLQMNSLKTEDTAVYFCTRVQLDYGPGYQYYGM DVWGQGTTVTVSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSHEDPEVKE NWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPEN NYKTTPPVLDSDGSFFLYSKLTVDKSRWQQGNVFSCSVLHEALHSHYTQKSLSLSPG K [SEQ ID NO: 19] |
| DNA for Light Chain | GAGTCTGTGCTGACGCAGCCGCCCTCAGTGTCTGGGGCCCCAGGGCAGAGGGTCACC ATCTCCTGCACTGGGATGAACTCCAACATCGGGGCAGGTTATGATGTATACTGGTAC CAACAACTTCCAGGAAGAGCCCCCAAACTCCTCATCTATGGTAACAGCAATCGGCCC TCAGGGGTCCCTGACCGATTCTCTGGCTCCAGGTCTGGCACCTCAGCCTCCCTGGCC ATCACTGGGCTCCAGGCTGAGGATGAGGCTGATTATTACTGCCAGTCCTATGACACC AGCCTGAATGGTTGGGCTTTCGGCGGAGGGACCAAGTTGACCGTCCTAGGCCAGCCC AAGGCTGCCCCCTCGGTCACTCTGTTCCCACCCTCCTCTGAGGAGCTTCAAGCCAAC AAGGCCACACTGGTGTGTCTCGTAAGTGACTTCTACCCGGGAGCCGTGACAGTGGCC TGGAAGGCAGATGGCAGCCCCGTCAAGGTGGGAGTGGAGACCACCAAACCCTCCAAA CAAAGCAACAACAAGTATGCGGCCAGCAGCTACCTGAGCCTGACGCCCGAGCAGTGG AAGTCCCACAGAAGCTACAGCTGCCGGGTCACGCATGAAGGGAGCACCGTGGAGAAG ACAGTGGCCCCTGCAGAATGCTCT [SEQ ID NO: 20] |
| DNA for Heavy Chain version 1 | GAGGTGCAGCTGGTGGAGTCTGGGGGAGGCTTGG TACAGCCAGGGCGGTCCCTGAGACTCCCCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCATTGTCTATCTGCAAATGAACAGCCTGAAAACCGAGGACACAGCCGT GTATTTCTGTACTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCAGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT |

TABLE 5-continued

| AB-000224 variable region and full chain sequences | |
|---|---|
| | GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA<br>[SEQ ID NO: 21] |
| DNA for Heavy Chain version 2 | GAGGTGCAGCTGGTGGAGTCTGGGGGAGGCTTGG<br>TACAGCCAGGGCGGTCCCTGAGACTCCCCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAACCGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 22] |

In certain embodiments, a variant of an anti-CSP antibody includes one, two, or three CDRs of a VL sequence of Table 5. In certain embodiments, a variant of an anti-CSP antibody includes at least one mutation, e.g., substitution, and no more than 10, 20, 30, 40, or 50 mutations in the VL amino acid sequence set forth in SEQ ID NO: 13. In certain embodiments, the VL of the variant of an anti-CSP antibody includes at least one, at least two, or at least three mutations, e.g., substitutions, in the CDR1 amino acid sequence set forth in SEQ ID NO: 1. In certain embodiments, the VL of the variant of an anti-CSP antibody includes at least one, at least two, or at least three mutations, e.g., substitutions, in the CDR2 amino acid sequence set forth in SEQ ID NO: 2. In certain embodiments, the VL of the variant of an anti-CSP antibody includes at least one, at least two, or at least three mutations, e.g., substitutions, in the CDR3 amino acid sequence set forth in SEQ ID NO: 3. In certain embodiments, the VL of the variant of an anti-CSP antibody includes at least one, at least two, or at least three mutations, e.g., substitutions, in the CDR1 amino acid sequence set forth in SEQ ID NO: 7. In certain embodiments, the VL of the variant of an anti-CSP antibody includes at least one, at least two, or at least three mutations, e.g., substitutions, in the CDR2 amino acid sequence set forth in SEQ ID NO: 8. In certain embodiments, the VL of the variant of an anti-CSP antibody includes at least one, at least two, or at least three mutations, e.g., substitutions, in the CDR3 amino acid sequence set forth in SEQ ID NO: 9. In certain embodiments, the mutation is a conservative substitution. In certain embodiments, the VL of the variant of an anti-CSP antibody includes at least one, at least two, or at least three mutations, e.g., substitutions, in the framework of the amino acid sequence set forth in SEQ ID NO: 13. An exemplary nucleic acid sequence of SEQ ID NO: 13 is set forth in SEQ ID NO: 15. In certain embodiments, the VL of the variant of an anti-CSP antibody includes a substitution at position 1 of the SEQ ID NO: 13. In certain embodiments, the substitution is E1Q. In certain embodiments, the VL of the variant of an anti-CSP antibody includes a substitution at position 4 of the SEQ ID NO: 13. In certain embodiments, the substitution is R44T.

In certain embodiments, a variant of an anti-CSP antibody includes one, two, or three CDRs of a VH sequence of Table 5. In certain embodiments, a variant of an anti-CSP antibody includes at least one mutation, e.g., substitutions, and no more than 10, 20, 30, 40, or 50 mutations in the VH amino acid sequence set forth in SEQ ID NO: 14. In certain embodiments, the VH of the variant of an anti-CSP antibody includes at least one, at least two, or at least three mutations, e.g., substitutions, in the CDR1 amino acid sequence set forth in SEQ ID NO: 4. In certain embodiments, the VH of the variant of an anti-CSP antibody includes at least one, at least two, or at least three mutations, e.g., substitutions, in the CDR2 amino acid sequence set forth in SEQ ID NO: 5. In certain embodiments, the VH of the variant of an anti-CSP antibody includes at least one, at least two, or at least three mutations, e.g., substitutions, in the CDR3 amino acid sequence set forth in SEQ ID NO: 6. In certain embodiments, the VH of the variant of an anti-CSP antibody includes at least one, at least two, or at least three mutations, e.g., substitutions, in the CDR1 amino acid sequence set forth in SEQ ID NO: 10. In certain embodiments, the VH of the variant of an anti-CSP antibody includes at least one, at least two, or at least three mutations, e.g., substitutions, in the CDR2 amino acid sequence set forth in SEQ ID NO: 11. In certain embodiments, the VH of the variant of an anti-CSP antibody includes at least one, at least two, or at least three mutations, e.g., substitutions, in the CDR3 amino acid sequence set forth in SEQ ID NO: 12. In certain embodiments, the mutation is a conservative substitution. In certain embodiments, the VH of the variant of an anti-CSP antibody includes a CDR2 having a substitution at position 12 of the SEQ ID NO: 5. In certain embodiments, the substitution is H12K. In certain embodiments, the VH of the variant of an anti-CSP antibody includes a CDR2 having a substitution at position 18 of the SEQ ID NO: 5. In certain embodiments, the substitution is R18K. In certain embodiments, the mutation is a conservative substitution. In certain embodiments, the VH of the variant of an anti-CSP antibody includes a CDR2 having a substitution at position 12 of the SEQ ID NO: 11. In certain embodiments, the substitution is H12K. In certain embodiments, the VH of the variant of an anti-CSP antibody includes a CDR2 having a substitution at position 18 of the SEQ ID NO: 11. In certain embodiments, the substitution is R18K. In certain embodiments, the VH of the variant of an anti-CSP antibody includes at least one, at least two, at least three mutations, or at least four mutations, e.g., substitutions, in the framework of the amino acid sequence set forth in SEQ ID NO: 14. An exemplary nucleic acid sequence of SEQ ID NO: 14 is set forth in SEQ ID NO: 16. In certain embodiments, the VH of the variant of an anti-CSP antibody includes a substitution at position 21 of the SEQ ID NO: 14. In certain embodiments, the substitution is P21S. In certain embodiments, the VH of the variant of an anti-CSP antibody includes a substitution at position 23 of the SEQ ID NO: 14. In certain embodiments, the substitution is T23A. In certain embodiments, the VH of the variant of an anti-CSP antibody includes a substitution at position 80 of the SEQ ID NO: 14. In certain embodiments, the substitution is I80T. In certain embodiments, the VH of the variant of an anti-CSP antibody includes a substitution at position 90 of the SEQ ID NO: 14. In certain embodiments, the substitution is T90A. In certain embodiments, the VH of the variant of an anti-CSP antibody includes a substitution at position 99 of the SEQ ID NO: 14. In certain embodiments, the substitution is T99A.

In certain embodiments, a variant of an anti-CSP antibody includes at least one mutation, e.g., substitution, and no more than 10, 20, 30, 40, or 50 mutations in the Fc region of the heavy chain amino acid sequence set forth in SEQ ID NO: 18. In certain embodiments, the heavy chain of the variant of an anti-CSP antibody has an amino acid sequence set forth in SEQ ID NO: 18. An exemplary nucleic acid sequence of SEQ ID NO: 18 is set forth in SEQ ID NO: 21. In certain embodiments, the heavy chain of the variant of an anti-CSP antibody includes a substitution at position 438 of the SEQ ID NO: 18. In certain embodiments, the substitution is M438L. In certain embodiments, the heavy chain of the variant of an anti-CSP antibody includes a substitution at position 444 of the SEQ ID NO: 18. In certain embodiments, the substitution is N444S. In certain embodiments, the heavy chain of the variant of an anti-CSP antibody includes a substitution at position 438 of the SEQ ID NO: 18 and a substitution at position 444 of the SEQ ID NO: 18. In certain embodiments, the substitutions are M438L and N444S. In certain embodiments, the heavy chain of the variant of an anti-CSP antibody has an amino acid sequence set forth in SEQ ID NO: 19. An exemplary nucleic acid sequence of SEQ ID NO: 19 is set forth in SEQ ID NO: 22.

In certain embodiments, the light chain of the anti-CSP antibody AB-000224 and variants thereof comprises a signal peptide. In certain embodiments, the signal peptide is an IGLV2-8 signal peptide. In certain embodiments, the signal peptide has an amino acid sequence set forth in SEQ ID NO: 277. In certain embodiments, the heavy chain of the anti-CSP antibody AB-000224 and variants thereof comprises a signal peptide. In certain embodiments, the signal peptide is an IGKV1-39 signal peptide. In certain embodiments, the signal peptide has an amino acid sequence set forth in SEQ ID NO: 278. SEQ ID NO: 277 and SEQ ID NO: 278 are provided below:

[SEQ ID NO: 277]
MAWALLLLTLLTQGTGSWA

[SEQ ID NO: 278]
MDMRVPAQLLGLLLLWLRGARC

In certain embodiments, the anti-CSP antibody variant comprises a light chain variable region comprising a CDR1, a CDR2, and a CDR3 and having the amino acid sequence set forth in SEQ ID NO: 23, as shown in Table 6. In certain embodiments, the anti-CSP antibody variant comprises a heavy chain variable region comprising a CDR1, a CDR2, and a CDR3 and having the amino acid sequence set forth in SEQ ID NO: 24, as shown in Table 6. In certain embodiments, the anti-CSP antibody variant comprises a light chain having the amino acid sequence set forth in SEQ ID NO: 27, as shown in Table 6. In certain embodiments, the anti-CSP antibody variant comprises a heavy chain having the amino acid sequence set forth in SEQ ID NO: 28, as shown in Table 6. In certain embodiments, the anti-CSP antibody variant comprises a heavy chain having the amino acid sequence set forth in SEQ ID NO: 29, as shown in Table 6. Exemplary nucleic acid sequences of SEQ ID NOS: 23, 24, 27, 28, and 29 are provided in Table 6 below.

TABLE 6

| Antibody ID: AB-000224.001 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |

TABLE 6-continued

| Antibody ID: AB-000224.001 | | |
|---|---|---|
| | KABAT | ASN |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGAGYDVYWYQQLPGTAPKLLIYGNSNRPS<br>GVPDRFSGSRSGTSASLAITGLQAEDEADYYCQSYDTSLNGWAFGGGTKLTVLG<br>[SEQ ID NO: 23] | |
| VH | EVQLVESGGGLVQPGRSLRLSCTASGFSFGDHAMSWVRQAPGKGLEWVGFIRKTTYGA<br>TTHYAAAVRGRFTISRDDSKSIVYLQMNSLKTEDTAVYFCTRVQLDYGPGYQYYGMDV<br>WGQGTTVTVSS [SEQ ID NO: 24] | |
| DNA for VL | CAGTCTGTGCTGACGCAGCCGCCCTCAGTGTCTGGGGCCCCAGGGCAGAGGGTCACCA<br>TCTCCTGCACTGGGATGAACTCCAACATCGGGGCAGGTTATGATGTATACTGGTACCA<br>ACAACTTCCAGGAACTGCCCCCAAACTCCTCATCTATGGTAACAGCAATCGGCCCTCA<br>GGGGTCCCTGACCGATTCTCTGGCTCCAGGTCTGGCACCTCAGCCTCCCTGGCCATCA<br>CTGGGCTCCAG<br>GCTGAGGATGAGGCTGATTATTACTGCCAGTCCTATGACACCAGCCTGAATGGTTGGG<br>CTTTCGGCGGAGGGACCAAGTTGACCGTCCTAGGC [SEQ ID NO: 25] | |
| DNA for VH | GAGGTGCAGCTGGTGGAGTCTGGGGGAGGCTTGGTACAGCCAGGGCGGTCCCTGAGAC<br>TCAGCTGTACAGCCTCTGGGTTTAGTTTTGGTGATCATGCTATGAGCTGGGTCCGCCA<br>GGCTCCAGGGAAGGGGCTGGAGTGGGTAGGTTTCATTAGAAAGACAACTTATGGTGCG<br>ACAACACACTACGCCGCGGCTGTGAGAGGCAGATTCACCATCTCGCGAGATGATTCTA<br>AAAGCATTGTCTATCTGCAAATGAACAGCCTGAAAACCGAGGACACAGCCGTGTATTT<br>CTGTACTAGAGTGCAGCTTGACTATGGCCCGGGATACCAGTACTACGGTATGGACGTC<br>TGGGGCCAAGGGACCACGGTCACCGTCTCCTCA [SEQ ID NO: 26] | |
| Light Chain | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLGQPKAAPSVTLFPPSSEELQ<br>ANKATLVCLVSDFYPGAVTVAWKADGSPVKVGVETTKPSKQSNNKYAASS<br>YLSLTPEQWKSHRSYSCRVTHEGSTVEKTVAPAECS [SEQ ID NO: 27] | |
| Heavy Chain version 1 | EVQLVESGGGLVQPGRSLRLSCTASGFSFGDHAMSWVRQAPGKGLEWVGFIRKTTYGA<br>TTHYAAAVRGRFTISRDDSKSIVYLQMNSLKTEDTAVYFCTRVQLDYGPGYQYYGMDV<br>WGQGTTVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKALPAPIEKTISK<br>AKGQPREPQVYTLPPSRDELTKNQVSLTCLVKGFYPSDIAVEWESNGQPENNYKTTPP<br>VLDSDGSFFLYSKLTVDKSRWQQGNVFSCSVMHEALHNHYTQKSLSLSPGK [SEQ<br>ID NO: 28] | |
| Heavy Chain version 2 | EVQLVESGGGLVQPGRSLRLSCTASGFSFGDHAMSWVRQAPGKGLEWVGFIRKTTYGA<br>TTHYAAAVRGRFTISRDDSKSIVYLQMNSLKTEDTAVYFCTRVQLDYGPGYQYYGMDV<br>WGQGTTVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKALPAPIEKTISK<br>AKGQPREPQVYTLPPSRDELTKNQVSLTCLVKGFYPSDIAVEWESNGQPENNYKTTPP<br>VLDSDGSFFLYSKLTVDKSRWQQGNVFSCSVLHEALHSHYTQKSLSLSPGK [SEQ<br>ID NO: 29] | |
| DNA for Light Chain | CAGTCTGTGCTGACGCAGCCGCCCTCAGTGTCTGGGGCCCCAGGGCAGAGGGTCACCA<br>TCTCCTGCACTGGGATGAACTCCAACATCGGGGCAGGTTATGATGTATACTGGTACCA<br>ACAACTTCCAGGAACTGCCCCCAAACTCCTCATCTATGGTAACAGCAATCGGCCCTCA<br>GGGGTCCCTGACCGATTCTCTGGCTCCAGGTCTGGCACCTCAGCCTCCCTGGCCATCA<br>CTGGGCTCCAGGCTGAGGATGAGGCTGATTATTACTGCCAGTCCTATGACACCAGCCT<br>GAATGGTTGGGCTTTCGGCGGAGGGACCAAGTTGACCGTCCTAGGCCAGCCCAAGGCT<br>GCCCCCTCGGTCACTCTGTTCCCACCCTCCTCTGAGGAGCTTCAAGCCAACAAGGCCA<br>CACTGGTGTGTCTCGTAAGTGACTTCTACCCGGGAGCCGTGACAGTGGCCTGGAAGGC<br>AGATGGCAGCCCCGTCAAGGTGGGAGTGGAGACCACCAAACCCTCCAAACAAAGCAAC<br>AACAAGTATGCGGCCAGCAGCTACCTGAGCCTGACGCCCGAGCAGTGGAAGTCCCACA<br>GAAGCTACAGCTGCCGGGTCACGCATGAAGGGAGCACCGTGGAGAAGACAGTGGCCCC<br>TGCAGAATGCTCT [SEQ ID NO: 30] | |

TABLE 6-continued

| Antibody ID: AB-000224.001 | | |
|---|---|---|
| | KABAT | ASN |
| DNA for Heavy Chain version 1 | GAGGTGCAGCTGGTGGAGTCTGGGGGAGGCTTGGTACAGCCAGGGCGGTCCCTGAGAC<br>TCAGCTGTACAGCCTCTGGGTTTAGTTTTGGTGATCATGCTATGAGCTGGGTCCGCCA<br>GGCTCCAGGGAAGGGGCTGGAGTGGGTAGGTTTCATTAGAAAGACAACTTATGGTGCG<br>ACAACACACTACGCCGCGGCTGTGAGAGGCAGATTCACCATCTCGCGAGATGATTCTA<br>AAAGCATTGTCTATCTGCAAATGAACAGCCTGAAAACCGAGGACACAGCCGTGTATTT<br>CTGTACTAGAGTGCAGCTTGACTATGGCCCGGGATACCAGTACTACGGTATGGACGTC<br>TGGGGCCAAGGGACCACGGTCACCGTCTCCTCAGCCTCCACCAAGGGCCCATCGGTCT<br>TCCCCCTGGCACCCTCCTCCAAGAGCACCTCTGGGGGCACAGCAGCCCTGGGCTGCCT<br>GGTCAAGGACTACTTCCCCGAACCGGTGACGGTGTCGTGGAACTCAGGCGCCCTGACC<br>AGCGGCGTGCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGCAACGTGAA<br>TCACAAGCCCAGCAACACCAAGGTGGACAAGAAAGTTGAGCCCAAATCTTGTGACAAA<br>ACTCACACATGCCCACCGTGCCCAGCACCTGAACTCCTGGGGGGACCGTCAGTCTTCC<br>TCTTCCCCCCAAAACCCAAGGACACCCTCATGATCTCCCGGACCCCTGAGGTCACATG<br>CGTGGTGGTGGACGTGAGCCACGAAGACCCTGAGGTCAAGTTCAACTGGTACGTGGAC<br>GGCGTGGAGGTGCATAATGCCAAGACAAAGCCGCGGGAGGAGCAGTACAACAGCACGT<br>ACCGTGTGGTCAGCGTCCTCACCGTCCTGCACCAGGACTGGCTGAATGGCAAGGAGTA<br>CAAGTGCAAGGTCTCCAACAAAGCCCTCCCAGCCCCCATCGAGAAAACCATCTCCAAA<br>GCCAAAGGGCAGCCCCGAGAACCACAGGTGTACACCCTGCCCCCATCCCGGGATGAGC<br>TGACCAAGAACCAGGTCAGCCTGACCTGCCTGGTCAAAGGCTTCTATCCCAGCGACAT<br>CGCCGTGGAGTGGGAGAGCAATGGGCAGCCGGAGAACAACTACAAGACCACGCCTCCC<br>GTGCTGGACTCCGACGGCTCCTTCTTCCTCTACAGCAAGCTCACCGTGGACAAGAGCA<br>GGTGGCAGCAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 31] | |
| DNA for Heavy Chain version 2 | GAGGTGCAGCTGGTGGAGTCTGGGGGAGGCTTGGTACAGCCAGGGCGGTCCCTGAGAC<br>TCAGCTGTACAGCCTCTGGGTTTAGTTTTGGTGATCATGCTATGAGCTGGGTCCGCCA<br>GGCTCCAGGGAAGGGGCTGGAGTGGGTAGGTTTCATTAGAAAGACAACTTATGGTGCG<br>ACAACACACTACGCCGCGGCTGTGAGAGGCAGATTCACCATCTCGCGAGATGATTCTA<br>AAAGCATTGTCTATCTGCAAATGAACAGCCTGAAAACCGAGGACACAGCCGTGTATTT<br>CTGTACTAGAGTGCAGCTTGACTATGGCCCGGGATACCAGTACTACGGTATGGACGTC<br>TGGGGCCAAGGGACCACGGTCACCGTCTCCTCAGCCTCCACCAAGGGCCCATCGGTCT<br>TCCCCCTGGCACCCTCCTCCAAGAGCACCTCTGGGGGCACAGCAGCCCTGGGCTGCCT<br>GGTCAAGGACTACTTCCCCGAACCGGTGACGGTGTCGTGGAACTCAGGCGCCCTGACC<br>AGCGGCGTGCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGCAACGTGAA<br>TCACAAGCCCAGCAACACCAAGGTGGACAAGAAAGTTGAGCCCAAATCTTGTGACAAA<br>ACTCACACATGCCCACCGTGCCCAGCACCTGAACTCCTGGGGGGACCGTCAGTCTTCC<br>TCTTCCCCCCAAAACCCAAGGACACCCTCATGATCTCCCGGACCCCTGAGGTCACATG<br>CGTGGTGGTGGACGTGAGCCACGAAGACCCTGAGGTCAAGTTCAACTGGTACGTGGAC<br>GGCGTGGAGGTGCATAATGCCAAGACAAAGCCGCGGGAGGAGCAGTACAACAGCACGT<br>ACCGTGTGGTCAGCGTCCTCACCGTCCTGCACCAGGACTGGCTGAATGGCAAGGAGTA<br>CAAGTGCAAGGTCTCCAACAAAGCCCTCCCAGCCCCCATCGAGAAAACCATCTCCAAA<br>GCCAAAGGGCAGCCCCGAGAACCACAGGTGTACACCCTGCCCCCATCCCGGGATGAGC<br>TGACCAAGAACCAGGTCAGCCTGACCTGCCTGGTCAAAGGCTTCTATCCCAGCGACAT<br>CGCCGTGGAGTGGGAGAGCAATGGGCAGCCGGAGAACAACTACAAGACCACGCCTCCC<br>GTGCTGGACTCCGACGGCTCCTTCTTCCTCTACAGCAAGCTCACCGTGGACAAGAGCA<br>GGTGGCAGCAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 32] | |

In certain embodiments, the anti-CSP antibody variant comprises a light chain variable region comprising a CDR1, a CDR2, and a CDR3 and having the amino acid sequence set forth in SEQ ID NO: 33, as shown in Table 7. In certain embodiments, the anti-CSP antibody variant comprises a heavy chain variable region comprising a CDR1, a CDR2, and a CDR3 and having the amino acid sequence set forth in SEQ ID NO: 34, as shown in Table 75. In certain embodiments, the anti-CSP antibody variant comprises a light chain having the amino acid sequence set forth in SEQ ID NO: 37, as shown in Table 7. In certain embodiments, the anti-CSP antibody variant comprises a heavy chain having the amino acid sequence set forth in SEQ ID NO: 38, as shown in Table 7. In certain embodiments, the anti-CSP antibody variant comprises a heavy chain having the amino acid sequence set forth in SEQ ID NO: 39, as shown in Table 7. Exemplary nucleic acid sequences of SEQ ID NOS: 33, 34, 37, 38, and 39 are provided in Table 7 below.

TABLE 7

| Antibody ID: AB-000224.002 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |

TABLE 7-continued

| Antibody ID: AB-000224.002 | | |
|---|---|---|
| | KABAT | ASN |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGAGYDVYWYQQLPGTAPKLLIYGNSNRPSGVP DRFSGSRSGTSASLAITGLQAEDEADYYCQSYDTSLNGWAFGGGTKLTVLG [SEQ ID NO: 33] | |
| VH | EVQLVESGGGLVQPGRSLRLSCAASGFSFGDHAMSWVRQAPGKGLEWVGFIRKTTYGATTH YAAAVRGRFTISRDDSKSIVYLQMNSLKTEDTAVYFCTRVQLDYGPGYQYYGMDVWGQGTT VTVSS [SEQ ID NO: 34] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 35] | |
| DNA for VH | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCATTGTCTATCTGCAAATGAACAGCCTGAAAACCGAGGACACAGCCGT GTATTTCTGTACTAGAGTGCAGCTTGACTATGGCCCGGGATACCAGTACT ACGGTATGGACGTCTGGGGCCAAGGGACCACGGTCACCGTCTCCTCA [SEQ ID NO: 36] | |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADGSPVKVGVETTKPSKQSNNKYAASS YLSLTPEQWKSHRSYSCRVTHEGSTVEKTVAPAECS [SEQ ID NO: 37] | |
| Heavy Chain version 1 | EVQLVESGGGLVQPGRSLRLSCAASGFS FGDHAMSWVRQAPGKGLEWVGFIRKTTYGATTHYAAAVRGRFTISRDDSK SIVYLQMNSLKTEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 38] | |
| Heavy Chain version 2 | EVQLVESGGGLVQPGRSLRLSCAASGFS FGDHAMSWVRQAPGKGLEWVGFIRKTTYGATTHYAAAVRGRFTISRDDSK SIVYLQMNSLKTEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVLHEALHSHYTQKSLSLSPGK [SEQ ID NO: 39] | |
| DNA for Light Chain | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGCCAGCCCA AGGCTGCCCCCTCGGTCACTCTGTTCCCACCCTCCTCTGAGGAGCTTCAA GCCAACAAGGCCACACTGGTGTGTCTCGTAAGTGACTTCTACCCGGGAGC | |

TABLE 7-continued

| Antibody ID: AB-000224.002 | | |
|---|---|---|
| | KABAT | ASN |
| | CGTGACAGTGGCCTGGAAGGCAGATGGCAGCCCCGTCAAGGTGGGAGTGG<br>AGACCACCAAACCCTCCAAACAAAGCAACAACAAGTATGCGGCCAGCAGC<br>TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT [SEQ ID NO: 40] | |
| DNA for Heavy Chain version 1 | GAGGTGCAGCTGGTGGAGTCTGGGGGAGGCTTGGTACAGCCAGGGCGGTCCCTGAGACTCA<br>GCTGTGCGGCCTCTGGGTTTAGTTTTGGTGATCATGCTATGAGCTGGGTCCGCCAGGCTCC<br>AGGGAAGGGGCTGGAGTGGGTAGGTTTCATTAGAAAGACAACTTATGGTGCGACAACACAC<br>TACGCCGCGGCTGTGAGAGGCAGATTCACCATCTCGCGAGATGATTCTAAAAGCATTGTCT<br>ATCTGCAAATGAACAGCCTGAAAACCGAGGACACAGCCGTGTATTTCTGTACTAGAGTGCA<br>GCTTGACTATGGCCCGGGATACCAGTACTACGGTATGGACGTCTGGGGCCAAGGGACCACG<br>GTCACCGTCTCCTCAGCCTCCACCAAGGGCCCATCGGTCTTCCCCCTGGCACCCTCCTCCA<br>AGAGCACCTCTGGGGGCACAGCAGCCCTGGGCTGCCTGGTCAAGGACTACTTCCCCGAACC<br>GGTGACGGTGTCGTGGAACTCAGGCGCCCTGACCAGCGGCGTGCACACCTTCCCGGCTGTC<br>CTACAGTCCTCAGGACTCTACTCCCTCAGCAGCGTGGTGACCGTGCCCTCCAGCAGCTTGG<br>GCACCCAGACCTACATCTGCAACGTGAATCACAAGCCCAGCAACACCAAGGTGGACAAGAA<br>AGTTGAGCCCAAATCTTGTGACAAAACTCACACATGCCCACCGTGCCCAGCACCTGAACTC<br>CTGGGGGGACCGTCAGTCTTCCTCTTCCCCCCAAAACCCAAGGACACCCTCATGATCTCCC<br>GGACCCCTGAGGTCACATGCGTGGTGGTGGACGTGAGCCACGAAGACCCTGAGGTCAAGTT<br>CAACTGGTACGTGGACGGCGTGGAGGTGCATAATGCCAAGACAAAGCCGCGGGAGGAGCAG<br>TACAACAGCACGTACCGTGTGGTCAGCGTCCTCACCGTCCTGCACCAGGACTGGCTGAATG<br>GCAAGGAGTACAAGTGCAAGGTCTCCAACAAAGCCCTCCCAGCCCCCATCGAGAAAACCAT<br>CTCCAAAGCCAAAGGGCAGCCCCGAGAACCACAGGTGTACACCCTGCCCCCATCCCGGGAT<br>GAGCTGACCAAGAACCAGGTCAGCCTGACCTGCCTGGTCAAAGGCTTCTATCCCAGCGACA<br>TCGCCGTGGAGTGGGAGAGCAATGGGCAGCCGGAGAACAACTACAAGACCACGCCTCCCGT<br>GCTGGACTCCGACGGCTCCTTCTTCCTCTACAGCAAGCTCACCGTGGACAAGAGCAGGTGG<br>CAGCAGGGGAACGTCTTCTCATGCTCCGTGATGCATGAGGCTCTGCACAACCACTACACAC<br>AGAAGAGCCTCTCCCTGTCTCCGGGTAAA [SEQ ID NO: 41] | |
| DNA for Heavy Chain version 1 | GAGGTGCAGCTGGTGGAGTCTGGGGGAGGCTTGGTACAGCCAGGGCGGTCCCTGAGACTCA<br>GCTGTGCGGCCTCTGGGTTTAGTTTTGGTGATCATGCTATGAGCTGGGTCCGCCAGGCTCC<br>AGGGAAGGGGCTGGAGTGGGTAGGTTTCATTAGAAAGACAACTTATGGTGCGACAACACAC<br>TACGCCGCGGCTGTGAGAGGCAGATTCACCATCTCGCGAGATGATTCTAAAAGCATTGTCT<br>ATCTGCAAATGAACAGCCTGAAAACCGAGGACACAGCCGTGTATTTCTGTACTAGAGTGCA<br>GCTTGACTATGGCCCGGGATACCAGTACTACGGTATGGACGTCTGGGGCCAAGGGACCACG<br>GTCACCGTCTCCTCAGCCTCCACCAAGGGCCCATCGGTCTTCCCCCTGGCACCCTCCTCCA<br>AGAGCACCTCTGGGGGCACAGCAGCCCTGGGCTGCCTGGTCAAGGACTACTTCCCCGAACC<br>GGTGACGGTGTCGTGGAACTCAGGCGCCCTGACCAGCGGCGTGCACACCTTCCCGGCTGTC<br>CTACAGTCCTCAGGACTCTACTCCCTCAGCAGCGTGGTGACCGTGCCCTCCAGCAGCTTGG<br>GCACCCAGACCTACATCTGCAACGTGAATCACAAGCCCAGCAACACCAAGGTGGACAAGAA<br>AGTTGAGCCCAAATCTTGTGACAAAACTCACACATGCCCACCGTGCCCAGCACCTGAACTC<br>CTGGGGGGACCGTCAGTCTTCCTCTTCCCCCCAAAACCCAAGGACACCCTCATGATCTCCC<br>GGACCCCTGAGGTCACATGCGTGGTGGTGGACGTGAGCCACGAAGACCCTGAGGTCAAGTT<br>CAACTGGTACGTGGACGGCGTGGAGGTGCATAATGCCAAGACAAAGCCGCGGGAGGAGCAG<br>TACAACAGCACGTACCGTGTGGTCAGCGTCCTCACCGTCCTGCACCAGGACTGGCTGAATG<br>GCAAGGAGTACAAGTGCAAGGTCTCCAACAAAGCCCTCCCAGCCCCCATCGAGAAAACCAT<br>CTCCAAAGCCAAAGGGCAGCCCCGAGAACCACAGGTGTACACCCTGCCCCCATCCCGGGAT<br>GAGCTGACCAAGAACCAGGTCAGCCTGACCTGCCTGGTCAAAGGCTTCTATCCCAGCGACA<br>TCGCCGTGGAGTGGGAGAGCAATGGGCAGCCGGAGAACAACTACAAGACCACGCCTCCCGT<br>GCTGGACTCCGACGGCTCCTTCTTCCTCTACAGCAAGCTCACCGTGGACAAGAGCAGGTGG<br>CAGCAGGGGAACGTCTTCTCATGCTCCGTGCTGCATGAGGCTCTGCACTCCCACTACACAC<br>AGAAGAGCCTCTCCCTGTCTCCGGGTAAA [SEQ ID NO: 42] | |

In certain embodiments, the anti-CSP antibody variant comprises a light chain variable region comprising a CDR1, a CDR2, and a CDR3 and having the amino acid sequence set forth in SEQ ID NO: 43, as shown in Table 8. In certain embodiments, the anti-CSP antibody variant comprises a heavy chain variable region comprising a CDR1, a CDR2, and a CDR3 and having the amino acid sequence set forth in SEQ ID NO: 44, as shown in Table 8. In certain embodiments, the anti-CSP antibody variant comprises a light chain having the amino acid sequence set forth in SEQ ID NO: 47, as shown in Table 8. In certain embodiments, the anti-CSP antibody variant comprises a heavy chain having the amino acid sequence set forth in SEQ ID NO: 48, as shown in Table 8. In certain embodiments, the anti-CSP antibody variant comprises a heavy chain having the amino acid sequence set forth in SEQ ID NO: 49, as shown in Table 8. Exemplary nucleic acid sequences of SEQ ID NOS: 43, 44, 47, 48, and 49 are provided in Table 8 below.

TABLE 8

| Antibody ID: AB-000224.003 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |

TABLE 8-continued

| Antibody ID: AB-000224.003 | | |
|---|---|---|
| | KABAT | ASN |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 43] | |
| VH | EVQLVESGGGLVQPGRSLRLSCTASGFS FGDHAMSWVRQAPGKGLEWVGFIRKTTYGATTHYAAAVRGRFTISRDDSK STVYLQMNSLKTEDTAVYFCTRVQLDYGPGYQYYGMDVWGQGTTVTVSS [SEQ ID NO: 44] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 45] | |
| DNA for VH | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCACTGTCTATCTGCAAATGAACAGCCTGAAAACCGAGGACACAGCCGT GTATTTCTGTACTAGAGTGCAGCTTGACTATGGCCCGGGATACCAGTACT ACGGTATGGACGTCTGGGGCCAAGGGACCACGGTCACCGTCTCCTCA [SEQ ID NO: 46] | |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADGSPVKVGVETTKPSKQSNNKYAASS YLSLTPEQWKSHRSYSCRVTHEGSTVEKTVAPAECS [SEQ ID NO: 47] | |
| Heavy Chain version 1 | EVQLVESGGGLVQPGRSLRLSCTASGFS FGDHAMSWVRQAPGKGLEWVGFIRKTTYGATTHYAAAVRGRFTISRDDSK STVYLQMNSLKTEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRWSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 48] | |
| Heavy Chain version 2 | EVQLVESGGGLVQPGRSLRLSCTASGFS FGDHAMSWVRQAPGKGLEWVGFIRKTTYGATTHYAAAVRGRFTISRDDSK STVYLQMNSLKTEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVLHEALHSHYTQKSLSLSPGK [SEQ ID NO: 49] | |

TABLE 8-continued

| | Antibody ID: AB-000224.003 | |
|---|---|---|
| | KABAT | ASN |
| DNA for Light Chain | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGCCAGCCCA<br>AGGCTGCCCCCTCGGTCACTCTGTTCCCACCCTCCTCTGAGGAGCTTCAA<br>GCCAACAAGGCCACACTGGTGTGTCTCGTAAGTGACTTCTACCCGGGAGC<br>CGTGACAGTGGCCTGGAAGGCAGATGGCAGCCCCGTCAAGGTGGGAGTGG<br>AGACCACCAAACCCTCCAAACAAAGCAACAACAAGTATGCGGCCAGCAGC<br>TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT [SEQ ID NO: 50] | |
| DNA for Heavy Chain version 1 | GAGGTGCAGCTGGTGGAGTCTGGGGGAGGCTTGGTACAGCCAGGGCGGTCCCTGAGACTCA<br>GCTGTACAGCCTCTGGGTTTAGTTTTGGTGATCATGCTATGAGCTGGGTCCGCCAGGCTCC<br>AGGGAAGGGGCTGGAGTGGGTAGGTTTCATTAGAAAGACAACTTATGGTGCGACAACACAC<br>TACGCCGCGGCTGTGAGAGGCAGATTCACCATCTCGCGAGATGATTCTAAAAGCACTGTCT<br>ATCTGCAAATGAACAGCCTGAAAACCGAGGACACAGCCGTGTATTTCTGTACTAGAGTGCA<br>GCTTGACTATGGCCCGGGATACCAGTACTACGGTATGGACGTCTGGGGCCAAGGGACCACG<br>GTCACCGTCTCCTCAGCCTCCACCAAGGGCCCATCGGTCTTCCCCCTGGCACCCTCCTCCA<br>AGAGCACCTCTGGGGGCACAGCAGCCCTGGGCTGCCTGGTCAAGGACTACTTCCCCGAACC<br>GGTGACGGTGTCGTGGAACTCAGGCGCCCTGACCAGCGGCGTGCACACCTTCCCGGCTGTC<br>CTACAGTCCTCAGGACTCTACTCCCTCAGCAGCGTGGTGACCGTGCCCTCCAGCAGCTTGG<br>GCACCCAGACCTACATCTGCAACGTGAATCACAAGCCCAGCAACACCAAGGTGGACAAGAA<br>AGTTGAGCCCAAATCTTGTGACAAAACTCACACATGCCCACCGTGCCCAGCACCTGAACTC<br>CTGGGGGGACCGTCAGTCTTCCTCTTCCCCCCAAAACCCAAGGACACCCTCATGATCTCCC<br>GGACCCCTGAGGTCACATGCGTGGTGGTGGACGTGAGCCACGAAGACCCTGAGGTCAAGTT<br>CAACTGGTACGTGGACGGCGTGGAGGTGCATAATGCCAAGACAAAGCCGCGGGAGGAGCAG<br>TACAACAGCACGTACCGTGTGGTCAGCGTCCTCACCGTCCTGCACCAGGACTGGCTGAATG<br>GCAAGGAGTACAAGTGCAAGGTCTCCAACAAAGCCCTCCCAGCCCCCATCGAGAAAACCAT<br>CTCCAAAGCCAAAGGGCAGCCCCGAGAACCACAGGTGTACACCCTGCCCCCATCCCGGGAT<br>GAGCTGACCAAGAACCAGGTCAGCCTGACCTGCCTGGTCAAAGGCTTCTATCCCAGCGACA<br>TCGCCGTGGAGTGGGAGAGCAATGGGCAGCCGGAGAACAACTACAAGACCACGCCTCCCGT<br>GCTGGACTCCGACGGCTCCTTCTTCCTCTACAGCAAGCTCACCGTGGACAAGAGCAGGTGG<br>CAGCAGGGGAACGTCTTCTCATGCTCCGTGATGCATGAGGCTCTGCACAACCACTACACAC<br>AGAAGAGCCTCTCCCTGTCTCCGGGTAAA [SEQ ID NO: 51] | |
| DNA for Heavy Chain version 2 | GAGGTGCAGCTGGTGGAGTCTGGGGGAGGCTTGGTACAGCCAGGGCGGTCCCTGAGACTCA<br>GCTGTACAGCCTCTGGGTTTAGTTTTGGTGATCATGCTATGAGCTGGGTCCGCCAGGCTCC<br>AGGGAAGGGGCTGGAGTGGGTAGGTTTCATTAGAAAGACAACTTATGGTGCGACAACACAC<br>TACGCCGCGGCTGTGAGAGGCAGATTCACCATCTCGCGAGATGATTCTAAAAGCACTGTCT<br>ATCTGCAAATGAACAGCCTGAAAACCGAGGACACAGCCGTGTATTTCTGTACTAGAGTGCA<br>GCTTGACTATGGCCCGGGATACCAGTACTACGGTATGGACGTCTGGGGCCAAGGGACCACG<br>GTCACCGTCTCCTCAGCCTCCACCAAGGGCCCATCGGTCTTCCCCCTGGCACCCTCCTCCA<br>AGAGCACCTCTGGGGGCACAGCAGCCCTGGGCTGCCTGGTCAAGGACTACTTCCCCGAACC<br>GGTGACGGTGTCGTGGAACTCAGGCGCCCTGACCAGCGGCGTGCACACCTTCCCGGCTGTC<br>CTACAGTCCTCAGGACTCTACTCCCTCAGCAGCGTGGTGACCGTGCCCTCCAGCAGCTTGG<br>GCACCCAGACCTACATCTGCAACGTGAATCACAAGCCCAGCAACACCAAGGTGGACAAGAA<br>AGTTGAGCCCAAATCTTGTGACAAAACTCACACATGCCCACCGTGCCCAGCACCTGAACTC<br>CTGGGGGGACCGTCAGTCTTCCTCTTCCCCCCAAAACCCAAGGACACCCTCATGATCTCCC<br>GGACCCCTGAGGTCACATGCGTGGTGGTGGACGTGAGCCACGAAGACCCTGAGGTCAAGTT<br>CAACTGGTACGTGGACGGCGTGGAGGTGCATAATGCCAAGACAAAGCCGCGGGAGGAGCAG<br>TACAACAGCACGTACCGTGTGGTCAGCGTCCTCACCGTCCTGCACCAGGACTGGCTGAATG<br>GCAAGGAGTACAAGTGCAAGGTCTCCAACAAAGCCCTCCCAGCCCCCATCGAGAAAACCAT<br>CTCCAAAGCCAAAGGGCAGCCCCGAGAACCACAGGTGTACACCCTGCCCCCATCCCGGGAT<br>GAGCTGACCAAGAACCAGGTCAGCCTGACCTGCCTGGTCAAAGGCTTCTATCCCAGCGACA<br>TCGCCGTGGAGTGGGAGAGCAATGGGCAGCCGGAGAACAACTACAAGACCACGCCTCCCGT<br>GCTGGACTCCGACGGCTCCTTCTTCCTCTACAGCAAGCTCACCGTGGACAAGAGCAGGTGG<br>CAGCAGGGGAACGTCTTCTCATGCTCCGTGCTGCATGAGGCTCTGCACTCCCACTACACAC<br>AGAAGAGCCTCTCCCTGTCTCCGGGTAAA [SEQ ID NO: 52] | |

In certain embodiments, the anti-CSP antibody variant comprises a light chain variable region comprising a CDR1, a CDR2, and a CDR3 and having the amino acid sequence set forth in SEQ ID NO: 53, as shown in Table 9. In certain embodiments, the anti-CSP antibody variant comprises a heavy chain variable region comprising a CDR1, a CDR2, and a CDR3 and having the amino acid sequence set forth in SEQ ID NO: 55, as shown in Table 9. In certain embodiments, the anti-CSP antibody variant comprises a light chain having the amino acid sequence set forth in SEQ ID NO: 57, as shown in Table 9. In certain embodiments, the anti-CSP antibody variant comprises a heavy chain having the amino acid sequence set forth in SEQ ID NO: 58, as shown in Table 9. In certain embodiments, the anti-CSP antibody variant comprises a heavy chain having the amino acid sequence set forth in SEQ ID NO: 59, as shown in Table 9. Exemplary nucleic acid sequences of SEQ ID NOS: 53, 54, 57, 58, and 59 are provided in Table 9 below.

TABLE 9

| Antibody ID: AB-000224.004 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGAGYDVYWYQQLPGTAPKLLIYGNSNRPSGVP DRFSGSRSGTSASLAITGLQAEDEADYYCQSYDTSLNGWAFGGGTKLTVLG [SEQ ID NO: 53] | |
| VH | EVQLVESGGGLVQPGRSLRLSCTASGFSFGDHAMSWVRQAPGKGLEWVGFIRKTTYGATTH YAAAVRGRFTISRDDSKSIVYLQMNSLKAEDTAVYFCTRVQLDYGPGYQYYGMDVWGQGTT VTVSS [SEQ ID NO: 54] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 55] | |
| DNA for VH | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGOATTGTOTATCTGCAAATGAACAGCCTGAAAGCAGAGGACACAGCCGT GTATTTCTGTACTAGAGTGCAGCTTGACTATGGCCCGGGATACCAGTACT ACGGTATGGACGTCTGGGGCCAAGGGACCACGGTCACCGTCTCCTCA [SEQ ID NO: 56] | |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADGSPVKVGVETTKPSKQSNNKYAASS YLSLTPEQWKSHRSYSCRVTHEGSTVEKTVAPAECS [SEQ ID NO: 57] | |
| Heavy Chain version 1 | EVQLVESGGGLVQPGRSLRLSCTASGFS FGDHAMSWVRQAPGKGLEWVGFIRKTTYGATTHYAAAVRGRFTISRDDSK SIVYLQMNSLKAEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 58] | |
| Heavy Chain version 2 | EVQLVESGGGLVQPGRSLRLSCTASGFS FGDHAMSWVRQAPGKGLEWVGFIRKTTYGATTHYAAAVRGRFTISRDDSK SIVYLQMNSLKAEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVLHEALHSHYTQKSLSLSPGK [SEQ ID NO: 59] | |
| DNA for Light Chain | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT | |

TABLE 9-continued

| Antibody ID: AB-000224.004 | |
|---|---|
| KABAT | ASN |
| | CTGGCTCCAGGTCTGGCACCTCAGCCTCCCTGGCCATCACTGGGCTCCAG |
| | GCTGAGGATGAGGCTGATTATTACTGCCAGTCCTATGACACCAGCCTGAA |
| | TGGTTGGGCTTTCGGCGGAGGGACCAAGTTGACCGTCCTAGGCCAGCCCA |
| | AGGCTGCCCCCTCGGTCACTCTGTTCCCACCCTCCTCTGAGGAGCTTCAA |
| | GCCAACAAGGCCACACTGGTGTGTCTCGTAAGTGACTTCTACCCGGGAGC |
| | CGTGACAGTGGCCTGGAAGGCAGATGGCAGCCCCGTCAAGGTGGGAGTGG |
| | AGACCACCAAACCCTCCAAACAAAGCAACAACAAGTATGCGGCCAGCAGC |
| | TACCTGAGCCTGACGCCCGAGCAGTGGAAGTCCCACAGAAGCTACAGCTG |
| | CCGGGTCACGCATGAAGGGAGCACCGTGGAGAAGACAGTGGCCCCTGCAG |
| | AATGCTCT [SEQ ID NO: 60] |
| DNA | GAGGTGCAGCTGGTGGAGTCTGGGGGAGGCTTGG |
| for | TACAGCCAGGGCGGTCCCTGAGACTCAGCTGTACAGCCTCTGGGTTTAGT |
| Heavy | TTTGGTGATCATGCTATGAGCTGGGTCCGCCAGGCTCCAGGGAAGGGGCT |
| Chain | GGAGTGGGTAGGTTTCATTAGAAAGACAACTTATGGTGCGACAACACACT |
| version | ACGCCGCGGCTGTGAGAGGCAGATTCACCATCTCGCGAGATGATTCTAAA |
| 1 | AGCATTGTCTATCTGCAAATGAACAGCCTGAAAGCAGAGGACACAGCCGT |
| | GTATTTCTGTACTAGAGTGCAGCTTGACTATGGCCCGGGATACCAGTACT |
| | ACGGTATGGACGTCTGGGGCCAAGGGACCACGGTCACCGTCTCCTCAGCC |
| | TCCACCAAGGGCCCATCGGTCTTCCCCCTGGCACCCTCCTCCAAGAGCAC |
| | CTCTGGGGGCACAGCAGCCCTGGGCTGCCTGGTCAAGGACTACTTCCCCG |
| | AACCGGTGACGGTGTCGTGGAACTCAGGCGCCCTGACCAGCGGCGTGCAC |
| | ACCTTCCCGGCTGTCCTACAGTCCTCAGGACTCTACTCCCTCAGCAGCGT |
| | GGTGACCGTGCCCTCCAGCAGCTTGGGCACCCAGACCTACATCTGCAACG |
| | TGAATCACAAGCCCAGCAACACCAAGGTGGACAAGAAAGTTGAGCCCAAA |
| | TCTTGTGACAAAACTCACACATGCCCACCGTGCCCAGCACCTGAACTCCT |
| | GGGGGGACCGTCAGTCTTCCTCTTCCCCCCAAAACCCAAGGACACCCTCA |
| | TGATCTCCCGGACCCCTGAGGTCACATGCGTGGTGGTGGACGTGAGCCAC |
| | GAAGACCCTGAGGTCAAGTTCAACTGGTACGTGGACGGCGTGGAGGTGCA |
| | TAATGCCAAGACAAAGCCGCGGGAGGAGCAGTACAACAGCACGTACCGTG |
| | TGGTCAGCGTCCTCACCGTCCTGCACCAGGACTGGCTGAATGGCAAGGAG |
| | TACAAGTGCAAGGTCTCCAACAAAGCCCTCCCAGCCCCCATCGAGAAAAC |
| | CATCTCCAAAGCCAAAGGGCAGCCCCGAGAACCACAGGTGTACACCCTGC |
| | CCCCATCCCGGGATGAGCTGACCAAGAACCAGGTCAGCCTGACCTGCCTG |
| | GTCAAAGGCTTCTATCCCAGCGACATCGCCGTGGAGTGGGAGAGCAATGG |
| | GCAGCCGGAGAACAACTACAAGACCACGCCTCCCGTGCTGGACTCCGACG |
| | GCTCCTTCTTCCTCTACAGCAAGCTCACCGTGGACAAGAGCAGGTGGCAG |
| | CAGGGGAACGTCTTCTCATGCTCCGTGATGCATGAGGCTCTGCACAACCA |
| | CTACACACAGAAGAGCCTCTCCCTGTCTCCGGGTAAA [SEQ ID NO: 61] |
| DNA | GAGGTGCAGCTGGTGGAGTCTGGGGGAGGCTTGG |
| for | TACAGCCAGGGCGGTCCCTGAGACTCAGCTGTACAGCCTCTGGGTTTAGT |
| Heavy | TTTGGTGATCATGCTATGAGCTGGGTCCGCCAGGCTCCAGGGAAGGGGCT |
| Chain | GGAGTGGGTAGGTTTCATTAGAAAGACAACTTATGGTGCGACAACACACT |
| version | ACGCCGCGGCTGTGAGAGGCAGATTCACCATCTCGCGAGATGATTCTAAA |
| 2 | AGCATTGTCTATGTGCAAATGAACAGCCTGAAAGCAGAGGACACAGCCGT |
| | GTATTTCTGTACTAGAGTGCAGCTTGACTATGGCCCGGGATACCAGTACT |
| | ACGGTATGGACGTCTGGGGCCAAGGGACCACGGTCACCGTCTCCTCAGCC |
| | TCCACCAAGGGCCCATCGGTCTTCCCCCTGGCACCCTCCTCCAAGAGCAC |
| | CTCTGGGGGCACAGCAGCCCTGGGCTGCCTGGTCAAGGACTACTTCCCCG |
| | AACCGGTGACGGTGTCGTGGAACTCAGGCGCCCTGACCAGCGGCGTGCAC |
| | ACCTTCCCGGCTGTCCTACAGTCCTCAGGACTCTACTCCCTCAGCAGCGT |
| | GGTGACCGTGCCCTCCAGCAGCTTGGGCACCCAGACCTACATCTGCAACG |
| | TGAATCACAAGCCCAGCAACACCAAGGTGGACAAGAAAGTTGAGCCCAAA |
| | TCTTGTGACAAAACTCACACATGCCCACCGTGCCCAGCACCTGAACTCCT |
| | GGGGGGACCGTCAGTCTTCCTCTTCCCCCCAAAACCCAAGGACACCCTCA |
| | TGATCTCCCGGACCCCTGAGGTCACATGCGTGGTGGTGGACGTGAGCCAC |
| | GAAGACCCTGAGGTCAAGTTCAACTGGTACGTGGACGGCGTGGAGGTGCA |
| | TAATGCCAAGACAAAGCCGCGGGAGGAGCAGTACAACAGCACGTACCGTG |
| | TGGTCAGCGTCCTCACCGTCCTGCACCAGGACTGGCTGAATGGCAAGGAG |
| | TACAAGTGCAAGGTCTCCAACAAAGCCCTCCCAGCCCCCATCGAGAAAAC |
| | CATCTCCAAAGCCAAAGGGCAGCCCCGAGAACCACAGGTGTACACCCTGC |
| | CCCCATCCCGGGATGAGCTGACCAAGAACCAGGTCAGCCTGACCTGCCTG |
| | GTCAAAGGCTTCTATCCCAGCGACATCGCCGTGGAGTGGGAGAGCAATGG |
| | GCAGCCGGAGAACAACTACAAGACCACGCCTCCCGTGCTGGACTCCGACG |
| | GCTCCTTCTTCCTCTACAGCAAGCTCACCGTGGACAAGAGCAGGTGGCAG |
| | CAGGGGAACGTCTTCTCATGCTCCGTGCTGCATGAGGCTCTGCACTCCCA |
| | CTACACACAGAAGAGCCTCTCCCTGTCTCCGGGTAAA [SEQ ID NO: 62] |

In certain embodiments, the anti-CSP antibody variant comprises a light chain variable region comprising a CDR1, a CDR2, and a CDR3 and having the amino acid sequence set forth in SEQ ID NO: 63, as shown in Table 10. In certain embodiments, the anti-CSP antibody variant comprises a heavy chain variable region comprising a CDR1, a CDR2, and a CDR3 and having the amino acid sequence set forth in SEQ ID NO: 64, as shown in Table 10. In certain embodiments, the anti-CSP antibody variant comprises a light chain having the amino acid sequence set forth in SEQ ID NO: 67, as shown in Table 10. In certain embodiments, the anti-CSP antibody variant comprises a heavy chain having the amino acid sequence set forth in SEQ ID NO: 68, as shown in Table 10. In certain embodiments, the anti-CSP antibody variant comprises a heavy chain having the amino acid sequence set forth in SEQ ID NO: 69, as shown in Table 10. Exemplary nucleic acid sequences of SEQ ID NOS: 63, 64, 67, 68, and 69 are provided in Table 10 below.

TABLE 10

| Antibody ID: AB-000224.005 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLG<br>[SEQ ID NO: 63] | |
| VH | EVQLVESGGGLVQPGRSLRLSCTASGFS<br>FGDHAMSWVRQAPGKGLEWVGFIRKTTYGATTHYAAAVRGRFTISRDDSK<br>STVYLQMNSLKTEDTAVYFCARVQLDYGPGYQYYGMDVWGQGTTVTVSS<br>[SEQ ID NO: 64] | |
| DNA for VL | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGC<br>[SEQ ID NO: 65] | |
| DNA for VH | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAACCGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCA<br>[SEQ ID NO: 66] | |
| Light Chain | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLGQPKAAPSVTLFPPSSEELQ<br>ANKATLVCLVSDFYPGAVTVAWKADGSPVKVGVETTKPSKQSNNKYAASS<br>YLSLTPEQWKSHRSYSCRVTHEGSTVEKTVAPAECS<br>[SEQ ID NO: 67] | |
| Heavy Chain version 1 | EVQLVESGGGLVQPGRSLRLSCTASGFS<br>FGDHAMSWVRQAPGKGLEWVGFIRKTTYGATTHYAAAVRGRFTISRDDSK<br>SIVYLQMNSLKTEDTAVYFCARVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVMHEALHNHYTQKSLSLSPGK<br>[SEQ ID NO: 68] | |
| Heavy Chain version 2 | EVQLVESGGGLVQPGRSLRLSCTASGFS<br>FGDHAMSWVRQAPGKGLEWVGFIRKTTYGATTHYAAAVRGRFTISRDDSK<br>SIVYLQMNSLKTEDTAVYFCARVQLDYGPGYQYYGMDVWGQGTTVTVSSA<br>STKGPSVFPLAPSSKSTSGGTAALGCLVKDYFPEPVTVSWNSGALTSGVH | |

TABLE 10-continued

Antibody ID: AB-000224.005

| | KABAT | ASN |
|---|---|---|
| | TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVLHEALHSHYTQKSLSLSPGK [SEQ ID NO: 69] | |
| DNA for Light Chain | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGCCAGCCCA<br>AGGCTGCCCCCTCGGTCACTCTGTTCCCACCCTCCTCTGAGGAGCTTCAA<br>GCCAACAAGGCCACACTGGTGTGTCTCGTAAGTGACTTCTACCCGGGAGC<br>CGTGACAGTGGCCTGGAAGGCAGATGGCAGCCCCGTCAAGGTGGGAGTGG<br>AGACCACCAAACCCTCCAAACAAAGCAACAACAAGTATGCGGCCAGCAGC<br>TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT<br>[SEQ ID NO: 70] | |
| DNA for Heavy Chain version 1 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAACCGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 71] | |
| DNA for Heavy Chain version 2 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAACCGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG | |

TABLE 10-continued

| Antibody ID: AB-000224.005 | |
|---|---|
| KABAT | ASN |
| GCAGCCGGAGAACAACTACAAGACCACGCCTCCCGTGCTGGACTCCGACG GCTCCTTCTTCCTCTACAGCAAGCTCACCGTGGACAAGAGCAGGTGGCAG CAGGGGAACGTCTTCTCATGCTCCGTGCTGCATGAGGCTCTGCACTCCCA CTACACACAGAAGAGCCTCTCCCTGTCTCCGGGTAAA [SEQ ID NO: 72] | |

In certain embodiments, the anti-CSP antibody variant comprises a light chain variable region comprising a CDR1, a CDR2, and a CDR3 and having the amino acid sequence set forth in SEQ ID NO: 73, as shown in Table 11. In certain embodiments, the anti-CSP antibody variant comprises a heavy chain variable region comprising a CDR1, a CDR2, and a CDR3 and having the amino acid sequence set forth in SEQ ID NO: 74, as shown in Table 11. In certain embodiments, the anti-CSP antibody variant comprises a light chain having the amino acid sequence set forth in SEQ ID NO: 77, as shown in Table 11. In certain embodiments, the anti-CSP antibody variant comprises a heavy chain having the amino acid sequence set forth in SEQ ID NO: 78, as shown in Table 11. In certain embodiments, the anti-CSP antibody variant comprises a heavy chain having the amino acid sequence set forth in SEQ ID NO: 79, as shown in Table 11. Exemplary nucleic acid sequences of SEQ ID NOS: 73, 74, 77, 78, and 79 are provided in Table 11 below.

TABLE 11

| Antibody ID: AB-000224.006 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 73] | |
| VH | EVQLVESGGGLVQPGRSLRLSCAASGFS FGDHAMSWVRQAPGKGLEWVGFIRKTTYGATTHYAAAVRGRFTISRDDSK STVYLQMNSLKTEDTAVYFCTRVQLDYGPGYQYYGMDVWGQGTTVTVSS [SEQ ID NO: 74] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 75] | |
| DNA for VH | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCACTGTCTATCTGCAAATGAACAGCCTGAAAACCGAGGACACAGCCGT GTATTTCTGTACTAGAGTGCAGCTTGACTATGGCCCGGGATACCAGTACT ACGGTATGGACGTCTGGGGCCAAGGGACCACGGTCACCGTCTCCTCA [SEQ ID NO: 76] | |

TABLE 11-continued

| Antibody ID: AB-000224.006 | |
|---|---|
| | KABAT ASN |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADGSPVKVGVETTKPSKQSNNKYAASS YLSLTPEQWKSHRSYSCRVTHEGSTVEKTVAPAECS [SEQ ID NO: 77] |
| Heavy Chain version 1 | EVQLVESGGGLVQPGRSLRLSCAASGFS FGDHAMSWVRQAPGKGLEWVGFIRKTTYGATTHYAAAVRGRFTISRDDSK STVYLQMNSLKTEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 78] |
| Heavy Chain version 2 | EVQLVESGGGLVQPGRSLRLSCAASGFS FGDHAMSWVRQAPGKGLEWVGFIRKTTYGATTHYAAAVRGRFTISRDDSK STVYLQMNSLKTEDTAVYFCTRVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVLHEALHSHYTQKSLSLSPGK [SEQ ID NO: 79] |
| DNA for Light Chain | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGCCAGCCCA AGGCTGCCCCCTCGGTCACTCTGTTCCCACCCTCCTCTGAGGAGCTTCAA GCCAACAAGGCCACACTGGTGTGTCTCGTAAGTGACTTCTACCCGGGAGC CGTGACAGTGGCCTGGAAGGCAGATGGCAGCCCCGTCAAGGTGGGAGTGG AGACCACCAAACCCTCCAAACAAAGCAACAACAAGTATGCGGCCAGCAGC TACCTGAGCCTGACGCCCGAGCAGTGGAAGTCCCACAGAAGCTACAGCTG CCGGGTCACGCATGAAGGGAGCACCGTGGAGAAGACAGTGGCCCCTGCAG AATGCTCT [SEQ ID NO: 80] |
| DNA for Heavy Chain version 1 | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCACTGTCTATCTGCAAATGAACAGCCTGAAAACCGAGGACACAGCCGT GTATTTCTGTACTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCAGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT GGGGGGACCGTCAGTCTTCCTCTTCCCCCCAAAACCCAAGGACACCCTCA TGATCTCCCGGACCCCTGAGGTCACATGCGTGGTGGTGGACGTGAGCCAC GAAGACCCTGAGGTCAAGTTCAACTGGTACGTGGACGGCGTGGAGGTGCA TAATGCCAAGACAAAGCCGCGGGAGGAGCAGTACAACAGCACGTACCGTG TGGTCAGCGTCCTCACCGTCCTGCACCAGGACTGGCTGAATGGCAAGGAG TACAAGTGCAAGGTCTCCAACAAAGCCCTCCCAGCCCCCATCGAGAAAAC CATCTCCAAAGCCAAAGGGCAGCCCCGAGAACCACAGGTGTACACCCTGC CCCCATCCCGGGATGAGCTGACCAAGAACCAGGTCAGCCTGACCTGCCTG GTCAAAGGCTTCTATCCCAGCGACATCGCCGTGGAGTGGGAGAGCAATGG GCAGCCGGAGAACAACTACAAGACCACGCCTCCCGTGCTGGACTCCGACG GCTCCTTCTTCCTCTACAGCAAGCTCACCGTGGACAAGAGCAGGTGGCAG CAGGGGAACGTCTTCTCATGCTCCGTGATGCATGAGGCTCTGCACAACCA CTACACACAGAAGAGCCTCTCCCTGTCTCCGGGTAAA [SEQ ID NO: 81] |

TABLE 11-continued

| Antibody ID: AB-000224.006 | | |
|---|---|---|
| | KABAT | ASN |
| DNA for Heavy Chain version 2 | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCACTGTCTATCTGCAAATGAACAGCCTGAAAACCGAGGACACAGCCGT GTATTTCTGTACTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCAGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT GGGGGGACCGTCAGTCTTCCTCTTCCCCCCAAAACCCAAGGACACCCTCA TGATCTCCCGGACCCCTGAGGTCACATGCGTGGTGGTGGACGTGAGCCAC GAAGACCCTGAGGTCAAGTTCAACTGGTACGTGGACGGCGTGGAGGTGCA TAATGCCAAGACAAAGCCGCGGGAGGAGCAGTACAACAGCACGTACCGTG TGGTCAGCGTCCTCACCGTCCTGCACCAGGACTGGCTGAATGGCAAGGAG TACAAGTGCAAGGTCTCCAACAAAGCCCTCCCAGCCCCCATCGAGAAAAC CATCTCCAAAGCCAAAGGGCAGCCCCGAGAACCACAGGTGTACACCCTGC CCCCATCCCGGGATGAGCTGACCAAGAACCAGGTCAGCCTGACCTGCCTG GTCAAAGGCTTCTATCCCAGCGACATCGCCGTGGAGTGGGAGAGCAATGG GCAGCCGGAGAACAACTACAAGACCACGCCTCCCGTGCTGGACTCCGACG GCTCCTTCTTCCTCTACAGCAAGCTCACCGTGGACAAGAGCAGGTGGCAG CAGGGGAACGTCTTCTCATGCTCCGTGCTGCATGAGGCTCTGCACTCCCA CTACACACAGAAGAGCCTCTCCCTGTCTCCGGGTAAA [SEQ ID NO: 82] | |

In certain embodiments, the anti-CSP antibody variant comprises a light chain variable region comprising a CDR1, a CDR2, and a CDR3 and having the amino acid sequence set forth in SEQ ID NO: 83, as shown in Table 12. In certain embodiments, the anti-CSP antibody variant comprises a heavy chain variable region comprising a CDR1, a CDR2, and a CDR3 and having the amino acid sequence set forth in SEQ ID NO: 84, as shown in Table 12. In certain embodiments, the anti-CSP antibody variant comprises a light chain having the amino acid sequence set forth in SEQ ID NO: 87, as shown in Table 12. In certain embodiments, the anti-CSP antibody variant comprises a heavy chain having the amino acid sequence set forth in SEQ ID NO: 88, as shown in Table 12. In certain embodiments, the anti-CSP antibody variant comprises a heavy chain having the amino acid sequence set forth in SEQ ID NO: 89, as shown in Table 12. Exemplary nucleic acid sequences of SEQ ID NOS: 83, 84, 87, 88, and 89 are provided in Table 12 below.

TABLE 12

| Antibody ID: AB-000224.007 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 83] | |
| VH | EVQLVESGGGLVQPGRSLRLSCAASGFS FGDHAMSWVRQAPGKGLEWVGFIRKTTYGATTHYAAAVRGRFTISRDDSK SIVYLQMNSLKAEDTAVYFCTRVQLDYGPGYQYYGMDVWGQGTTVTVSS [SEQ ID NO: 84] | |

TABLE 12-continued

| | |
|---|---|
| Antibody ID: AB-000224.007 | |
| | KABAT ASN |
| DNA for VL | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGC<br>[SEQ ID NO: 85] |
| DNA for VH | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGOATTGTOTATCTGCAAATGAACAGCCTGAAAGCAGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCA<br>[SEQ ID NO: 86] |
| Light Chain | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLGQPKAAPSVTLFPPSSEELQ<br>ANKATLVCLVSDFYPGAVTVAWKADGSPVKVGVETTKPSKQSNNKYAASS<br>YLSLTPEQWKSHRSYSCRVTHEGSTVEKTVAPAECS<br>[SEQ ID NO: 87] |
| Heavy Chain version 1 | EVQLVESGGGLVQPGRSLRLSCAASGFS<br>FGDHAMSWVRQAPGKGLEWVGFIRKTTYGATTHYAAAVRGRFTISRDDSK<br>SIVYLQMNSLKAEDTAVYFCTRVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVMHEALHNHYTQKSLSLSPGK<br>[SEQ ID NO: 88] |
| Heavy Chain version 2 | EVQLVESGGGLVQPGRSLRLSCAASGFS<br>FGDHAMSWVRQAPGKGLEWVGFIRKTTYGATTHYAAAVRGRFTISRDDSK<br>SIVYLQMNSLKAEDTAVYFCTRVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVLHEALHSHYTQKSLSLSPGK [SEQ ID NO: 89] |
| DNA for Light Chain | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGCCAGCCCA<br>AGGCTGCCCCCTCGGTCACTCTGTTCCCACCCTCCTCTGAGGAGCTTCAA<br>GCCAACAAGGCCACACTGGTGTGTCTCGTAAGTGACTTCTACCCGGGAGC<br>CGTGACAGTGGCCTGGAAGGCAGATGGCAGCCCCGTCAAGGTGGGAGTGG<br>AGACCACCAAACCCTCCAAACAAAGCAACAACAAGTATGCGGCCAGCAGC<br>TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT<br>[SEQ ID NO: 90] |
| DNA for Heavy Chain version 1 | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGGATTGTCTATGTGCAAATGAACAGCCTGAAAGCAGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG |

TABLE 12-continued

| Antibody ID: AB-000224.007 | | |
|---|---|---|
| | KABAT | ASN |
| | AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 91] | |
| DNA for Heavy Chain version 2 | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCATTGTCTATCTGCAAATGAACAGCCTGAAAGCAGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 92] | |

In certain embodiments, the anti-CSP antibody variant comprises a light chain variable region comprising a CDR1, a CDR2, and a CDR3 and having the amino acid sequence set forth in SEQ ID NO: 93, as shown in Table 13. In certain embodiments, the anti-CSP antibody variant comprises a heavy chain variable region comprising a CDR1, a CDR2, and a CDR3 and having the amino acid sequence set forth in SEQ ID NO: 94, as shown in Table 13. In certain embodiments, the anti-CSP antibody variant comprises a light chain having the amino acid sequence set forth in SEQ ID NO: 97, as shown in Table 13. In certain embodiments, the anti-CSP antibody variant comprises a heavy chain having the amino acid sequence set forth in SEQ ID NO: 98, as shown in Table 13. In certain embodiments, the anti-CSP antibody variant comprises a heavy chain having the amino acid sequence set forth in SEQ ID NO: 99, as shown in Table 13. Exemplary nucleic acid sequences of SEQ ID NOS: 93, 94, 97, 98, and 99 are provided in Table 13 below.

TABLE 13

| Antibody ID: AB-000224.008 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |

TABLE 13-continued

| Antibody ID: AB-000224.008 | | |
|---|---|---|
| | KABAT | ASN |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 93] | |
| VH | EVQLVESGGGLVQPGRSLRLSCAASGFS FGDHAMSWVRQAPGKGLEWVGFIRKTTYGATTHYAAAVRGRFTISRDDSK SIVYLQMNSLKTEDTAVYFCARVQLDYGPGYQYYGMDVWGQGTTVTVSS [SEQ ID NO: 94] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 95] | |
| DNA for VH | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCATTGTCTATCTGCAAATGAACAGCCTGAAAACCGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCA [SEQ ID NO: 96] | |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADGSPVKVGVETTKPSKQSNNKYAASS YLSLTPEQWKSHRSYSCRVTHEGSTVEKTVAPAECS [SEQ ID NO: 97] | |
| Heavy Chain version 1 | EVQLVESGGGLVQPGRSLRLSCAASGFS FGDHAMSWVRQAPGKGLEWVGFIRKTTYGATTHYAAAVRGRFTISRDDSK SIVYLQMNSLKTEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 98] | |
| Heavy Chain version 2 | EVQLVESGGGLVQPGRSLRLSCAASGFS FGDHAMSWVRQAPGKGLEWVGFIRKTTYGATTHYAAAVRGRFTISRDDSK SIVYLQMNSLKTEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVLHEALHSHYTQKSLSLSPGK [SEQ ID NO: 99] | |
| DNA for Light Chain | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGCCAGCCCA | |

TABLE 13-continued

| Antibody ID: AB-000224.008 | |
|---|---|
| | KABAT ASN |
| | AGGCTGCCCCCTCGGTCACTCTGTTCCCACCCTCCTCTGAGGAGCTTCAA GCCAACAAGGCCACACTGGTGTGTCTCGTAAGTGACTTCTACCCGGGAGC CGTGACAGTGGCCTGGAAGGCAGATGGCAGCCCCGTCAAGGTGGGAGTGG AGACCACCAAACCCTCCAAACAAAGCAACAACAAGTATGCGGCCAGCAGC TACCTGAGCCTGACGCCCGAGCAGTGGAAGTCCCACAGAAGCTACAGCTG CCGGGTCACGCATGAAGGGAGCACCGTGGAGAAGACAGTGGCCCCTGCAG AATGCTCT [SEQ ID NO: 100] |
| DNA for Heavy Chain version 1 | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCATTGTCTATCTGCAAATGAACAGCCTGAAAACCGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCAGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT GGGGGGACCGTCAGTCTTCCTCTTCCCCCCAAAACCCAAGGACACCCTCA TGATCTCCCGGACCCCTGAGGTCACATGCGTGGTGGTGGACGTGAGCCAC GAAGACCCTGAGGTCAAGTTCAACTGGTACGTGGACGGCGTGGAGGTGCA TAATGCCAAGACAAAGCCGCGGGAGGAGCAGTACAACAGCACGTACCGTG TGGTCAGCGTCCTCACCGTCCTGCACCAGGACTGGCTGAATGGCAAGGAG TACAAGTGCAAGGTCTCCAACAAAGCCCTCCCAGCCCCCATCGAGAAAAC CATCTCCAAAGCCAAAGGGCAGCCCCGAGAACCACAGGTGTACACCCTGC CCCCATCCCGGGATGAGCTGACCAAGAACCAGGTCAGCCTGACCTGCCTG GTCAAAGGCTTCTATCCCAGCGACATCGCCGTGGAGTGGGAGAGCAATGG GCAGCCGGAGAACAACTACAAGACCACGCCTCCCGTGCTGGACTCCGACG GCTCCTTCTTCCTCTACAGCAAGCTCACCGTGGACAAGAGCAGGTGGCAG CAGGGGAACGTCTTCTCATGCTCCGTGATGCATGAGGCTCTGCACAACCA CTACACACAGAAGAGCCTCTCCCTGTCTCCGGGTAAA [SEQ ID NO: 101] |
| DNA for Heavy Chain version 2 | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCATTGTCTATCTGCAAATGAACAGCCTGAAAACCGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCAGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT GGGGGGACCGTCAGTCTTCCTCTTCCCCCCAAAACCCAAGGACACCCTCA TGATCTCCCGGACCCCTGAGGTCACATGCGTGGTGGTGGACGTGAGCCAC GAAGACCCTGAGGTCAAGTTCAACTGGTACGTGGACGGCGTGGAGGTGCA TAATGCCAAGACAAAGCCGCGGGAGGAGCAGTACAACAGCACGTACCGTG TGGTCAGCGTCCTCACCGTCCTGCACCAGGACTGGCTGAATGGCAAGGAG TACAAGTGCAAGGTCTCCAACAAAGCCCTCCCAGCCCCCATCGAGAAAAC CATCTCCAAAGCCAAAGGGCAGCCCCGAGAACCACAGGTGTACACCCTGC CCCCATCCCGGGATGAGCTGACCAAGAACCAGGTCAGCCTGACCTGCCTG GTCAAAGGCTTCTATCCCAGCGACATCGCCGTGGAGTGGGAGAGCAATGG GCAGCCGGAGAACAACTACAAGACCACGCCTCCCGTGCTGGACTCCGACG GCTCCTTCTTCCTCTACAGCAAGCTCACCGTGGACAAGAGCAGGTGGCAG CAGGGGAACGTCTTCTCATGCTCCGTGCTGCATGAGGCTCTGCACTCCCA CTACACACAGAAGAGCCTCTCCCTGTCTCCGGGTAAA [SEQ ID NO: 102] |

In certain embodiments, the anti-CSP antibody variant comprises a light chain variable region comprising a CDR1, a CDR2, and a CDR3 and having the amino acid sequence set forth in SEQ ID NO: 103, as shown in Table 14. In certain embodiments, the anti-CSP antibody variant comprises a heavy chain variable region comprising a CDR1, a CDR2, and a CDR3 and having the amino acid sequence set forth in SEQ ID NO: 104, as shown in Table 14. In certain embodiments, the anti-CSP antibody variant comprises a light chain having the amino acid sequence set forth in SEQ ID NO: 107, as shown in Table 14. In certain embodiments, the anti-CSP antibody variant comprises a heavy chain having the amino acid sequence set forth in SEQ ID NO: 108, as shown in Table 14. In certain embodiments, the anti-CSP antibody variant comprises a heavy chain having the amino acid sequence set forth in SEQ ID NO: 109, as shown in Table 14. Exemplary nucleic acid sequences of SEQ ID NOS: 103, 104, 107, 108, and 109 are provided in Table 14 below.

TABLE 14

| Antibody ID: AB-000224.009 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLG<br>[SEQ ID NO: 103] | |
| VH | EVQLVESGGGLVQPGRSLRLSCTASGFS<br>FGDHAMSWVRQAPGKGLEWVGFIRKTTYGATTHYAAAVRGRFTISRDDSK<br>STVYLQMNSLKAEDTAVYFCTRVQLDYGPGYQYYGMDVWGQGTTVTVSS<br>[SEQ ID NO: 104] | |
| DNA for VL | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGC<br>[SEQ ID NO: 105] | |
| DNA for VH | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGOACTGTOTATCTGCAAATGAACAGCCTGAAAGCAGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCA<br>[SEQ ID NO: 106] | |
| Light Chain | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLGQPKAAPSVTLFPPSSEELQ<br>ANKATLVCLVSDFYPGAVTVAWKADGSPVKVGVETTKPSKQSNNKYAASS<br>YLSLTPEQWKSHRSYSCRVTHEGSTVEKTVAPAECS<br>[SEQ ID NO: 107] | |
| Heavy Chain version 1 | EVQLVESGGGLVQPGRSLRLSCTASGFS<br>FGDHAMSWVRQAPGKGLEWVGFIRKTTYGATTHYAAAVRGRFTISRDDSK<br>STVYLQMNSLKAEDTAVYFCTRVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE | |

TABLE 14-continued

| Antibody ID: AB-000224.009 | |
|---|---|
| | KABAT ASN |
| | YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVMHEALHNHYTQKSLSLSPGK<br>[SEQ ID NO: 108] |
| Heavy Chain version 2 | EVQLVESGGGLVQPGRSLRLSCTASGFS<br>FGDHAMSWVRQAPGKGLEWVGFIRKTTYGATTHYAAAVRGRFTISRDDSK<br>STVYLQMNSLKAEDTAVYFCTRVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVLHEALHSHYTQKSLSLSPGK [SEQ ID NO: 109] |
| DNA for Light Chain | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGCCAGCCCA<br>AGGCTGCCCCCTCGGTCACTCTGTTCCCACCCTCCTCTGAGGAGCTTCAA<br>GCCAACAAGGCCACACTGGTGTGTCTCGTAAGTGACTTCTACCCGGGAGC<br>CGTGACAGTGGCCTGGAAGGCAGATGGCAGCCCCGTCAAGGTGGGAGTGG<br>AGACCACCAAACCCTCCAAACAAAGCAACAACAAGTATGCGGCCAGCAGC<br>TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT<br>[SEQ ID NO: 110] |
| DNA for Heavy Chain version 1 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGOACTGTOTATCTGCAAATGAACAGCCTGAAAGCAGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 111] |
| DNA for Heavy Chain version 2 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCACTGTCTATCTGCAAATGAACAGCCTGAAAGCAGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT |

TABLE 14-continued

| Antibody ID: AB-000224.009 | | |
|---|---|---|
| | KABAT | ASN |
| | GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 112] | |

In certain embodiments, the anti-CSP antibody variant comprises a light chain variable region comprising a CDR1, a CDR2, and a CDR3 and having the amino acid sequence set forth in SEQ ID NO: 113, as shown in Table 15. In certain embodiments, the anti-CSP antibody variant comprises a heavy chain variable region comprising a CDR1, a CDR2, and a CDR3 and having the amino acid sequence set forth in SEQ ID NO: 114, as shown in Table 15. In certain embodiments, the anti-CSP antibody variant comprises a light chain having the amino acid sequence set forth in SEQ ID NO: 117, as shown in Table 15. In certain embodiments, the anti-CSP antibody variant comprises a heavy chain having the amino acid sequence set forth in SEQ ID NO: 118, as shown in Table 15. In certain embodiments, the anti-CSP antibody variant comprises a heavy chain having the amino acid sequence set forth in SEQ ID NO: 119, as shown in Table 15. Exemplary nucleic acid sequences of SEQ ID NOS: 113, 114, 117, 118, and 119 are provided in Table 15 below.

TABLE 15

| Antibody ID: AB-000224.010 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLG<br>[SEQ ID NO: 113] | |
| VH | EVQLVESGGGLVQPGRSLRLSCTASGFS<br>FGDHAMSWVRQAPGKGLEWVGFIRKTTYGATTHYAAAVRGRFTISRDDSK<br>STVYLQMNSLKTEDTAVYFCARVQLDYGPGYQYYGMDVWGQGTTVTVSS<br>[SEQ ID NO: 114] | |
| DNA for VL | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGC<br>[SEQ ID NO: 115] | |
| DNA for VH | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT | |

TABLE 15-continued

| Antibody ID: AB-000224.010 | | |
|---|---|---|
| | KABAT | ASN |
| | ACGCCGCGGCTGTGAGAGGCAGATTCACCATCTCGCGAGATGATTCTAAA<br>AGCACTGTCTATCTGCAAATGAACAGCCTGAAAACCGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCA<br>[SEQ ID NO: 116] | |
| Light Chain | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLGQPKAAPSVTLFPPSSEELQ<br>ANKATLVCLVSDFYPGAVTVAWKADGSPVKVGVETTKPSKQSNNKYAASS<br>YLSLTPEQWKSHRSYSCRVTHEGSTVEKTVAPAECS<br>[SEQ ID NO: 117] | |
| Heavy Chain version 1 | EVQLVESGGGLVQPGRSLRLSCTASGFS<br>FGDHAMSWVRQAPGKGLEWVGFIRKTTYGATTHYAAAVRGRFTISRDDSK<br>STVYLQMNSLKTEDTAVYFCARVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVMHEALHNHYTQKSLSLSPGK<br>[SEQ ID NO: 118] | |
| Heavy Chain version 2 | EVQLVESGGGLVQPGRSLRLSCTASGFS<br>FGDHAMSWVRQAPGKGLEWVGFIRKTTYGATTHYAAAVRGRFTISRDDSK<br>STVYLQMNSLKTEDTAVYFCARVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVLHEALHSHYTQKSLSLSPGK [SEQ ID NO: 119] | |
| DNA for Light Chain | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGCCAGCCCA<br>AGGCTGCCCCCTCGGTCACTCTGTTCCCACCCTCCTCTGAGGAGCTTCAA<br>GCCAACAAGGCCACACTGGTGTGTCTCGTAAGTGACTTCTACCCGGGAGC<br>CGTGACAGTGGCCTGGAAGGCAGATGGCAGCCCCGTCAAGGTGGGAGTGG<br>AGACCACCAAACCCTCCAAACAAAGCAACAACAAGTATGCGGCCAGCAGC<br>TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT<br>[SEQ ID NO: 120] | |
| DNA for Heavy Chain version 1 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCACTGTCTATCTGCAAATGAACAGCCTGAAAACCGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG | |

TABLE 15-continued

| Antibody ID: AB-000224.010 | | |
|---|---|---|
| | KABAT | ASN |
| | GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 121] | |
| DNA for Heavy Chain version 2 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCACTGTCTATCTGCAAATGAACAGCCTGAAAACCGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 122] | |

In certain embodiments, the anti-CSP antibody variant comprises a light chain variable region comprising a CDR1, a CDR2, and a CDR3 and having the amino acid sequence set forth in SEQ ID NO: 123, as shown in Table 16. In certain embodiments, the anti-CSP antibody variant comprises a heavy chain variable region comprising a CDR1, a CDR2, and a CDR3 and having the amino acid sequence set forth in SEQ ID NO: 124, as shown in Table 16. In certain embodiments, the anti-CSP antibody variant comprises a light chain having the amino acid sequence set forth in SEQ ID NO: 127, as shown in Table 16. In certain embodiments, the anti-CSP antibody variant comprises a heavy chain having the amino acid sequence set forth in SEQ ID NO: 128, as shown in Table 16. In certain embodiments, the anti-CSP antibody variant comprises a heavy chain having the amino acid sequence set forth in SEQ ID NO: 129, as shown in Table 16. Exemplary nucleic acid sequences of SEQ ID NOS: 123, 124, 127, 128, and 129 are provided in Table 16 below.

TABLE 16

| Antibody ID: AB-000224.011 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |

TABLE 16-continued

| Antibody ID: AB-000224.011 | |
|---|---|
| | KABAT ASN |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 123] |
| VH | EVQLVESGGGLVQPGRSLRLSCTASGFS FGDHAMSWVRQAPGKGLEWVGFIRKTTYGATTHYAAAVRGRFTISRDDSK SIVYLQMNSLKAEDTAVYFCARVQLDYGPGYQYYGMDVWGQGTTVTVSS [SEQ ID NO: 124] |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 125] |
| DNA for VH | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCATTGTCTATCTGCAAATGAACAGCCTGAAAGCAGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCA [SEQ ID NO: 126] |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADGSPVKVGVETTKPSKQSNNKYAASS YLSLTPEQWKSHRSYSCRVTHEGSTVEKTVAPAECS [SEQ ID NO: 127] |
| Heavy Chain version 1 | EVQLVESGGGLVQPGRSLRLSCTASGFS FGDHAMSWVRQAPGKGLEWVGFIRKTTYGATTHYAAAVRGRFTISRDDSK SIVYLQMNSLKAEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 128] |
| Heavy Chain version 2 | EVQLVESGGGLVQPGRSLRLSCTASGFS FGDHAMSWVRQAPGKGLEWVGFIRKTTYGATTHYAAAVRGRFTISRDDSK SIVYLQMNSLKAEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVLHEALHSHYTQKSLSLSPGK [SEQ ID NO: 129] |
| DNA for Light Chain | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGCCAGCCCA AGGCTGCCCCCTCGGTCACTCTGTTCCCACCCTCCTCTGAGGAGCTTCAA GCCAACAAGGCCACACTGGTGTGTCTCGTAAGTGACTTCTACCCGGGAGC CGTGACAGTGGCCTGGAAGGCAGATGGCAGCCCCGTCAAGGTGGGAGTGG AGACCACCAAACCCTCCAAACAAAGCAACAACAAGTATGCGGCCAGCAGC TACCTGAGCCTGACGCCCGAGCAGTGGAAGTCCCACAGAAGCTACAGCTG CCGGGTCACGCATGAAGGGAGCACCGTGGAGAAGACAGTGGCCCCTGCAG AATGCTCT [SEQ ID NO: 130] |

TABLE 16-continued

| Antibody ID: AB-000224.011 | | |
|---|---|---|
| | KABAT | ASN |
| DNA for Heavy Chain version 1 | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCATTGTCTATCTGCAAATGAACAGCCTGAAAGCAGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCAGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT GGGGGGACCGTCAGTCTTCCTCTTCCCCCCAAAACCCAAGGACACCCTCA TGATCTCCCGGACCCCTGAGGTCACATGCGTGGTGGTGGACGTGAGCCAC GAAGACCCTGAGGTCAAGTTCAACTGGTACGTGGACGGCGTGGAGGTGCA TAATGCCAAGACAAAGCCGCGGGAGGAGCAGTACAACAGCACGTACCGTG TGGTCAGCGTCCTCACCGTCCTGCACCAGGACTGGCTGAATGGCAAGGAG TACAAGTGCAAGGTCTCCAACAAAGCCCTCCCAGCCCCCATCGAGAAAAC CATCTCCAAAGCCAAAGGGCAGCCCCGAGAACCACAGGTGTACACCCTGC CCCCATCCCGGGATGAGCTGACCAAGAACCAGGTCAGCCTGACCTGCCTG GTCAAAGGCTTCTATCCCAGCGACATCGCCGTGGAGTGGGAGAGCAATGG GCAGCCGGAGAACAACTACAAGACCACGCCTCCCGTGCTGGACTCCGACG GCTCCTTCTTCCTCTACAGCAAGCTCACCGTGGACAAGAGCAGGTGGCAG CAGGGGAACGTCTTCTCATGCTCCGTGATGCATGAGGCTCTGCACAACCA CTACACACAGAAGAGCCTCTCCCTGTCTCCGGGTAAA [SEQ ID NO: 131] | |
| DNA for Heavy Chain version 2 | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGGATTGTCTATGTGCAAATGAACAGCCTGAAAGCAGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCAGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT GGGGGGACCGTCAGTCTTCCTCTTCCCCCCAAAACCCAAGGACACCCTCA TGATCTCCCGGACCCCTGAGGTCACATGCGTGGTGGTGGACGTGAGCCAC GAAGACCCTGAGGTCAAGTTCAACTGGTACGTGGACGGCGTGGAGGTGCA TAATGCCAAGACAAAGCCGCGGGAGGAGCAGTACAACAGCACGTACCGTG TGGTCAGCGTCCTCACCGTCCTGCACCAGGACTGGCTGAATGGCAAGGAG TACAAGTGCAAGGTCTCCAACAAAGCCCTCCCAGCCCCCATCGAGAAAAC CATCTCCAAAGCCAAAGGGCAGCCCCGAGAACCACAGGTGTACACCCTGC CCCCATCCCGGGATGAGCTGACCAAGAACCAGGTCAGCCTGACCTGCCTG GTCAAAGGCTTCTATCCCAGCGACATCGCCGTGGAGTGGGAGAGCAATGG GCAGCCGGAGAACAACTACAAGACCACGCCTCCCGTGCTGGACTCCGACG GCTCCTTCTTCCTCTACAGCAAGCTCACCGTGGACAAGAGCAGGTGGCAG CAGGGGAACGTCTTCTCATGCTCCGTGCTGCATGAGGCTCTGCACTCCCA CTACACACAGAAGAGCCTCTCCCTGTCTCCGGGTAAA [SEQ ID NO: 132] | |

In certain embodiments, the anti-CSP antibody variant comprises a light chain variable region comprising a CDR1, a CDR2, and a CDR3 and having the amino acid sequence set forth in SEQ ID NO: 133, as shown in Table 17. In certain embodiments, the anti-CSP antibody variant comprises a heavy chain variable region comprising a CDR1, a CDR2, and a CDR3 and having the amino acid sequence set forth in SEQ ID NO: 134, as shown in Table 17. In certain embodiments, the anti-CSP antibody variant comprises a light chain having the amino acid sequence set forth in SEQ ID NO: 137, as shown in Table 17. In certain embodiments, the anti-CSP antibody variant comprises a heavy chain having the amino acid sequence set forth in SEQ ID NO: 138, as shown in Table 17. In certain embodiments, the anti-CSP antibody variant comprises a heavy chain having the amino acid sequence set forth in SEQ ID NO: 139, as shown in Table 17. Exemplary nucleic acid sequences of SEQ ID NOS: 133, 134, 137, 138, and 139 are provided in Table 17 below.

TABLE 17

| Antibody ID: AB-000224.012 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLG<br>[SEQ ID NO: 133] | |
| VH | EVQLVESGGGLVQPGRSLRLSCAASGFS<br>FGDHAMSWVRQAPGKGLEWVGFIRKTTYGATTHYAAAVRGRFTISRDDSK<br>STVYLQMNSLKAEDTAVYFCTRVQLDYGPGYQYYGMDVWGQGTTVTVSS<br>[SEQ ID NO: 134] | |
| DNA for VL | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGC<br>[SEQ ID NO: 135] | |
| DNA for VH | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGOACTGTOTATCTGCAAATGAACAGCCTGAAAGCAGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCA<br>[SEQ ID NO: 136] | |
| Light Chain | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLGQPKAAPSVTLFPPSSEELQ<br>ANKATLVCLVSDFYPGAVTVAWKADGSPVKVGVETTKPSKQSNNKYAASS<br>YLSLTPEQWKSHRSYSCRVTHEGSTVEKTVAPAECS<br>[SEQ ID NO: 137] | |
| Heavy Chain version 1 | EVQLVESGGGLVQPGRSLRLSCAASGFS<br>FGDHAMSWVRQAPGKGLEWVGFIRKTTYGATTHYAAAVRGRFTISRDDSK<br>STVYLQMNSLKAEDTAVYFCTRVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVMHEALHNHYTQKSLSLSPGK<br>[SEQ ID NO: 138] | |
| Heavy Chain version 2 | EVQLVESGGGLVQPGRSLRLSCAASGFS<br>FGDHAMSWVRQAPGKGLEWVGFIRKTTYGATTHYAAAVRGRFTISRDDSK<br>STVYLQMNSLKAEDTAVYFCTRVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH | |

TABLE 17-continued

| Antibody ID: AB-000224.012 | | |
|---|---|---|
| | KABAT | ASN |
| | EDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVLHEALHSHYTQKSLSLSPGK<br>[SEQ ID NO: 139] | |
| DNA for Light Chain | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGCCAGCCCA<br>AGGCTGCCCCCTCGGTCACTCTGTTCCCACCCTCCTCTGAGGAGCTTCAA<br>GCCAACAAGGCCACACTGGTGTGTCTCGTAAGTGACTTCTACCCGGGAGC<br>CGTGACAGTGGCCTGGAAGGCAGATGGCAGCCCCGTCAAGGTGGGAGTGG<br>AGACCACCAAACCCTCCAAACAAAGCAACAACAAGTATGCGGCCAGCAGC<br>TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT<br>[SEQ ID NO: 140] | |
| DNA for Heavy Chain version 1 | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCACTGTCTATCTGCAAATGAACAGCCTGAAAGCAGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 141] | |
| DNA for Heavy Chain version 2 | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGGACTGTCTATCTGCAAATGAACAGCCTGAAAGCAGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG | |

TABLE 17-continued

| Antibody ID: AB-000224.012 | |
|---|---|
| KABAT | ASN |
| GCTCCTTCTTCCTCTACAGCAAGCTCACCGTGGACAAGAGCAGGTGGCAG CAGGGGAACGTCTTCTCATGCTCCGTGCTGCATGAGGCTCTGCACTCCCA CTACACACAGAAGAGCCTCTCCCTGTCTCCGGGTAAA [SEQ ID NO: 142] | |

In certain embodiments, the anti-CSP antibody variant comprises a light chain variable region comprising a CDR1, a CDR2, and a CDR3 and having the amino acid sequence set forth in SEQ ID NO: 143, as shown in Table 18. In certain embodiments, the anti-CSP antibody variant comprises a heavy chain variable region comprising a CDR1, a CDR2, and a CDR3 and having the amino acid sequence set forth in SEQ ID NO: 144, as shown in Table 18. In certain embodiments, the anti-CSP antibody variant comprises a light chain having the amino acid sequence set forth in SEQ ID NO: 147, as shown in Table 18. In certain embodiments, the anti-CSP antibody variant comprises a heavy chain having the amino acid sequence set forth in SEQ ID NO: 148, as shown in Table 18. In certain embodiments, the anti-CSP antibody variant comprises a heavy chain having the amino acid sequence set forth in SEQ ID NO: 149, as shown in Table 18. Exemplary nucleic acid sequences of SEQ ID NOS: 143, 144, 147, 148, and 149 are provided in Table 18 below.

TABLE 18

| Antibody ID: AB-000224.013 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 143] | |
| VH | EVQLVESGGGLVQPGRSLRLSCAASGFS FGDHAMSWVRQAPGKGLEWVGFIRKTTYGATTHYAAAVRGRFTISRDDSK STVYLQMNSLKTEDTAVYFCARVQLDYGPGYQYYGMDVWGQGTTVTVSS [SEQ ID NO: 144] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 145] | |
| DNA for VH | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCACTGTCTATCTGCAAATGAACAGCCTGAAAACCGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCA [SEQ ID NO: 146] | |

TABLE 18-continued

| Antibody ID: AB-000224.013 | |
|---|---|
| | KABAT ASN |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADGSPVKVGVETTKPSKQSNNKYAASS YLSLTPEQWKSHRSYSCRVTHEGSTVEKTVAPAECS [SEQ ID NO: 147] |
| Heavy Chain version 1 | EVQLVESGGGLVQPGRSLRLSCAASGFS FGDHAMSWVRQAPGKGLEWVGFIRKTTYGATTHYAAAVRGRFTISRDDSK STVYLQMNSLKTEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 148] |
| Heavy Chain version 2 | EVQLVESGGGLVQPGRSLRLSCAASGFS FGDHAMSWVRQAPGKGLEWVGFIRKTTYGATTHYAAAVRGRFTISRDDSK STVYLQMNSLKTEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVLHEALHSHYTQKSLSLSPGK [SEQ ID NO: 149] |
| DNA for Light Chain | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGCCAGCCCA AGGCTGCCCCCTCGGTCACTCTGTTCCCACCCTCCTCTGAGGAGCTTCAA GCCAACAAGGCCACACTGGTGTGTCTCGTAAGTGACTTCTACCCGGGAGC CGTGACAGTGGCCTGGAAGGCAGATGGCAGCCCCGTCAAGGTGGGAGTGG AGACCACCAAACCCTCCAAACAAAGCAACAACAAGTATGCGGCCAGCAGC TACCTGAGCCTGACGCCCGAGCAGTGGAAGTCCCACAGAAGCTACAGCTG CCGGGTCACGCATGAAGGGAGCACCGTGGAGAAGACAGTGGCCCCTGCAG AATGCTCT [SEQ ID NO: 150] |
| DNA for Heavy Chain version 1 | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCACTGTCTATCTGCAAATGAACAGCCTGAAAACCGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCAGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT GGGGGGACCGTCAGTCTTCCTCTTCCCCCCAAAACCCAAGGACACCCTCA TGATCTCCCGGACCCCTGAGGTCACATGCGTGGTGGTGGACGTGAGCCAC GAAGACCCTGAGGTCAAGTTCAACTGGTACGTGGACGGCGTGGAGGTGCA TAATGCCAAGACAAAGCCGCGGGAGGAGCAGTACAACAGCACGTACCGTG TGGTCAGCGTCCTCACCGTCCTGCACCAGGACTGGCTGAATGGCAAGGAG TACAAGTGCAAGGTCTCCAACAAAGCCCTCCCAGCCCCCATCGAGAAAAC CATCTCCAAAGCCAAAGGGCAGCCCCGAGAACCACAGGTGTACACCCTGC CCCCATCCCGGGATGAGCTGACCAAGAACCAGGTCAGCCTGACCTGCCTG GTCAAAGGCTTCTATCCCAGCGACATCGCCGTGGAGTGGGAGAGCAATGG GCAGCCGGAGAACAACTACAAGACCACGCCTCCCGTGCTGGACTCCGACG GCTCCTTCTTCCTCTACAGCAAGCTCACCGTGGACAAGAGCAGGTGGCAG CAGGGGAACGTCTTCTCATGCTCCGTGATGCATGAGGCTCTGCACAACCA CTACACACAGAAGAGCCTCTCCCTGTCTCCGGGTAAA [SEQ ID NO: 151] |

TABLE 18-continued

| Antibody ID: AB-000224.013 | | |
|---|---|---|
| | KABAT | ASN |
| DNA for Heavy Chain version 2 | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCACTGTCTATCTGCAAATGAACAGCCTGAAAACCGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCAGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT GGGGGGACCGTCAGTCTTCCTCTTCCCCCCAAAACCCAAGGACACCCTCA TGATCTCCCGGACCCCTGAGGTCACATGCGTGGTGGTGGACGTGAGCCAC GAAGACCCTGAGGTCAAGTTCAACTGGTACGTGGACGGCGTGGAGGTGCA TAATGCCAAGACAAAGCCGCGGGAGGAGCAGTACAACAGCACGTACCGTG TGGTCAGCGTCCTCACCGTCCTGCACCAGGACTGGCTGAATGGCAAGGAG TACAAGTGCAAGGTCTCCAACAAAGCCCTCCCAGCCCCCATCGAGAAAAC CATCTCCAAAGCCAAAGGGCAGCCCCGAGAACCACAGGTGTACACCCTGC CCCCATCCCGGGATGAGCTGACCAAGAACCAGGTCAGCCTGACCTGCCTG GTCAAAGGCTTCTATCCCAGCGACATCGCCGTGGAGTGGGAGAGCAATGG GCAGCCGGAGAACAACTACAAGACCACGCCTCCCGTGCTGGACTCCGACG GCTCCTTCTTCCTCTACAGCAAGCTCACCGTGGACAAGAGCAGGTGGCAG CAGGGGAACGTCTTCTCATGCTCCGTGCTGCATGAGGCTCTGCACTCCCA CTACACACAGAAGAGCCTCTCCCTGTCTCCGGGTAAA [SEQ ID NO: 152] | |

In certain embodiments, the anti-CSP antibody variant comprises a light chain variable region comprising a CDR1, a CDR2, and a CDR3 and having the amino acid sequence set forth in SEQ ID NO: 153, as shown in Table 19. In certain embodiments, the anti-CSP antibody variant comprises a heavy chain variable region comprising a CDR1, a CDR2, and a CDR3 and having the amino acid sequence set forth in SEQ ID NO: 154, as shown in Table 19. In certain embodiments, the anti-CSP antibody variant comprises a light chain having the amino acid sequence set forth in SEQ ID NO: 157, as shown in Table 19. In certain embodiments, the anti-CSP antibody variant comprises a heavy chain having the amino acid sequence set forth in SEQ ID NO: 158, as shown in Table 19. In certain embodiments, the anti-CSP antibody variant comprises a heavy chain having the amino acid sequence set forth in SEQ ID NO: 159, as shown in Table 19. Exemplary nucleic acid sequences of SEQ ID NOS: 153, 154, 157, 158, and 159 are provided in Table 19 below.

TABLE 19

| Antibody ID: AB-000224.014 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 153] | |

TABLE 19-continued

| Antibody ID: AB-000224.014 | |
|---|---|
| | KABAT ASN |
| VH | EVQLVESGGGLVQPGRSLRLSCAASGFS<br>FGDHAMSWVRQAPGKGLEWVGFIRKTTYGATTHYAAAVRGRFTISRDDSK<br>SIVYLQMNSLKAEDTAVYFCARVQLDYGPGYQYYGMDVWGQGTTVTVSS<br>[SEQ ID NO: 154] |
| DNA for VL | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGC<br>[SEQ ID NO: 155] |
| DNA for VH | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGOATTGTOTATCTGCAAATGAACAGCCTGAAAGCAGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCA<br>[SEQ ID NO: 156] |
| Light Chain | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLGQPKAAPSVTLFPPSSEELQ<br>ANKATLVCLVSDFYPGAVTVAWKADGSPVKVGVETTKPSKQSNNKYAASS<br>YLSLTPEQWKSHRSYSCRVTHEGSTVEKTVAPAECS<br>[SEQ ID NO: 157] |
| Heavy Chain version 1 | EVQLVESGGGLVQPGRSLRLSCAASGFS<br>FGDHAMSWVRQAPGKGLEWVGFIRKTTYGATTHYAAAVRGRFTISRDDSK<br>SIVYLQMNSLKAEDTAVYFCARVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVMHEALHNHYTQKSLSLSPGK<br>[SEQ ID NO: 158] |
| Heavy Chain version 2 | EVQLVESGGGLVQPGRSLRLSCAASGFS<br>FGDHAMSWVRQAPGKGLEWVGFIRKTTYGATTHYAAAVRGRFTISRDDSK<br>SIVYLQMNSLKAEDTAVYFCARVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVLHEALHSHYTQKSLSLSPGK [SEQ ID NO: 159] |
| DNA for Light Chain | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGCCAGCCCA<br>AGGCTGCCCCCTCGGTCACTCTGTTCCCACCCTCCTCTGAGGAGCTTCAA<br>GCCAACAAGGCCACACTGGTGTGTCTCGTAAGTGACTTCTACCCGGGAGC<br>CGTGACAGTGGCCTGGAAGGCAGATGGCAGCCCCGTCAAGGTGGGAGTGG<br>AGACCACCAAACCCTCCAAACAAAGCAACAACAAGTATGCGGCCAGCAGC<br>TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT<br>[SEQ ID NO: 160] |
| DNA for Heavy Chain version 1 | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGOATTGTOTATCTGCAAATGAACAGCCTGAAAGCAGAGGACACAGCCGT |

TABLE 19-continued

| Antibody ID: AB-000224.014 | | |
| --- | --- | --- |
| | KABAT | ASN |
| | GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 161] | |
| DNA for Heavy Chain version 2 | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGGATTGTCTATGTGCAAATGAACAGCCTGAAAGCAGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 162] | |

In certain embodiments, the anti-CSP antibody variant comprises a light chain variable region comprising a CDR1, a CDR2, and a CDR3 and having the amino acid sequence set forth in SEQ ID NO: 163, as shown in Table 20. In certain embodiments, the anti-CSP antibody variant comprises a heavy chain variable region comprising a CDR1, a CDR2, and a CDR3 and having the amino acid sequence set forth in SEQ ID NO: 164, as shown in Table 20. In certain embodiments, the anti-CSP antibody variant comprises a light chain having the amino acid sequence set forth in SEQ ID NO: 167, as shown in Table 20. In certain embodiments, the anti-CSP antibody variant comprises a heavy chain having the amino acid sequence set forth in SEQ ID NO: 168, as shown in Table 20. In certain embodiments, the anti-CSP antibody variant comprises a heavy chain having the amino acid sequence set forth in SEQ ID NO: 169, as shown in Table 20. Exemplary nucleic acid sequences of SEQ ID NOS: 163, 164, 167, 168, and 169 are provided in Table 20 below.

TABLE 20

| Antibody ID: AB-000224.015 | | |
| --- | --- | --- |
| | KABAT | ASN |
| CDR1-VL | TGMNSNIGAGYDVY [SEQ ID NO: 1] | TGMNSNIGAGYDVY [SEQ ID NO: 7] |

TABLE 20-continued

| Antibody ID: AB-000224.015 | | |
|---|---|---|
| | KABAT | ASN |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLG [SEQ ID NO: 163] | |
| VH | EVQLVESGGGLVQPGRSLRLSCTASGFS FGDHAMSWVRQAPGKGLEWVGFIRKTTYGATTHYAAAVRGRFTISRDDSK STVYLQMNSLKAEDTAVYFCARVQLDYGPGYQYYGMDVWGQGTTVTVSS [SEQ ID NO: 164] | |
| DNA for VL | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGC [SEQ ID NO: 165] | |
| DNA for VH | GAGGTGCAGCTGGTGGAGTCTGGGGGAGGCTTGG TACAGCCAGGGCGGTCCCTGAGACTCAGCTGTACAGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCACTGTGTATCTGCAAATGAACAGCCTGAAAGCAGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCA [SEQ ID NO: 166] | |
| Light Chain | QSVLTQPPSVSGAPGQRVTISCTGMNSNIGA GYDVYWYQQLPGTAPKLLIYGNSNRPSGVPDRFSGSRSGTSASLAITGLQ AEDEADYYCQSYDTSLNGWAFGGGTKLTVLGQPKAAPSVTLFPPSSEELQ ANKATLVCLVSDFYPGAVTVAWKADGSPVKVGVETTKPSKQSNNKYAASS YLSLTPEQWKSHRSYSCRVTHEGSTVEKTVAPAECS [SEQ ID NO: 167] | |
| Heavy Chain version 1 | EVQLVESGGGLVQPGRSLRLSCTASGFS FGDHAMSWVRQAPGKGLEWVGFIRKTTYGATTHYAAAVRGRFTISRDDSK STVYLQMNSLKAEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 168] | |
| Heavy Chain version 2 | EVQLVESGGGLVQPGRSLRLSCTASGFS FGDHAMSWVRQAPGKGLEWVGFIRKTTYGATTHYAAAVRGRFTISRDDSK STVYLQMNSLKAEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVLHEALHSHYTQKSLSLSPGK [SEQ ID NO: 169] | |
| DNA for | CAGTCTGTGCTGACGCAGCCGCCCTCAGTGTCTGGGGCCCCAG GGCAGAGGGTCACCATCTCCTGCACTGGGATGAACTCCAACATCGGGGCA | |

TABLE 20-continued

| Antibody ID: AB-000224.015 | |
|---|---|
| | KABAT ASN |
| Light Chain | GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGCCAGCCCA<br>AGGCTGCCCCCTCGGTCACTCTGTTCCCACCCTCCTCTGAGGAGCTTCAA<br>GCCAACAAGGCCACACTGGTGTGTCTCGTAAGTGACTTCTACCCGGGAGC<br>CGTGACAGTGGCCTGGAAGGCAGATGGCAGCCCCGTCAAGGTGGGAGTGG<br>AGACCACCAAACCCTCCAAACAAAGCAACAACAAGTATGCGGCCAGCAGC<br>TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT<br>[SEQ ID NO: 170] |
| DNA for Heavy Chain version 1 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGOACTGTOTATCTGCAAATGAACAGCCTGAAAGCAGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 171] |
| DNA for Heavy Chain version 2 | GAGGTGCAGCTGGTGGAGTCTGGGGGAGGCTTGG<br>TACAGCCAGGGCGGTCCCTGAGACTCAGCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGCACTGTCTATCTGCAAATGAACAGCCTGAAAGCAGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 172] |

In certain embodiments, the anti-CSP antibody variant comprises a light chain variable region comprising a CDR1, a CDR2, and a CDR3 and having the amino acid sequence set forth in SEQ ID NO: 173, as shown in Table 21. In certain embodiments, the anti-CSP antibody variant comprises a heavy chain variable region comprising a CDR1, a CDR2, and a CDR3 and having the amino acid sequence set forth in SEQ ID NO: 174, as shown in Table 21. In certain embodiments, the anti-CSP antibody variant comprises a light chain having the amino acid sequence set forth in SEQ ID NO: 177, as shown in Table 21. In certain embodiments, the anti-CSP antibody variant comprises a heavy chain having the amino acid sequence set forth in SEQ ID NO: 178, as shown in Table 21. In certain embodiments, the anti-CSP antibody variant comprises a heavy chain having the amino acid sequence set forth in SEQ ID NO: 179, as shown in Table 21. Exemplary nucleic acid sequences of SEQ ID NOS: 173, 174, 177, 178, and 179 are provided in Table 21 below.

TABLE 21

| Antibody ID: AB-000224.016 | | |
|---|---|---|
| | KABAT | ASN |
| CDR1-VL | TGMNSNIGAGYDVY [SEQ ID NO: 1] | TGMNSNIGAGYDVY [SEQ ID NO: 7] |
| CDR2-VL | GNSNRPS [SEQ ID NO: 2] | GNSNRPS [SEQ ID NO: 8] |
| CDR3-VL | QSYDTSLNGWA [SEQ ID NO: 3] | QSYDTSLNGWA [SEQ ID NO: 9] |
| CDR1-VH | DHAMS [SEQ ID NO: 4] | DHAMS [SEQ ID NO: 10] |
| CDR2-VH | FIRKTTYGATTHYAAAVRG [SEQ ID NO: 5] | FIRKTTYGATTHYAAAVRG [SEQ ID NO: 11] |
| CDR3-VH | VQLDYGPGYQYYGMDV [SEQ ID NO: 6] | VQLDYGPGYQYYGMDV [SEQ ID NO: 12] |
| VL | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLG<br>[SEQ ID NO: 173] | |
| VH | EVQLVESGGGLVQPGRSLRLSCAASGFS<br>FGDHAMSWVRQAPGKGLEWVGFIRKTTYGATTHYAAAVRGRFTISRDDSK<br>STVYLQMNSLKAEDTAVYFCARVQLDYGPGYQYYGMDVWGQGTTVTVSS<br>[SEQ ID NO: 174] | |
| DNA for VL | CAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAACTGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGAA<br>TGGTTGGGCTTTCGGCGGAGGGACCAAGTTGACCGTCCTAGGC<br>[SEQ ID NO: 175] | |
| DNA for VH | GAGGTGCAGCTGGTGGAGTCTGGGGGAGGCTTGG<br>TACAGCCAGGGCGGTCCCTGAGACTCAGCTGTGCGGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACACACT<br>ACGCCGCGGCTGTGAGAGGCAGATTCACCATCTCGCGAGATGATTCTAAA<br>AGOACTGTOTATCTGCAAATGAACAGCCTGAAAGCAGAGGACACAGCCGT<br>GTATTTCTGTGCTAGAGTGCAGCTTGACTATGGCCCGGGATACCAGTACT<br>ACGGTATGGACGTCTGGGGCCAAGGGACCACGGTCACCGTCTCCTCA<br>[SEQ ID NO: 176] | |
| Light Chain | QSVLTQPPSVSGAPGQRVTISCTGMNSNIGA<br>GYDVYWYQQLPGTAPKLLIYGNSNRPSGVPDRFSGSRSGTSASLAITGLQ<br>AEDEADYYCQSYDTSLNGWAFGGGTKLTVLGQPKAAPSVTLFPPSSEELQ<br>ANKATLVCLVSDFYPGAVTVAWKADGSPVKVGVETTKPSKQSNNKYAASS<br>YLSLTPEQWKSHRSYSCRVTHEGSTVEKTVAPAECS<br>[SEQ ID NO: 177] | |
| Heavy Chain version 1 | EVQLVESGGGLVQPGRSLRLSCAASGFS<br>FGDHAMSWVRQAPGKGLEWVGFIRKTTYGATTHYAAAVRGRFTISRDDSK<br>STVYLQMNSLKAEDTAVYFCARVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE | |

TABLE 21-continued

| Antibody ID: AB-000224.016 | |
|---|---|
| KABAT | ASN |
| | YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVMHEALHNHYTQKSLSLSPGK [SEQ ID NO: 178] |
| Heavy Chain version 2 | EVQLVESGGGLVQPGRSLRLSCAASGFS FGDHAMSWVRQAPGKGLEWVGFIRKTTYGATTHYAAAVRGRFTISRDDSK STVYLQMNSLKAEDTAVYFCARVQLDYGPGYQYYGMDVWGQGTTVTVSSA STKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQ QGNVFSCSVLHEALHSHYTQKSLSLSPGK [SEQ ID NO: 179] |
| DNA for Light Chain | CAGTCTGTGCTGACGCAGCCGCCCTCAGTGTCTGGGGCCCCAG GGCAGAGGGTCACCATCTCCTGCACTGGGATGAACTCCAACATCGGGGCA GGTTATGATGTATACTGGTACCAACAACTTCCAGGAACTGCCCCCAAACT CCTCATCTATGGTAACAGCAATCGGCCCTCAGGGGTCCCTGACCGATTCT CTGGCTCCAGGTCTGGCACCTCAGCCTCCCTGGCCATCACTGGGCTCCAG GCTGAGGATGAGGCTGATTATTACTGCCAGTCCTATGACACCAGCCTGAA TGGTTGGGCTTTCGGCGGAGGGACCAAGTTGACCGTCCTAGGCCAGCCCA AGGCTGCCCCCTCGGTCACTCTGTTCCCACCCTCCTCTGAGGAGCTTCAA GCCAACAAGGCCACACTGGTGTGTCTCGTAAGTGACTTCTACCCGGGAGC CGTGACAGTGGCCTGGAAGGCAGATGGCAGCCCCGTCAAGGTGGGAGTGG AGACCACCAAACCCTCCAAACAAAGCAACAACAAGTATGCGGCCAGCAGC TACCTGAGCCTGACGCCCGAGCAGTGGAAGTCCCACAGAAGCTACAGCTG CCGGGTCACGCATGAAGGGAGCACCGTGGAGAAGACAGTGGCCCCTGCAG AATGCTCT [SEQ ID NO: 180] |
| DNA for Heavy Chain version 1 | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGOACTGTOTATCTGCAAATGAACAGCCTGAAAGCAGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCAGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT GGGGGGACCGTCAGTCTTCCTCTTCCCCCCAAAACCCAAGGACACCCTCA TGATCTCCCGGACCCCTGAGGTCACATGCGTGGTGGTGGACGTGAGCCAC GAAGACCCTGAGGTCAAGTTCAACTGGTACGTGGACGGCGTGGAGGTGCA TAATGCCAAGACAAAGCCGCGGGAGGAGCAGTACAACAGCACGTACCGTG TGGTCAGCGTCCTCACCGTCCTGCACCAGGACTGGCTGAATGGCAAGGAG TACAAGTGCAAGGTCTCCAACAAAGCCCTCCCAGCCCCCATCGAGAAAAC CATCTCCAAAGCCAAAGGGCAGCCCCGAGAACCACAGGTGTACACCCTGC CCCCATCCCGGGATGAGCTGACCAAGAACCAGGTCAGCCTGACCTGCCTG GTCAAAGGCTTCTATCCCAGCGACATCGCCGTGGAGTGGGAGAGCAATGG GCAGCCGGAGAACAACTACAAGACCACGCCTCCCGTGCTGGACTCCGACG GCTCCTTCTTCCTCTACAGCAAGCTCACCGTGGACAAGAGCAGGTGGCAG CAGGGGAACGTCTTCTCATGCTCCGTGATGCATGAGGCTCTGCACAACCA CTACACACAGAAGAGCCTCTCCCTGTCTCCGGGTAAA [SEQ ID NO: 181] |
| DNA for Heavy Chain version 2 | GAGGTGCAGCTGGTGGAGTCTGGGGGAGGCTTGG TACAGCCAGGGCGGTCCCTGAGACTCAGCTGTGCGGCCTCTGGGTTTAGT TTTGGTGATCATGCTATGAGCTGGGTCCGCCAGGCTCCAGGGAAGGGGCT GGAGTGGGTAGGTTTCATTAGAAAGACAACTTATGGTGCGACAACACACT ACGCCGCGGCTGTGAGAGGCAGATTCACCATCTCGCGAGATGATTCTAAA AGCACTGTCTATCTGCAAATGAACAGCCTGAAAGCAGAGGACACAGCCGT GTATTTCTGTGCTAGAGTGCAGCTTGACTATGGCCCGGGATACCAGTACT ACGGTATGGACGTCTGGGGCCAAGGGACCACGGTCACCGTCTCCTCAGCC TCCACCAAGGGCCCATCGGTCTTCCCCCTGGCACCCTCCTCCAAGAGCAC CTCTGGGGGCACAGCAGCCCTGGGCTGCCTGGTCAAGGACTACTTCCCCG AACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGT GGTGACCGTGCCCTCCAGCAGCTTGGGCACCCAGACCTACATCTGCAACG TGAATCACAAGCCCAGCAACACCAAGGTGGACAAGAAAGTTGAGCCCAAA TCTTGTGACAAAACTCACACATGCCCACCGTGCCCAGCACCTGAACTCCT |

TABLE 21-continued

| Antibody ID: AB-000224.016 | |
|---|---|
| KABAT | ASN |
| GGGGGGACCGTCAGTCTTCCTCTTCCCCCCAAAACCCAAGGACACCCTCA TGATCTCCCGGACCCCTGAGGTCACATGCGTGGTGGTGGACGTGAGCCAC GAAGACCCTGAGGTCAAGTTCAACTGGTACGTGGACGGCGTGGAGGTGCA TAATGCCAAGACAAAGCCGCGGGAGGAGCAGTACAACAGCACGTACCGTG TGGTCAGCGTCCTCACCGTCCTGCACCAGGACTGGCTGAATGGCAAGGAG TACAAGTGCAAGGTCTCCAACAAAGCCCTCCCAGCCCCCATCGAGAAAAC CATCTCCAAAGCCAAAGGGCAGCCCCGAGAACCACAGGTGTACACCCTGC CCCCATCCCGGGATGAGCTGACCAAGAACCAGGTCAGCCTGACCTGCCTG GTCAAAGGCTTCTATCCCAGCGACATCGCCGTGGAGTGGGAGAGCAATGG GCAGCCGGAGAACAACTACAAGACCACGCCTCCCGTGCTGGACTCCGACG GCTCCTTCTTCCTCTACAGCAAGCTCACCGTGGACAAGAGCAGGTGGCAG CAGGGGAACGTCTTCTCATGCTCCGTGCTGCATGAGGCTCTGCACTCCCA CTACACACAGAAGAGCCTCTCCCTGTCTCCGGGTAAA [SEQ ID NO: 182] | |

In certain embodiments, the VL of the variant of an anti-CSP antibody includes at least one, at least two, or at least three mutations, e.g., substitutions, in the CDR1 amino acid sequence set forth in SEQ ID NO: 183. In certain embodiments, the VL of the variant of an anti-CSP antibody includes at least one, at least two, or at least three mutations, e.g., substitutions, in the CDR2 amino acid sequence set forth in SEQ ID NO: 184. In certain embodiments, the VL of the variant of an anti-CSP antibody includes at least one, at least two, or at least three mutations, e.g., substitutions, in the CDR3 amino acid sequence set forth in SEQ ID NO: 185. In certain embodiments, the VH of the variant of an anti-CSP antibody includes at least one, at least two, or at least three mutations, e.g., substitutions, in the CDR1 amino acid sequence set forth in SEQ ID NO: 186. In certain embodiments, the VL of the variant of an anti-CSP antibody includes at least one, at least two, or at least three mutations, e.g., substitutions, in the CDR2 amino acid sequence set forth in SEQ ID NO: 187. In certain embodiments, the VL of the variant of an anti-CSP antibody includes at least one, at least two, or at least three mutations, e.g., substitutions, in the CDR3 amino acid sequence set forth in SEQ ID NO: 188.

In certain embodiments, the VL of the variant of an anti-CSP antibody includes at least one, at least two, or at least three mutations, e.g., substitutions, in the CDR1 amino acid sequence set forth in SEQ ID NO: 189. In certain embodiments, the VL of the variant of an anti-CSP antibody includes at least one, at least two, or at least three mutations, e.g., substitutions, in the CDR2 amino acid sequence set forth in SEQ ID NO: 190. In certain embodiments, the VL of the variant of an anti-CSP antibody includes at least one, at least two, or at least three mutations, e.g., substitutions, in the CDR3 amino acid sequence set forth in SEQ ID NO: 191. In certain embodiments, the VH of the variant of an anti-CSP antibody includes at least one, at least two, or at least three mutations, e.g., substitutions, in the CDR1 amino acid sequence set forth in SEQ ID NO: 192. In certain embodiments, the VL of the variant of an anti-CSP antibody includes at least one, at least two, or at least three mutations, e.g., substitutions, in the CDR2 amino acid sequence set forth in SEQ ID NO: 193. In certain embodiments, the VL of the variant of an anti-CSP antibody includes at least one, at least two, or at least three mutations, e.g., substitutions, in the CDR3 amino acid sequence set forth in SEQ ID NO: 194.

In certain embodiments, the anti-CSP antibody variant comprises a light chain variable region comprising a CDR1, a CDR2, and a CDR3 and having the amino acid sequence set forth in SEQ ID NO: 195, as shown in Table 22. In certain embodiments, the anti-CSP antibody variant comprises a heavy chain variable region comprising a CDR1, a CDR2, and a CDR3 and having the amino acid sequence set forth in SEQ ID NO: 196, as shown in Table 22. In certain embodiments, the anti-CSP antibody variant comprises a light chain having the amino acid sequence set forth in SEQ ID NO: 199, as shown in Table 22. In certain embodiments, the anti-CSP antibody variant comprises a heavy chain having the amino acid sequence set forth in SEQ ID NO: 200, as shown in Table 22. In certain embodiments, the anti-CSP antibody variant comprises a heavy chain having the amino acid sequence set forth in SEQ ID NO: 201, as shown in Table 22. Exemplary nucleic acid sequences of SEQ ID NOS: 195, 196, 199, 200, and 201 are provided in Table 22 below.

TABLE 22

| Antibody ID: AB-000224.017 | | |
|---|---|---|
| | KABAT | ASN |
| CDR1-VL | TGMNSNIGAGYDVY [SEQ ID NO: 183] | TGMNSNIGAGYDVY [SEQ ID NO: 189] |
| CDR2-VL | GNSNRPS [SEQ ID NO: 184] | GNSNRPS [SEQ ID NO: 190] |
| CDR3-VL | QSYDTSLDGWA [SEQ ID NO: 185] | QSYDTSLDGWA [SEQ ID NO: 191] |
| CDR1-VH | DHAMS [SEQ ID NO: 186] | DHAMS [SEQ ID NO: 192] |

TABLE 22-continued

| Antibody ID: AB-000224.017 | | |
|---|---|---|
| | KABAT | ASN |
| CDR2-VH | FIRKTTYGATTKYAAAVKG [SEQ ID NO: 187] | FIRKTTYGATTKYAAAVKG [SEQ ID NO: 193] |
| CDR3-VH | VQLDYGPGYQYYGMDV [SEQ ID NO: 188] | VQLDYGPGYQYYGMDV [SEQ ID NO: 194] |
| VL | ESVLTQPPSVSGAPGQRVTISCTGMNSNIGA<br>GYDVYWYQQLPGRAPKLLIYGNSNRPSGVPDRFSGSRSGTSASLAITGLQ<br>AEDEADYYCQSYDTSLDGWAFGGGTKLTVLG<br>[SEQ ID NO: 195] | |
| VH | EVQLVESGGGLVQPGRSLRLPCTASGFS<br>FGDHAMSWVRQAPGKGLEWVGFIRKTTYGATTKYAAAVKGRFTISRDDSK<br>SIVYLQMNSLKTEDTAVYFCTRVQLDYGPGYQYYGMDVWGQGTTVTVSS<br>[SEQ ID NO: 196] | |
| DNA for VL | GAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAAGAGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGGA<br>CGGTTGGGCTTTCGGCGGAGGGACCAAGTTGACCGTCCTAGGC<br>[SEQ ID NO: 197] | |
| DNA forVH | GAGGTGCAGCTGGTGGAGTCTGGGGGAGGCTTGG<br>TACAGCCAGGGCGGTCCCTGAGACTCCCCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACAAAGT<br>ACGCCGCGGCTGTGAAGGGCAGATTCACCATCTCGCGAGATGATTCTAAA<br>AGCATTGTCTATCTGCAAATGAACAGCCTGAAAACCGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCA<br>[SEQ ID NO: 198] | |
| Light Chain | ESVLTQPPSVSGAPGQRVTISCTGMNSNIGA<br>GYDVYWYQQLPGRAPKLLIYGNSNRPSGVPDRFSGSRSGTSASLAITGLQ<br>AEDEADYYCQSYDTSLDGWAFGGGTKLTVLGQPKAAPSVTLFPPSSEELQ<br>ANKATLVCLVSDFYPGAVTVAWKADGSPVKVGVETTKPSKQSNNKYAASS<br>YLSLTPEQWKSHRSYSCRVTHEGSTVEKTVAPAECS<br>[SEQ ID NO: 199] | |
| Heavy Chain version 1 | EVQLVESGGGLVQPGRSLRLPCTASGFS<br>FGDHAMSWVRQAPGKGLEWVGFIRKTTYGATTKYAAAVKGRFTISRDDSK<br>SIVYLQMNSLKTEDTAVYFCTRVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRWSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVMHEALHNHYTQKSLSLSPGK<br>[SEQ ID NO: 200] | |
| Heavy Chain version 2 | EVQLVESGGGLVQPGRSLRLPCTASGFS<br>FGDHAMSWVRQAPGKGLEWVGFIRKTTYGATTKYAAAVKGRFTISRDDSK<br>SIVYLQMNSLKTEDTAVYFCTRVQLDYGPGYQYYGMDVWGQGTTVTVSSA<br>STKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSH<br>EDPEVKFNWYVDGVEVHNAKTKPREEQYNSTYRWSVLTVLHQDWLNGKE<br>YKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQ<br>QGNVFSCSVLHEALHSHYTQKSLSLSPGK [SEQ ID NO: 201] | |
| DNA for Light Chain | GAGTCTGTGCTGACGCAGCCGCCCTCAGTGTCTGGGGCCCCAG<br>GGCAGAGGGTCACCATCTCCTGCACTGGGATGAACTCCAACATCGGGGCA<br>GGTTATGATGTATACTGGTACCAACAACTTCCAGGAAGAGCCCCCAAACT<br>CCTCATCTATGGTAACAGCAATCGGCCCTCAGGGGTCCCTGACCGATTCT<br>CTGGCTCCAGGTCTGGCACCTCAGCCTCCCTGGCCATCACTGGGCTCCAG<br>GCTGAGGATGAGGCTGATTATTACTGCCAGTCCTATGACACCAGCCTGGA<br>CGGTTGGGCTTTCGGCGGAGGGACCAAGTTGACCGTCCTAGGCCAGCCCA<br>AGGCTGCCCCCTCGGTCACTCTGTTCCCACCCTCCTCTGAGGAGCTTCAA<br>GCCAACAAGGCCACACTGGTGTGTCTCGTAAGTGACTTCTACCCGGGAGC<br>CGTGACAGTGGCCTGGAAGGCAGATGGCAGCCCCGTCAAGGTGGGAGTGG<br>AGACCACCAAACCCTCCAAACAAAGCAACAACAAGTATGCGGCCAGCAGC | |

TABLE 22-continued

| Antibody ID: AB-000224.017 | |
|---|---|
| KABAT | ASN |
| | TACCTGAGCCTGACGCCCGAGCAGTGGAAGTCCCACAGAAGCTACAGCTG<br>CCGGGTCACGCATGAAGGGAGCACCGTGGAGAAGACAGTGGCCCCTGCAG<br>AATGCTCT<br>[SEQ ID NO: 202] |
| DNA for Heavy Chain version 1 | GAGGTGCAGCTGGTGGAGTCTGGGGGAGGCTTGG<br>TACAGCCAGGGCGGTCCCTGAGACTCCCCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACAAAGT<br>ACGCCGCGGCTGTGAAGGGCAGATTCACCATCTCGCGAGATGATTCTAAA<br>AGCATTGTCTATCTGCAAATGAACAGCCTGAAAACCGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCA<br>CTACACACAGAAGAGCCTCTCCCTGTCTCCGGGTAAA [SEQ ID NO: 203] |
| DNA for Heavy Chain version 2 | GAGGTGCAGCTGGTGGAGTCTGGGGGAGGCTTGG<br>TACAGCCAGGGCGGTCCCTGAGACTCCCCTGTACAGCCTCTGGGTTTAGT<br>TTTGGTGATCATGCTATGAGCTGGGTCCGCCAGGCTCCAGGGAAGGGGCT<br>GGAGTGGGTAGGTTTCATTAGAAAGACAACTTATGGTGCGACAACAAAGT<br>ACGCCGCGGCTGTGAAGGGCAGATTCACCATCTCGCGAGATGATTCTAAA<br>AGCATTGTCTATCTGCAAATGAACAGCCTGAAAACCGAGGACACAGCCGT<br>GTATTTCTGTACTAGAGTGCAGCTTGACTATGGCCCGGGATACCAGTACT<br>ACGGTATGGACGTCTGGGGCCAAGGGACCACGGTCACCGTCTCCTCAGCC<br>TCCACCAAGGGCCCATCGGTCTTCCCCCTGGCACCCTCCTCCAAGAGCAC<br>CTCTGGGGGCACAGCAGCCCTGGGCTGCCTGGTCAAGGACTACTTCCCCG<br>AACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGT<br>GGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAA<br>TCTTGTGACAAAACTCACACATGCCCACCGTGCCCAGCACCTGAACTCCT<br>GGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCA<br>TAATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAG<br>CAGGGGAACGTCTTCTCATGCTCCGTGCTGCATGAGGCTCTGCACTCCCA<br>CTACACACAGAAGAGCCTCTCCCTGTCTCCGGGTAAA [SEQ ID NO: 2 04] |

3. Anti-CSP Antibody Variants of AB-007088

In certain embodiments, a variant of an anti-CSP antibody AB-007088 disclosed herein comprises modifications compared to AB-007088 that provide improved pharmacokinetic properties, increased serum stability, stronger binding, and/or improved in vivo protective effects compared to AB-007088. In certain embodiments, a variant of an anti-CSP antibody AB-007088 disclosed herein exhibits reduced immunogenicity and/or increased manufacturability as compared to AB-007088. In certain embodiments, a variant of an anti-CSP antibody AB-007088 disclosed herein has at least one modification, e.g., substitution, relative to the native AB-007088 variable heavy chain amino acid sequence (SEQ ID NO: 196) or variable light chain amino acid sequence (SEQ ID NO: 195), and has improved developability, e.g., decreased heterogeneity, increased yield, increased stability, improved net charges to improve pharmacokinetics, and/or reduced immunogenicity. In certain embodiments, a VH region or a VL region of such a variant of an anti-CSP antibody AB-007088 disclosed herein has at least two, three, four, five, or six, or more modifications, e.g., substitutions. In certain embodiments, a variant of the an anti-CSP antibody AB-007088 disclosed herein has a total of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 modifications, e.g. substitutions, including both variable regions, compared to AB-007088.

In certain embodiments, a variant of an anti-CSP antibody AB-007088 disclosed herein exhibits increased serum half-life as compared to AB-007088. In certain embodiments, a variant of an anti-CSP antibody AB-007088 disclosed herein has at least one modification, e.g., substitution, relative to the native AB-007088 Fc region of the heavy chain herein, and has improved pharmacokinetics properties, e.g., half-life. In certain embodiments, an Fc region of the heavy chain of such a variant of an anti-CSP antibody AB-007088 disclosed herein has at least two, three, four, five, or six, or more modifications, e.g., substitutions. In certain embodiments, a variant of the an anti-CSP antibody AB-007088 disclosed herein has a total of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 modifications, e.g. substitutions, including both heavy and light chains, compared to AB-007088. In certain non-limiting embodiments, an Fc region of the heavy chain of a variant of an anti-CSP antibody AB-007088 disclosed herein can include an isoleucine at position 250, a tyrosine at position 252, an isoleucine at position 259, a glutamine at position 307, a phenylalanine at position 308, a leucine at position 319, a leucine at position 428, a histidine at position 434, a phenylalanine at position 434, an alanine at position 434, a serine at position 434, a methionine at position 434, or a combination thereof, wherein the numbering is defined by EU index as in Kabat. In certain embodiments, an Fc region of the heavy chain of a variant of an anti-CSP antibody AB-007088 disclosed herein includes a leucine at position 428 and a serine at position 434, wherein the numbering is defined by EU index as in Kabat.

The light and heavy chain CDRs of AB-007088 as defined by Kabat numbering system are shown in Table 23 below:

TABLE 23

| AB-007088 CDR sequences (Kabat) | | | |
|---|---|---|---|
| | CDR1 | CDR2 | CDR3 |
| VL region | RASQSISSWLA (SEQ ID NO: 205) | DASSLES (SEQ ID NO: 206) | QQYNSYSFWT (SEQ ID NO: 207) |
| VH region | TYGMH (SEQ ID NO: 208) | IIWYDGSQKYYAD SVQG (SEQ ID NO: 209) | VRFSVGPHGSA FDL (SEQ ID NO: 210) |

The light and heavy chain CDRs of AB-007088 as defined by ASN are shown in Table 24 below:

TABLE 24

| AB-007088 CDR sequences (ASN) | | | |
|---|---|---|---|
| | CDR1 | CDR2 | CDR3 |
| VL region | RASQSISSWLA (SEQ ID NO: 211) | DASSLES (SEQ ID NO: 212) | QQYNSYWT (SEQ ID NO: 213) |
| VH region | TYGMH (SEQ ID NO: 214) | IIWYDGSQKYYADSVQG (SEQ ID NO: 215) | SAFDL (SEQ ID NO: 216) |

The heavy chain variable region (VH) and light chain variable region (VL) sequences and heavy and light chain sequences of AB-007088 are shown in Table 25 below:

TABLE 25

| 6AB-007088 variable region and full-length sequences | |
|---|---|
| VL region | GVQMTQSPSTLSASVGDRVTLTCRASQSISSWLAWYQQKPGKAPKLLIYDAS SLESGVPSRFSGSGSGTEFTLTISSLQPDDFATYYCQQYNSYSFWTFGQGTK VEIKR (SEQ ID NO: 217) |
| VH region | QVQLVESGGGWQPGRSLRLSCAASGFAFNTYGMHWVRQTPGKGLEWVAIIWY DGSQKYYADSVQGRFIISRDNHKNTLSLQMNGLRAEDTAVYFCVRVRFSVGP HGSAFDLWGQGTMVIVSS (SEQ ID NO: 218) |
| DNA for VL region | GGCGTCCAGATGACCCAGTCTCCTTCCACCCTGT CTGCATCTGTGGGAGACAGAGTCACCCTCACTTGCCGGGCCAGTCAGAGT ATTAGTAGTTGGTTGGCCTGGTATCAGCAGAAACCAGGGAAAGCCCCTAA ACTCCTGATCTATGATGCCTCCAGTTTGGAAAGTGGGGTCCCATCAAGGT TCAGCGGCAGTGGATCTGGGACAGAATTCACTCTCACCATCAGCAGCCTG CAACCTGATGATTTTGCAACTTATTACTGCCAACAGTATAATAGTTATTC TTTTTGGACGTTCGGCCAAGGGACCAAGGTGGAAATCAAACGC [SEQ ID NO: 219] |
| DNA for VH region | CAGGTGCAACTGGTGGAGTCTGGGGGAGGCGTGG TCCAGCCTGGGAGGTCCCTGAGACTCTCCTGTGCAGCGTCTGGGTTCGCT TTCAATACCTATGGCATGCACTGGGTCCGCCAGACTCCAGGCAAGGGGCT GGAGTGGGTGGCAATTATCTGGTATGATGGGAGCCAGAAATACTATGCAG ACTCCGTGCAGGGCCGATTCATCATCTCCAGAGACAATCACAAGAACACG TTGTCTCTGCAAATGAACGGCCTGAGAGCCGAGGACACGGCTGTGTATTT CTGTGTGAGAGTCCGCTTTAGCGTTGGCCCCCACGGGAGTGCTTTTGATC TCTGGGGCCAGGGGACAATGGTCATCGTCTCTTCA [SEQ ID NO: 220] |

TABLE 25-continued

| 6AB-007088 variable region and full-length sequences | |
|---|---|
| Light Chain | GVQMTQSPSTLSASVGDRVTLTCRASQS<br>ISSWLAWYQQKPGKAPKLLIYDASSLESGVPSRFSGSGSGTEFTLTISSL<br>QPDDFATYYCQQYNSYSFWTFGQGTKVEIKRTVAAPSVFIFPPSDEQLKS<br>GTASVVCLLNNFYPREAKVQWKVDNALQSGNSQESVTEQDSKDSTYSLSS<br>TLTLSKADYEKHKVYACEVTHQGLSSPVTKSFNRGEC<br>[SEQ ID NO: 221] |
| Heavy Chain version 1 | QVQLVESGGGVVQPGRSLRLSCAASGFA<br>FNTYGMHWVRQTPGKGLEWVAIIWYDGSQKYYADSVQGRFIISRDNHKNT<br>LSLQMNGLRAEDTAVYFCVRVRFSVGPHGSAFDLWGQGTMVIVSSASTKG<br>PSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHEDPE<br>VKFNWYVDGVEVHNAKTKPREEQYNSTYRWSVLTVLHQDWLNGKEYKCK<br>VSNKALPAPIEKTISKAKGQPREPQVYTLPPSRDELTKNQVSLTCLVKGF<br>YPSDIAVEWESNGQPENNYKTTPPVLDSDGSFFLYSKLTVDKSRWQQGNV<br>FSCSVMHEALHNHYTQKSLSLSPGK [SEQ ID NO: 222] |
| Heavy Chain version 2 | QVQLVESGGGVVQPGRSLRLSCAASGFA<br>FNTYGMHWVRQTPGKGLEWVAIIWYDGSQKYYADSVQGRFIISRDNHKNT<br>LSLQMNGLRAEDTAVYFCVRVRFSVGPHGSAFDLWGQGTMVIVSSASTKG<br>PSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHEDPE<br>VKFNWYVDGVEVHNAKTKPREEQYNSTYRWSVLTVLHQDWLNGKEYKCK<br>VSNKALPAPIEKTISKAKGQPREPQVYTLPPSRDELTKNQVSLTCLVKGF<br>YPSDIAVEWESNGQPENNYKTTPPVLDSDGSFFLYSKLTVDKSRWQQGNV<br>FSCSVLHEALHSHYTQKSLSLSPGK [SEQ ID NO: 223] |
| DNA for Light Chain | GGCGTCCAGATGACCCAGTCTCCTTCCACCCTGT<br>CTGCATCTGTGGGAGACAGAGTCACCCTCACTTGCCGGGCCAGTCAGAGT<br>ATTAGTAGTTGGTTGGCCTGGTATCAGCAGAAACCAGGGAAAGCCCCTAA<br>ACTCCTGATCTATGATGCCTCCAGTTTGGAAAGTGGGGTCCCATCAAGGT<br>TCAGCGGCAGTGGATCTGGGACAGAATTCACTCTCACCATCAGCAGCCTG<br>CAACCTGATGATTTTGCAACTTATTACTGCCAACAGTATAATAGTTATTC<br>TTTTTGGACGTTCGGCCAAGGGACCAAGGTGGAAATCAAACGCACTGTGG<br>CTGCACCATCTGTCTTCATCTTCCCGCCATCTGATGAGCAGTTGAAATCT<br>GGAACTGCCTCTGTTGTGTGCCTGCTGAATAACTTCTATCCCAGAGAGGC<br>CAAAGTACAGTGGAAGGTGGATAACGCCCTCCAATCGGGTAACTCCCAGG<br>AGAGTGTCACAGAGCAGGACAGCAAGGACAGCACCTACAGCCTCAGCAGC<br>ACCCTGACGCTGAGCAAAGCAGACTACGAGAAACACAAAGTCTACGCCTG<br>CGAAGTCACCCATCAGGGCCTGAGCTCGCCCGTCACAAAGAGCTTCAACA<br>GGGGAGAGTGT<br>[SEQ ID NO: 224] |
| DNA for Heavy Chain version 1 | CAGGTGCAACTGGTGGAGTCTGGGGGAGGCGTGG<br>TCCAGCCTGGGAGGTCCCTGAGACTCTCCTGTGCAGCGTCTGGGTTCGCT<br>TTCAATACCTATGGCATGCACTGGGTCCGCCAGACTCCAGGCAAGGGGCT<br>GGAGTGGGTGGCAATTATCTGGTATGATGGGAGCCAGAAATACTATGCAG<br>ACTCCGTGCAGGGCCGATTCATCATCTCCAGAGACAATCACAAGAACACG<br>TTGTCTCTGCAAATGAACGGCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCATCGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGATGCATGAGGCTCTGCACAACCACTACACACAGAA<br>GAGCCTCTCCCTGTCTCCGGGTAAA [SEQ ID NO: 225] |
| DNA for Heavy Chain version 2 | CAGGTGCAACTGGTGGAGTCTGGGGGAGGCGTGG<br>TCCAGCCTGGGAGGTCCCTGAGACTCTCCTGTGCAGCGTCTGGGTTCGCT<br>TTCAATACCTATGGCATGCACTGGGTCCGCCAGACTCCAGGCAAGGGGCT<br>GGAGTGGGTGGCAATTATCTGGTATGATGGGAGCCAGAAATACTATGCAG |

TABLE 25-continued

| 6AB-007088 variable region and full-length sequences |
|---|
| ACTCCGTGCAGGGCCGATTCATCATCTCCAGAGACAATCACAAGAACACG<br>TTGTCTCTGCAAATGAACGGCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCATCGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGCTGCATGAGGCTCTGCACTCCCACTACACACAGAA<br>GAGCCTCTCCCTGTCTCCGGGTAAA [SEQ ID NO: 226] |

In certain embodiments, a variant of an anti-CSP antibody includes one, two, or three CDRs of a VL sequence of Table 25. In certain embodiments, a variant of an anti-CSP antibody includes at least one mutation, e.g., a substitution, and no more than 10, 20, 30, 40, or 50 mutations in the VL amino acid sequence set forth in SEQ ID NO: 217. In certain embodiments, the VL of the variant of an anti-CSP antibody includes at least one, at least two, or at least three mutations, e.g., substitutions, in the CDR1 amino acid sequence set forth in SEQ ID NO: 205. In certain embodiments, the VL of the variant of an anti-CSP antibody includes at least one, at least two, or at least three mutations, e.g., substitutions, in the CDR2 amino acid sequence set forth in SEQ ID NO: 206. In certain embodiments, the VL of the variant of an anti-CSP antibody includes at least one, at least two, or at least three mutations, e.g., substitutions, in the CDR3 amino acid sequence set forth in SEQ ID NO: 207. In certain embodiments, the VL of the variant of an anti-CSP antibody includes at least one, at least two, or at least three mutations, e.g., substitutions, in the CDR1 amino acid sequence set forth in SEQ ID NO: 211. In certain embodiments, the VL of the variant of an anti-CSP antibody includes at least one, at least two, or at least three mutations, e.g., substitutions, in the CDR2 amino acid sequence set forth in SEQ ID NO: 212. In certain embodiments, the VL of the variant of an anti-CSP antibody includes at least one, at least two, or at least three mutations, e.g., substitutions, in the CDR3 amino acid sequence set forth in SEQ ID NO: 213. In certain embodiments, the mutation is a conservative substitution. In certain embodiments, the VL of the variant of an anti-CSP antibody includes at least one, at least two, or at least three mutations, e.g., substitutions, in the framework of the amino acid sequence set forth in SEQ ID NO: 217. An exemplary nucleic acid sequence of SEQ ID NO: 217 is set forth in SEQ ID NO: 219.

In certain embodiments, a variant of an anti-CSP antibody includes one, two, or three CDRs of a VH sequence of Table 25. In certain embodiments, a variant of an anti-CSP antibody includes at least one mutation, e.g., a substitution, and no more than 10, 20, 30, 40, or 50 mutations in the VH amino acid sequence set forth in SEQ ID NO: 218. In certain embodiments, the VH of the variant of an anti-CSP antibody includes at least one, at least two, or at least three mutations, e.g., substitutions, in the CDR1 amino acid sequence set forth in SEQ ID NO: 208. In certain embodiments, the VH of the variant of an anti-CSP antibody includes at least one, at least two, or at least three mutations, e.g., substitutions, in the CDR2 amino acid sequence set forth in SEQ ID NO: 209. In certain embodiments, the VH of the variant of an anti-CSP antibody includes at least one, at least two, or at least three mutations, e.g., substitutions, in the CDR3 amino acid sequence set forth in SEQ ID NO: 210. In certain embodiments, the VH of the variant of an anti-CSP antibody includes at least one, at least two, or at least three mutations, e.g., substitutions, in the CDR1 amino acid sequence set forth in SEQ ID NO: 214. In certain embodiments, the VH of the variant of an anti-CSP antibody includes at least one, at least two, or at least three mutations, e.g., substitutions, in the CDR2 amino acid sequence set forth in SEQ ID NO: 215. In certain embodiments, the VH of the variant of an anti-CSP antibody includes at least one, at least two, or at least three mutations, e.g., substitutions, in the CDR3 amino acid sequence set forth in SEQ ID NO: 216. In certain embodiments, the mutation is a conservative substitution. In certain embodiments, the VH of the variant of an anti-CSP antibody includes at least one, at least two, at least three mutations, at least four mutations, at least five mutations, or at least six mutations, e.g., substitutions, in the framework of the amino acid sequence set forth in SEQ ID NO: 218. An exemplary nucleic acid sequence of SEQ ID NO: 218 is set forth in SEQ ID NO: 220. In certain embodiments, the VH of the variant of an anti-CSP antibody includes a substitution at position 28 of the SEQ ID NO: 218. In certain embodiments, the substitution is A28T. In certain embodiments, the VH of the variant of an anti-CSP antibody includes a substitution at position 40 of the SEQ ID NO: 218. In certain embodiments, the substitution is T40A. In certain embodiments, the VH of the variant of an anti-CSP antibody includes a substitution at position 69 of the SEQ ID NO: 218. In certain embodiments, the substitution is I69T. In certain embodiments, the VH of the variant of an anti-CSP antibody includes a substitution at position 80 of the SEQ ID NO: 218. In certain embodiments, the substitution is S80Y. In certain embodiments, the VH of the variant of an anti- CSP antibody includes a substitution at position 85 of the SEQ ID NO: 218. In certain embodiments, the substitution is G85S. In certain embodiments, the VH of the variant of an anti-CSP antibody includes a substitution at position 120 of the SEQ ID NO: 218. In certain embodiments, the substitution is I120T.

In certain embodiments, the light chain of the variant of an anti-CSP antibody has an amino acid sequence set forth in SEQ ID NO: 221. An exemplary nucleic acid sequence of SEQ ID NO: 221 is set forth in SEQ ID NO: 224. In certain embodiments, a variant of an anti-CSP antibody includes at least one mutation, e.g., substitution, and no more than 10, 20, 30, 40, or 50 mutations in the Fc region of the heavy chain amino acid sequence set forth in SEQ ID NO: 222. In certain embodiments, the heavy chain of the variant of an anti-CSP antibody has an amino acid sequence set forth in SEQ ID NO: 222. An exemplary nucleic acid sequence of SEQ ID NO: 222 is set forth in SEQ ID NO: 225. In certain embodiments, the heavy chain of the variant of an anti-CSP antibody includes a substitution at position 434 of the SEQ ID NO: 222. In certain embodiments, the substitution is M434L. In certain embodiments, the heavy chain of the variant of an anti-CSP antibody includes a substitution at position 440 of the SEQ ID NO: 222. In certain embodiments, the substitution is L440S. In certain embodiments, the heavy chain of the variant of an anti-CSP antibody includes a substitution at position 434 of the SEQ ID NO: 222 and a substitution at position 440 of the SEQ ID NO: 222. In certain embodiments, the substitutions are M434L and N440S. In certain embodiments, the heavy chain of the variant of an anti-CSP antibody has an amino acid sequence set forth in SEQ ID NO: 223. An exemplary nucleic acid sequence of SEQ ID NO: 223 is set forth in SEQ ID NO: 226.

In certain embodiments, the light chain of the anti-CSP antibody AB-007088 and variants thereof comprises a signal peptide. In certain embodiments, the signal peptide is an IGLV2-8 signal peptide. In certain embodiments, the signal peptide has an amino acid sequence set forth in SEQ ID NO: 277. In certain embodiments, the heavy chain of the anti-CSP antibody AB-007088 and variants thereof comprises a signal peptide. In certain embodiments, the signal peptide is an IGKV1-39 signal peptide. In certain embodiments, the signal peptide has an amino acid sequence set forth in SEQ ID NO: 278.

In certain embodiments, the anti-CSP antibody variant comprises a light chain variable region comprising a CDR1, a CDR2, and a CDR3 and having the amino acid sequence set forth in SEQ ID NO: 227, as shown in Table 26. In certain embodiments, the anti-CSP antibody variant comprises a heavy chain variable region comprising a CDR1, a CDR2, and a CDR3 and having the amino acid sequence set forth in SEQ ID NO: 228, as shown in Table 26. In certain embodiments, the anti-CSP antibody variant comprises a light chain having the amino acid sequence set forth in SEQ ID NO: 231, as shown in Table 26. In certain embodiments, the anti-CSP antibody variant comprises a heavy chain having the amino acid sequence set forth in SEQ ID NO: 232, as shown in Table 26. In certain embodiments, the anti-CSP antibody variant comprises a heavy chain having the amino acid sequence set forth in SEQ ID NO: 233, as shown in Table 26. Exemplary nucleic acid sequences of SEQ ID NOS: 227, 228, 231, 232, and 233 are provided in Table 26 below.

TABLE 26

| Antibody ID: AB-007088.001 | | |
|---|---|---|
| | KABAT | ASN |
| CDR1-VL | RASQSISSWLA [SEQ ID NO: 205] | RASQSISSWLA [SEQ ID NO: 211] |
| CDR2-VL | DASSLES [SEQ ID NO: 206] | DASSLES [SEQ ID NO: 212] |
| CDR3-VL | QQYNSYSFWT [SEQ ID NO: 207] | QQYNSYSFWTF [SEQ ID NO: 213] |
| CDR1-VH | TYGMH [SEQ ID NO: 208] | TYGMH [SEQ ID NO: 214] |
| CDR2-VH | IIWYDGSQKYYADSVQG [SEQ ID NO: 209] | IIWYDGSQKYYADSVQG [SEQ ID NO: 215] |
| CDR3-VH | VRFSVGPHGSAFDL [SEQ ID NO: 210] | SAFDL [SEQ ID NO: 216] |
| VL | GVQMTQSPSTLSASVGDRVTLTCRASQS ISSWLAWYQQKPGKAPKLLIYDASSLESGVPSRFSGSGSGTEFTLTISSL QPDDFATYYCQQYNSYSFWTFGQGTKVEIKR [SEQ ID NO: 227] | |
| VH | QVQLVESGGGVVQPGRSLRLSCAASGFA FNTYGMHWVRQAPGKGLEWVAIIWYDGSQKYYADSVQGRFIISRDNHKNT LSLQMNSLRAEDTAVYFCVRVRFSVGPHGSAFDLWGQGTMVTVSS [SEQ ID NO: 228] | |
| DNA for VL | GGCGTCCAGATGACCCAGTCTCCTTCCACCCTGT CTGCATCTGTGGGAGACAGAGTCACCCTCACTTGCCGGGCCAGTCAGAGT ATTAGTAGTTGGTTGGCCTGGTATCAGCAGAAACCAGGGAAAGCCCCTAA ACTCCTGATCTATGATGCCTCCAGTTTGGAAAGTGGGGTCCCATCAAGGT | |

TABLE 26-continued

| Antibody ID: AB-007088.001 | |
|---|---|
| KABAT | ASN |
| | TCAGCGGCAGTGGATCTGGGACAGAATTCACTCTCACCATCAGCAGCCTG<br>CAACCTGATGATTTTGCAACTTATTACTGCCAACAGTATAATAGTTATTC<br>TTTTTGGACGTTCGGCCAAGGGACCAAGGTGGAAATCAAACGC<br>[SEQ ID NO: 229] |
| DNA forVH | CAGGTGCAACTGGTGGAGTCTGGGGGAGGCGTGG<br>TCCAGCCTGGGAGGTCCCTGAGACTCTCCTGTGCAGCGTCTGGGTTCGCT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCATCATCTCCAGAGACAATCACAAGAACACG<br>TTGTCTCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCA<br>[SEQ ID NO: 230] |
| Light Chain | GVQMTQSPSTLSASVGDRVTLTCRASQS<br>ISSWLAWYQQKPGKAPKLLIYDASSLESGVPSRFSGSGSGTEFTLTISSL<br>QPDDFATYYCQQYNSYSFWTFGQGTKVEIKRTVAAPSVFIFPPSDEQLKS<br>GTASVVCLLNNFYPREAKVQWKVDNALQSGNSQESVTEQDSKDSTYSLSS<br>TLTLSKADYEKHKVYACEVTHQGLSSPVTKSFNRGEC<br>[SEQ ID NO: 231] |
| Heavy Chain version 1 | QVQLVESGGGVVQPGRSLRLSCAASGFA<br>FNTYGMHWVRQAPGKGLEWVAIIWYDGSQKYYADSVQGRFIISRDNHKNT<br>LSLQMNSLRAEDTAVYFCVRVRFSVGPHGSAFDLWGQGTMVTVSSASTKG<br>PSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCK<br>VSNKALPAPIEKTISKAKGQPREPQVYTLPPSRDELTKNQVSLTCLVKGF<br>YPSDIAVEWESNGQPENNYKTTPPVLDSDGSFFLYSKLTVDKSRWQQGNV<br>FSCSVMHEALHNHYTQKSLSLSPGK<br>[SEQ ID NO: 232] |
| Heavy Chain version 2 | QVQLVESGGGVVQPGRSLRLSCAASGFA<br>FNTYGMHWVRQAPGKGLEWVAIIWYDGSQKYYADSVQGRFIISRDNHKNT<br>LSLQMNSLRAEDTAVYFCVRVRFSVGPHGSAFDLWGQGTMVTVSSASTKG<br>PSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCK<br>VSNKALPAPIEKTISKAKGQPREPQVYTLPPSRDELTKNQVSLTCLVKGF<br>YPSDIAVEWESNGQPENNYKTTPPVLDSDGSFFLYSKLTVDKSRWQQGNV<br>FSCSVLHEALHSHYTQKSLSLSPGK [SEQ ID NO: 233] |
| DNA for Light Chain | GGCGTCCAGATGACCCAGTCTCCTTCCACCCTGT<br>CTGCATCTGTGGGAGACAGAGTCACCCTCACTTGCCGGGCCAGTCAGAGT<br>ATTAGTAGTTGGTTGGCCTGGTATCAGCAGAAACCAGGGAAAGCCCCTAA<br>ACTCCTGATCTATGATGCCTCCAGTTTGGAAAGTGGGGTCCCATCAAGGT<br>TCAGCGGCAGTGGATCTGGGACAGAATTCACTCTCACCATCAGCAGCCTG<br>CAACCTGATGATTTTGCAACTTATTACTGCCAACAGTATAATAGTTATTC<br>TTTTTGGACGTTCGGCCAAGGGACCAAGGTGGAAATCAAACGCACTGTGG<br>CTGCACCATCTGTCTTCATCTTCCCGCCATCTGATGAGCAGTTGAAATCT<br>GGAACTGCCTCTGTTGTGTGCCTGCTGAATAACTTCTATCCCAGAGAGGC<br>CAAAGTACAGTGGAAGGTGGATAACGCCCTCCAATCGGGTAACTCCCAGG<br>AGAGTGTCACAGAGCAGGACAGCAAGGACAGCACCTACAGCCTCAGCAGC<br>ACCCTGACGCTGAGCAAAGCAGACTACGAGAAACACAAAGTCTACGCCTG<br>CGAAGTCACCCATCAGGGCCTGAGCTCGCCCGTCACAAAGAGCTTCAACA<br>GGGGAGAGTGT<br>[SEQ ID NO: 234] |
| DNA for Heavy Chain version 1 | CAGGTGCAACTGGTGGAGTCTGGGGGAGGCGTGG<br>TCCAGCCTGGGAGGTCCCTGAGACTCTCCTGTGCAGCGTCTGGGTTCGCT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCATCATCTCCAGAGACAATCACAAGAACACG<br>TTGTCTCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC |

TABLE 26-continued

| Antibody ID: AB-007088.001 | | |
|---|---|---|
| | KABAT | ASN |
| | AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGATGCATGAGGCTCTGCACAACCACTACACACAGAA<br>GAGCCTCTCCCTGTCTCCGGGTAAA [SEQ ID NO: 235] | |
| DNA for Heavy Chain version 2 | CAGGTGCAACTGGTGGAGTCTGGGGGAGGCGTGG<br>TCCAGCCTGGGAGGTCCCTGAGACTCTCCTGTGCAGCGTCTGGGTTCGCT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCATCATCTCCAGAGACAATCACAAGAACACG<br>TTGTCTCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGCTGCATGAGGCTCTGCACTCCCACTACACACAGAA<br>GAGCCTCTCCCTGTCTCCGGGTAAA [SEQ ID NO: 236] | |

In certain embodiments, the anti-CSP antibody variant comprises a light chain variable region comprising a CDR1, a CDR2, and a CDR3 and having the amino acid sequence set forth in SEQ ID NO: 237, as shown in Table 27. In certain embodiments, the anti-CSP antibody variant comprises a heavy chain variable region comprising a CDR1, a CDR2, and a CDR3 and having the amino acid sequence set forth in SEQ ID NO: 238, as shown in Table 27. In certain embodiments, the anti-CSP antibody variant comprises a light chain having the amino acid sequence set forth in SEQ ID NO: 241, as shown in Table 27. In certain embodiments, the anti-CSP antibody variant comprises a heavy chain having the amino acid sequence set forth in SEQ ID NO: 242, as shown in Table 27. In certain embodiments, the anti-CSP antibody variant comprises a heavy chain having the amino acid sequence set forth in SEQ ID NO: 243, as shown in Table 27. Exemplary nucleic acid sequences of SEQ ID NOS: 237, 238, 241, 242, and 243 are provided in Table 27 below.

TABLE 27

| Antibody ID: AB-007088.002 | | |
|---|---|---|
| | KABAT | ASN |
| CDR1-VL | RASQSISSWLA [SEQ ID NO: 205] | RASQSISSWLA [SEQ ID NO: 211] |
| CDR2-VL | DASSLES [SEQ ID NO: 206] | DASSLES [SEQ ID NO: 212] |
| CDR3-VL | QQYNSYSFWT [SEQ ID NO: 207] | QQYNSYSFWTF [SEQ ID NO: 213] |
| CDR1-VH | TYGMH [SEQ ID NO: 208] | TYGMH [SEQ ID NO: 214] |

TABLE 27-continued

| Antibody ID: AB-007088.002 | | |
|---|---|---|
| | KABAT | ASN |
| CDR2-VH | IIWYDGSQKYYADSVQG [SEQ ID NO: 209] | IIWYDGSQKYYADSVQG [SEQ ID NO: 215] |
| CDR3-VH | VRFSVGPHGSAFDL [SEQ ID NO: 210] | SAFDL [SEQ ID NO: 216] |
| VL | GVQMTQSPSTLSASVGDRVTLTCRASQS ISSWLAWYQQKPGKAPKLLIYDASSLESGVPSRFSGSGSGTEFTLTISSL QPDDFATYYCQQYNSYSFWTFGQGTKVEIKR [SEQ ID NO: 237] | |
| VH | QVQLVESGGGVVQPGRSLRLSCAASGFT FNTYGMHWVRQAPGKGLEWVAIIWYDGSQKYYADSVQGRFIISRDNHKNT LSLQMNSLRAEDTAVYFCVRVRFSVGPHGSAFDLWGQGTMVTVSS [SEQ ID NO: 238] | |
| DNA for VL | GGCGTCCAGATGACCCAGTCTCCTTCCACCCTGT CTGCATCTGTGGGAGACAGAGTCACCCTCACTTGCCGGGCCAGTCAGAGT ATTAGTAGTTGGTTGGCCTGGTATCAGCAGAAACCAGGGAAAGCCCCTAA ACTCCTGATCTATGATGCCTCCAGTTTGGAAAGTGGGGTCCCATCAAGGT TCAGCGGCAGTGGATCTGGGACAGAATTCACTCTCACCATCAGCAGCCTG CAACCTGATGATTTTGCAACTTATTACTGCCAACAGTATAATAGTTATTC TTTTTGGACGTTCGGCCAAGGGACCAAGGTGGAAATCAAACGC [SEQ ID NO: 239] | |
| DNA forVH | CAGGTGCAACTGGTGGAGTCTGGGGGAGGCGTGG TCCAGCCTGGGAGGTCCCTGAGACTCTCCTGTGCAGCGTCTGGGTTCACT TTCAATACCTATGGCATGCACTGGGTCCGCCAGGCACCAGGCAAGGGGCT GGAGTGGGTGGCAATTATCTGGTATGATGGGAGCCAGAAATACTATGCAG ACTCCGTGCAGGGCCGATTCATCATCTCCAGAGACAATCACAAGAACACG TTGTCTCTGCAAATGAACTCCCTGAGAGCCGAGGACACGGCTGTGTATTT CTGTGTGAGAGTCCGCTTTAGCGTTGGCCCCCACGGGAGTGCTTTTGATC TCTGGGGCCAGGGGACAATGGTCACAGTCTCTTCA [SEQ ID NO: 240] | |
| Light Chain | GVQMTQSPSTLSASVGDRVTLTCRASQS ISSWLAWYQQKPGKAPKLLIYDASSLESGVPSRFSGSGSGTEFTLTISSL QPDDFATYYCQQYNSYSFWTFGQGTKVEIKRTVAAPSVFIFPPSDEQLKS GTASVVCLLNNFYPREAKVQWKVDNALQSGNSQESVTEQDSKDSTYSLSS TLTLSKADYEKHKVYACEVTHQGLSSPVTKSFNRGEC [SEQ ID NO: 241] | |
| Heavy Chain version 1 | QVQLVESGGGVVQPGRSLRLSCAASGFT FNTYGMHWVRQAPGKGLEWVAIIWYDGSQKYYADSVQGRFIISRDNHKNT LSLQMNSLRAEDTAVYFCVRVRFSVGPHGSAFDLWGQGTMVTVSSASTKG PSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGF YPSDIAVEWESNGQPENNYKTTPPVLDSDGSFFLYSKLTVDKSRWQQGNV FSCSVMHEALHNHYTQKSLSLSPGK [SEQ ID NO: 242] | |
| Heavy Chain version 2 | QVQLVESGGGVVQPGRSLRLSCAASGFT FNTYGMHWVRQAPGKGLEWVAIIWYDGSQKYYADSVQGRFIISRDNHKNT LSLQMNSLRAEDTAVYFCVRVRFSVGPHGSAFDLWGQGTMVTVSSASTKG PSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGF YPSDIAVEWESNGQPENNYKTTPPVLDSDGSFFLYSKLTVDKSRWQQGNV FSCSVLHEALHSHYTQKSLSLSPGK [SEQ ID NO: 243] | |
| DNA for Light Chain | GGCGTCCAGATGACCCAGTCTCCTTCCACCCTGT CTGCATCTGTGGGAGACAGAGTCACCCTCACTTGCCGGGCCAGTCAGAGT ATTAGTAGTTGGTTGGCCTGGTATCAGCAGAAACCAGGGAAAGCCCCTAA ACTCCTGATCTATGATGCCTCCAGTTTGGAAAGTGGGGTCCCATCAAGGT TCAGCGGCAGTGGATCTGGGACAGAATTCACTCTCACCATCAGCAGCCTG CAACCTGATGATTTTGCAACTTATTACTGCCAACAGTATAATAGTTATTC TTTTTGGACGTTCGGCCAAGGGACCAAGGTGGAAATCAAACGCACTGTGG CTGCACCATCTGTCTTCATCTTCCCGCCATCTGATGAGCAGTTGAAATCT GGAACTGCCTCTGTTGTGTGCCTGCTGAATAACTTCTATCCCAGAGAGGC CAAAGTACAGTGGAAGGTGGATAACGCCCTCCAATCGGGTAACTCCCAGG AGAGTGTCACAGAGCAGGACAGCAAGGACAGCACCTACAGCCTCAGCAGC | |

TABLE 27-continued

| Antibody ID: AB-007088.002 | |
|---|---|
| KABAT | ASN |
| | ACCCTGACGCTGAGCAAAGCAGACTACGAGAAACACAAAGTCTACGCCTG<br>CGAAGTCACCCATCAGGGCCTGAGCTCGCCCGTCACAAAGAGCTTCAACA<br>GGGGAGAGTGT<br>[SEQ ID NO: 244] |
| DNA for Heavy Chain version 1 | CAGGTGCAACTGGTGGAGTCTGGGGGAGGCGTGG<br>TCCAGCCTGGGAGGTCCCTGAGACTCTCCTGTGCAGCGTCTGGGTTCACT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCATCATCTCCAGAGACAATCACAAGAACACG<br>TTGTCTCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGATGCATGAGGCTCTGCACAACCACTACACACAGAA<br>GAGCCTCTCCCTGTCTCCGGGTAAA [SEQ ID NO: 245] |
| DNA for Heavy Chain version 2 | CAGGTGCAACTGGTGGAGTCTGGGGGAGGCGTGG<br>TCCAGCCTGGGAGGTCCCTGAGACTCTCCTGTGCAGCGTCTGGGTTCACT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCATCATCTCCAGAGACAATCACAAGAACACG<br>TTGTCTCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGCTGCATGAGGCTCTGCACTCCCACTACACACAGAA<br>GAGCCTCTCCCTGTCTCCGGGTAAA [SEQ ID NO: 246] |

In certain embodiments, the anti-CSP antibody variant comprises a light chain variable region comprising a CDR1, a CDR2, and a CDR3 and having the amino acid sequence set forth in SEQ ID NO: 247, as shown in Table 28. In certain embodiments, the anti-CSP antibody variant comprises a heavy chain variable region comprising a CDR1, a CDR2, and a CDR3 and having the amino acid sequence set forth in SEQ ID NO: 248, as shown in Table 28. In certain embodiments, the anti-CSP antibody variant comprises a light chain having the amino acid sequence set forth in SEQ ID NO: 251, as shown in Table 28. In certain embodiments, the anti-CSP antibody variant comprises a heavy chain having the amino acid sequence set forth in SEQ ID NO: 252, as shown in Table 28. In certain embodiments, the anti-CSP antibody variant comprises a heavy chain having the amino acid sequence set forth in SEQ ID NO: 253, as shown in Table 28. Exemplary nucleic acid sequences of SEQ ID NOS: 247, 248, 251, 252, and 253 are provided in Table 28 below.

TABLE 28

| Antibody ID: AB-007088.003 | | |
|---|---|---|
| | KABAT | ASN |
| CDR1-VL | RASQSISSWLA [SEQ ID NO: 205] | RASQSISSWLA [SEQ ID NO: 211] |
| CDR2-VL | DASSLES [SEQ ID NO: 206] | DASSLES [SEQ ID NO: 212] |
| CDR3-VL | QQYNSYSFWT [SEQ ID NO: 207] | QQYNSYSFWTF [SEQ ID NO: 213] |
| CDR1-VH | TYGMH [SEQ ID NO: 208] | TYGMH [SEQ ID NO: 214] |
| CDR2-VH | IIWYDGSQKYYADSVQG [SEQ ID NO: 209] | IIWYDGSQKYYADSVQG [SEQ ID NO: 215] |
| CDR3-VH | VRFSVGPHGSAFDL [SEQ ID NO: 210] | SAFDL [SEQ ID NO: 216] |
| VL | GVQMTQSPSTLSASVGDRVTLTCRASQS ISSWLAWYQQKPGKAPKLLIYDASSLESGVPSRFSGSGSGTEFTLTISSL QPDDFATYYCQQYNSYSFWTFGQGTKVEIKR [SEQ ID NO: 247] | |
| VH | QVQLVESGGGVVQPGRSLRLSCAASGFA FNTYGMHWVRQAPGKGLEWVAIIWYDGSQKYYADSVQGRFTISRDNHKNT LSLQMNSLRAEDTAVYFCVRVRFSVGPHGSAFDLWGQGTMVTVSS [SEQ ID NO: 248] | |
| DNA for VL | GGCGTCCAGATGACCCAGTCTCCTTCCACCCTGT CTGCATCTGTGGGAGACAGAGTCACCCTCACTTGCCGGGCCAGTCAGAGT ATTAGTAGTTGGTTGGCCTGGTATCAGCAGAAACCAGGGAAAGCCCCTAA ACTCCTGATCTATGATGCCTCCAGTTTGGAAAGTGGGGTCCCATCAAGGT TCAGCGGCAGTGGATCTGGGACAGAATTCACTCTCACCATCAGCAGCCTG CAACCTGATGATTTTGCAACTTATTACTGCCAACAGTATAATAGTTATTC TTTTTGGACGTTCGGCCAAGGGACCAAGGTGGAAATCAAACGC [SEQ ID NO: 249] | |
| DNA forVH | CAGGTGCAACTGGTGGAGTCTGGGGGAGGCGTGG TCCAGCCTGGGAGGTCCCTGAGACTCTCCTGTGCAGCGTCTGGGTTCGCT TTCAATACCTATGGCATGCACTGGGTCCGCCAGGCACCAGGCAAGGGGCT GGAGTGGGTGGCAATTATCTGGTATGATGGGAGCCAGAAATACTATGCAG ACTCCGTGCAGGGCCGATTCACTATCTCCAGAGACAATCACAAGAACACG TTGTCTCTGCAAATGAACTCCCTGAGAGCCGAGGACACGGCTGTGTATTT CTGTGTGAGAGTCCGCTTTAGCGTTGGCCCCCACGGGAGTGCTTTTGATC TCTGGGGCCAGGGGACAATGGTCACAGTCTCTTCA [SEQ ID NO: 250] | |
| Light Chain | GVQMTQSPSTLSASVGDRVTLTCRASQS ISSWLAWYQQKPGKAPKLLIYDASSLESGVPSRFSGSGSGTEFTLTISSL QPDDFATYYCQQYNSYSFWTFGQGTKVEIKRTVAAPSVFIFPPSDEQLKS GTASVVCLLNNFYPREAKVQWKVDNALQSGNSQESVTEQDSKDSTYSLSS TLTLSKADYEKHKVYACEVTHQGLSSPVTKSFNRGEC [SEQ ID NO: 251] | |
| Heavy Chain version 1 | QVQLVESGGGVVQPGRSLRLSCAASGFA FNTYGMHWVRQAPGKGLEWVAIIWYDGSQKYYADSVQGRFTISRDNHKNT LSLQMNSLRAEDTAVYFCVRVRFSVGPHGSAFDLWGQGTMVTVSSASTKG PSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGF YPSDIAVEWESNGQPENNYKTTPPVLDSDGSFFLYSKLTVDKSRWQQGNV FSCSVMHEALHNHYTQKSLSLSPGK [SEQ ID NO: 252] | |
| Heavy Chain version 2 | QVQLVESGGGVVQPGRSLRLSCAASGFA FNTYGMHWVRQAPGKGLEWVAIIWYDGSQKYYADSVQGRFTISRDNHKNT LSLQMNSLRAEDTAVYFCVRVRFSVGPHGSAFDLWGQGTMVTVSSASTKG PSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGF YPSDIAVEWESNGQPENNYKTTPPVLDSDGSFFLYSKLTVDKSRWQQGNV FSCSVLHEALHSHYTQKSLSLSPGK [SEQ ID NO: 253] | |

TABLE 28-continued

| Antibody ID: AB-007088.003 | |
|---|---|
| KABAT | ASN |
| DNA for Light Chain | GGCGTCCAGATGACCCAGTCTCCTTCCACCCTGT<br>CTGCATCTGTGGGAGACAGAGTCACCCTCACTTGCCGGGCCAGTCAGAGT<br>ATTAGTAGTTGGTTGGCCTGGTATCAGCAGAAACCAGGGAAAGCCCCTAA<br>ACTCCTGATCTATGATGCCTCCAGTTTGGAAAGTGGGGTCCCATCAAGGT<br>TCAGCGGCAGTGGATCTGGGACAGAATTCACTCTCACCATCAGCAGCCTG<br>CAACCTGATGATTTTGCAACTTATTACTGCCAACAGTATAATAGTTATTC<br>TTTTTGGACGTTCGGCCAAGGGACCAAGGTGGAAATCAAACGCACTGTGG<br>CTGCACCATCTGTCTTCATCTTCCCGCCATCTGATGAGCAGTTGAAATCT<br>GGAACTGCCTCTGTTGTGTGCCTGCTGAATAACTTCTATCCCAGAGAGGC<br>CAAAGTACAGTGGAAGGTGGATAACGCCCTCCAATCGGGTAACTCCCAGG<br>AGAGTGTCACAGAGCAGGACAGCAAGGACAGCACCTACAGCCTCAGCAGC<br>ACCCTGACGCTGAGCAAAGCAGACTACGAGAAACACAAAGTCTACGCCTG<br>CGAAGTCACCCATCAGGGCCTGAGCTCGCCCGTCACAAAGAGCTTCAACA<br>GGGGAGAGTGT<br>[SEQ ID NO: 254] |
| DNA for Heavy Chain version 1 | CAGGTGCAACTGGTGGAGTCTGGGGGAGGCGTGG<br>TCCAGCCTGGGAGGTCCCTGAGACTCTCCTGTGCAGCGTCTGGGTTCGCT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCACTATCTCCAGAGACAATCACAAGAACACG<br>TTGTCTCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGATGCATGAGGCTCTGCACAACCACTACACACAGAA<br>GAGCCTCTCCCTGTCTCCGGGTAAA [SEQ ID NO: 255] |
| DNA for Heavy Chain version 2 | CAGGTGCAACTGGTGGAGTCTGGGGGAGGCGTGG<br>TCCAGCCTGGGAGGTCCCTGAGACTCTCCTGTGCAGCGTCTGGGTTCGCT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCACTATCTCCAGAGACAATCACAAGAACACG<br>TTGTCTCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGCTGCATGAGGCTCTGCACTCCCACTACACACAGAA<br>GAGCCTCTCCCTGTCTCCGGGTAAA [SEQ ID NO: 256] |

In certain embodiments, the anti-CSP antibody variant comprises a light chain variable region comprising a CDR1, a CDR2, and a CDR3 and having the amino acid sequence set forth in SEQ ID NO: 257, as shown in Table 29. In certain embodiments, the anti-CSP antibody variant comprises a heavy chain variable region comprising a CDR1, a CDR2, and a CDR3 and having the amino acid sequence set forth in SEQ ID NO: 258, as shown in Table 29. In certain embodiments, the anti-CSP antibody variant comprises a light chain having the amino acid sequence set forth in SEQ ID NO: 261, as shown in Table 29. In certain embodiments, the anti-CSP antibody variant comprises a heavy chain having the amino acid sequence set forth in SEQ ID NO: 262, as shown in Table 29. In certain embodiments, the anti-CSP antibody variant comprises a heavy chain having the amino acid sequence set forth in SEQ ID NO: 263, as shown in Table 29. Exemplary nucleic acid sequences of SEQ ID NOS: 257, 258, 261, 262, and 263 are provided in Table 29 below.

TABLE 29

| Antibody ID: AB-007088.004 | | |
|---|---|---|
| | KABAT | ASN |
| CDR1-VL | RASQSISSWLA [SEQ ID NO: 205] | RASQSISSWLA [SEQ ID NO: 211] |
| CDR2-VL | DASSLES [SEQ ID NO: 206] | DASSLES [SEQ ID NO: 212] |
| CDR3-VL | QQYNSYSFWT [SEQ ID NO: 207] | QQYNSYSFWTF [SEQ ID NO: 213] |
| CDR1-VH | TYGMH [SEQ ID NO: 208] | TYGMH [SEQ ID NO: 214] |
| CDR2-VH | IIWYDGSQKYYADSVQG [SEQ ID NO: 209] | IIWYDGSQKYYADSVQG [SEQ ID NO: 215] |
| CDR3-VH | VRFSVGPHGSAFDL [SEQ ID NO: 210] | SAFDL [SEQ ID NO: 216] |
| VL | GVQMTQSPSTLSASVGDRVTLTCRASQS<br>ISSWLAWYQQKPGKAPKLLIYDASSLESGVPSRFSGSGSGTEFTLTISSL<br>QPDDFATYYCQQYNSYSFWTFGQGTKVEIKR<br>[SEQ ID NO: 257] | |
| VH | QVQLVESGGGVVQPGRSLRLSCAASGFT<br>FNTYGMHWVRQAPGKGLEWVAIIWYDGSQKYYADSVQGRFTISRDNHKNT<br>LSLQMNSLRAEDTAVYFCVRVRFSVGPHGSAFDLWGQGTMVTVSS<br>[SEQ ID NO: 258] | |
| DNA for VL | GGCGTCCAGATGACCCAGTCTCCTTCCACCCTGT<br>CTGCATCTGTGGGAGACAGAGTCACCCTCACTTGCCGGGCCAGTCAGAGT<br>ATTAGTAGTTGGTTGGCCTGGTATCAGCAGAAACCAGGGAAAGCCCCTAA<br>ACTCCTGATCTATGATGCCTCCAGTTTGGAAAGTGGGGTCCCATCAAGGT<br>TCAGCGGCAGTGGATCTGGGACAGAATTCACTCTCACCATCAGCAGCCTG<br>CAACCTGATGATTTTGCAACTTATTACTGCCAACAGTATAATAGTTATTC<br>TTTTTGGACGTTCGGCCAAGGGACCAAGGTGGAAATCAAACGC<br>[SEQ ID NO: 259] | |
| DNA forVH | CAGGTGCAACTGGTGGAGTCTGGGGGAGGCGTGG<br>TCCAGCCTGGGAGGTCCCTGAGACTCTCCTGTGCAGCGTCTGGGTTCACT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCACTATCTCCAGAGACAATCACAAGAACACG<br>TTGTCTCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCA<br>[SEQ ID NO: 260] | |
| Light Chain | GVQMTQSPSTLSASVGDRVTLTCRASQS<br>ISSWLAWYQQKPGKAPKLLIYDASSLESGVPSRFSGSGSGTEFTLTISSL<br>QPDDFATYYCQQYNSYSFWTFGQGTKVEIKRTVAAPSVFIFPPSDEQLKS<br>GTASVVCLLNNFYPREAKVQWKVDNALQSGNSQESVTEQDSKDSTYSLSS<br>TLTLSKADYEKHKVYACEVTHQGLSSPVTKSFNRGEC<br>[SEQ ID NO: 261] | |
| Heavy Chain version 1 | QVQLVESGGGVVQPGRSLRLSCAASGFT<br>FNTYGMHWVRQAPGKGLEWVAIIWYDGSQKYYADSVQGRFTISRDNHKNT<br>LSLQMNSLRAEDTAVYFCVRVRFSVGPHGSAFDLWGQGTMVTVSSASTKG<br>PSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCK<br>VSNKALPAPIEKTISKAKGQPREPQVYTLPPSRDELTKNQVSLTCLVKGF<br>YPSDIAVEWESNGQPENNYKTTPPVLDSDGSFFLYSKLTVDKSRWQQGNV | |

TABLE 29-continued

| Antibody ID: AB-007088.004 | |
|---|---|
| KABAT | ASN |
| | FSCSVMHEALHNHYTQKSLSLSPGK [SEQ ID NO: 262] |
| Heavy Chain version 2 | QVQLVESGGGVVQPGRSLRLSCAASGFT FNTYGMHWVRQAPGKGLEWVAIIWYDGSQKYYADSVQGRFTISRDNHKNT LSLQMNSLRAEDTAVYFCVRVRFSVGPHGSAFDLWGQGTMVTVSSASTKG PSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGF YPSDIAVEWESNGQPENNYKTTPPVLDSDGSFFLYSKLTVDKSRWQQGNV FSCSVLHEALHSHYTQKSLSLSPGK [SEQ ID NO: 263] |
| DNA for Light Chain | GGCGTCCAGATGACCCAGTCTCCTTCCACCCTGT CTGCATCTGTGGGAGACAGAGTCACCCTCACTTGCCGGGCCAGTCAGAGT ATTAGTAGTTGGTTGGCCTGGTATCAGCAGAAACCAGGGAAAGCCCCTAA ACTCCTGATCTATGATGCCTCCAGTTTGGAAAGTGGGGTCCCATCAAGGT TCAGCGGCAGTGGATCTGGGACAGAATTCACTCTCACCATCAGCAGCCTG CAACCTGATGATTTTGCAACTTATTACTGCCAACAGTATAATAGTTATTC TTTTTGGACGTTCGGCCAAGGGACCAAGGTGGAAATCAAACGCACTGTGG CTGCACCATCTGTCTTCATCTTCCCGCCATCTGATGAGCAGTTGAAATCT GGAACTGCCTCTGTTGTGTGCCTGCTGAATAACTTCTATCCCAGAGAGGC CAAAGTACAGTGGAAGGTGGATAACGCCCTCCAATCGGGTAACTCCCAGG AGAGTGTCACAGAGCAGGACAGCAAGGACAGCACCTACAGCCTCAGCAGC ACCCTGACGCTGAGCAAAGCAGACTACGAGAAACACAAAGTCTACGCCTG CGAAGTCACCCATCAGGGCCTGAGCTCGCCCGTCACAAAGAGCTTCAACA GGGGAGAGTGT [SEQ ID NO: 264] |
| DNA for Heavy Chain version 1 | CAGGTGCAACTGGTGGAGTCTGGGGGAGGCGTGG TCCAGCCTGGGAGGTCCCTGAGACTCTCCTGTGCAGCGTCTGGGTTCACT TTCAATACCTATGGCATGCACTGGGTCCGCCAGGCACCAGGCAAGGGGCT GGAGTGGGTGGCAATTATCTGGTATGATGGGAGCCAGAAATACTATGCAG ACTCCGTGCAGGGCCGATTCACTATCTCCAGAGACAATCACAAGAACACG TTGTCTCTGCAAATGAACTCCCTGAGAGCCGAGGACACGGCTGTGTATTT CTGTGTGAGAGTCCGCTTTAGCGTTGGCCCCCACGGGAGTGCTTTTGATC TCTGGGGCCAGGGGACAATGGTCACAGTCTCTTCAGCCTCCACCAAGGGC CCATCGGTCTTCCCCCTGGCACCCTCCTCCAAGAGCACCTCTGGGGGCAC AGCAGCCCTGGGCTGCCTGGTCAAGGACTACTTCCCCGAACCGGTGACGG TGTCGTGGAACTCAGGCGCCCTGACCAGCGGCGTGCACACCTTCCCGGCT GTCCTACAGTCCTCAGGACTCTACTCCCTCAGCAGCGTGGTGACCGTGCC CTCCAGCAGCTTGGGCACCCAGACCTACATCTGCAACGTGAATCACAAGC CCAGCAACACCAAGGTGGACAAGAAAGTTGAGCCCAAATCTTGTGACAAA ACTCACACATGCCCACCGTGCCCAGCACCTGAACTCCTGGGGGGACCGTC AGTCTTCCTCTTCCCCCCAAAACCCAAGGACACCCTCATGATCTCCCGGA CCCCTGAGGTCACATGCGTGGTGGTGGACGTGAGCCACGAAGACCCTGAG GTCAAGTTCAACTGGTACGTGGACGGCGTGGAGGTGCATAATGCCAAGAC AAAGCCGCGGGAGGAGCAGTACAACAGCACGTACCGTGTGGTCAGCGTCC TCACCGTCCTGCACCAGGACTGGCTGAATGGCAAGGAGTACAAGTGCAAG GTCTCCAACAAAGCCCTCCCAGCCCCCATCGAGAAAACCATCTCCAAAGC CAAAGGGCAGCCCCGAGAACCACAGGTGTACACCCTGCCCCCATCCCGGG ATGAGCTGACCAAGAACCAGGTCAGCCTGACCTGCCTGGTCAAAGGCTTC TATCCCAGCGACATCGCCGTGGAGTGGGAGAGCAATGGGCAGCCGGAGAA CAACTACAAGACCACGCCTCCCGTGCTGGACTCCGACGGCTCCTTCTTCC TCTACAGCAAGCTCACCGTGGACAAGAGCAGGTGGCAGCAGGGGAACGTC TTCTCATGCTCCGTGATGCATGAGGCTCTGCACAACCACTACACACAGAA GAGCCTCTCCCTGTCTCCGGGTAAA [SEQ ID NO: 265] |
| DNA for Heavy Chain version 2 | CAGGTGCAACTGGTGGAGTCTGGGGGAGGCGTGG TCCAGCCTGGGAGGTCCCTGAGACTCTCCTGTGCAGCGTCTGGGTTCACT TTCAATACCTATGGCATGCACTGGGTCCGCCAGGCACCAGGCAAGGGGCT GGAGTGGGTGGCAATTATCTGGTATGATGGGAGCCAGAAATACTATGCAG ACTCCGTGCAGGGCCGATTCACTATCTCCAGAGACAATCACAAGAACACG TTGTCTCTGCAAATGAACTCCCTGAGAGCCGAGGACACGGCTGTGTATTT CTGTGTGAGAGTCCGCTTTAGCGTTGGCCCCCACGGGAGTGCTTTTGATC TCTGGGGCCAGGGGACAATGGTCACAGTCTCTTCAGCCTCCACCAAGGGC CCATCGGTCTTCCCCCTGGCACCCTCCTCCAAGAGCACCTCTGGGGGCAC AGCAGCCCTGGGCTGCCTGGTCAAGGACTACTTCCCCGAACCGGTGACGG TGTCGTGGAACTCAGGCGCCCTGACCAGCGGCGTGCACACCTTCCCGGCT GTCCTACAGTCCTCAGGACTCTACTCCCTCAGCAGCGTGGTGACCGTGCC CTCCAGCAGCTTGGGCACCCAGACCTACATCTGCAACGTGAATCACAAGC CCAGCAACACCAAGGTGGACAAGAAAGTTGAGCCCAAATCTTGTGACAAA ACTCACACATGCCCACCGTGCCCAGCACCTGAACTCCTGGGGGGACCGTC AGTCTTCCTCTTCCCCCCAAAACCCAAGGACACCCTCATGATCTCCCGGA CCCCTGAGGTCACATGCGTGGTGGTGGACGTGAGCCACGAAGACCCTGAG |

TABLE 29-continued

| Antibody ID: AB-007088.004 | |
|---|---|
| KABAT | ASN |
| GTCAAGTTCAACTGGTACGTGGACGGCGTGGAGGTGCATAATGCCAAGAC AAAGCCGCGGGAGGAGCAGTACAACAGCACGTACCGTGTGGTCAGCGTCC TCACCGTCCTGCACCAGGACTGGCTGAATGGCAAGGAGTACAAGTGCAAG GTCTCCAACAAAGCCCTCCCAGCCCCCATCGAGAAAACCATCTCCAAAGC CAAAGGGCAGCCCCGAGAACCACAGGTGTACACCCTGCCCCCATCCCGGG ATGAGCTGACCAAGAACCAGGTCAGCCTGACCTGCCTGGTCAAAGGCTTC TATCCCAGCGACATCGCCGTGGAGTGGGAGAGCAATGGGCAGCCGGAGAA CAACTACAAGACCACGCCTCCCGTGCTGGACTCCGACGGCTCCTTCTTCC TCTACAGCAAGCTCACCGTGGACAAGAGCAGGTGGCAGCAGGGGAACGTC TTCTCATGCTCCGTGCTGCATGAGGCTCTGCACTCCCACTACACACAGAA GAGCCTCTCCCTGTCTCCGGGTAAA [SEQ ID NO: 266] | |

In certain embodiments, the anti-CSP antibody variant comprises a light chain variable region comprising a CDR1, a CDR2, and a CDR3 and having the amino acid sequence set forth in SEQ ID NO: 267, as shown in Table 30. In certain embodiments, the anti-CSP antibody variant comprises a heavy chain variable region comprising a CDR1, a CDR2, and a CDR3 and having the amino acid sequence set forth in SEQ ID NO: 268, as shown in Table 30. In certain embodiments, the anti-CSP antibody variant comprises a light chain having the amino acid sequence set forth in SEQ ID NO: 271, as shown in Table 30. In certain embodiments, the anti-CSP antibody variant comprises a heavy chain having the amino acid sequence set forth in SEQ ID NO: 272, as shown in Table 30. In certain embodiments, the anti-CSP antibody variant comprises a heavy chain having the amino acid sequence set forth in SEQ ID NO: 273, as shown in Table 30. Exemplary nucleic acid sequences of SEQ ID NOS: 267, 268, 271, 272, and 273 are provided in Table 30 below.

TABLE 30

| Antibody ID: AB-007088.005 | | |
|---|---|---|
| | KABAT | ASN |
| CDR1-VL | RASQSISSWLA [SEQ ID NO: 205] | RASQSISSWLA [SEQ ID NO: 211] |
| CDR2-VL | DASSLES [SEQ ID NO: 206] | DASSLES [SEQ ID NO: 212] |
| CDR3-VL | QQYNSYSFWT [SEQ ID NO: 207] | QQYNSYSFWTF [SEQ ID NO: 213] |
| CDR1-VH | TYGMH [SEQ ID NO: 208] | TYGMH [SEQ ID NO: 214] |
| CDR2-VH | IIWYDGSQKYYADSVQG [SEQ ID NO: 209] | IIWYDGSQKYYADSVQG [SEQ ID NO: 215] |
| CDR3-VH | VRFSVGPHGSAFDL [SEQ ID NO: 210] | SAFDL [SEQ ID NO: 216] |
| VL | GVQMTQSPSTLSASVGDRVTLTCRASQS ISSWLAWYQQKPGKAPKLLIYDASSLESGVPSRFSGSGSGTEFTLTISSL QPDDFATYYCQQYNSYSFWTFGQGTKVEIKR [SEQ ID NO: 267] | |
| VH | QVQLVESGGGVVQPGRSLRLSCAASGFT FNTYGMHWVRQAPGKGLEWVAIIWYDGSQKYYADSVQGRFTISRDNHKNT LYLQMNSLRAEDTAVYFCVRVRFSVGPHGSAFDLWGQGTMVTVSS [SEQ ID NO: 268] | |
| DNA for VL | GGCGTCCAGATGACCCAGTCTCCTTCCACCCTGT CTGCATCTGTGGGAGACAGAGTCACCCTCACTTGCCGGGCCAGTCAGAGT ATTAGTAGTTGGTTGGCCTGGTATCAGCAGAAACCAGGGAAAGCCCCTAA ACTCCTGATCTATGATGCCTCCAGTTTGGAAAGTGGGGTCCCATCAAGGT TCAGCGGCAGTGGATCTGGGACAGAATTCACTCTCACCATCAGCAGCCTG CAACCTGATGATTTTGCAACTTATTACTGCCAACAGTATAATAGTTATTC TTTTTGGACGTTCGGCCAAGGGACCAAGGTGGAAATCAAACGC [SEQ ID NO: 269] | |
| DNA for VH | CAGGTGCAACTGGTGGAGTCTGGGGGAGGCGTGG TCCAGCCTGGGAGGTCCCTGAGACTCTCCTGTGCAGCGTCTGGGTTCACT TTCAATACCTATGGCATGCACTGGGTCCGCCAGGCACCAGGCAAGGGGCT GGAGTGGGTGGCAATTATCTGGTATGATGGGAGCCAGAAATACTATGCAG ACTCCGTGCAGGGCCGATTCACTATCTCCAGAGACAATCACAAGAACACG TTGTACCTGCAAATGAACTCCCTGAGAGCCGAGGACACGGCTGTGTATTT | |

TABLE 30-continued

| Antibody ID: AB-007088.005 | |
|---|---|
| KABAT | ASN |
| | CTGTGTGAGAGTCCGCTTTAGCGTTGGCCCCCACGGGAGTGCTTTTGATC<br>TCTGGGGCCAGGGGACAATGGTCACAGTCTCTTCA<br>[SEQ ID NO: 270] |
| Light Chain | GVQMTQSPSTLSASVGDRVTLTCRASQS<br>ISSWLAWYQQKPGKAPKLLIYDASSLESGVPSRFSGSGSGTEFTLTISSL<br>QPDDFATYYCQQYNSYSFWTFGQGTKVEIKRTVAAPSVFIFPPSDEQLKS<br>GTASVVCLLNNFYPREAKVQWKVDNALQSGNSQESVTEQDSKDSTYSLSS<br>TLTLSKADYEKHKVYACEVTHQGLSSPVTKSFNRGEC<br>[SEQ ID NO: 271] |
| Heavy Chain version 1 | QVQLVESGGGVVQPGRSLRLSCAASGFT<br>FNTYGMHWVRQAPGKGLEWVAIIWYDGSQKYYADSVQGRFTISRDNHKNT<br>LYLQMNSLRAEDTAVYFCVRVRFSVGPHGSAFDLWGQGTMVTVSSASTKG<br>PSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCK<br>VSNKALPAPIEKTISKAKGQPREPQVYTLPPSRDELTKNQVSLTCLVKGF<br>YPSDIAVEWESNGQPENNYKTTPPVLDSDGSFFLYSKLTVDKSRWQQGNV<br>FSCSVMHEALHNHYTQKSLSLSPGK<br>[SEQ ID NO: 272] |
| Heavy Chain version 2 | QVQLVESGGGVVQPGRSLRLSCAASGFT<br>FNTYGMHWVRQAPGKGLEWVAIIWYDGSQKYYADSVQGRFTISRDNHKNT<br>LYLQMNSLRAEDTAVYFCVRVRFSVGPHGSAFDLWGQGTMVTVSSASTKG<br>PSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCK<br>VSNKALPAPIEKTISKAKGQPREPQVYTLPPSRDELTKNQVSLTCLVKGF<br>YPSDIAVEWESNGQPENNYKTTPPVLDSDGSFFLYSKLTVDKSRWQQGNV<br>FSCSVLHEALHSHYTQKSLSLSPGK [SEQ ID NO: 273] |
| DNA for Light Chain | GGCGTCCAGATGACCCAGTCTCCTTCCACCCTGT<br>CTGCATCTGTGGGAGACAGAGTCACCCTCACTTGCCGGGCCAGTCAGAGT<br>ATTAGTAGTTGGTTGGCCTGGTATCAGCAGAAACCAGGGAAAGCCCCTAA<br>ACTCCTGATCTATGATGCCTCCAGTTTGGAAAGTGGGGTCCCATCAAGGT<br>TCAGCGGCAGTGGATCTGGGACAGAATTCACTCTCACCATCAGCAGCCTG<br>CAACCTGATGATTTTGCAACTTATTACTGCCAACAGTATAATAGTTATTC<br>TTTTTGGACGTTCGGCCAAGGGACCAAGGTGGAAATCAAACGCACTGTGG<br>CTGCACCATCTGTCTTCATCTTCCCGCCATCTGATGAGCAGTTGAAATCT<br>GGAACTGCCTCTGTTGTGTGCCTGCTGAATAACTTCTATCCCAGAGAGGC<br>CAAAGTACAGTGGAAGGTGGATAACGCCCTCCAATCGGGTAACTCCCAGG<br>AGAGTGTCACAGAGCAGGACAGCAAGGACAGCACCTACAGCCTCAGCAGC<br>ACCCTGACGCTGAGCAAAGCAGACTACGAGAAACACAAAGTCTACGCCTG<br>CGAAGTCACCCATCAGGGCCTGAGCTCGCCCGTCACAAAGAGCTTCAACA<br>GGGGAGAGTGT<br>[SEQ ID NO: 274] |
| DNA for Heavy Chain version 1 | CAGGTGCAACTGGTGGAGTCTGGGGGAGGCGTGG<br>TCCAGCCTGGGAGGTCCCTGAGACTCTCCTGTGCAGCGTCTGGGTTCACT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCACTATCTCCAGAGACAATCACAAGAACACG<br>TTGTACCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC |

TABLE 30-continued

| Antibody ID: AB-007088.005 | |
|---|---|
| KABAT | ASN |
| | TTCTCATGCTCCGTGATGCATGAGGCTCTGCACAACCACTACACACAGAA<br>GAGCCTCTCCCTGTCTCCGGGTAAA [SEQ ID NO: 275] |
| DNA for Heavy Chain version 2 | CAGGTGCAACTGGTGGAGTCTGGGGGAGGCGTGG<br>TCCAGCCTGGGAGGTCCCTGAGACTCTCCTGTGCAGCGTCTGGGTTCACT<br>TTCAATACCTATGGCATGCACTGGGTCCGCCAGGCACCAGGCAAGGGGCT<br>GGAGTGGGTGGCAATTATCTGGTATGATGGGAGCCAGAAATACTATGCAG<br>ACTCCGTGCAGGGCCGATTCACTATCTCCAGAGACAATCACAAGAACACG<br>TTGTACCTGCAAATGAACTCCCTGAGAGCCGAGGACACGGCTGTGTATTT<br>CTGTGTGAGAGTCCGCTTTAGCGTTGGCCCCCACGGGAGTGCTTTTGATC<br>TCTGGGGCCAGGGGACAATGGTCACAGTCTCTTCAGCCTCCACCAAGGGC<br>CCATCGGTCTTCCCCCTGGCACCCTCCTCCAAGAGCACCTCTGGGGGCAC<br>AGCAGCCCTGGGCTGCCTGGTCAAGGACTACTTCCCCGAACCGGTGACGG<br>TGTCGTGGAACTCAGGCGCCCTGACCAGCGGCGTGCACACCTTCCCGGCT<br>GTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGC<br>CCAGCAACACCAAGGTGGACAAGAAAGTTGAGCCCAAATCTTGTGACAAA<br>ACTCACACATGCCCACCGTGCCCAGCACCTGAACTCCTGGGGGGACCGTC<br>AGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGG<br>ATGAGCTGACCAAGAACCAGGTCAGCCTGACCTGCCTGGTCAAAGGCTTC<br>TATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTC<br>TTCTCATGCTCCGTGCTGCATGAGGCTCTGCACTCCCACTACACACAGAA<br>GAGCCTCTCCCTGTCTCCGGGTAAA [SEQ ID NO: 276] |

4. Glycosylation of Anti-CSP Antibodies and Variants Thereof

Glycosylation of antibodies and engineered antibodies has been previously disclosed (see, e.g., U.S. Pat. No. 6,602,684, the content of which is incorporated in its entirety). Antibody Fc regions are generally post-translationally modified via the addition of N-glycans at specific asparagine residues on the antibody heavy chain. IgG molecules bear a N-linked glycosylation asparagine of each heavy chain. It has been shown that a modified glycosylation profile can regulate the antibody functions. For example, without any limitation, altered glycosylation can improve the binding affinity or the half-life of the antibody as compared to the non-modified form.

In certain embodiments, the present disclosure provides anti-CSP antibodies and variants thereof with modified glycosylation. In certain embodiments, the antibodies disclosed herein include an Fc region with increased glycosylation. In certain non-limiting embodiments, the Fc region with increased glycosylation includes increased amounts of bisected oligosaccharides. In certain embodiments, the Fc region with increased glycosylation includes increased amounts of nonfucosylated oligosaccharides. In certain embodiments, the Fc region with increased glycosylation includes increased amounts of fucose-containing oligosaccharides.

In certain embodiments, the antibodies disclosed herein include an Fc region with decreased glycosylation. In certain non-limiting embodiments, the Fc region with decreased glycosylation includes reduced amounts of bisected oligosaccharides. In certain embodiments, the Fc region with decreased glycosylation includes reduced amounts of non-fucosylated oligosaccharides. In certain embodiments, the Fc region with increased glycosylation includes reduced amounts of fucose-containing oligosaccharides.

In certain embodiments, the antibodies disclosed herein include a V region with increased glycosylation. In certain non-limiting embodiments, the V region with increased glycosylation includes increased amounts of bisected oligosaccharides. In certain embodiments, the V region with increased glycosylation includes increased amounts of non-fucosylated oligosaccharides. In certain embodiments, the V region with increased glycosylation includes increased amounts of fucose-containing oligosaccharides.

In certain embodiments, the antibodies disclosed herein include a V region with decreased glycosylation. In certain non-limiting embodiments, the V region with decreased glycosylation includes reduced amounts of bisected oligosaccharides. In certain embodiments, the V region with decreased glycosylation includes reduced amounts of non-fucosylated oligosaccharides. In certain embodiments, the V region with increased glycosylation includes reduced amounts of fucose-containing oligosaccharides.

In certain embodiments, the modified glycosylation can be obtained by expressing any of the antibodies disclosed herein in a host cell with altered glycosylation machinery. For example, without any limitation, a host cell can include a functional disruption of the fucosyltransferase gene and antibodies expressed in this host cell with show reduced glycosylation, e.g., reduced fucosylation (see PCT Patent Publication No. WO 99/54342).

In certain embodiments, the present disclosure provides anti-CSP antibody variants disclosed herein including one or more amino acid substitution resulting in the alteration of a glycosylation acceptor site. In certain embodiments, the alteration includes the elimination of the glycosylation acceptor site. In certain embodiments, the alteration includes modification of a glycosylation acceptor site. In certain embodiments, the alteration includes insertion of a glycosylation acceptor site.

As used herein, "glycosylation acceptor site" refers to an amino acid residue of the light chain or heavy chain of the antibody which can be N- or O-glycosylated. In certain embodiments, the N-linked glycosylation acceptor site can be an asparagine residue. In certain embodiments, the O-linked glycosylation acceptor site can be a serine residue, a threonine residue, a tyrosine residue, a hydroxylysine residue, or a hydroxyproline residue.

In certain embodiments, the Fc region of the antibodies disclosed herein includes one or more glycosylation acceptor site. In certain embodiments, the V region of any of the antibodies disclosed herein includes one or more glycosylation acceptor site. In certain embodiments, the light chain of any of the antibodies disclosed herein includes one or more glycosylation acceptor site. In certain embodiments, the heavy chain of any one of the antibodies disclosed herein includes one or more glycosylation acceptor site. In certain embodiments, the light chain variable region of any of the antibodies disclosed herein includes one or more glycosylation acceptor site. In certain embodiments, the heavy chain variable region of any of the antibodies disclosed herein includes one or more glycosylation acceptor site.

5. PEGylation and Other Chemical Modifications of Anti-CSP Antibodies and Variants Thereof The present disclosure provides anti-CSP antibodies and variants thereof including additional modifications. In certain embodiments, the modifications can improve pharmacological properties of the antibodies, e.g., half-life. In certain non-limiting embodiments, the modification includes PEGylation, deamination, derivatization with polymers, lipidation, removal and/or introduction of disulfide bonds, oxidation, and removal of C-terminal lysine In certain embodiments, the modification is a PEGylation. PEGylation of antibodies and engineered antibodies includes attachment of one or more polyethylene glycol (PEG) to the antibody. In certain non-limitation embodiments, for example, the PEGylation can be carried out by an acylation reaction or an alkylation reaction with a reactive PEG molecule (or an analogous reactive water-soluble polymer). As used herein, the term "polyethylene glycol" refers to any of the forms of PEG that have been used to derivatize other proteins, such as mono (C1-C10) alkoxy- or aryloxy-polyethylene glycol or polyethylene glycol-maleimide.

In certain embodiments, the modification is the derivatization with a hydrophilic polymer. In certain non-limiting embodiments, for example, the hydrophilic polymer can be carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof.

In certain embodiments, the modification is a lipidation. Lipidation is the conjugation of a protein with a lipid. Lipidation of peptides improves metabolic stability, membrane permeability, bioavailability, and changes the pharmacokinetic and pharmacodynamic properties of the peptides. For example, a lipidated peptide has a high affinity with serum albumin resulting in increased half-life and stability. In certain non-limiting embodiments, for example, the lipid can be myristic acid, palmitic acid, stearic acid, lauric acid, cholesterol, and mixtures thereof.

In certain embodiments, the modification is a substitution of an amino acid residue to form a disulfide bond. In certain embodiments, the amino acid substitution introduces a cysteine. Under certain redox conditions, two cysteines can form a non-natural disulfide bond. In certain non-limiting embodiments, the disulfide bond improves the stability of the antibody, e.g., corrected pairing of the antibody chains. In certain embodiments, the cysteine is introduced in the V region. In certain embodiments, the cysteine is introduced in the Fc region. In certain embodiments, the modification is a substitution of an amino acid residue to remove a disulfide bond. In certain embodiments, the amino acid substitution removes a cysteine. In certain embodiments, the cysteine is substituted with a serine. In certain non-limiting embodiments, removing a cysteine improves the stability of the antibody, e.g., improved long-term stability. In certain embodiments, the cysteine is removed in the V region. In certain embodiments, the cysteine is removed in the Fc region.

6. Anti-CSP Antibody and Anti-CSP Antibody Variants Conjugates

In certain embodiments, the present disclosure provides an anti-CSP antibody or variant thereof conjugated or linked to therapeutic and/or imaging/detectable moieties. For example, without any limitation, the anti-CSP antibody or variant thereof can be conjugated to a detectable marker, a toxin, or a therapeutic agent. The moiety may be linked to the antibody covalently or by non-covalent linkages.

In certain embodiments, the antibody or variant thereof is conjugated to cytotoxic moiety or other moiety that inhibits cell proliferation. In certain embodiments, the antibody or variant thereof is conjugated to a cytotoxic agent including, but not limited to, a ricin A chain, doxorubicin, daunorubicin, a maytansinoid, taxol, ethidium bromide, mitomycin, etoposide, tenoposide, vincristine, vinblastine, colchicine, dihydroxy anthracin dione, actinomycin, a diphtheria toxin, extotoxin A from *Pseudomonas, Pseudomonas* exotoxin (PE) A, PE40, abrin, abrin A chain, modeccin A chain, alpha sarcin, gelonin, mitogellin, restrictocin, cobran venom factor, a ribonuclease, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, or a cisplatin. In certain embodiments, the antibody or variant thereof can be linked to an agent such as an enzyme inhibitor, a proliferation inhibitor, a lytic agent, a DNA or RNA synthesis inhibitors, a membrane permeability modifier, a DNA metabolites, a dichloroethyl sulfide derivative, a protein production inhibitor, a ribosome inhibitor, or an inducer of apoptosis.

In certain embodiments, the antibody or variant thereof can be linked to a radionuclide, an iron-related compound, a dye, a fluorescent agent, or an imaging agent. In certain embodiments, an antibody may be linked to agents, such as, but not limited to, metals; metal chelators; lanthanides; lanthanide chelators; radiometals; radiometal chelators; positron-emitting nuclei; microbubbles (for ultrasound); liposomes; molecules microencapsulated in liposomes or nanosphere; monocrystalline iron oxide nano-compounds; magnetic resonance imaging contrast agents; light absorbing, reflecting and/or scattering agents; colloidal particles; fluorophores, such as near-infrared fluorophores.

In certain embodiments, the present disclosure provides bispecific molecules comprising an anti-CSP antibody, a variant thereof, or a fragment thereof, disclosed herein. The anti-CSP antibody, anti-CSP antibody variant or antigen-binding portions thereof can be derivatized or linked to another functional molecule, e.g., another peptide or protein (e.g., another antibody or ligand for a receptor) to generate a bispecific molecule that binds to at least two different binding sites or target molecules. The anti-CSP antibody or variant thereof disclosed herein can be derivatized or linked to more than one other functional molecule to generate multispecific molecules that bind to more than two different binding sites (e.g., two different epitopes on the CSP protein) and/or target molecules; such multispecific molecules are also intended to be encompassed by the term “bispecific molecule” as used herein. To create a bispecific molecule of the invention, an antibody of the invention can be functionally linked (e.g., by chemical coupling, genetic fusion, noncovalent association, or otherwise) to one or more other binding molecules, such as another antibody, antibody fragment, peptide or binding mimetic, such that a bispecific molecule results. In certain non-limiting embodiments, for example and without any limitation, the bispecific antibody can be created using the knobs-into-holes strategy. This strategy typically involves creation of a first half of a first antibody that recognizes a first antigen, e.g., CSP, and a second half of the antibody that recognizes a second antigen or binding site, and then joining the two halves to create the bispecific antibody. In certain embodiments, the first antigen and the second antigen are different epitopes of the CSP protein.

7. Activity

The activity of any of the anti-CSP antibodies disclosed herein can be assessed by using different endpoints. In certain embodiments, the activity is assessed for binding to CSP, either binding to a series of linear peptides with varying lengths representing the immunodominant regions of the CSP protein or to the entire CSP protein. In certain embodiments, the activity is assessed for the ability to protect against challenge with *Plasmodium* that comprises *P. falciparum* CSP, e.g., in in vivo animal models of malaria. In certain embodiments, effector function, e.g., ADCC, is also evaluated.

In certain embodiments, the binding activity of an anti-CSP antibody disclosed herein to *P. falciparum* CSP protein can be assessed by surface plasmon resonance (SPR) using a biosensor system. Systems suitable for use in SPR are, for example, and without any limitation, LSA™ (Carterra, Dublin, CA), Biacore™ (General Electric, Boston, MA), and OpenSPR (Nicoya, East Kitchener, ON, Canada). In an exemplary SPR assay, each antibody can be either directly immobilized to a Carterra CMD200M Chip or captured to the CMD200M Carterra Chip with a goat anti-human IgG Fc antibody. The uncoupled antibodies can be washed off and various concentration gradients of the targets can be flowed over the antibodies. In certain experimental conditions, the highest concentration of each target can be in the range of 0.5-8 μg/mL. For better accuracy, each antibody can be immobilized in different locations (e.g., at least 2) on the chip, and the affinity for each antibody-target combination can be determined using multiple (e.g., 4-5) target concentrations according to standard methods. If the variation between the two duplicates is >3-fold, the antibody-target measurement is repeated.

In certain embodiments, the binding activity of an anti-CSP antibody disclosed herein to *P. falciparum* CSP protein can be assessed by bio-layer interferometry (BLI). For BLI, each of the antigens (e.g., those disclosed in Table 35) can be immobilized on sensors according to the manufacturer's instructions. Systems suitable for use in BLI include, but are not limited to, Octet™ (ForteBio, Fremont, CA) and Gator™ (Probelife, Palo Alto, CA). In certain embodiments, for example and without any limitation, the antigen can be biotinylated and immobilized to streptavidin sensors. For better accuracy, each antibody can be evaluated in replicates at a suitable concentration (e.g., 5 μg/mL). If the variation between the two duplicates is >3-fold, the antibody-target measurement is repeated. The assays are typically performed under conditions according to the manufacturer's instructions. The assays can be performed under a temperature in the range of 20° C. to 37° C., for example, 20° C.-25° C. In certain embodiments, the assay is performed at 25° C. In certain embodiments, the assay is performed at 37° C.

In certain embodiments, binding to CSP protein is assessed in a competitive assay format with a reference antibody AB-000224 or a reference antibody having the variable regions of AB-000224. In certain embodiments, binding to CSP protein is assessed in a competitive assay format with a reference antibody AB-007088 or a reference antibody having the variable regions of AB-007088. In certain embodiments, a variant anti-CSP antibody disclosed herein can block binding of the reference antibody in a competition assay by about 50% or more.

Anti-CSP antibodies and anti-CSP antibody variants of the present disclosure may also be evaluated in various assays for their ability to mediate FcR-dependent activity. In certain embodiments, an antibody of the present disclosure has enhanced ADCC and/or serum stability compared to antibody AB-000224 when the antibodies are assayed in a human IgG1 isotype format. In certain embodiments, an antibody of the present disclosure has enhanced ADCC and/or serum stability compared to antibody AB-007088 when the antibodies are assayed in a human IgG1 isotype format.

In certain embodiments, the activity of an anti-CSP antibody can be evaluated in vivo in an animal model, e.g., as described in the Examples section. In certain non-limiting embodiments, for example, the mouse malaria liver burden assay can be used, as disclosed in, for example, Flores-Garcia Y, et al. Malar J. 2019; 18(1):426, doi:10.1186/s12936-019-3055-9, the content of which is herein incorporated by reference. Mice are administered antibody and infected with chimeric *P. berghei* expressing GFP-luciferase and *P. falciparum* CSP protein. Parasite liver load can be evaluated, e.g., by RT-qPCR or by measuring bioluminescence with an IVIS Spectrum imager. A reduction in parasite liver load reflects the prophylactic activity of an antibody.

In certain embodiments, the activity of an anti-CSP antibody can be determined by evaluating the in vivo protection and survival of animal models, e.g., mice. For example, but without any limitation, mice are administered antibody and challenged with chimeric *P. berghei* expressing *P. falciparum* CSP protein as disclosed in, for example, Espinosa, D., et al. npj Vaccines 2017; 2, 10 (2017); Espinosa, D., et al. Infect Immun. 2013 August; 81(8): 2882-2887. The in vivo protection can be determined by detecting blood-stage parasitaemia in microscopy. The survival rate can be determined using the absence of parasitaemia during an observation period, e.g., two weeks, immediately following the challenge. An increased survival rate reflects the prophylactic and/or therapeutic activity of an antibody.

In certain embodiments, an anti-CSP antibody, e.g., AB-000224 or AB-007088, disclosed herein has at least 20%, or at least 30%, or at least 40%, or at least 50%, or at least 60%, or 70%, or greater, of the activity of antibody AB-000317 when evaluated under the same assay conditions. In certain embodiments, an anti-CSP antibody exhibits improved activity, i.e., greater than 100%, activity compared to antibody AB-000317. In certain non-limiting embodiments, an anti-CSP antibody disclosed herein exhibits at least 20%, or at least 30%, or at least 40%, or at least 50%, or at least 60%, or 70%, or greater reduction in parasite liver load as compared to antibody AB-000317. In certain non-limiting embodiments, an anti-CSP antibody disclosed herein exhibits at least 20%, or at least 30%, or at least 40%, or at least 50%, or at least 60%, or 70%, or greater increase in survival rate as compared to antibody AB-000317.

In certain embodiments, an anti-CSP antibody variant disclosed herein has at least 50%, or at least 60%, or 70%, or greater, of the activity of AB-000224 when evaluated under the same assay conditions. In certain embodiments, an anti-CSP antibody exhibits improved activity, i.e., greater than 100%, activity compared to AB-000224. In certain embodiments, the anti-CSP antibody variants disclosed herein have similar activity against malaria infection as compared to AB-000224. In certain embodiment, an anti-CSP antibody variant disclosed herein has at least 50%, or at least 60%, or 70%, or greater, of the activity of AB-007088 when evaluated under the same assay conditions. In certain embodiments, an anti-CSP antibody exhibits improved activity, i.e., greater than 100%, activity compared to AB-007088. In certain embodiments, the anti-CSP antibody variants disclosed herein have similar activity against malaria infection as compared to AB-007088. The term "similar activity," when used to compare in vivo activity of antibodies, refers to that two measurements of the activity is no more than 30%, no more than 25%, no more than 20%, no more than 15% different, no more than 10%, no more than 8%, or no more than 5% different from each other.

In certain embodiments, the native anti-CSP antibody, AB-000224, is modified to have improved developability (i.e., reduced development liabilities), including but not limited to, decreased heterogeneity, increased yield, increased stability, improved net charges to improve pharmacokinetics, and or/reduced immunogenicity. In certain embodiments, antibodies having improved developability can be obtained by introducing mutations to reduce or eliminate potential development liabilities, as described in Table 1. In certain embodiments, antibodies having improved developability possess modifications as compared to AB-000224 in their amino acid sequence, as disclosed in Table 2.

In certain embodiments, the native anti-CSP antibody, AB-007088, is modified to have improved developability (i.e., reduced development liabilities), including but not limited to, decreased heterogeneity, increased yield, increased stability, improved net charges to improve pharmacokinetics, and or/reduced immunogenicity. In certain embodiments, antibodies having improved developability can be obtained by introducing mutations to reduce or eliminate potential development liabilities, as described in Table 1. In certain embodiments, antibodies having improved developability possess modifications as compared to AB-007088 in their amino acid sequence, as disclosed in Table 2.

In certain embodiments, the anti-CSP antibody variants disclosed herein have improved developability while maintaining comparable or improved binding affinity to the target as compared to AB-000224. Non-limiting examples of such anti-CSP antibody variants are disclosed herein. In certain embodiments, the anti-CSP antibody variants disclosed herein have improved developability while maintaining activities that are similar to AB-000224.

In certain embodiments, the anti-CSP antibody variants disclosed herein have improved developability while maintaining comparable or improved binding affinity to the target as compared to AB-007088. Non-limiting examples of such anti-CSP antibody variants are disclosed herein. In certain embodiments, the anti-CSP antibody variants disclosed herein have improved developability while maintaining activities that are similar to AB-007088.

8. Generation of Antibodies

CSP antibodies and variants thereof disclosed herein can be produced using vectors and recombinant methodology (see, e.g., Sambrook & Russell, Molecular Cloning: A Laboratory Manual, Cold Spring Harbor Laboratory Press; Ausubel, Current Protocols in Molecular Biology). Reagents, cloning vectors, and kits for genetic manipulation are available from commercial vendors.

The present disclosure provides isolated nucleic acids encoding a VH and/or VL region, or fragment thereof, of any of the anti-CSP antibodies and anti-CSP antibody variants disclosed herein. In certain embodiments, the present disclosure provides vectors comprising said nucleic acids and host cells into which the nucleic acids are introduced that are used to replicate the antibody-encoding nucleic acids and/or to express the antibodies. These nucleic acids can encode an amino acid sequence containing the VL, and/or an amino acid sequence containing the VH of the anti-CSP antibody or variant thereof (e.g., the light and/or heavy chains of the antibody). In certain embodiments, the host cell contains (1) a vector containing a polynucleotide that encodes the VL amino acid sequence and a polynucleotide that encodes the VH amino acid sequence, or (2) a first vector containing a polynucleotide that encodes the VL amino acid sequence and a second vector containing a polynucleotide that encodes the VH amino acid sequence.

In certain embodiments, the present disclosure provides a method of making an anti-CSP antibody disclosed herein. In certain embodiments, the method includes culturing a host cell previously described under conditions suitable for expression of the antibody. In certain embodiments, the antibody is subsequently recovered from the host cell (or host cell culture medium).

Suitable vectors containing polynucleotides encoding antibodies of the present disclosure, or fragments thereof, include cloning vectors and expression vectors. While the cloning vector selected can vary according to the host cell intended to be used, useful cloning vectors generally can self-replicate, can possess a single target for a particular restriction endonuclease, and/or may carry genes for a marker that can be used in selecting clones containing the vector. Non-limiting examples include plasmids and bacterial viruses, e.g., pUC18, pUC19, Bluescript (e.g., pBS SK+) and its derivatives, mp18, mp19, pBR322, pMB9, ColEl plasmids, pCR1, RP4, phage DNAs, and shuttle vectors.

Expression vectors generally are replicable polynucleotide constructs that contain a nucleic acid of the present disclosure. The expression vector can replicate in the host cells either as episomes or as an integral part of the chromosomal DNA. Suitable expression vectors include, but are not limited to, plasmids and viral vectors, including adenoviruses, adeno-associated viruses, retroviruses, and any other vector.

Suitable host cells for expressing an anti-CSP antibody or anti-CSP antibody variant disclosed herein include both prokaryotic or eukaryotic cells. For example, but without any limitation, anti-CSP antibodies can be produced in bacteria, in particular when glycosylation and Fc effector function are not needed. After expression, the antibody can be isolated from the bacterial cell lysate in a soluble fraction and can be further purified. Alternatively, the host cell can be a eukaryotic host cell, including, without limitation, eukaryotic microorganisms, such as filamentous fungi or yeast, fungi and yeast strains whose glycosylation pathways have been "humanized," resulting in the production of an antibody with a partially or fully human glycosylation pattern, vertebrate, invertebrate, and plant cells. Non-limiting examples of invertebrate cells include insect cells. Numerous baculoviral strains have been identified which may be used in conjunction with insect cells. Plant cell cultures can also be utilized as host cells.

In certain embodiments, vertebrate host cells are used for producing anti-CSP antibodies of the present disclosure. For example, without any limitation, mammalian cell lines that can be used to express anti-CSP antibodies include monkey kidney CV1 line transformed by SV40 (COS-7); human embryonic kidney line (293 or 293 cells); baby hamster kidney cells (BHK); mouse Sertoli cells (TM4 cells); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells; MRC 5 cells; and FS4 cells. In certain embodiments, the mammalian cell line used to express anti-CSP antibodies can be Chinese hamster ovary (CHO) cell line; DHFR-CHO cell line (Urlaub et al., Proc. Natl. Acad. Sci. USA 77:4216, 1980); and myeloma cell lines such as YO, NSO, and Sp2/0. Host cells of the present disclosure also include, without limitation, isolated cells, in vitro cultured cells, and ex vivo cultured cells.

A host cell transfected with an expression vector encoding an anti-CSP antibody of the present disclosure, or fragment thereof, can be cultured under appropriate conditions to allow expression of the polypeptide to occur. The polypeptides can be secreted and isolated from a mixture of cells and medium containing the polypeptides. Alternatively, the polypeptide can be retained in the cytoplasm or a membrane fraction and the cells harvested, lysed, and the polypeptide isolated using a desired method.

In certain embodiments, the present disclosure provides a method of generating variants of an anti-CSP antibody disclosed herein. In certain non-limiting embodiments, for example and without any limitation, a construct encoding a variant of VH CDR2 as described in the "anti-CSP Antibody Variant" section can be additionally modified and the VH region encoded by the additionally modified construct can be tested for binding activity to CSP and/or in vivo protective efficacy in the context of a VH region comprising the native AB-000224 CDR1 and CDR3, or a variant CDR1 or CDR3 as described herein, that is paired with a native AB-000224 VL region or variant region as described herein. Similarly, a construct encoding a variant VL CDR3 as described in the "anti-CSP Antibody Variant" section can be additionally modified and the VL region encoded by the additionally modified construct can be tested for binding activity to CSP and/or protective efficacy. Such an analysis can also be performed with other CDRs or framework regions and an antibody having the desired activity can then be selected.

Pharmaceutical Compositions and Methods of Treatment

In certain embodiments, the present disclosure provides pharmaceutical compositions for the administration of an anti-CSP antibody and variants thereof. In certain embodiments, the pharmaceutical compositions can be administered to a mammalian subject, e.g., a human, who has malaria or is at risk for malaria, in a therapeutically effective amount and according to a schedule sufficient to prevent *Plasmodium* infection, e.g., infection with *Plasmodium falciparum* or a *Plasmodium* sp. having a cross-reactive CSP protein, or to reduce a symptom of malaria in the subject. In certain embodiments, the pharmaceutical compositions can include any of the anti-CSP antibodies and variants thereof disclosed herein, or a polynucleotide encoding the same, and a pharmaceutically acceptable diluent or carrier. In certain embodiments, a polynucleotide encoding the antibody can be contained in a plasmid vector for delivery, or a viral vector. In certain embodiments, the pharmaceutical composition comprises a therapeutically effective amount of the antibody. As used herein, a "therapeutically effective dose" or a "therapeutically effective amount" refers to an amount sufficient to prevent, cure, or at least partially arrest malaria or symptoms of malaria. A therapeutically effective dose can be determined by monitoring a patient's response to therapy. Typical benchmarks indicative of a therapeutically effective dose include amelioration or prevention of symptoms of malaria in the patient, including, for example, and without limitation, reduction in the number of parasites. Amounts effective for this use will depend upon the severity of the disease and the general state of the patient's health, including other factors such as age, weight, gender, administration route, etc. Single or multiple administrations of the antibody will be dependent on the dosage and frequency as required and tolerated by the patient.

In certain embodiments, the antibody is administered at a pre-erythrocyte stage of infection, i.e., the antibody is administered in a time frame to prevent or reduce hepatocyte infection.

Various pharmaceutically acceptable diluents, carriers, and excipients, and techniques for the preparation and use of pharmaceutical compositions are also disclosed herein. Illustrative pharmaceutical compositions and pharmaceutically acceptable diluents, carriers, and excipients are also described in Remington: The Science and Practice of Pharmacy 20th Ed. (Lippincott, Williams & Wilkins 2012). In certain embodiments, each carrier, diluent, or excipient is "acceptable" in the sense of being compatible with the other ingredients of the pharmaceutical composition and not injurious to the subject. Often, the pharmaceutically acceptable carrier is an aqueous pH-buffered solution. In certain non-limiting embodiments, for example, pharmaceutically-acceptable carriers, diluents or excipients include water; buffers, e.g., phosphate-buffered saline; sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

In certain embodiments, the pharmaceutical composition can be formulated for any suitable route of administration, including for example, parenteral, intrapulmonary, intranasal, or local administration. Parenteral administration can include intramuscular, intravenous, intraarterial, intraperitoneal, oral, or subcutaneous administration. In certain embodiments, the pharmaceutical composition is formulated for intravenous administration and has a concentration of antibody of 10-100 mg/ml, 10-50 mg/ml, 20 to 40 mg/ml, or about 30 mg/ml. In certain embodiments, the pharmaceutical composition is formulated for subcutaneous injection and has a concentration of antibody of 50-500 mg/ml, 50-250 mg/ml, or 100 to 150 mg/ml, and a viscosity less than 50 cP, less than 30 cP, less than 20 cP, or about 10 cP. In certain embodiments, the pharmaceutical compositions are liquids or solids. In certain embodiments, the pharmaceutical compositions are formulated for parenteral, e.g., intravenous, subcutaneous, intraperitoneal, or intramuscular administration.

In certain embodiments, the formulation of and delivery methods of pharmaceutical compositions are adapted according to the site and the disease to be treated. For example, without any limitation, formulations include those in which the antibody is encapsulated in micelles, liposomes, or drug-release capsules (active agents incorporated within a biocompatible coating designed for slow-release); ingestible formulations; formulations for topical use, such as creams, ointments, and gels; and other formulations such as inhalants, aerosols, and sprays.

In certain non-limiting embodiments, for example for parenteral administration, the antibodies or antigen-binding fragments thereof are formulated in a unit dosage injectable form (solution, suspension, emulsion) in association with a pharmaceutically acceptable, parenteral vehicle. Non-limiting examples of vehicles include water, saline, Ringer's solution, dextrose solution, and 5% human serum albumin. Nonaqueous vehicles such as fixed oils and ethyl oleate may also be used.

The dose and dosage regimen depend upon a variety of factors readily determined by a physician, such as the nature of the infection, the characteristics of the subject, and the subject's history. In certain embodiments, the amount of antibody or antigen-binding fragment thereof administered or provided to the subject is in the range of about 0.1 mg/kg to about 50 mg/kg of the subject's body weight. Depending on the type and severity of the infection, in certain embodiments, about 0.1 mg/kg to about 50 mg/kg body weight (e.g., about 0.1-15 mg/kg/dose) of antibody or antigen-binding fragment thereof may be provided as an initial candidate dosage to the patient, whether, for example, by one or more separate administrations, or by continuous infusion. The progress of the therapy is readily monitored by conventional methods and assays and based on criteria known to the physician or other persons of skill in the art.

An antibody or variant thereof of the present disclosure can be administered to a subject using any route of administration, e.g., systemic, parenterally, locally, in accordance with known methods. Such routes include, but are not limited to, intravenous administration, e.g., as a bolus or by continuous infusion over a period of time, by intramuscular, intraperitoneal, intracerobrospinal, subcutaneous, intraarticular, intrasynovial, intrathecal, oral, topical, or inhalation routes. A subject can be administered an antibody of the present invention one or more times; and can be administered before, after, or concurrently with another therapeutic agent as further described below.

In certain embodiments, the antibodies or variants thereof of the present disclosure can be administered to prevent malaria. In certain embodiments, the antibodies disclosed herein can inhibit or reduce the risk of *Plasmodium* infection. In certain embodiments, the antibodies disclosed herein can inhibit or reduce the pre-erythrocytic or sporozoite stage of infection. In certain embodiments, the antibodies disclosed herein can prevent malaria by targeting the *Plasmodium* at an early stage of entry to the vertebrate of a subject, to thereby arrest the infection from taking place.

In certain embodiments, antibody or variant thereof of the present disclosure can be administered to treat malaria. In certain embodiments, the antibodies disclosed herein can inhibit or reduce the progression of *Plasmodium* infection in the blood stream. In certain embodiments, the antibodies disclosed herein can inhibit or reduce the risk of transmission of *Plasmodium* from a subject to another via insect feeding, e.g., mosquito bite or via contact with infected blood.

In certain embodiments, the pharmaceutical compositions disclosed herein can be administered to a pediatric patient. As used herein, the term "pediatric patient" refers to a patient up to the age of 18 years old. In certain embodiments, the pediatric patient is a patient from age 3 months to less than 12 years old. In certain non-limiting embodiments, the pediatric patient can be a patient between from about 1 year old to about 2 years old, from about 2 years old to about 3 years old, from about 3 years old to about 4 years old, from about 4 years old to about 5 years old, from about 5 years old to about 6 years old, from about 6 years old to about 7 years old, from about 7 years old to about 8 years old, from about 8 years old to about 9 years old, from about 9 years old to about 10 years old, or from about 11 years old to about 12 years old. In certain embodiments, the pediatric patient is not responsive or poorly responsive to another treatment to malaria. In certain embodiments, the pediatric patient is human.

In certain embodiments, the dose of the pharmaceutical compositions disclosed herein is administered based on the weight of the pediatric patient. In certain non-limiting embodiments, the dose of the pharmaceutical compositions is about 5 mg/kg, about 10 mg/kg, about 15 mg/kg, about 20 mg/kg about 25 mg/kg, about 50 mg/kg, about 75 mg/kg, about 100 mg/kg, about 150 mg/kg, about 200 mg/kg, about 250 mg/kg, about 300 mg/kg, or about 350 mg/kg. In certain embodiments, the pediatric patient has a weight of from about 2.5 kg to about 5 kg, from about 5 kg to about 10 kg, from about 10 kg to about 15 kg, from about 15 kg to about 20 kg, from about 20 kg to about 30 kg, or from about 30 kg to about 40 kg.

In certain embodiments, the antibody is provided to the subject in combination with one or more additional therapeutic agents used to treat or prevent malaria or a related disease or disorder. In certain embodiments, a method for treating or preventing malaria is provided, comprising administering to the human a therapeutically effective amount of an antibody as disclosed herein, or a pharmaceutically acceptable salt thereof, in combination with a therapeutically effective amount of one or more additional therapeutic agents. In certain embodiments, a method for treating malaria in a human having or at risk of having the infection is provided, comprising administering to the human a therapeutically effective amount of an antibody as disclosed herein, or a pharmaceutically acceptable salt thereof, in combination with a therapeutically effective amount of one or more additional therapeutic agents.

In certain embodiments, when an antibody of the present disclosure as described herein is combined with one or more additional therapeutic agents as described above, the components of the composition are administered as a simultaneous or sequential regimen. When administered sequentially, the combination may be administered in two or more administrations.

In certain embodiments, an antibody as disclosed herein is combined with one or more additional therapeutic agents in a unitary dosage form for simultaneous administration to a patient.

A "patient" refers to any subject receiving the antibody regardless of whether they have malaria. In certain embodiments, a "patient" is a non-human subject, e.g., an animal that is used as a model for evaluating the effects of antibody administration.

"Co-administration" of an antibody disclosed herein with one or more additional therapeutic agents generally refers to simultaneous or sequential administration of an antibody or fragment thereof disclosed herein and one or more additional therapeutic agents, such that therapeutically effective amounts of the antibody or fragment thereof disclosed herein and one or more additional therapeutic agents are both present in the body of the patient. Co-administration includes administration of unit dosages of the antibody disclosed herein before or after administration of unit dosages of one or more additional therapeutic agents, for example, and without limitation, administration of the antibody within seconds, minutes, or hours of the administration of one or more additional therapeutic agents. In certain non-limiting embodiments, for example, a unit dose of an antibody disclosed herein is administered first, followed within seconds or minutes by administration of a unit dose of one or more additional therapeutic agents. In certain non-limiting embodiments, a unit dose of one or more additional therapeutic agents is administered first, followed by administration of a unit dose of an antibody within seconds or minutes. In certain embodiments, a unit dose of an antibody disclosed herein is administered first, followed, after a period of hours (e.g., 1-12 hours), by administration of a unit dose of one or more additional therapeutic agents. In certain embodiments, a unit dose of one or more additional therapeutic agents is administered first, followed, after a period of hours (e.g., 1-12 hours), by administration of a unit dose of the antibody.

The combined administration may be co-administration, using separate pharmaceutical compositions or a single pharmaceutical composition, or consecutive administration in either order, wherein there is optionally a time period while both (or all) therapeutic agents simultaneously exert their biological activities. Such combined therapy may result in a synergistic therapeutic effect. In certain embodiments, it is desirable to combine administration of an antibody of the invention with another antibody directed against another *Plasmodium falciparum* antigen, or against a different CSP target epitope.

CSP has multiple domains and regions that include the N-terminal domain, the immunogenic central NANP repeat region, and the C-terminal (ctCSP) domain or α-thrombospondin repeat (αTSR) domain. Between the N-terminal domain and the central repeat region is the junctional region that contains an NPDP sequence and a minor repeat region that contains three NVDP motifs that are both related to the dominant NANP motif (Pholcharee, T. et al., J. Mol. Bio. 432: 1048-1063 (2020). In certain embodiments, an antibody disclosed herein is co-administered with an antibody that binds to ctCSP. In certain embodiments, an antibody disclosed herein is co-administered with an antibody that binds to the alpha epitope (α-ctCSP) domain of ctCSP. The α-ctCSP consists of an α-helix that includes the T-cell epitope Th2R (region III), and the CS flap, which contains another T-cell epitope Th3R (Beutler N, PLoS Pathog 18(3): e1010409 (2022), FIG. 2, incorporated by reference herein). In certain embodiments, an antibody disclosed herein is co-administered with an antibody that binds to the beta epitope (β-ctCSP) domain of ctCSP (Beutler N, PLoS Pathog 18(3):e1010409 (2022), FIG. 2).

In certain embodiments, the antibody can be administered by gene therapy via a nucleic acid comprising one or more polynucleotides encoding the antibody. In certain embodiments, the polynucleotide encodes an scFv. In certain embodiments, the polynucleotide comprises DNA, cDNA or RNA. In certain embodiments, the polynucleotide is present in a vector, e.g., a viral vector.

Exemplary Embodiments of the Presently Disclosed Subject Matter

The present disclosure provides to antibodies targeting *Plasmodium falciparum*. In certain non-limiting embodiments, the antibody is a recombinant anti-circumsporozoite (CSP) antibody. In certain embodiments, the recombinant antibody comprises a light chain variable region (VL) and a heavy chain variable region (VH), wherein the light chain variable region comprises a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3; and the heavy chain variable region comprises a CDR1 comprising the amino acid sequence set forth in SEQ ID NO: 4, a CDR2 comprising the amino acid sequence set forth in SEQ ID NO: 5, and a CDR3 comprising the amino acid sequence set forth in SEQ ID NO: 6.

In certain embodiments, the VL of the recombinant antibodies disclosed herein comprises the amino acid sequence set forth in SEQ ID NO: 163; the amino acid sequence set forth in SEQ ID NO: 23; the amino acid sequence set forth in SEQ ID NO: 33; the amino acid sequence set forth in SEQ ID NO: 43; the amino acid sequence set forth in SEQ ID NO: 53; the amino acid sequence set forth in SEQ ID NO: 63; the amino acid sequence set forth in SEQ ID NO: 73; the amino acid sequence set forth in SEQ ID NO: 83; the amino acid sequence set forth in SEQ ID NO: 93; the amino acid sequence set forth in SEQ ID NO: 103; the amino acid sequence set forth in SEQ ID NO: 113; the amino acid sequence set forth in SEQ ID NO: 123; the amino acid sequence set forth in SEQ ID NO: 133; the amino acid sequence set forth in SEQ ID NO: 143; the amino acid sequence set forth in SEQ ID NO: 153; or the amino acid sequence set forth in SEQ ID NO: 173. In certain embodiments, the VH of the recombinant antibodies disclosed herein comprises the amino acid sequence set forth in SEQ ID NO: 164; the amino acid sequence set forth in SEQ ID NO: 24; the amino acid sequence set forth in SEQ ID NO: 34; the amino acid sequence set forth in SEQ ID NO: 44; the amino acid sequence set forth in SEQ ID NO: 54; the amino acid sequence set forth in SEQ ID NO: 64; the amino acid sequence set forth in SEQ ID NO: 74; the amino acid sequence set forth in SEQ ID NO: 84; the amino acid sequence set forth in SEQ ID NO: 94; the amino acid sequence set forth in SEQ ID NO: 104; the amino acid sequence set forth in SEQ ID NO: 114; the amino acid sequence set forth in SEQ ID NO: 124; the amino acid sequence set forth in SEQ ID NO: 134; the amino acid sequence set forth in SEQ ID NO: 144; the amino acid sequence set forth in SEQ ID NO: 154; or the amino acid sequence set forth in SEQ ID NO: 174.

In certain embodiments of the recombinant antibodies disclosed herein, the VL comprises the amino acid sequence set forth in SEQ ID NO: 163, and the VH comprises the amino acid sequence set forth in SEQ ID NO: 164; the VL comprises the amino acid sequence set forth in SEQ ID NO: 33, and the VH comprises the amino acid sequence set forth in SEQ ID NO: 34; the VL comprises the amino acid sequence set forth in SEQ ID NO: 43, and the VH comprises the amino acid sequence set forth in SEQ ID NO: 44; the VL comprises the amino acid sequence set forth in SEQ ID NO: 53, and the VH comprises the amino acid sequence set forth in SEQ ID NO: 54; the VL comprises the amino acid sequence set forth in SEQ ID NO: 63, and the VH comprises the amino acid sequence set forth in SEQ ID NO: 64; the VL comprises the amino acid sequence set forth in SEQ ID NO: 73, and the VH comprises the amino acid sequence set forth in SEQ ID NO: 74; the VL comprises the amino acid sequence set forth in SEQ ID NO: 83, and the VH comprises the amino acid sequence set forth in SEQ ID NO: 84; the VL comprises the amino acid sequence set forth in SEQ ID NO: 93, and the VH comprises the amino acid sequence set forth in SEQ ID NO: 94; the VL comprises the amino acid sequence set forth in SEQ ID NO: 103, and the VH comprises the amino acid sequence set forth in SEQ ID NO: 104; the VL comprises the amino acid sequence set forth in SEQ ID NO: 113, and the VH comprises the amino acid sequence set forth in SEQ ID NO: 114; the VL comprises the amino acid sequence set forth in SEQ ID NO: 123, and the VH comprises the amino acid sequence set forth in SEQ ID NO: 124; the VL comprises the amino acid sequence set forth in SEQ ID NO: 133, and the VH comprises the amino acid sequence set forth in SEQ ID NO: 134; the VL comprises the amino acid sequence set forth in SEQ ID NO: 143, and the VH comprises the amino acid sequence set forth in SEQ ID NO: 144; the VL comprises the amino acid sequence set forth in SEQ ID NO: 153, and the VH comprises the amino acid sequence set forth in SEQ ID NO: 154; or the VL comprises the amino acid sequence set forth in SEQ ID NO: 173, and the VH comprises the amino acid sequence set forth in SEQ ID NO: 174. In certain embodiments of the recombinant antibodies disclosed herein, the VL comprises the amino acid sequence set forth in SEQ ID NO: 63, and the VH comprises the amino acid sequence set forth in SEQ ID NO: 64. In certain embodiments of the recombinant antibodies disclosed herein, the VL comprises the amino acid sequence set forth in SEQ ID NO: 133, and the VH comprises the amino acid sequence set forth in SEQ ID NO: 134. In certain embodiments of the recombinant antibodies disclosed herein, the VL comprises the amino acid sequence set forth in SEQ ID NO: 163, and the VH comprises the amino acid sequence set forth in SEQ ID NO: 164.

In certain embodiments, the recombinant antibodies disclosed herein comprise a light chain (LC) and a heavy chain (HC). In certain embodiments, the LC of the recombinant antibodies disclosed herein comprises the amino acid sequence set forth in SEQ ID NO: 27; the amino acid sequence set forth in SEQ ID NO: 37; the amino acid sequence set forth in SEQ ID NO: 47; the amino acid sequence set forth in SEQ ID NO: 57; the amino acid sequence set forth in SEQ ID NO: 67; the amino acid sequence set forth in SEQ ID NO: 77; the amino acid sequence set forth in SEQ ID NO: 87; the amino acid sequence set forth in SEQ ID NO: 97; the amino acid sequence set forth in SEQ ID NO: 107; the amino acid sequence set forth in SEQ ID NO: 117; the amino acid sequence set forth in SEQ ID NO: 127; the amino acid sequence set forth in SEQ ID NO: 137; the amino acid sequence set forth in SEQ ID NO: 147; the amino acid sequence set forth in SEQ ID NO: 157; the amino acid sequence set forth in SEQ ID NO: 167; or the amino acid sequence set forth in SEQ ID NO: 177. In certain embodiments, the HC of the recombinant antibodies disclosed herein comprises the amino acid sequence set forth in SEQ ID NO: 28 or SEQ ID NO: 29; the amino acid sequence set forth in SEQ ID NO: 38 or SEQ ID NO: 39; the amino acid sequence set forth in SEQ ID NO: 48 or SEQ ID NO: 49; the amino acid sequence set forth in SEQ ID NO: 58 or SEQ ID NO: 59; the amino acid sequence set forth in SEQ ID NO: 68 or SEQ ID NO: 69; the amino acid sequence set forth in SEQ ID NO: 78 or SEQ ID NO: 79; the amino acid sequence set forth in SEQ ID NO: 88 or SEQ ID NO: 89; the amino acid sequence set forth in SEQ ID NO: 98 or SEQ ID NO: 99; the amino acid sequence set forth in SEQ ID NO: 108 or SEQ ID NO: 109; the amino acid sequence set forth in SEQ ID NO: 118 or SEQ ID NO: 119; the amino acid sequence set forth in SEQ ID NO: 128 or SEQ ID NO: 129; the amino acid sequence set forth in SEQ ID NO: 138 or SEQ ID NO: 139; the amino acid sequence set forth in SEQ ID NO: 148 or SEQ ID NO: 149; the amino acid sequence set forth in SEQ ID NO: 158 or SEQ ID NO: 159; the amino acid sequence set forth in SEQ ID NO: 168 or SEQ ID NO: 169; or the amino acid sequence set forth in SEQ ID NO: 178 or SEQ ID NO: 179.

In certain embodiments of the recombinant antibodies disclosed herein, the LC comprises the amino acid sequence set forth in SEQ ID NO: 27, and the HC comprises the amino acid sequence set forth in SEQ ID NO: 28 or SEQ ID NO: 29; the LC comprises the amino acid sequence set forth in SEQ ID NO: 37, and the HC comprises the amino acid sequence set forth in SEQ ID NO: 38 or SEQ ID NO: 39; the LC comprises the amino acid sequence set forth in SEQ ID NO: 47, and the HC comprises the amino acid sequence set forth in SEQ ID NO: 48 or SEQ ID NO: 49; the LC comprises the amino acid sequence set forth in SEQ ID NO: 57, and the HC comprises the amino acid sequence set forth in SEQ ID NO: 58 or SEQ ID NO: 59; the LC comprises the amino acid sequence set forth in SEQ ID NO: 67, and the HC comprises the amino acid sequence set forth in SEQ ID NO: 68 or SEQ ID NO: 69; the LC comprises the amino acid sequence set forth in SEQ ID NO: 77, and the HC comprises the amino acid sequence set forth in SEQ ID NO: 78 or SEQ ID NO: 79; the LC comprises the amino acid sequence set forth in SEQ ID NO: 87, and the HC comprises the amino acid sequence set forth in SEQ ID NO: 88 or SEQ ID NO: 89; the LC comprises the amino acid sequence set forth in SEQ ID NO: 97, and the HC comprises the amino acid sequence set forth in SEQ ID NO: 98 or SEQ ID NO: 99; the LC comprises the amino acid sequence set forth in SEQ ID NO: 107, and the HC comprises the amino acid sequence set forth in SEQ ID NO: 108 or SEQ ID NO: 109; the LC comprises the amino acid sequence set forth in SEQ ID NO: 117, and the HC comprises the amino acid sequence set forth in SEQ ID NO: 118 or SEQ ID NO: 119; the LC comprises the amino acid sequence set forth in SEQ ID NO: 127, and the HC comprises the amino acid sequence set forth in SEQ ID NO: 128 or SEQ ID NO: 129; the LC comprises the amino acid sequence set forth in SEQ ID NO: 137, and the HC comprises the amino acid sequence set forth in SEQ ID NO: 138 or SEQ ID NO: 139; the LC comprises the amino acid sequence set forth in SEQ ID NO: 147, and the HC comprises the amino acid sequence set forth in SEQ ID NO: 148 or SEQ ID NO: 149; the LC comprises the amino acid sequence set forth in SEQ ID NO: 157, and the HC comprises the amino acid sequence set forth in SEQ ID NO: 158 or SEQ ID NO: 159; the LC comprises the amino acid sequence set forth in SEQ ID NO: 167, and the HC comprises the amino acid sequence set forth in SEQ ID NO: 168 or SEQ ID NO: 169; or the LC comprises the amino acid sequence set forth in SEQ ID NO: 177, and the HC comprises the amino acid sequence set forth in SEQ ID NO: 178 or SEQ ID NO: 179. In certain embodiments of the recombinant antibodies disclosed herein, the LC comprises the amino acid sequence set forth in SEQ ID NO: 67, and the HC comprises the amino acid sequence set forth in SEQ ID NO: 69. In certain embodiments, the LC comprises the amino acid sequence set forth in SEQ ID NO: 137, and the HC comprises the amino acid sequence set forth in SEQ ID NO: 139. In certain embodiments, the LC comprises the amino acid sequence set forth in SEQ ID NO: 167, and the HC comprises the amino acid sequence set forth in SEQ ID NO: 169.

In certain embodiments, the VL of the recombinant antibodies disclosed herein comprises the amino acid sequence set forth in SEQ ID NO: 13. In certain embodiments of the recombinant antibodies disclosed herein, the VL comprises at least one amino acid substitution. In certain embodiments of the recombinant antibodies disclosed herein, the at least one amino acid substitution is at position 1 and/or at position 44. In certain embodiments of the recombinant antibodies disclosed herein, the amino acid substitution at position 1 is E1Q. In certain embodiments of the recombinant antibodies disclosed herein, the amino acid substitution at position 44 is R44T.

In certain embodiments, the VH of the recombinant antibodies disclosed herein comprises the amino acid sequence set forth in SEQ ID NO: 14. In certain embodiments of the recombinant antibodies disclosed herein, the VH comprises at least one amino acid substitution. In certain embodiments of the recombinant antibodies disclosed herein, the at least one amino acid substitution is at position 21, position 23, position 88, position 98, or a combination thereof. In certain embodiments of the recombinant antibodies disclosed herein, the amino acid substitution at position 1 is E1Q. In certain embodiments of the recombinant antibodies disclosed herein, the amino acid substitution at position 44 is R44T. In certain embodiments of the recombinant antibodies disclosed herein, the amino acid substitution at position 21 is P21S. In certain embodiments of the recombinant antibodies disclosed herein, the amino acid substitution at position 23 is T23A. In certain embodiments of the recombinant antibodies disclosed herein, the amino acid substitution at position 80 is I80T. In certain embodiments, the amino acid substitution at position 90 is T90A.

In certain embodiments, the HC of the recombinant antibodies disclosed herein comprises the amino acid sequence set forth in SEQ ID NO: 18. In certain embodiments of the recombinant antibodies disclosed herein, the HC comprises at least one amino acid substitution. In certain embodiments of the recombinant antibodies disclosed herein, the at least one amino acid substitution is at position 438 and/or or at position 444. In certain embodiments, the amino acid substitution at position 438 is M438L. In certain embodiments of the recombinant antibodies disclosed herein, the amino acid substitution at position 444 is N444S.

In certain non-limiting embodiments, the present disclosure provides a recombinant anti-circumsporozoite (CSP) antibody comprising a light chain variable region (VL) and a heavy chain variable region (VH), wherein the VL comprises the amino acid sequence set forth in SEQ ID NO: 63 and the VH comprises the amino acid sequence set forth in SEQ ID NO: 64. In certain embodiments, the recombinant antibody comprises a light chain (LC) and a heavy chain (HC), wherein the LC comprises the amino acid sequence set forth in SEQ ID NO: 67 and the HC comprises the amino acid sequence set forth in SEQ ID NO: 69.

In certain non-limiting embodiments, the present disclosure further provides a recombinant anti-circumsporozoite (CSP) antibody comprising a light chain variable region (VL) and a heavy chain variable region (VH), wherein the VL comprises the amino acid sequence set forth in SEQ ID NO: 133 and the VH comprises the amino acid sequence set forth in SEQ ID NO: 134. In certain embodiments, the recombinant antibody comprises a light chain (LC) and a heavy chain (HC), wherein the LC comprises the amino acid sequence set forth in SEQ ID NO: 137 and the HC comprises the amino acid sequence set forth in SEQ ID NO: 139.

In certain non-limiting embodiments, the present disclosure also provides a recombinant anti-circumsporozoite (CSP) antibody comprising a light chain variable region (VL) and a heavy chain variable region (VH), wherein the VL comprises the amino acid sequence set forth in SEQ ID NO: 163 and the VH comprises the amino acid sequence set forth in SEQ ID NO: 164. In certain embodiments, the recombinant antibody comprises a light chain (LC) and a heavy chain (HC), wherein the LC comprises the amino acid sequence set forth in SEQ ID NO: 167 and the HC comprises the amino acid sequence set forth in SEQ ID NO: 169.

In certain non-limiting embodiments, the present disclosure provides a recombinant anti-circumsporozoite (CSP) antibody comprising a light chain variable region (VL) and a heavy chain variable region (VH), wherein the light chain variable region comprises a CDR1 comprising the amino acid sequence set forth in SEQ ID NO: 183, a CDR2 comprising the amino acid sequence set forth in SEQ ID NO: 184, and a CDR3 comprising the amino acid sequence set forth in SEQ ID NO: 185; and the heavy chain variable region comprises a CDR1 comprising the amino acid sequence set forth in SEQ ID NO: 186, a CDR2 comprising the amino acid sequence set forth in SEQ ID NO: 187, and a CDR3 comprising the amino acid sequence set forth in SEQ ID NO: 188. In certain embodiments, the VL comprises the amino acid sequence set forth in SEQ ID NO: 195, and the VH comprises the amino acid sequence set forth in SEQ ID NO: 196. In certain embodiments, the recombinant antibody comprises comprising a LC and a HC. In certain embodiments of the recombinant antibodies disclosed herein, the LC comprises the amino acid sequence set forth in SEQ ID NO: 199, and the HC comprises the amino acid sequence set forth in SEQ ID NO: 200 or SEQ ID NO: 201.

In certain non-limiting embodiments, the present disclosure provides a recombinant anti-circumsporozoite (CSP) antibody comprising a light chain variable region (VL) and a heavy chain variable region (VH), wherein the light chain variable region comprises a CDR1 comprising the amino acid sequence set forth in SEQ ID NO: 205, a CDR2 comprising the amino acid sequence set forth in SEQ ID NO: 206, and a CDR3 comprising the amino acid sequence set forth in SEQ ID NO: 207; and the heavy chain variable region comprises a CDR1 comprising the amino acid sequence set forth in SEQ ID NO: 208, a CDR2 comprising the amino acid sequence set forth in SEQ ID NO: 209, and a CDR3 comprising the amino acid sequence set forth in SEQ ID NO: 210.

In certain embodiments, the VL of the recombinant antibodies disclosed herein comprises the amino acid sequence set forth in SEQ ID NO: 227; the amino acid sequence set forth in SEQ ID NO: 237; the amino acid sequence set forth in SEQ ID NO: 247; the amino acid sequence set forth in SEQ ID NO: 257; or the amino acid sequence set forth in SEQ ID NO: 267. In certain embodiments, the VH of the recombinant antibodies disclosed herein comprises the amino acid sequence set forth in SEQ ID NO: 228; the amino acid sequence set forth in SEQ ID NO: 238; the amino acid sequence set forth in SEQ ID NO: 248; the amino acid sequence set forth in SEQ ID NO: 258; or the amino acid sequence set forth in SEQ ID NO: 268. In certain embodiments of the recombinant antibodies disclosed herein, the VL comprises the amino acid sequence set forth in SEQ ID NO: 227, and the VH comprises the amino acid sequence set forth in SEQ ID NO: 228; the VL comprises the amino acid sequence set forth in SEQ ID NO: 237, and the VH comprises the amino acid sequence set forth in SEQ ID NO: 238; the VL comprises the amino acid sequence set forth in SEQ ID NO: 247, and the VH comprises the amino acid sequence set forth in SEQ ID NO: 248; the VL comprises the amino acid sequence set forth in SEQ ID NO: 257, and the VH comprises the amino acid sequence set forth in SEQ ID NO: 258; or the VL comprises the amino acid sequence set forth in SEQ ID NO: 267, and the VH comprises the amino acid sequence set forth in SEQ ID NO: 268.

In certain embodiments, the recombinant antibodies disclosed herein comprise a LC and a HC. In certain embodiments, the LC of the recombinant antibodies disclosed herein comprises the amino acid sequence set forth in SEQ ID NO: 231; the amino acid sequence set forth in SEQ ID NO: 241; the amino acid sequence set forth in SEQ ID NO: 251; the amino acid sequence set forth in SEQ ID NO: 261; or the amino acid sequence set forth in SEQ ID NO: 271. In certain embodiments, the HC of the recombinant antibodies disclosed herein comprises the amino acid sequence set forth in SEQ ID NO: 232 or SEQ ID NO: 233; the amino acid sequence set forth in SEQ ID NO: 242 or SEQ ID NO: 243; the amino acid sequence set forth in SEQ ID NO: 252 or SEQ ID NO: 253; the amino acid sequence set forth in SEQ ID NO: 262 or SEQ ID NO: 263; or the amino acid sequence set forth in SEQ ID NO: 272 or SEQ ID NO: 273. In certain embodiments of the recombinant antibodies disclosed herein, the LC comprises the amino acid sequence set forth in SEQ ID NO: 231, and the HC comprises the amino acid sequence set forth in SEQ ID NO: 232 or SEQ ID NO: 233; the LC comprises the amino acid sequence set forth in SEQ ID NO: 241, and the HC comprises the amino acid sequence set forth in SEQ ID NO: 242 or SEQ ID NO: 243; the LC comprises the amino acid sequence set forth in SEQ ID NO: 251, and the HC comprises the amino acid sequence set forth in SEQ ID NO: 252 or SEQ ID NO: 253; the LC comprises the amino acid sequence set forth in SEQ ID NO: 261, and the HC comprises the amino acid sequence set forth in SEQ ID NO: 262 or SEQ ID NO: 263; or the LC comprises the amino acid sequence set forth in SEQ ID NO: 271, and the HC comprises the amino acid sequence set forth in SEQ ID NO: 272 or SEQ ID NO: 273.

In certain embodiments, the VH of the recombinant antibodies disclosed herein comprises the amino acid sequence set forth in SEQ ID NO: 218. In certain embodiments of the recombinant antibodies disclosed herein, the VH comprises at least one amino acid substitution. In certain embodiments of the recombinant antibodies disclosed herein, the at least one amino acid substitution is at position 40, position 69, position 80, position 85, position 120, or a combination thereof. In certain embodiments of the recombinant antibodies disclosed herein, the amino acid substitution at position 40 is T40A. In certain embodiments of the recombinant antibodies disclosed herein, the amino acid substitution at position 69 is I69T. In certain embodiments of the recombinant antibodies disclosed herein, the amino acid substitution at position 80 is S80Y. In certain embodiments of the recombinant antibodies disclosed herein, the amino acid substitution at position 85 is G85S. In certain embodiments of the recombinant antibodies disclosed herein, the amino acid substitution at position 120 is I120T. In certain embodiment of the recombinant antibodies disclosed herein s, the HC comprises the amino acid sequence set forth in SEQ ID NO: 222. In certain embodiments of the recombinant antibodies disclosed herein, the HC comprises at least one amino acid substitution. In certain embodiments of the recombinant antibodies disclosed herein, the at least one amino acid substitution is at position 434 and/or at position 440. In certain embodiments of the recombinant antibodies disclosed herein, the amino acid substitution at position 434 is M434L. In certain embodiments of the recombinant antibodies disclosed herein, the amino acid substitution at position 440 is N440S.

In certain embodiments, the recombinant antibodies disclosed herein exhibit at least 20% reduction in parasite liver load as compared to a reference antibody. In certain embodiments, the recombinant antibodies disclosed herein exhibit at least 20% increase in survival rate as compared to a reference antibody. In certain embodiments, the recombinant antibodies disclosed herein exhibit increased conformational stability as compared to a reference antibody. In certain embodiments, the recombinant antibodies disclosed herein exhibit increased colloidal stability as compared to a reference antibody. In certain embodiments, the reference antibody is AB-000317. In certain embodiments, the reference antibody is AB-000224. In certain embodiments, the reference antibody is AB-007088.

In certain embodiments, the recombinant antibodies disclosed herein binds to a NANP repeat region. In certain embodiments, the recombinant antibodies disclosed herein binds to a polypeptide comprising or consisting of the amino acid sequence set forth in SEQ ID NO: 280.

In certain embodiments, the recombinant antibodies disclosed herein comprise at least one modification relative to the native AB-000224 variable heavy chain amino acid sequence set forth in SEQ ID NO: 14. In certain embodiments, the recombinant antibodies disclosed herein comprise at least one modification relative to the native AB-000224 variable light chain amino acid sequence set forth in SEQ ID NO: 13. In certain embodiments, the recombinant antibodies disclosed herein comprise at least one modification relative to the native AB-000224 variable heavy chain amino acid sequence set forth in SEQ ID NO: 14 and at least one modification relative to the native AB-000224 variable light chain amino acid sequence set forth in SEQ ID NO: 13.

In certain embodiments, the recombinant antibodies disclosed herein comprise at least one modification relative to the native AB-007088 variable heavy chain amino acid sequence set forth in SEQ ID NO: 218. In certain embodiments, the recombinant antibodies disclosed herein comprise at least one modification relative to the native AB-007088 variable light chain amino acid sequence set forth in SEQ ID NO: 217. In certain embodiments, the recombinant antibodies disclosed herein comprise at least one modification relative to the native AB-007088 variable heavy chain amino acid sequence set forth in SEQ ID NO: 218 and at least one modification relative to the native AB-000224 variable light chain amino acid sequence set forth in SEQ ID NO: 217. In certain non-limiting embodiments, the present disclosure provides a polynucleotide encoding a recombinant antibody disclosed herein. In certain non-limiting embodiments, the present disclosure provides an expression vector comprising the polynucleotide disclosed herein. In certain non-limiting embodiments, the present disclosure provides a host cell comprising the expression vector or the polynucleotide disclosed herein.

In certain non-limiting embodiments, the present disclosure provides a composition comprising the recombinant antibody disclosed herein. In certain embodiments, the composition further comprises a pharmaceutically acceptable carrier.

In certain non-limiting embodiments, the present disclosure provides a method of preventing and/or treating malaria in a subject in need thereof, comprising administering an effective amount of the recombinant antibody disclosed herein or of the composition disclosed herein. In certain embodiments, the subject is a pediatric patient.

In certain non-limiting embodiments, the present disclosure provides the recombinant antibodies or compositions disclosed herein for use in the prevention and/or treatment and/or prevention of malaria in a subject in need thereof. Additionally, in certain non-limiting embodiments, the present disclosure provides the recombinant antibodies or compositions disclosed herein for the manufacture of a medicament for the prevention and/or treatment and/or prevention of malaria in a subject in need thereof. Furthermore, the present disclosure provides use of the recombinant antibodies or compositions disclosed herein for the prevention and/or treatment and/or prevention of malaria in a subject in need thereof. In certain embodiments, the subject is a pediatric patient.

From the foregoing description, it will be apparent that variations and modifications may be made to the presently disclosed subject matter to adopt it to various usages and conditions. Such embodiments are also within the scope of the following claims.

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

The foregoing written description is considered to be sufficient to enable one skilled in the art to practice the methods and/or obtain the compositions described herein. The following examples and detailed description are offered by way of illustration and not by way of limitation.

EXAMPLES

The Examples are offered for illustrative purposes only, and are not intended to limit the scope of the present invention in any way. Indeed, various modifications in addition to those shown and described herein will become apparent to those skilled in the art from the foregoing description and fall within the scope of the appended claims.

It is understood that various other embodiments may be practiced, given the general description provided above.

Example 1. Identification of Functionally Active Anti-CSP Antibodies

AB-000224 and AB-007088 were discovered in antibody repertoires generated by Immune Repertoire Capture® (IRC®) technology from plasmablast B cells isolated from two donors enrolled in a Phase 2a study evaluating the efficacy of the RTS,S vaccine in preventing malaria infection. The IRC® technology and its use in antibody discovery is well known and disclosed in, e.g., WO 2012148497A2, the entire content of which is herein incorporated by reference. The RTS,S vaccine is a pseudo-viral particle vaccine that combines the hepatitis B surface antigen and the central repeat and C-terminal regions of the CSP protein. RTS,S consists of two polypeptides; RTS is a single polypeptide chain corresponding to amino acids 207 to 395 of *P. falciparum* (3D7) that is fused to HBsAg and S is a polypeptide of 226 amino acids that corresponds to HBsAg. Stoute, et. al., N Engl J Med; 336:86-91(1997); RTS,S Clinical Trials Partnership, PLoS Med. 11(7):e1001685, (2014), WO1993/10152. The RTS,S vaccine was administered with the adjuvant AS01B to increase efficacy. AS01B is a liposome-based formulation that contains the immunostimulants monophosphoryl lipid A (MPL) and QS21 and was shown to be more immunogenic than another adjuvant, AS02A, used in initial studies. Kester, et al., J Infect Dis 200: 337-346 (2009). All study participants were vaccinated with one of two vaccine schedules (standard full-dose: 0, 1, 2 M or fractional-third dose: 0, 1, 7 M), or placebo and subsequently challenged with a controlled human malaria parasite infection. The donors from whom AB-000224 and AB-007088 were identified and protected following challenge. Heavy and light chain AB-000224 sequences were expressed as a human IgG1 monoclonal antibody. Heavy and light chain AB-007088 sequences were expressed as a human IgG1 monoclonal antibody. Compared to other antibodies obtained from the same or different donors, AB-000224 and AB-007088 demonstrated strong binding and affinity to CSP protein in vitro, no binding to Hepatitis B protein, and exceptional functional activity when tested in vivo.

The present example provides the design of improved variants of AB-000224 or AB-007088. In certain embodiments, the variants generated have improved developability, e.g., as identified through various in vitro assays, such as aggregation assessment by HPLC or UPLC, hydrophobic interaction chromatography (HIC), polyspecificity assays (e.g., baculovirus particle binding), self-interaction nanoparticle spectroscopy (SINS), or mass spec analysis after incubation in an accelerated degradation condition such as high temperature, low pH, high pH, or oxidative $H_2O_2$. Mutations are successful if the activity is maintained (or enhanced) while removing or reducing the severity of the liability.

Example 2. Generation of Anti-CSP Antibody Variants

Assessment of AB-000224

Figure 4A:
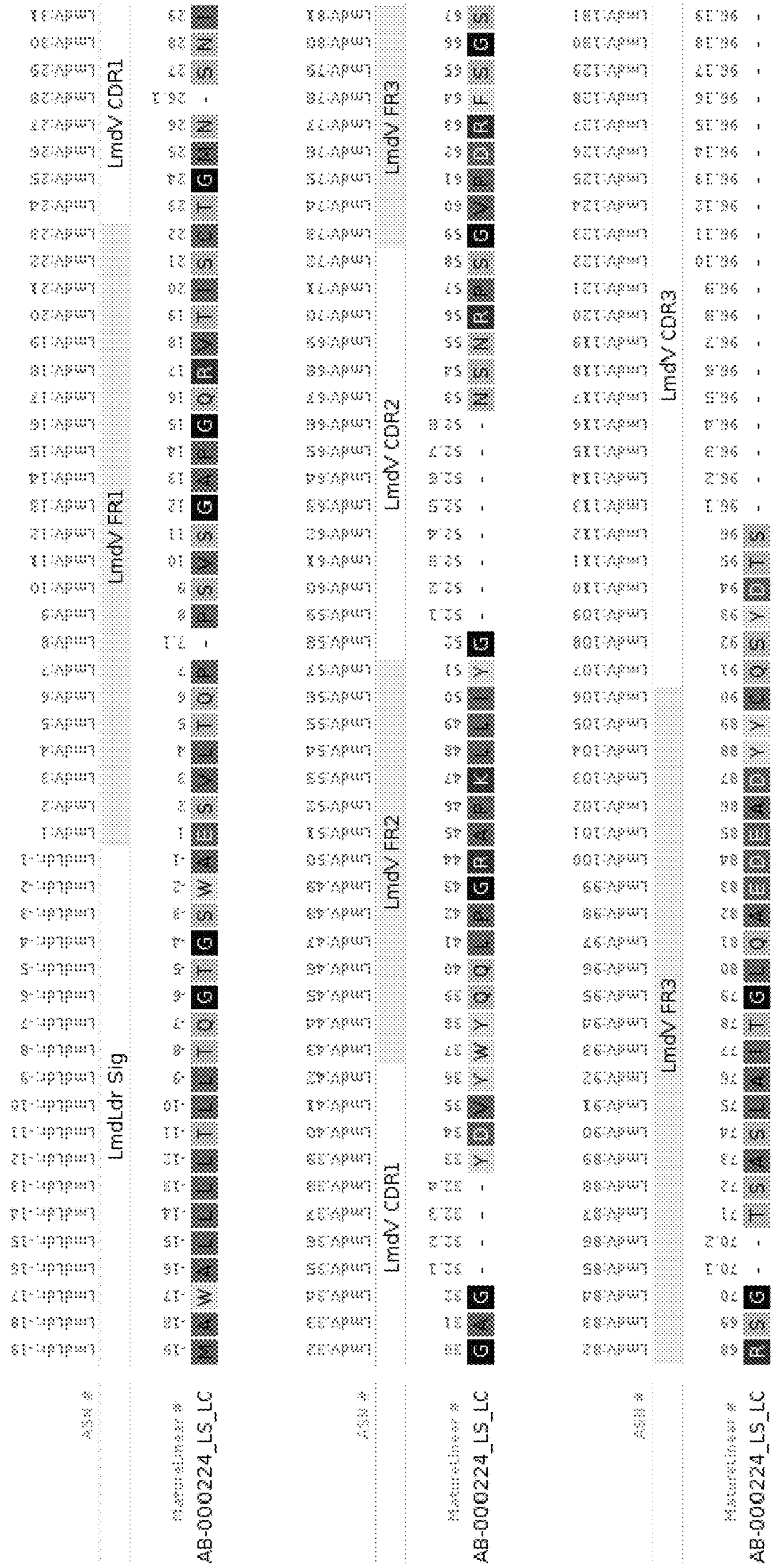
FIGS. 4A-4B illustrate sequences for the AB-000224 antibody.
Figure 4A:
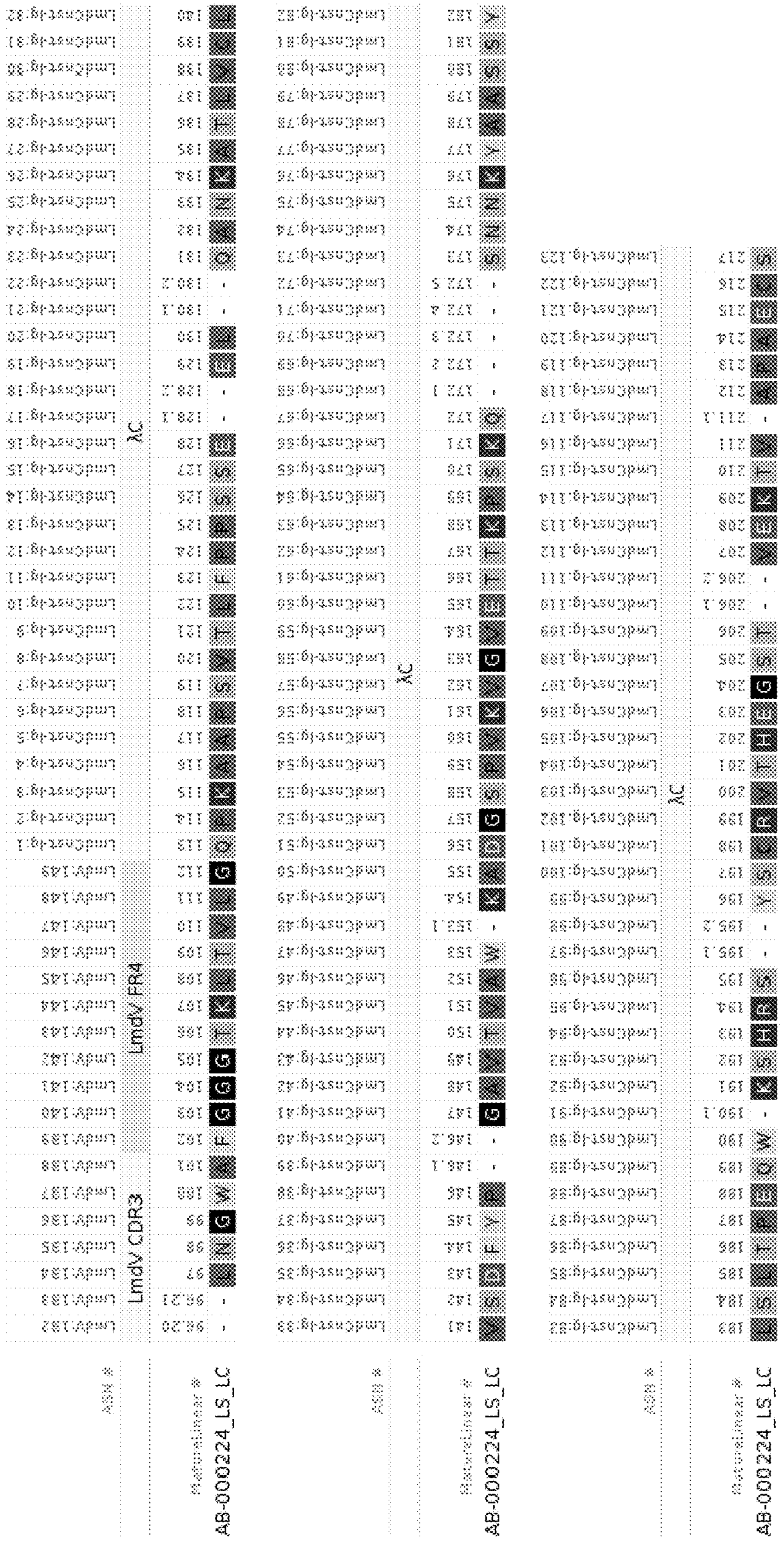
Figure 4B:
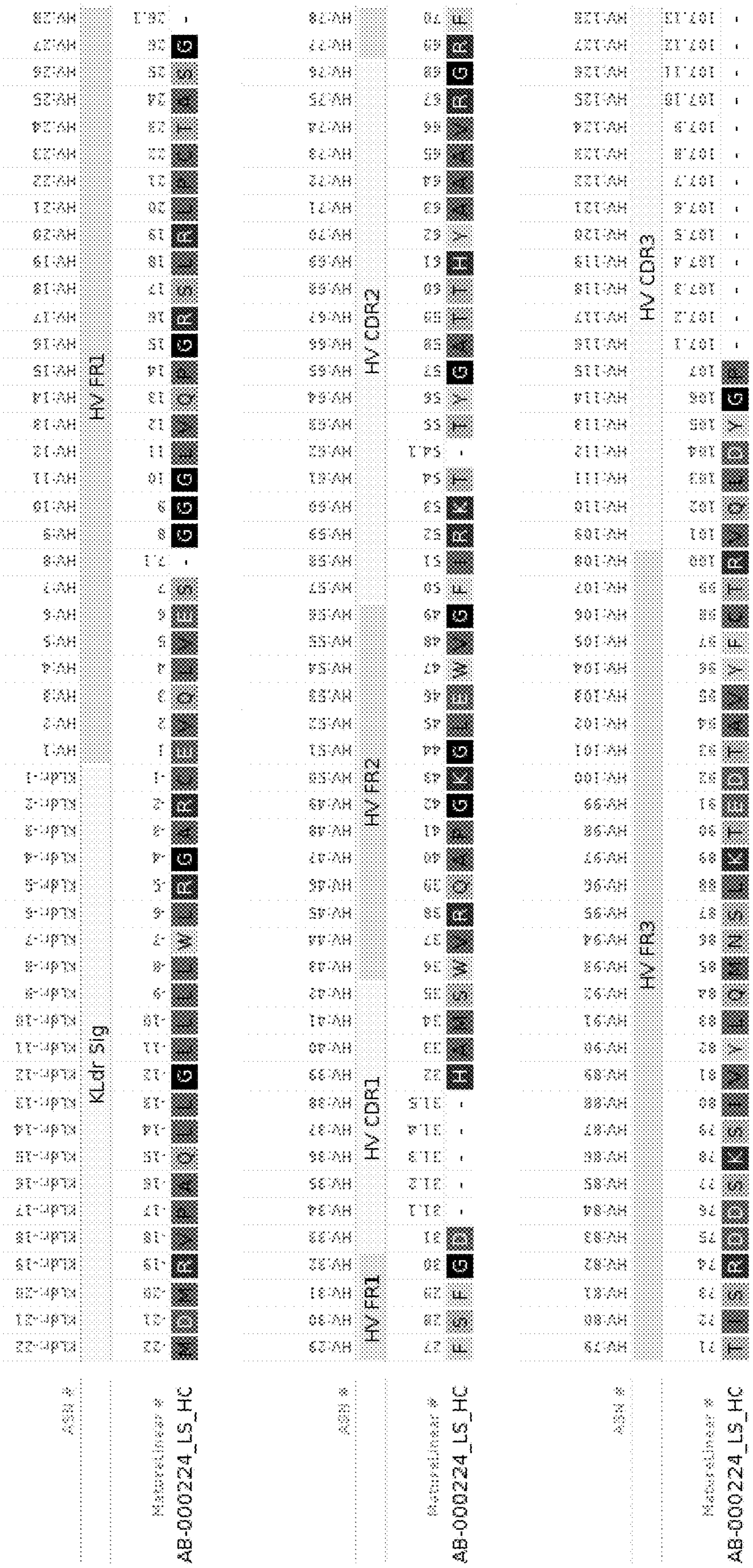
Figure 4B:
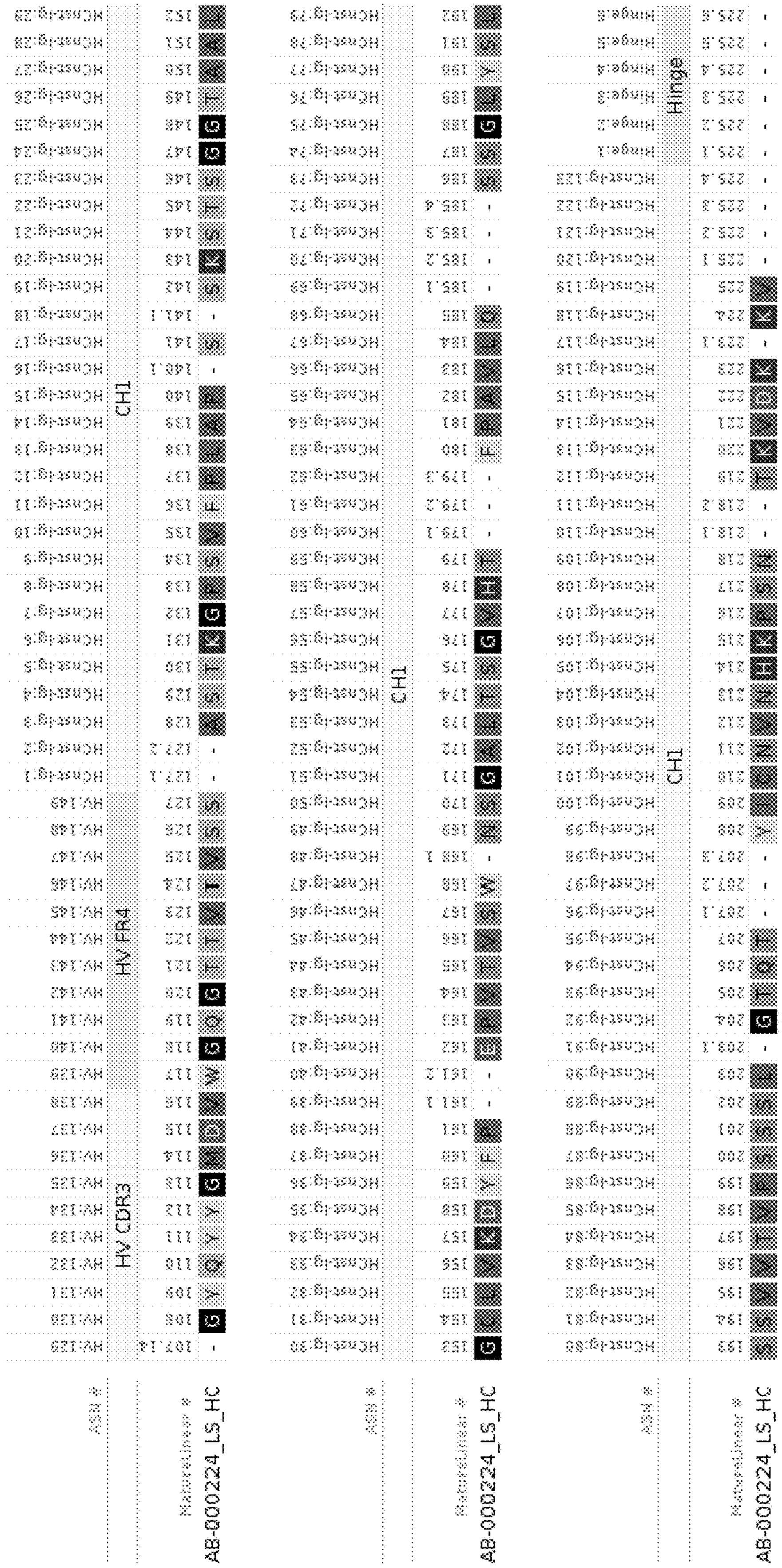
Figure 4B:
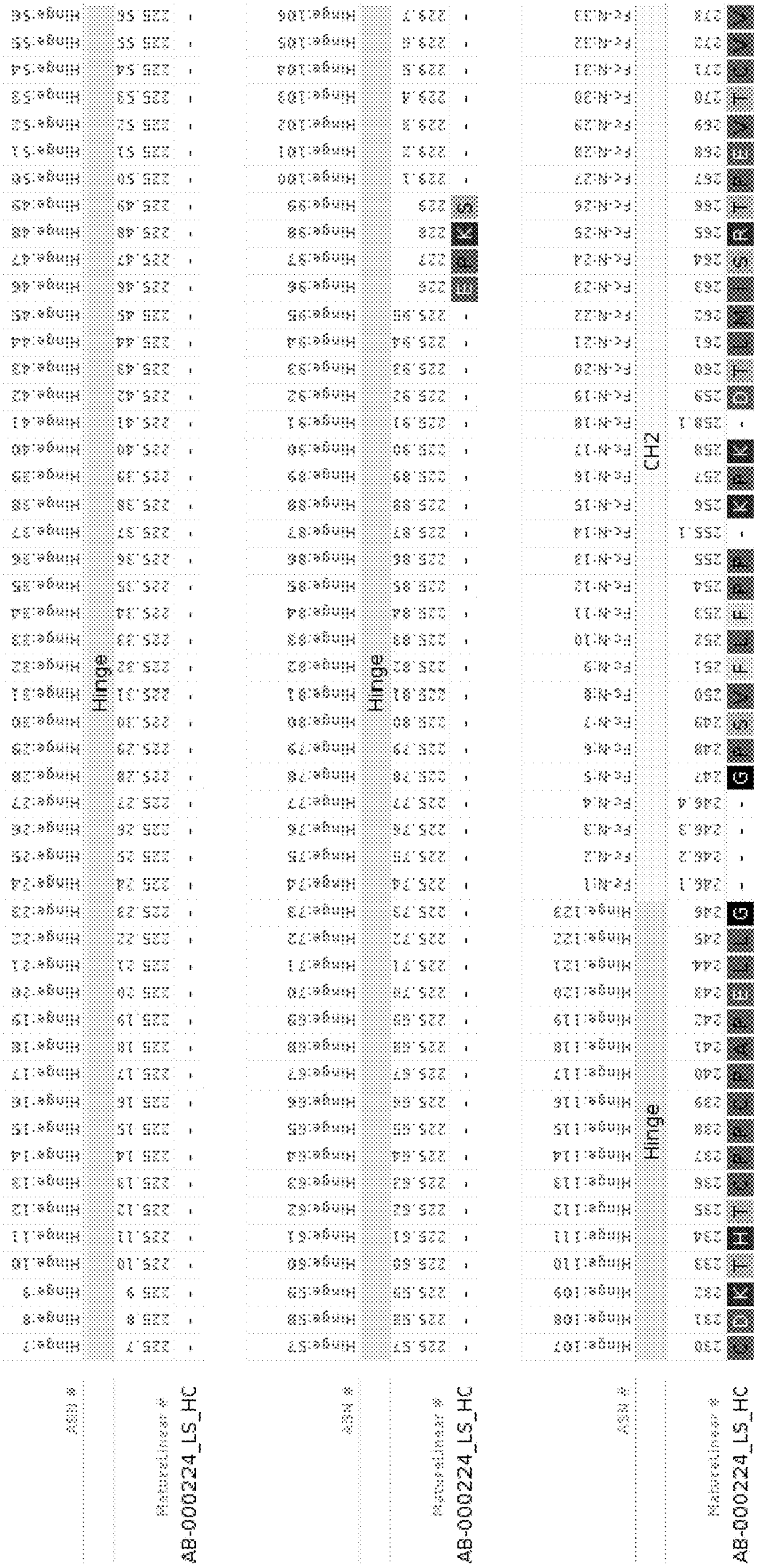
Figure 4B:
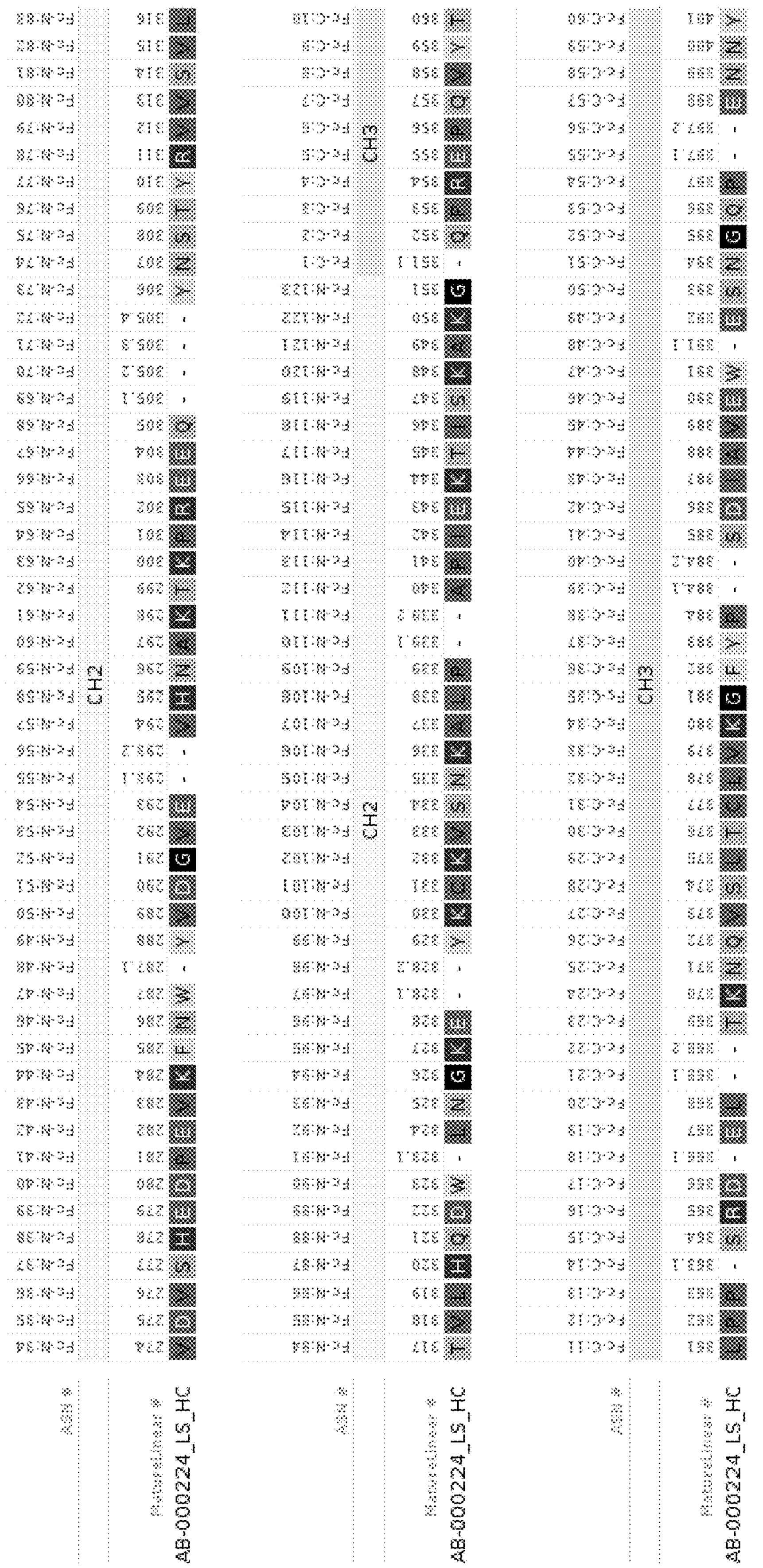
Figure 4B:
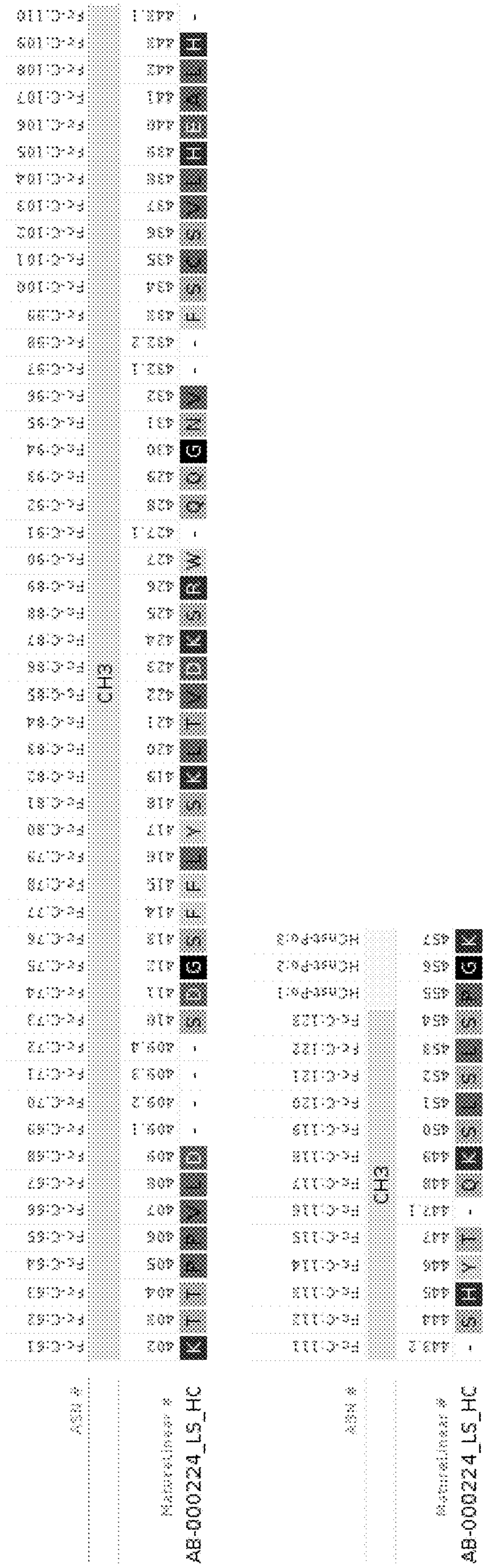

In vivo generated antibodies undergo genomic recombination followed by somatic hypermutation. Germline information was obtained from the AB-000224 antibody and used for the optimization of variant design. FIGS. 4A and 4B show the alignment of the AB-0002224 to the putative V and J germlines genes. CDRs, germline deviations, and potential liabilities were identified. N-linked glycosylation sites, non-typical cysteine residues, and other potential liability motifs were identified across the VH and VL.

The close siblings to AB-000224 are AB-007110, AB-007111, and AB-007112. These were evaluated at the sequence and structure level to find any possible beneficial modifications to AB-000224. AB-007110 in particular has been shown in biophysical characterization to have improved thermal stability over AB-000224. The positions evaluated below differ from AB-000224 and are either consistent amongst the siblings or of structural interest.

Mutations were built by grouping the "Standard" Design Group in all combinations. This results in 16 variants. Add a single variant using the "Sibling" Design Group with all three sites together. This totals 17 variants. Adding the parent results in 18 antibodies required for production. Mutation site positions in the AB-000224 variants according to the ASN numbering system are specified in the table below:

TABLE 32

| Variant | LC-LmdV:E1 | LC-LmdV:R50 | LC-LmdV:N135 | HV:P22 | HV:T24 | HV:H69 | HV:R75 | HV:I88 | HV:T98 | HV:T107 |
|---|---|---|---|---|---|---|---|---|---|---|
| AB-000224_LS | | | | | | | | | | |
| AB-000224.001 | Q | T | | S | | | | | | |
| AB-000224.002 | Q | T | | s | A | | | | | |
| AB-000224.003 | Q | T | | s | | | | T | | |
| AB-000224.004 | Q | T | | s | | | | | A | |
| AB-000224.005 | Q | T | | s | | | | | | A |
| AB-000224.006 | Q | T | | S | A | | | T | | |
| AB-000224.007 | Q | T | | S | A | | | | A | |
| AB-000224.008 | Q | T | | S | A | | | | | A |
| AB-000224.009 | Q | T | | S | | | | T | A | |
| AB-000224.010 | Q | T | | S | | | | T | | A |
| AB-000224.011 | Q | T | | S | | | | | A | A |
| AB-000224.012 | Q | T | | S | A | | | T | A | |
| AB-000224.013 | Q | T | | S | A | | | T | | A |
| AB-000224.014 | Q | T | | S | A | | | | A | A |
| AB-000224.015 | Q | T | | S | | | | T | A | A |
| AB-000224.016 | Q | T | | S | A | | | T | A | A |
| AB-000224.017 | | | D | | | K | K | | | |

Design of Variants of AB-000224

Framework and complementary-determining region (CDR) germline deviations in AB-000224 were analyzed for their potential to be mutated, individually or in combination, to germline sequence, without negatively impacting binding to the (NANP)3 region of the CSP protein or potency. For each of the candidate mutations from AB-000224 sequence to germline sequence, the risk of making the mutation was assessed based on: (1) the change in charge, if any, since change in charge is intrinsically risky, and a change to more positive charge is particularly risky given the already net positive charge of AB-000224 Fv; (2) conservation of the native AB-000224 residue in the lineage versus the presence of the germline residue or other mutations at that position in the lineage and (3) the structural location of the position with respect to the NANP motif. Some mutations were noted to be coupled to at least one other mutation, meaning that the risk prediction is based on making the mutation in conjunction with the other mutation(s). Proposed AB-000224 Residue Modifications according to the ASN numbering system are shown in Table 31 below:

TABLE 31

| Site | Mutation | Design Group |
|---|---|---|
| LmdV:E1 | Q | Standard |
| LmdV:R50 | T | Standard |
| LmdV:N135 | NS | Siblings |
| HV:P22 | S | Standard |
| HV:T24 | TA | Standard |
| HV:H69 | HK | Siblings |
| HV:R75 | RK | Siblings |
| HV:D84 | DN | Do not repair |
| HV:I88 | IT | Standard |
| HV:T98 | TA | Standard |
| HV:F105 | FY | Do not repair |
| HV:T107 | TA | Standard |

Assessment of AB-007088

Figure 5A:
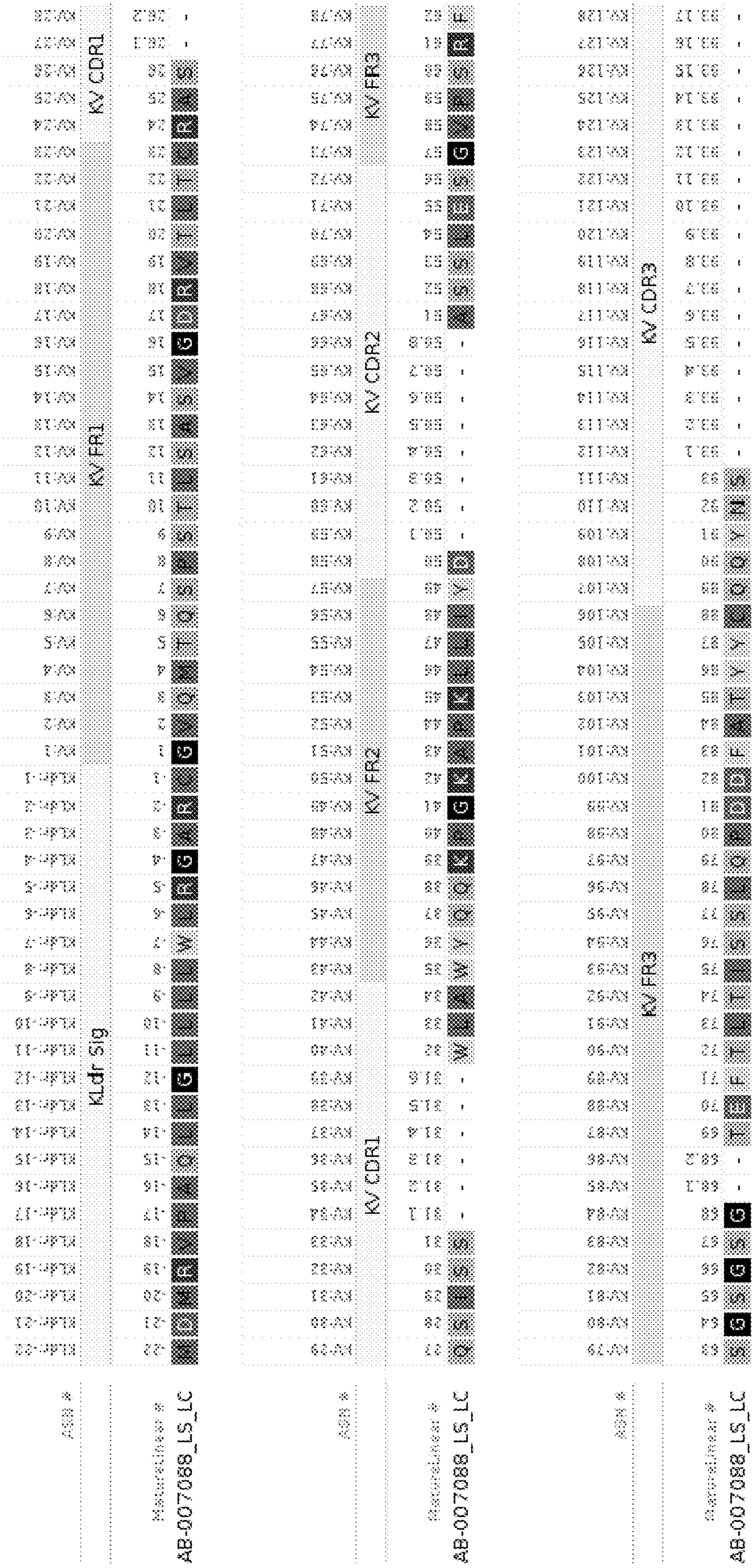
FIGS. 5A-5B illustrate sequences for the AB-007088 antibody.
Figure 5A:
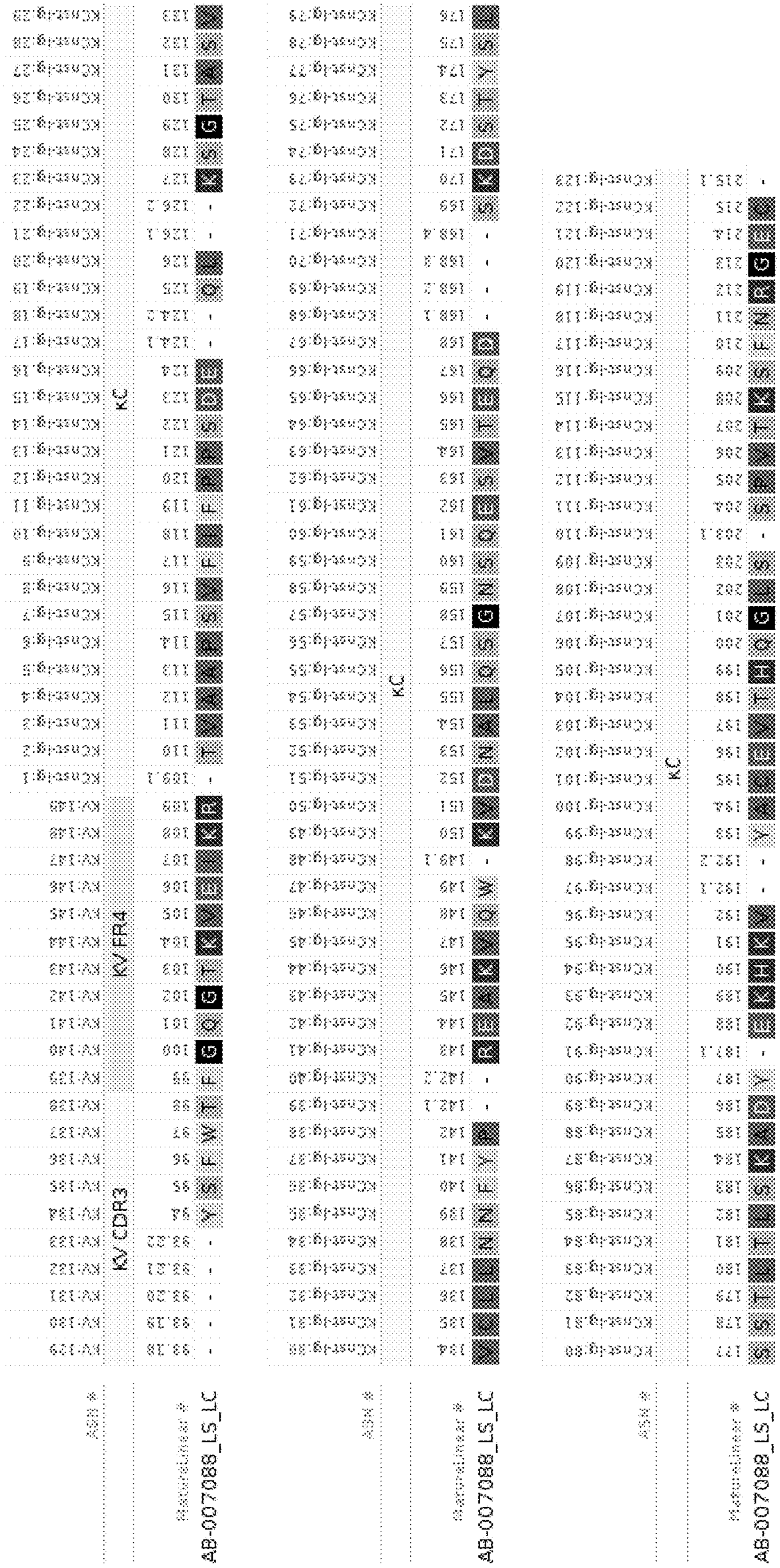
Figure 5B:
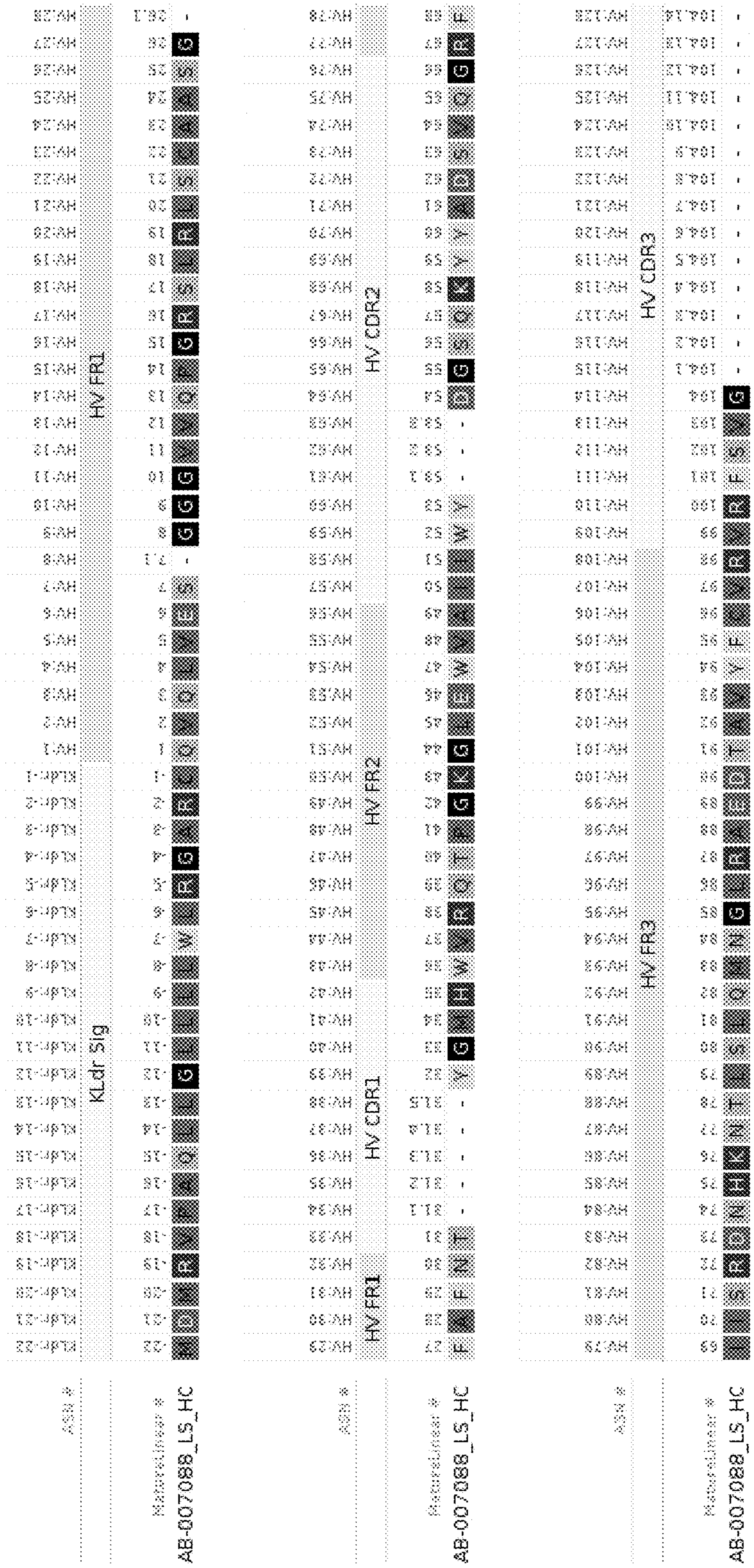
Figure 5B:
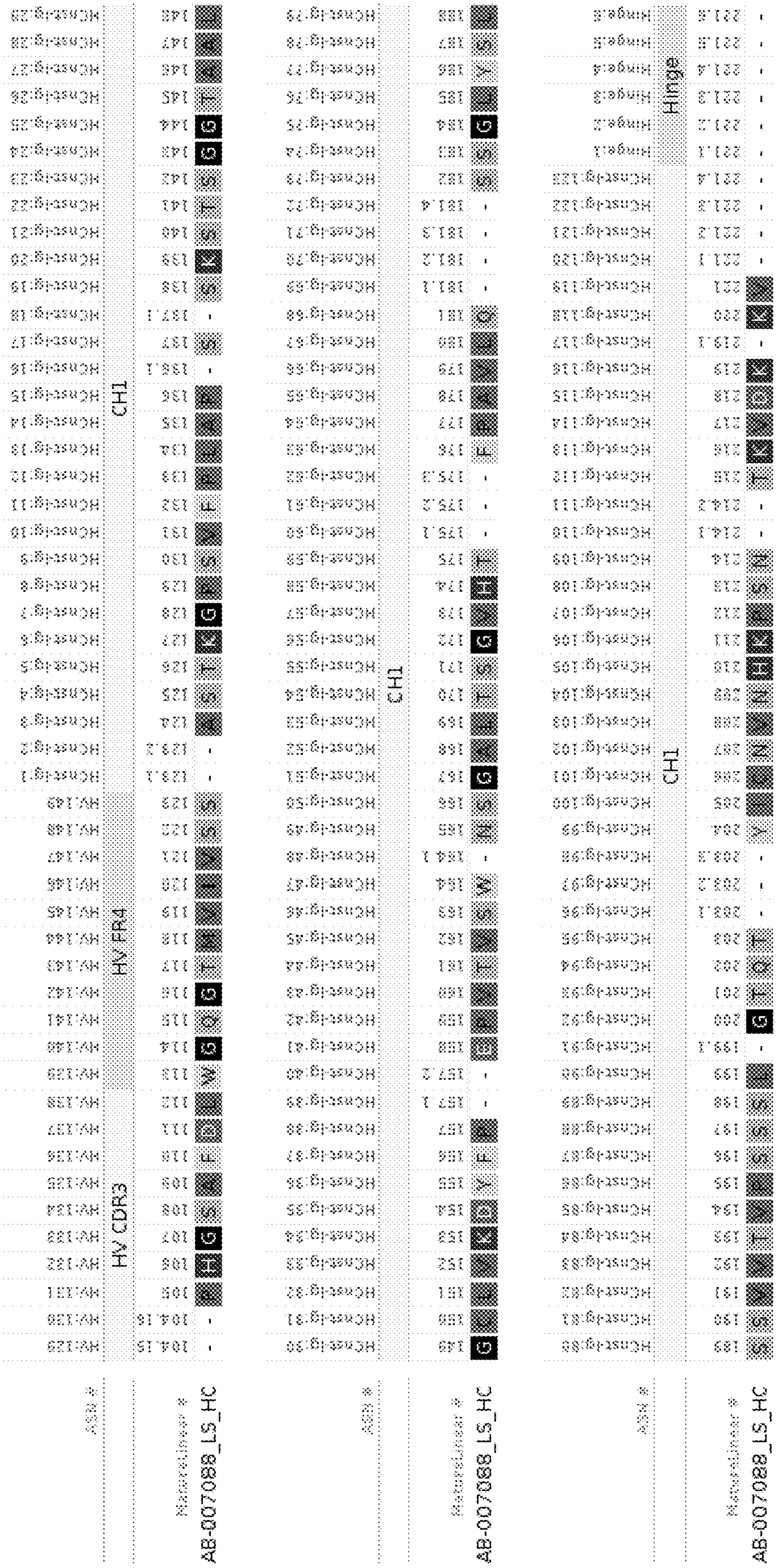
Figure 5B:
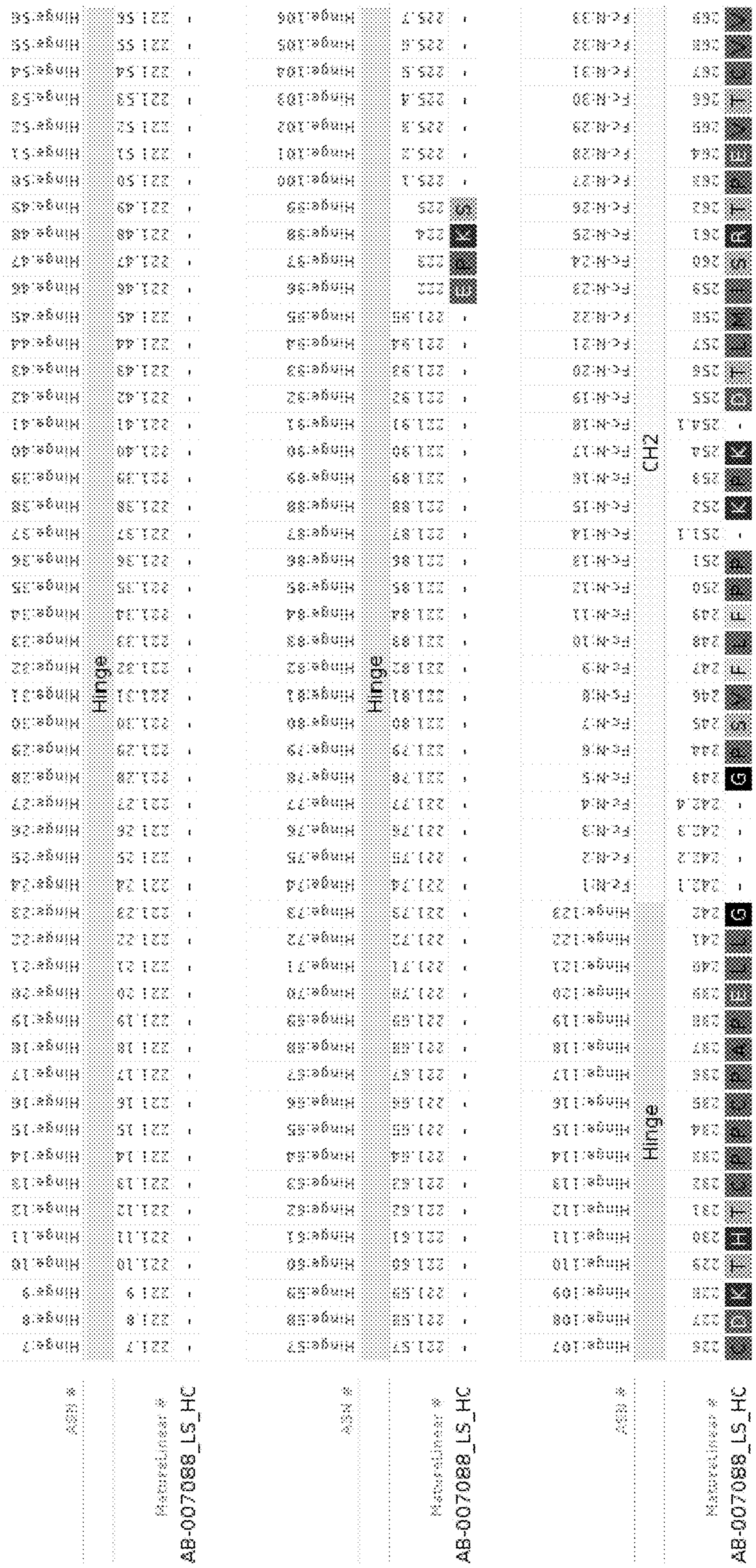
Figure 5B:
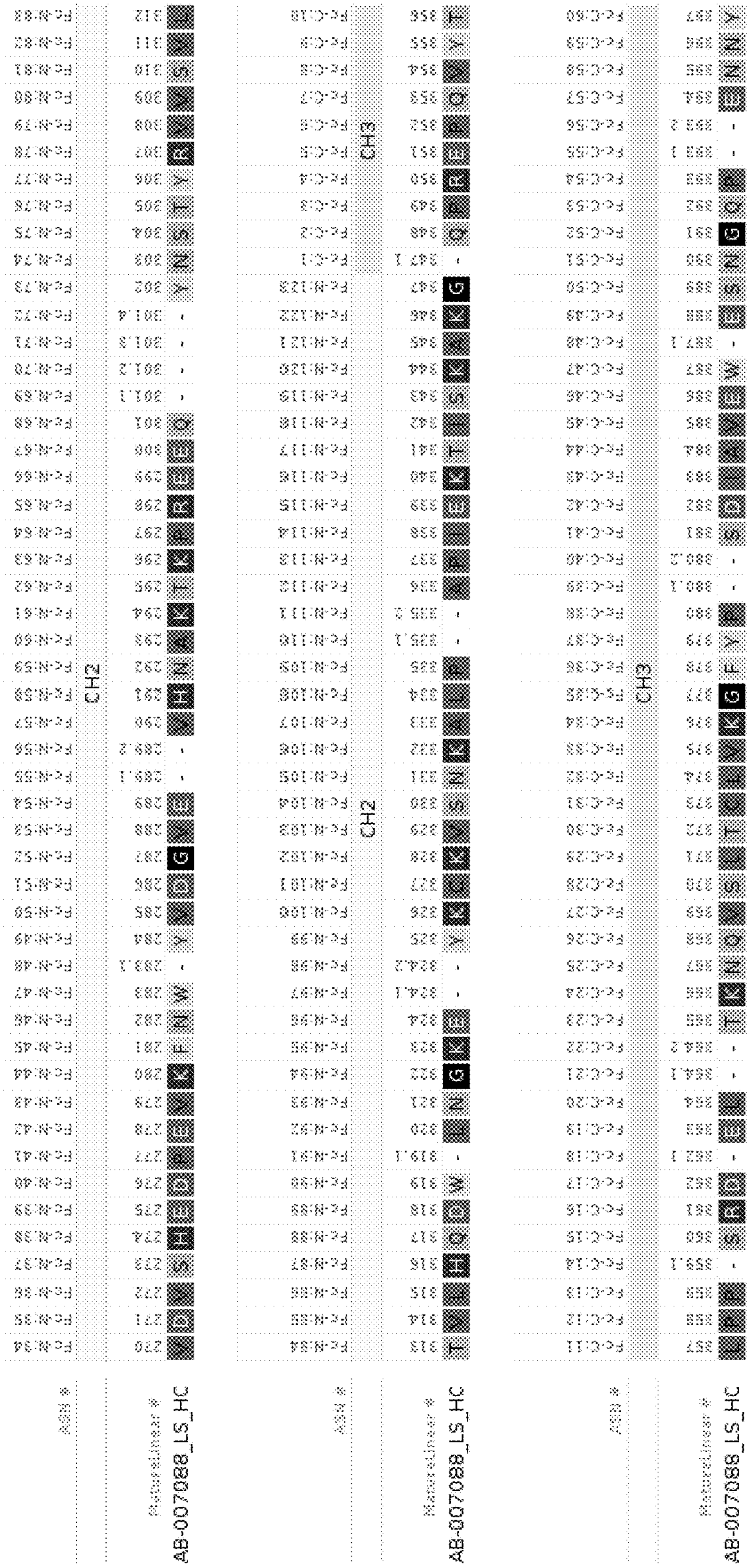
Figure 5B:
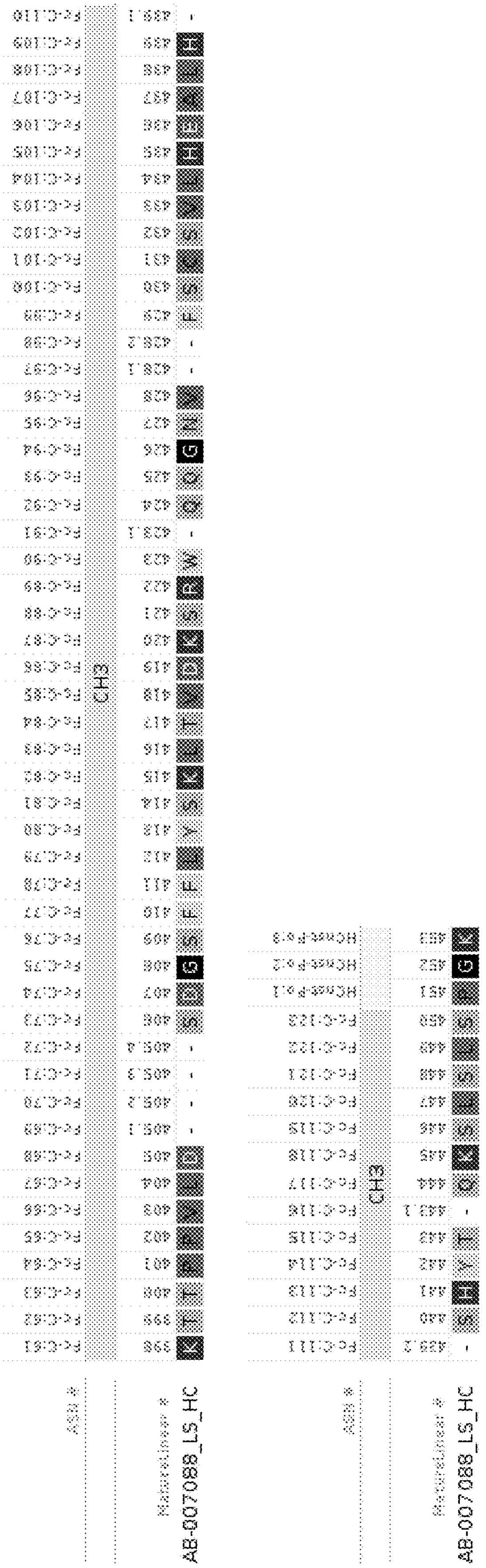

Germline information was obtained from the AB-007088 antibody and used for the optimization of variant design. FIGS. 5A and 5B show the alignment of the AB-0070884 to the putative V and J germlines genes. CDRs, germline deviations, and potential liabilities were identified. N-linked glycosylation sites, non-typical cysteine residues, and other potential liability motifs were identified across the VH and VL.

Design of Variants of AB-007088

Framework and complementary-determining region (CDR) germline deviations in AB-007088 were analyzed for their potential to be mutated, individually or in combination, to germline sequence, without negatively impacting binding to the (NANP)3 region of the CSP protein or potency. For each of the candidate mutations from AB-007088 sequence to germline sequence, the risk of making the mutation was assessed based on: (1) the change in charge, if any, since change in charge is intrinsically risky, and a change to more positive charge is particularly risky given the already net positive charge of AB-007088 Fv; (2) conservation of the native AB-007088 residue in the lineage versus the presence of the germline residue or other mutations at that position in the lineage and (3) the structural location of the position with respect to the NANP motif. Some mutations were noted to be coupled to at least one other mutation, meaning that the risk prediction is based on making the mutation in conjunction with the other mutation(s). Proposed AB-007088 Residue Modifications according to the ASN numbering system are shown in Table 33 below:

TABLE 33

| Site | Mutation | Design Group |
|---|---|---|
| HV:A30 | AT | Group 1 |
| HV:T47 | A | Group 1 |
| HV:I79 | IT | Group 1 |

TABLE 33-continued

| Site | Mutation | Design Group |
|---|---|---|
| HV:S90 | SY | Group 2 |
| HV:G95 | S | Group 1 |
| HV:I146 | T | Group 1 |

Mutations were built by grouping the "Group 1" Design Group in all combinations. This resulted in 4 variants. By adding a single variant using HV: S90Y to the design with all mutations, a total of five designs were obtained. Mutation site positions in the AB-007088 variants according to the ASN numbering system are specified in the table below:

TABLE 34

| Variant | HV:A30 | HV:T47 | HV:I79 | HV:S90 | HV:G95 | HV:I146 |
|---|---|---|---|---|---|---|
| AB-007088_LS | | | | | | |
| AB-007088.001 | | A | | | S | T |
| AB-007088.002 | T | A | | | S | T |
| AB-007088.003 | | A | T | | S | T |
| AB-007088.004 | T | A | T | | S | T |
| AB-007088.005 | T | A | T | Y | S | T |

Example 3. Binding Assays

AB-000224 and AB-007088 were evaluated for binding to the complete CSP protein and a series of linear peptides representing the immunodominant NANP repeat region. Two assay platforms, bio-layer interferometry (BLI) and surface plasmon resonance (SPR), were used to quantify antibody-target binding strength. Five binding targets were evaluated in the SPR assay and six targets were evaluated in the BLI platform and described in Table 35 below:

TABLE 35

| Target Name | Peptide Sequence | Used in BLI, SPR, or both assays |
|---|---|---|
| (NANP)6 | NANPNANPNANPNANPNANPNANP (SEQ ID NO: 279) | Both |
| (NPNA)3 | NPNANPNANPNA (SEQ ID NO: 280) | Both |
| (NVDP)3 (NANP)2 | NVDPNANPNVDPNANPNVDP (SEQ ID NO: 281) | Both |
| NANPNV DPNANP | NPDPNANPNVDPNANP (SEQ ID NO: 2 82) | Both |
| NANPNV DP | DPNANPNVDPNA (SEQ ID NO: 283) | BLI only |
| N-Interface | KQPADGNPDPNANPN (SEQ ID NO: 284) | BLI only |
| CSP Protein | MMRKLAILSVSSFLFVEALFQEYQCYGSSSNTRVLNELNYDNAGIN LYNELEMNYYGKQENWYSLKKNSRSLGENDDGNNNNGDNGREGKDE DKRDGNNEDNEKLRKPKHKKLKQPGDGNPDPNANPNVDPNANPNVD PNANPNVDPNANPNANPNANPNANPNANPNANPNANPNANPNANPN ANPNANPNANPNANPNANPNANPNANPNANPNANPNANPNANPNAN PNANPNANPNANPNANPNANPNANPNANPNANPNANPNANPNANPN ANPNANPNANPNANPNANPNANPNKNNQGNGQGHNMPNDPNRNVDE NANANNAVKNNNNEEPSDKHIEQYLKKIQNSLSTEWSPCSVTCGNG IQVRIKPGSANKPKDELDYENDIEKKICKMEKCSSVFNVVNSSIGL IMVLSFLFLN (SEQ ID NO: 285) | SPR only |

For BLI, each of the targets specified in Table 35 was biotinylated and immobilized to streptavidin sensors. Each antibody was evaluated in duplicate at 5 μg/mL. If the variation between the two duplicates was >3-fold, the antibody-target measurement was repeated.

For SPR, each antibody was either directly coupled to a Carterra Chip or coupled using a goat anti-human Fc antibody. The uncoupled antibodies were washed off and various concentration gradients of the targets were flowed over the antibodies, where the highest concentration of each target was in the range 0.5-8 μg/mL. Each antibody was immobilized in two different locations on the chip to allow for duplicate measurements. The affinity for each antibody-target combination was determined using 4-5 target concentrations in Mathematica software. If the variation between the two duplicates was >3-fold, the antibody-target measurement was repeated.

While the data generated by the BLI and SPR assays are similar, the assays were designed with opposite orientations of the target and antibody. Specifically, the target was immobilized while the antibody flowed over it in the BLI assay, while the SPR assay was designed so that the antibody was immobilized and the target flowed over it. Given these orientations, an antibody, when evaluated in the BLI assay, would be more likely to engage in binding interactions that involve multiple target molecules. As such, the binding of antibodies to targets in the BLI assay may exhibit more similarities to binding the complete CSP protein, which coats the surface of the malaria sporozoite. In contrast, the activity measured in the SPR assay would more accurately represent an interaction between an antibody F(ab) and a single target molecule. The data generated for the antibodies AB-000224 and AB-007088 are summarized in Table 36 below:

TABLE 36

| Antibody ID | AB-000224 | AB-007088 |
|---|---|---|
| NANP6 $K_{ON}$ BLI | 5.44 | 5.22 |
| NANP6 $K_{OFF}$ BLI | −4.75 | −4.32 |
| NANP6 $K_D$ BLI | −10.19 | −9.55 |
| NANP6 $K_{ON}$ SPR | 5.01 | 5.52 |
| NANP6 $K_{OFF}$ SPR | −5.00 | −4.14 |
| NANP6 $K_D$ SPR | −10.00 | −9.63 |
| NPNA3 $K_{ON}$ BLI | 5.35 | 5.23 |
| NPNA3 $K_{OFF}$ BLI | −4.32 | −6.00 |
| NPNA3 $K_D$ BLI | −9.67 | −11.23 |
| NPNA3 $K_{ON}$ SPR | 4.87 | 5.08 |
| NPNA3 $K_{OFF}$ SPR | −3.47 | −3.25 |
| NPNA3 $K_D$ SPR | −8.34 | −8.33 |
| NVDP3NANP2 $K_{ON}$ BLI | 5.53 | 4.94 |
| NVDP3NANP2 $K_{OFF}$ BLI | −5.12 | −6.00 |
| NVDP3NANP2 $K_D$ BLI | −10.65 | −10.94 |
| NVDP3NANP2 $K_{ON}$ SPR | 4.81 | 4.29 |
| NVDP3NANP2 $K_{OFF}$ SPR | −4.02 | −4.40 |
| NVDP3NANP2 $K_D$ SPR | −8.77 | −8.71 |
| NANPNVDPNANP $K_{ON}$ BLI | 5.59 | 5.03 |
| NANPNVDPNANP $K_{OFF}$ BLI | −2.68 | −6.00 |
| NANPNVDPNANP $K_D$ BLI | −8.27 | −11.03 |
| NANPNVDPNANP $K_{ON}$ SPR | 4.08 | <LLOQ |
| NANPNVDPNANP $K_{OFF}$ SPR | −1.77 | <LLOQ |
| NANPNVDPNANP $K_D$ SPR | −5.85 | <LLOQ |
| NANPNVDP $K_{ON}$ BLI | <LLOQ | 4.89 |
| NANPNVDP $K_{OFF}$ BLI | <LLOQ | −6.00 |
| NANPNVDP $K_D$ BLI | <LLOQ | −10.89 |
| NVDPNANP $K_{ON}$ BLI | 5.35 | 5.02 |
| NVDPNANP $K_{OFF}$ BLI | −4.50 | −6.00 |
| NVDPNANP $K_D$ BLI | −9.85 | −11.02 |
| N-Interface $K_{ON}$ BLI | 6.42 | 5.13 |
| N-Interface $K_{OFF}$ BLI | −1.92 | −6.00 |
| N-Interface $K_D$ BLI | −8.34 | −11.13 |
| N-Interface $K_{ON}$ SPR | <LLOQ | 4.17 |
| N-Interface $K_{OFF}$ SPR | <LLOQ | −2.42 |
| N-Interface $K_D$ SPR | <LLOQ | −6.60 |
| CSP $K_{ON}$ SPR | 5.47 | 5.08 |
| CSP $K_{OFF}$ SPR | −5.00 | −4.59 |
| CSP $K_D$ SPR | −10.44 | −9.67 |

Summary of AB-000224 Antibody Variants

Seventeen (17) variants (AB-000224.001, AB-000224.002, AB-000224.003, AB-000224.004, AB-000224.005, AB-000224.006, AB-000224.007, AB-000224.008, AB-000224.009, AB-000224.010, AB-000224.011, AB-000224.012, AB-000224.013, AB-000224.014, AB-000224.015, AB-000224.016, AB-000224.017)) were designed to germline antibodies by mutating residues in either the framework regions or CDRs to reduce the risk of antibody-directed immunogenicity.

Summary of AB-007088 Antibody Variants

Five (5) variants (AB-007088.001, AB-007088.002, AB-007088.003, AB-007088.004, AB-007088.005) were designed to germline antibodies by mutating residues in either the framework regions or CDRs to reduce the risk of antibody-directed immunogenicity.

Example 4. In Vivo Performance of the Antibodies

Liver Burden Assay

AB-000224 and AB-007088 and variants thereof (with those in format comprising Heavy Chain version 2 indicated with the "LS") were evaluated for in vivo activity in a mouse malaria liver burden assay, as described in Flores-Garcia Y, et al. Malar J. 2019; 18(1):426, doi:10.1186/s12936-019-3055-9. Experimental antibodies were compared to both positive (AB-000317) and negative (AB-001245) antibody controls. AB-000317 is an anti-CSP antibody described in WO2020/172220. AB-001245 is non-CSP isotype control.

For each antibody, five C57Bl/6 mice per experimental or control arm were administered 100 μg of antibody 16 hours prior to intravenous infection with fluorescent chimeric *P. berghei* sporozoites expressing *P. falciparum* CSP protein. Forty-two (42) hours following parasite challenge, the sporozoite liver load was quantified by bioluminescence. For each experimental mouse, the percent liver burden was calculated by subtracting the average background luminescence measured from two untreated, naive mice and calculating the percent reduction as compared to the average luminescence measured in five untreated, infected mice. The average percent reduction was reported for each of the experimental antibody groups.

Figure 1B:
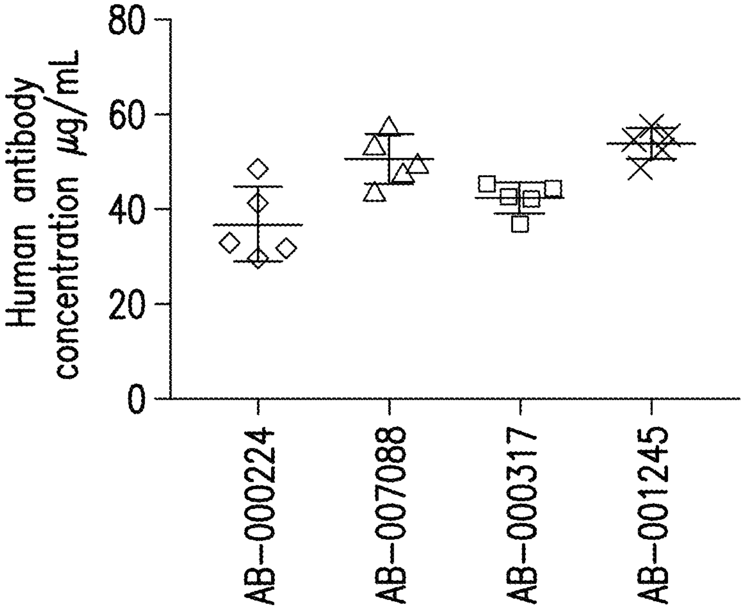
FIG. 1B illustrates the associated human IgG serum concentrations determined by ELISA obtained 15 hours following antibody administration. The individual points indicate the total amount of human IgG in a single mouse. AB-001245 is a non-malaria-specific antibody that was used as a negative control. AB-000317 is a positive control.

Mice administered AB-000224, AB-007088 or positive control antibody AB-000317 all exhibited a similar reduction in liver burden load as compared to naïve infected mice and mice treated with the negative control, AB-001245 (FIG. 1A). The level of experimental and control human antibodies circulating in the mice at the time of infection was quantified via an ELISA assay (FIG. 1B) and was similar between the experimental and control antibodies.

Figure 10A:
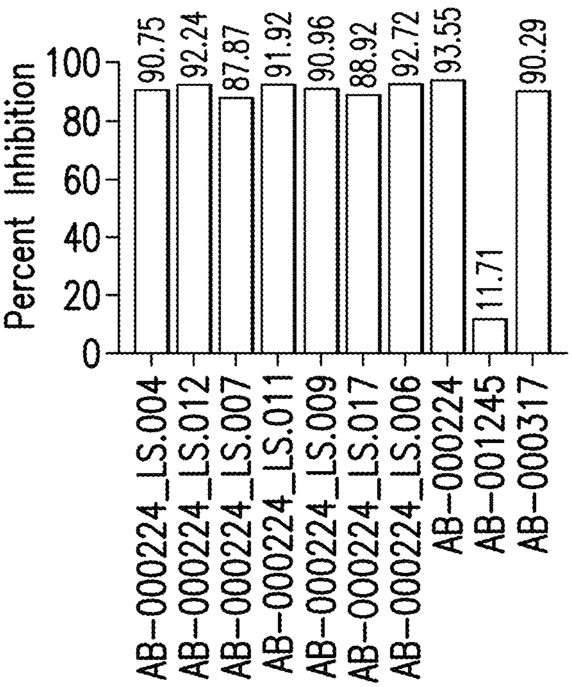
FIGS. 10A-10F illustrate parasite liver load following administration of experimental anti-CSP antibodies variants disclosed herein. Results are expressed as percentage inhibition, where naïve infected were considered as 100%.
Figure 10B:
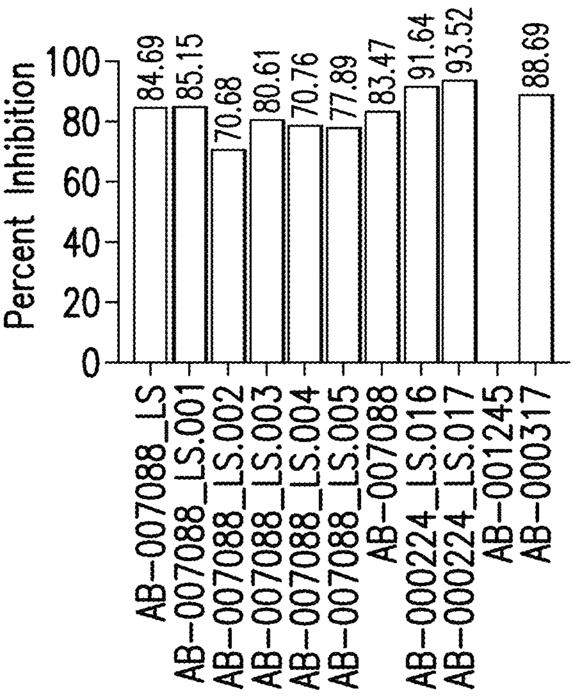
Figure 10C:
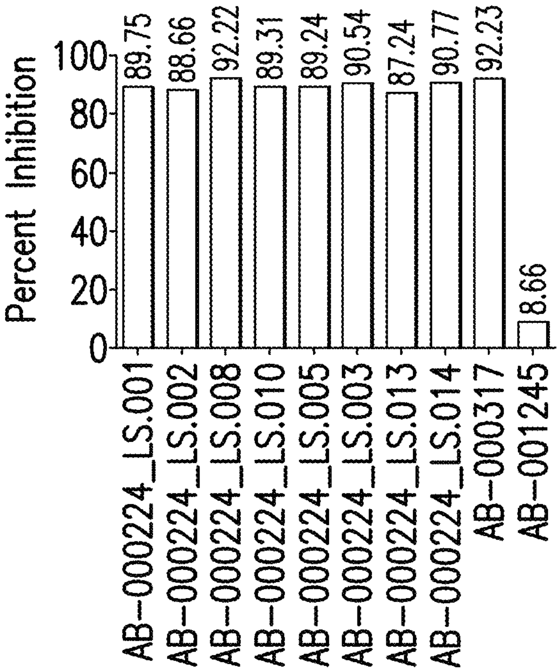
Figure 10D:
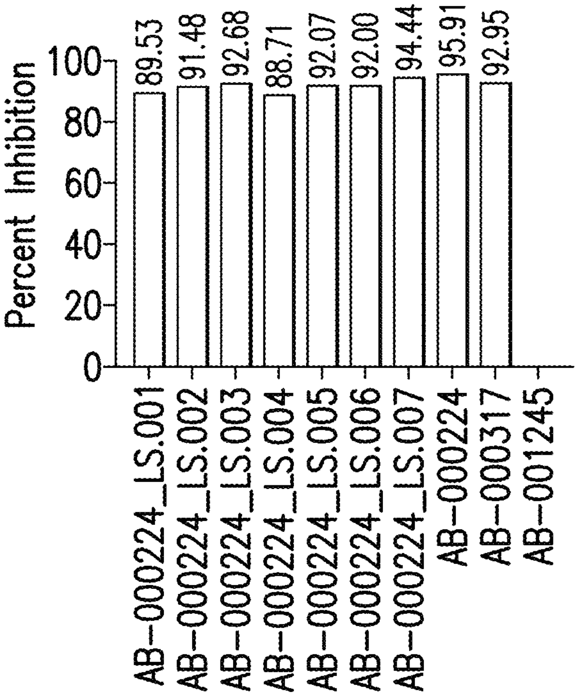
Figure 10E:
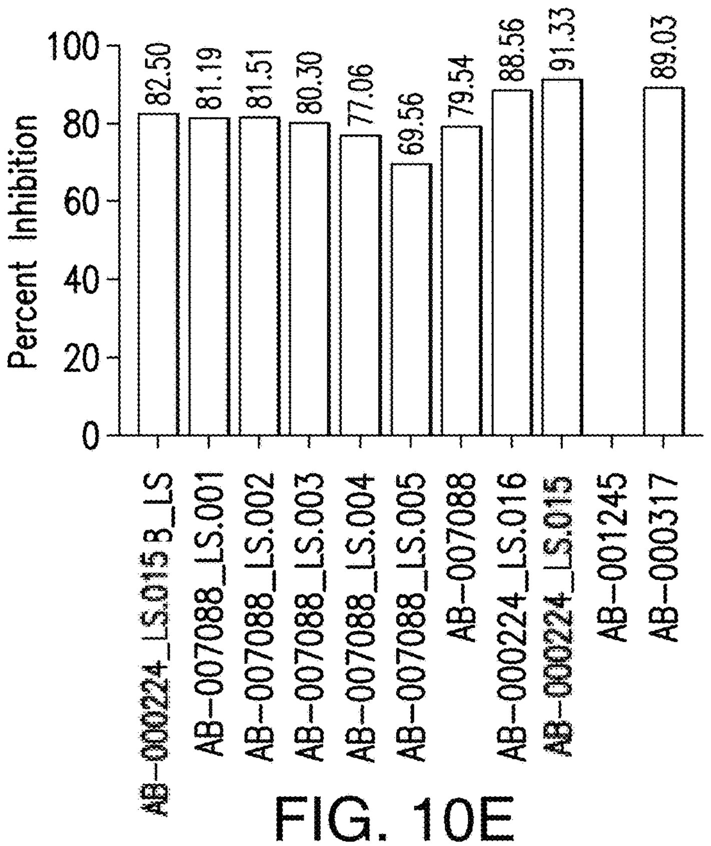
Figure 10F:
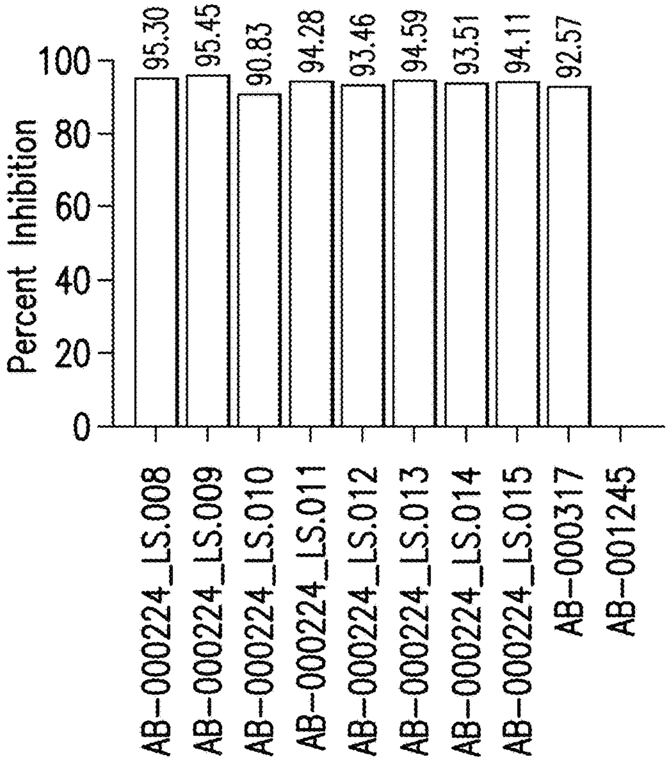
Figure 10G:
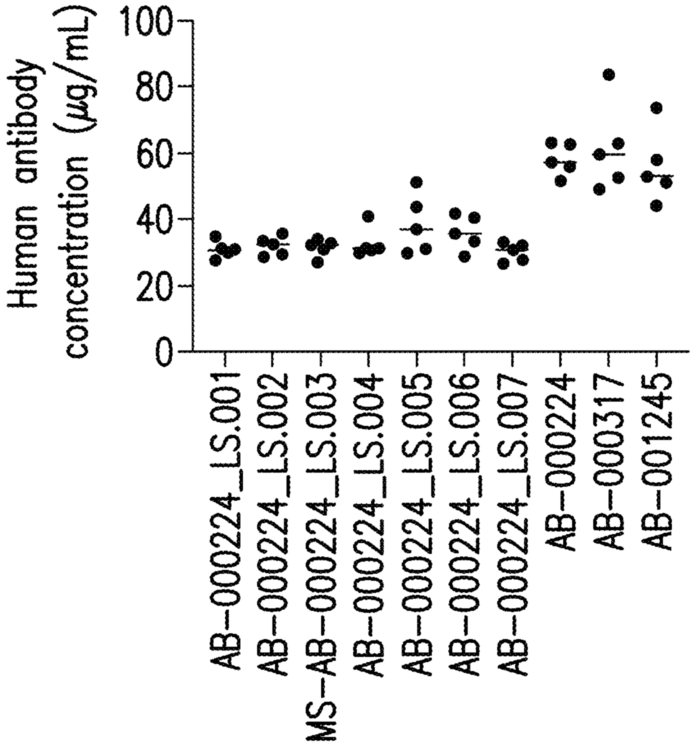
FIGS. 10G-10I show concentration of human antibodies that were circulating in the mice at the time of infection as determined by ELISA for the assays shown in FIGS. 10D-F, respectively. AB-001245 is a non-malaria-specific antibody that was used as a negative control. AB-000317 is a positive control.
Figure 10H:
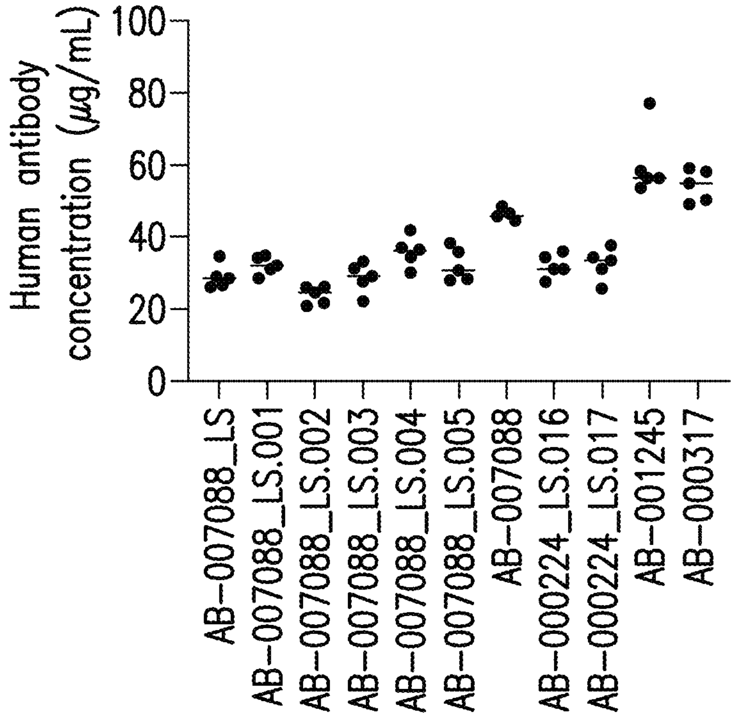
Figure 10I:
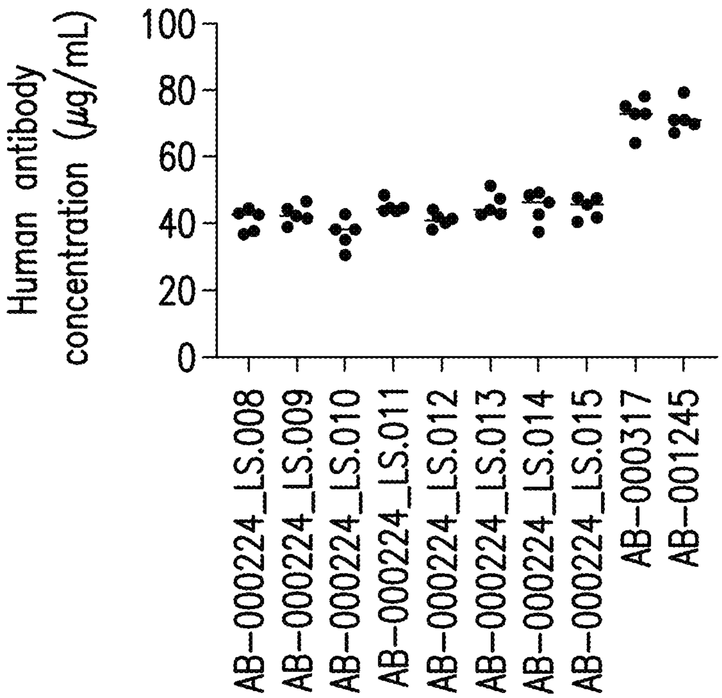

Variants of AB-000224 and AB-007088 drove reduction in liver burden load in treated mice that was comparable to the respective parent antibody AB-000224 or AB-007088 and the positive control antibody AB-000317. Liver burden levels measured in animals administered either the variants, the parent molecules or positive control antibody AB-000317 was significantly lower than liver burden levels in either the naïve infected mice or mice treated with the negative control, AB-001245 (FIGS. 10A-10F). Biological replicates of each antibody variant are shown in FIGS. 10A-10F. The concentration of human antibodies that were circulating in the mice at the time of infection was determined by ELISA and is shown in FIGS. 10G-10I.

Bite Parasitemia Assay

AB-000224 and AB-007088 and variants thereof were also evaluated for their ability to protect against infection (with those in format comprising Heavy Chain version 2 indicated with the "LS"). In this experiment, animals were exposed to mosquitoes infected with chimeric *P. berghei* expressing *P. falciparum* CSP protein, as described in Espinosa, D., et al. npj Vaccines 2017; 2, 10 (2017); Espinosa, D., et al. Infect Immun. 2013 August; 81(8): 2882-2887.

C57Bl/6 Mice were administered 150 μg of antibody and 16 hours later were exposed to six or seven chimeric *P. berghei*-infected mosquitoes. At least 70%-80% of the mosquito population are infected with chimeric *P. berghei* expressing *P. falciparum* CSP protein, resulting in exposure to at least one infectious event. Each mouse was subsequently evaluated for blood stage parasitemia from days 4-10 following infection by microscopy. Parasitemia data were recorded as positive or negative and the data used to generate a survival curve. Experimental antibodies were compared to both the positive (AB-000317) and negative (AB-001245) controls.

Figure 2A:
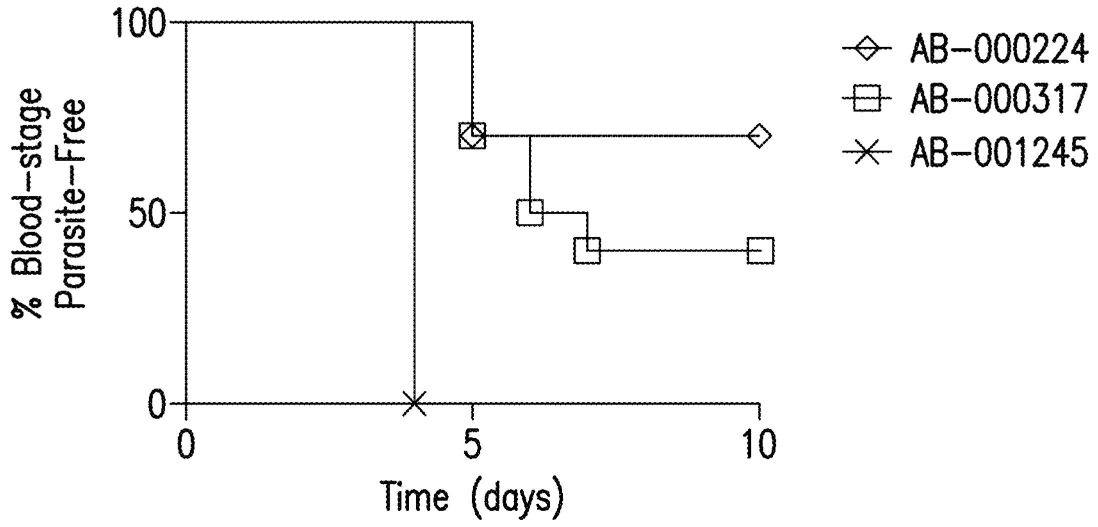
FIGS. 2A and 2C illustrate the survival rate of mice following administration of anti-CSP antibody AB-000224 and exposure to mosquitoes infected with chimeric *P. berghei* expressing *P. falciparum* CSP protein in two experiments.
Figure 2B:
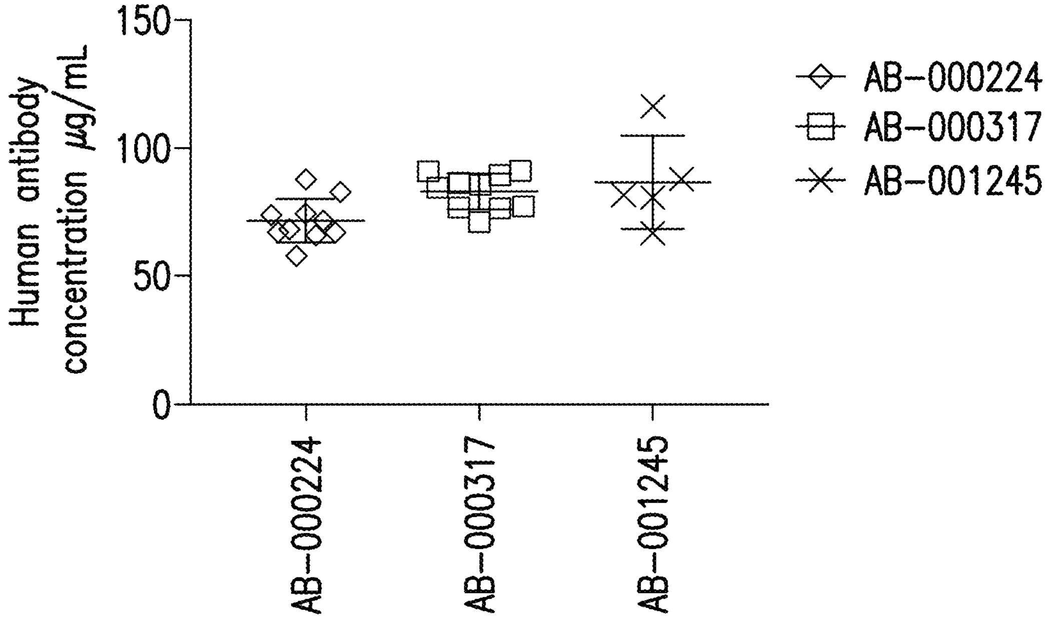
FIG. 2B shows the associated human IgG serum concentrations determined by ELISA obtained 15 hours following antibody administration in the experiment shown in FIG. 2A. AB-001245 is a non-malaria-specific antibody that was used as a negative control. AB-000317 is a positive control.
Figure 2C:
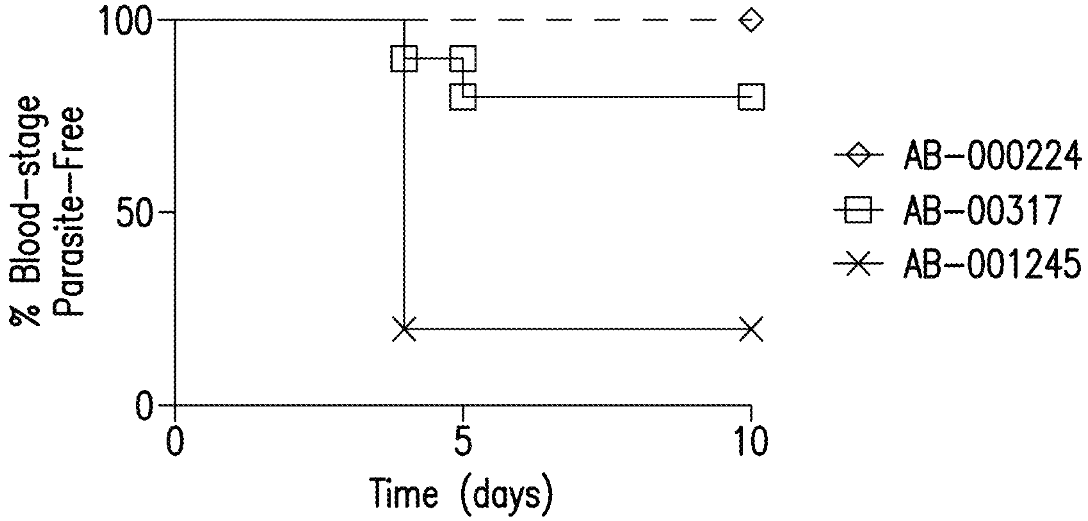
Figure 3A:
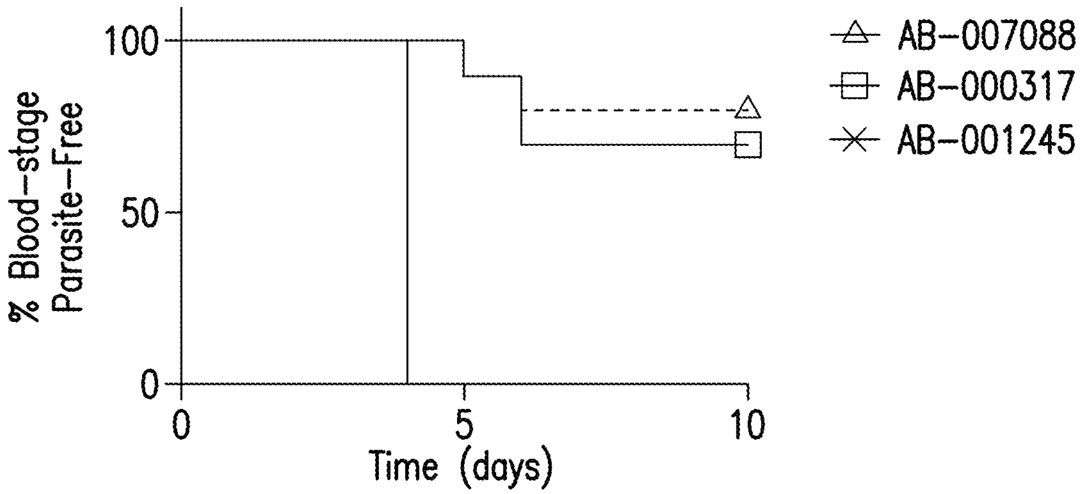
FIGS. 3A and 3C illustrate the survival rate of mice following administration of anti-CSP antibody AB-007088 and exposure to mosquitoes infected with chimeric *P. berghei* expressing *P. falciparum* CSP protein in two experiments.
Figure 3B:
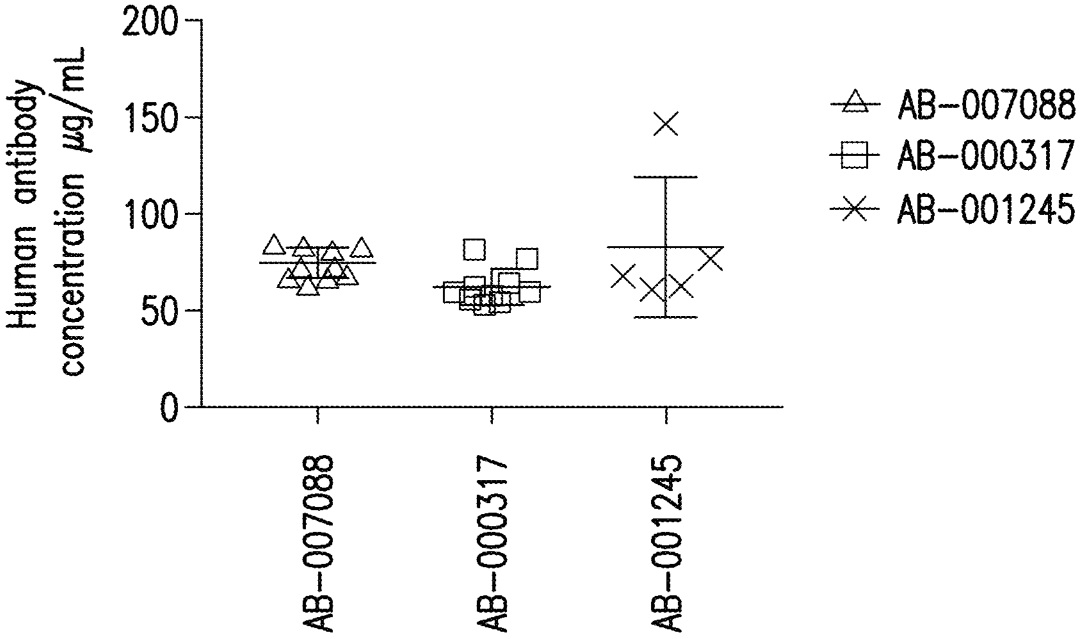
FIG. 3B shows the associated human IgG serum concentrations determined by ELISA obtained 15 hours following antibody administration in the experiment shown in FIG. 3A. AB-001245 is a non-malaria-specific antibody that was used as a negative control. AB-000317 is a positive control.
Figure 3C:
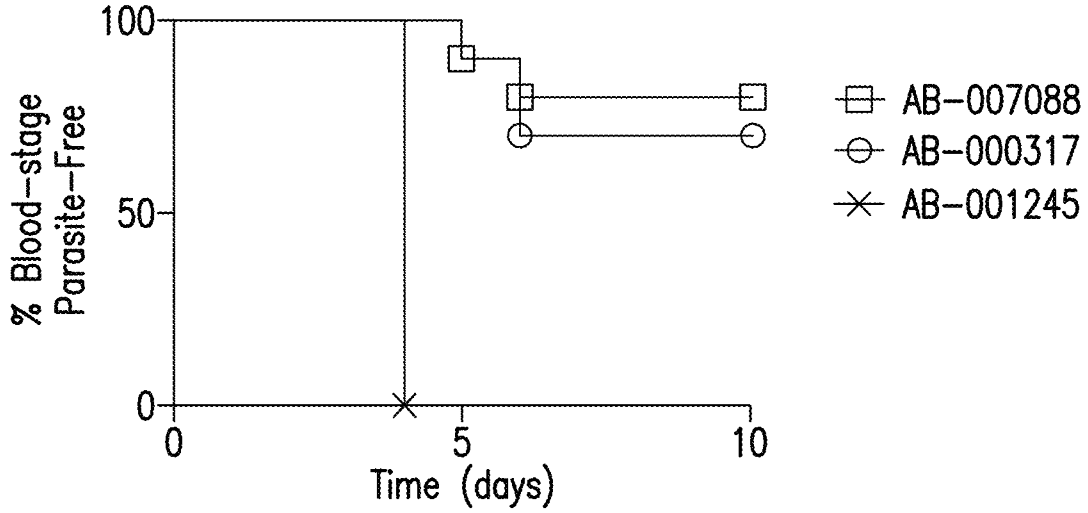

Mice treated with AB-000224, AB-007088 or the positive control AB-000317 were less likely to develop parasitemia as compared to mice treated with the negative control AB-001245. (FIGS. 2A and 2C show AB-000224 experimental data and FIGS. 3A and 3C show AB-007088 experimental data). The level of human antibodies circulating in the mice at the time of infection was quantified via an ELISA assay (FIGS. 2B and 3B) and was similar between the experimental and control antibodies.

Figure 11A:
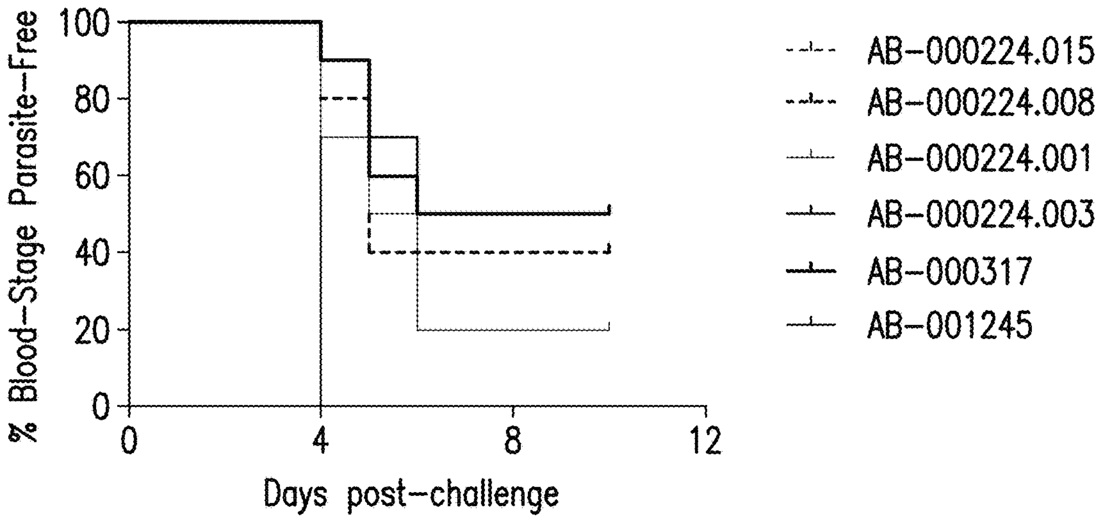
FIGS. 11A-11C illustrate the survival rate of mice following administration of anti-CSP antibody variants disclosed herein and exposure to mosquitoes infected with chimeric *P. berghei* expressing *P. falciparum* CSP protein.
Figure 11B:
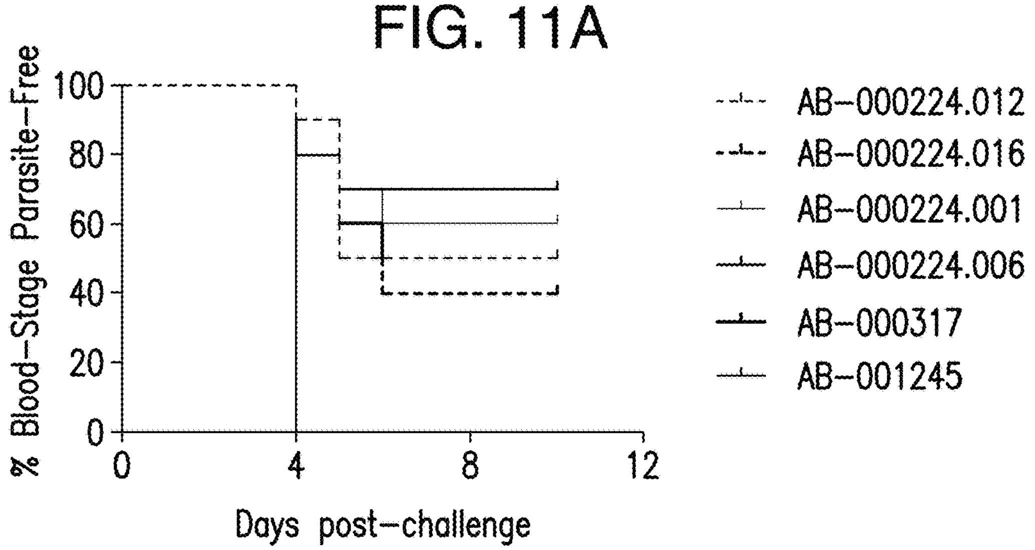
Figure 11C:
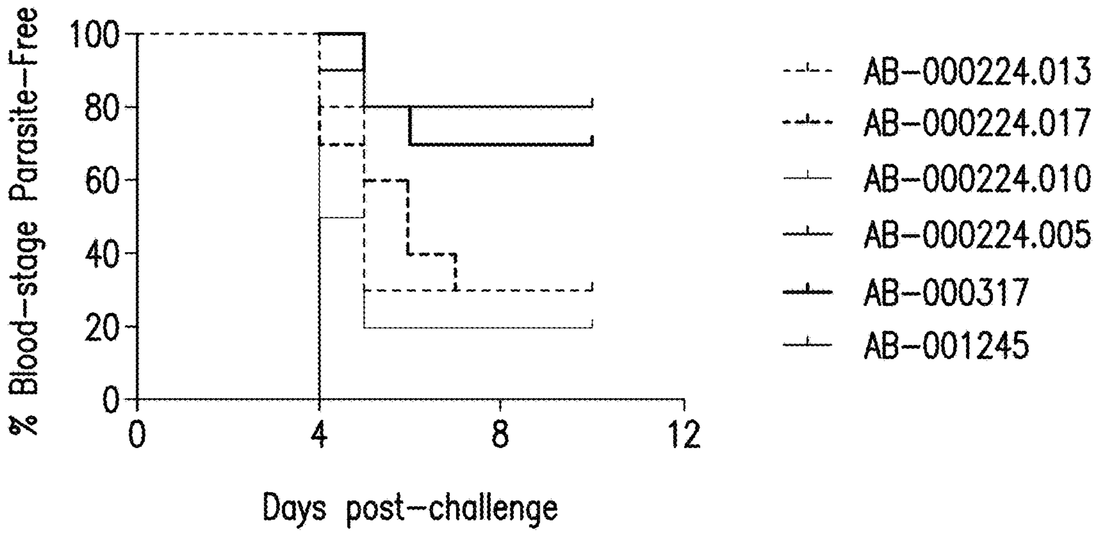
Figure 11D:
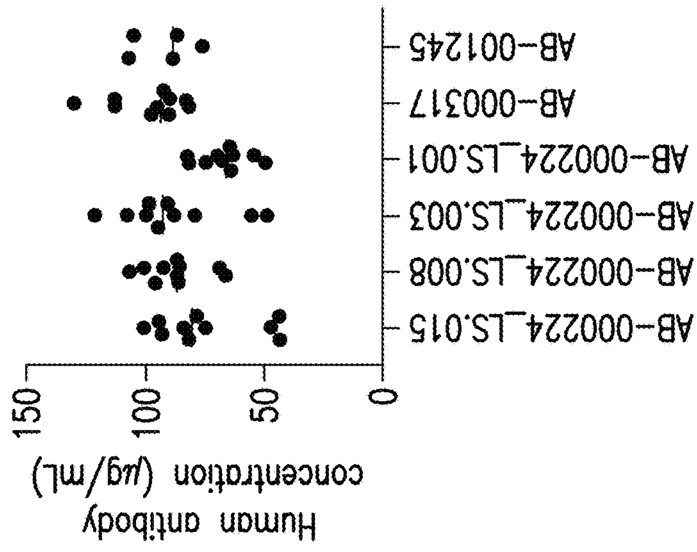
FIGS. 11D-F show concentration of human antibodies that were circulating in the mice at the time of infection as determined by ELISA for the assays shown in FIGS. 11A-C, respectively. AB-001245 is a non-malaria-specific antibody that was used as a negative control. AB-000317 is a positive control.
Figure 11E:
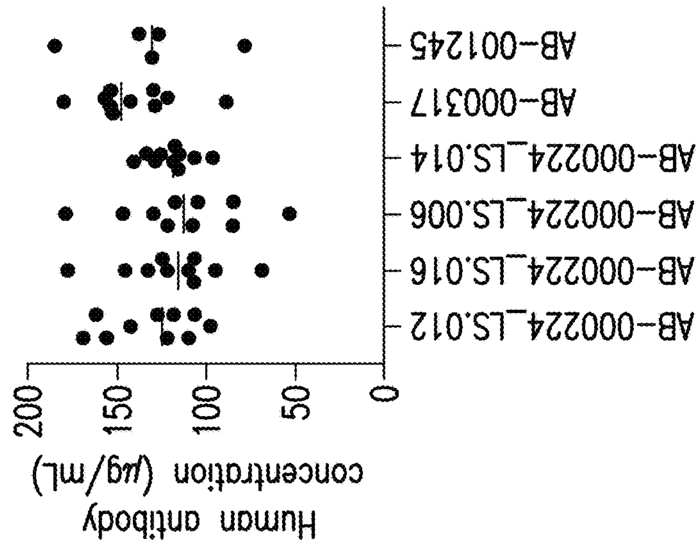
Figure 11F:
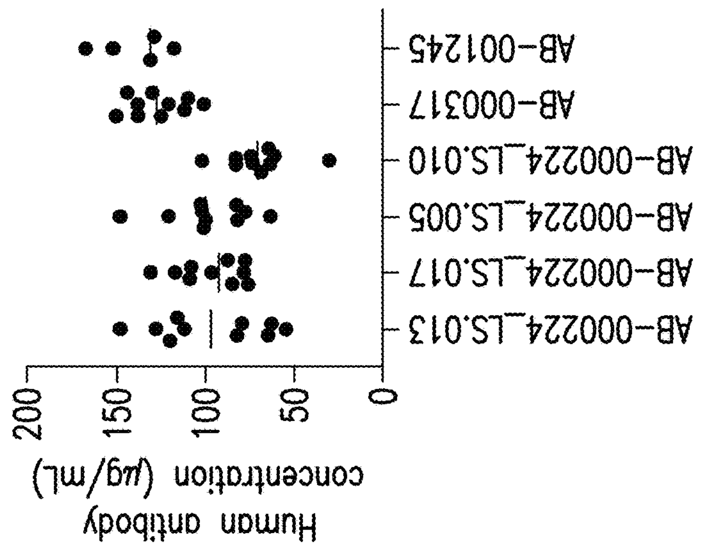

Finally, mice administered variants of AB-000224 or AB-007088 were comparably likely to remain parasite-free as mice treated with either of the parent antibodies, or the positive control antibody AB-000317 (FIGS. 11A-11C). The concentration of human antibodies that were circulating in the mice at the time of infection was determined by ELISA and is shown in FIGS. 11D-11F.

Example 5. Biophysical Characterization

The present example describes the biophysical hallmarks of the anti-CSP antibody variants. AB-000224 and AB-007088 and variants thereof (all in the format comprising Heavy Chain version 2) were evaluated for their conformational stability and colloidal stability. Several methods were used to analyze these endpoints and are summarized in the Tables 37 and 38 below:

TABLE 37

| Conformational Stability Methods | | | | |
|---|---|---|---|---|
| Method Name | Attribute Measured | Characterization | Desired Outcome | Values that indicate instability |
| Differential scanning fluorimetry (DSF) | Melting temperature | Lower Tm(app) is indicative of decreased conformational stability | Increase in Tm or formation of additional Tm's indicating increased domain stability | Weighted Shoulder Score (WSS) Below 20 |
| Thermal hold | Temperature induced aggregation | Define conditions for precipitation relating to potential destabilization during room temperature incubation | Increase in thermal stability indicated by the absence of precipitation | Absorbance at 350 nm is above 0.5 |
| Low pH Aggregation | Low pH stability by high molecular weight | Molecules with an increase in high molecule weight following neutralization after low pH exposure may show increased aggregation during low pH viral inactivation | No significant increase in high molecular weight species following low pH exposure and neutralization | More than 10% aggregation after low pH exposure |
| Chemical Unfolding | Conformational stability | Molecules with an increased inflection point may show lower rates of aggregation during storage and are more conformationally stable | Increased inflection point compared to the parent molecule | Less than 2.1M inflection point |

TABLE 38

| Colloidal Stability Methods | | | | |
|---|---|---|---|---|
| Method Name | Attribute Measured | Characterization | Desired Outcome | Values that indicate instability |
| Self-interaction nanoparticle spectroscopy (SINS) | Protein-protein interaction | Define relative protein self-association to help identify potential for higher viscosity during concentration and problems with filterability | Decrease in parameters indicating self-association of the molecule | Wavelength Maximum Above 550 nm |
| Standup Monolayer Affinity Chromatography (Zenix Column) | Colloidal stability | Molecules with reduced retention times may show increase solubility and lower rates of aggregation during storage | Decreased main peak retention time compared to parent molecule | Longer retention times, there is no established values correlating to instability at this time |
| Relative Solubility Analysis (RSA) | Polyethylene glycol based solubility analysis | Molecules with higher relative solubility may show lower rates of aggregation during storage | Increased solubility compared to parent molecule | 50% Loss of protein occurring less than 7% PEG |
| Polyreactivity | Non-specific binding | Molecules that have the potential to non-specifically bind to an array of different antigens can potentially have a higher clearance rate. | Decreased non-specific binding compared to the parent molecule | Absorbance at 405 nm is above 1.5-2.0 |

AB-000224 Variants Showed Improved Stability

AB-000224 and variants thereof showed comparable harvest yield and titer results. Thus, additional end-points were assessed. AB-000224 and variants thereof were evaluated for their thermal stability by differential scanning fluorimetry (DSF). Thermal unfolding was monitored by measuring the intensity of an extrinsic dye (sypro orange) as the sample was heated from 20° C. to 90° C. The data was reported as Tm1 and Tm2 with the first transition correlating with the CH2 domain and the 2nd transition correlating with the unfolding of the Fab and CH3 domain regions. Higher unfolding temperatures are desirable and have been linked with an increase in a product's conformational stability. Lack of a Tm2 is indicative of the Fab unfolding at the same or similar temperature to the CH2 domain, reported as Tm1. Additional information is also obtained from a proprietary parameter termed the weighted shoulder score which accounts for multiple pieces of information from the unfolding curve. Again, higher values are indicative of greater conformational stability. The DSF analysis was conducted in PBS buffer, with all samples being diluted down to a final antibody concentration of 0.15 mg/mL.

The propensity to aggregate at elevated temperatures was assessed using the thermal aggregation method. Samples were place in a 96 well Biorad PCR plate and heated to various temperatures for 5 minutes using a Biorad Thermal Cycler. After heating, protein precipitation was determined by reading the absorbance at 350 nm (A350) using a Spectrostar nano plate reader. Almost all AB-000224 variants showed higher WSS as compared to the parent antibody AB-000224, a T2 that approached 80° C., and no precipitation during thermal hold assays. However, AB-000224.017 did not have a T2 and showed precipitation during thermal hold assay.

Further, AB-000224 and variants thereof were also evaluated for their chemical stability. Sensitivity to low pH was assessed by titrating the samples to pH 3.3 using acetic acid, holding the samples for 30 minutes, neutralizing the samples to pH 5 with tris base, and measuring aggregation by size exclusion HPLC. Samples that were diluted with PBS using the same volume of acetic acid and tris base as used in the test samples were used as a control. AB-000224 and all variants thereof did not show low pH instability.

AB-000224 and variants thereof were tested for stability against chemical unfolding as assayed by denaturation with guanidine. Chemical unfolding curves were produced by exposing the antibodies to increasing concentrations of guanidine hydrochloride. After 24 hours, the intrinsic fluorescence of the samples is measured using a SUPR-UV plate reader. The collected raw data was then processed and the chemical unfolding curve and its inflection point calculated from the processed data as a function of denaturant condition. Antibodies with denaturation inflection points higher than 2.1 M guanidine are considered to be conformationally stable by this method. AB-000224 and all variants showed inflection points above 2 M guanidine (Gdn). Notably, AB-000224.005, AB-000224.008, AB-000224.010, AB-000224.011, AB-000224.013, and AB-000224.015 showed improved stability against chemical unfolding as compared to AB-000224, each having an inflection point above 2.3 M guanidine.

AB-000224 and variants thereof were also evaluated for their colloidal stability by self-interaction nanoparticle spectroscopy (SINS) which monitors protein-protein interactions by capture on the surface of a gold colloid and measuring shifts of the wavelength of maximum absorption. Maximum absorption values of wavelengths higher than 550 nm are consider interacting and could manifest in increase viscosity and filterability issues. All variants had maximum absorption values less than 550 nm and showed a slight improvement in the SINS values as compared to AB-000224.

AB-000224 and variants thereof were tested for potential hydrophobic interactions that might results in manufacturability challenges by monitoring retention time on a Zenix HPLC column. Undiluted samples were loaded onto the Zenix column and eluted isocratically with a 100 mM sodium phosphate, pH 7.0 running buffer and monitored at 220 nm. Longer retention times indicates hydrophobic interactions. Most antibodies have a retention time of 8.5-9.0 minutes under conditions tested. AB-00224 and all variants thereof showed comparable retention times of approximately 10 minutes.

Solubility of AB-000224 and variants thereof was assayed by precipitating the antibody samples with increasing amounts of PEG 10,000, filtering the samples, and measuring the soluble protein concentration. For each parent molecule, an initial experiment was performed to determine the ideal PEG concentration to precipitate the parent by approximately 50%, subsequent experiments used this PEG concentration on all variants to assess if a variant is more or less soluble than the parent molecule. Antibodies that precipitate above 8-10% PEG are considered highly soluble while poorly soluble antibodies precipitate at 4-5% PEG. AB-000224 and all variants thereof showed high solubility.

Polyreactivity of AB-000224 and variants thereof was determined by testing the antibodies for binding to KLH, insulin and dsDNA by Elisa. Samples were diluted to 1 μg/mL and a secondary anti-human antibody was used to detect the amount of protein that has bound to the different antigens. After substrate addition, absorbance was measured at 405 nm. A polyreactive antibody was used as a positive control. Non-specific binding to such common physiological components can cause an increase clearance rate, negatively impacting pK. Absorbance values above 1.5 for KLH and Insulin and 2.0 for dsDNA could indicate non-specific binding issues for a molecule. While most of the AB-000224 variants did not show any polyreactivity, some variants showed polyreactive signal against insulin (AB-000224.006, AB-000224.007, AB-000224.008, AB-000224.009, AB-000224.010).

Figure 12A:
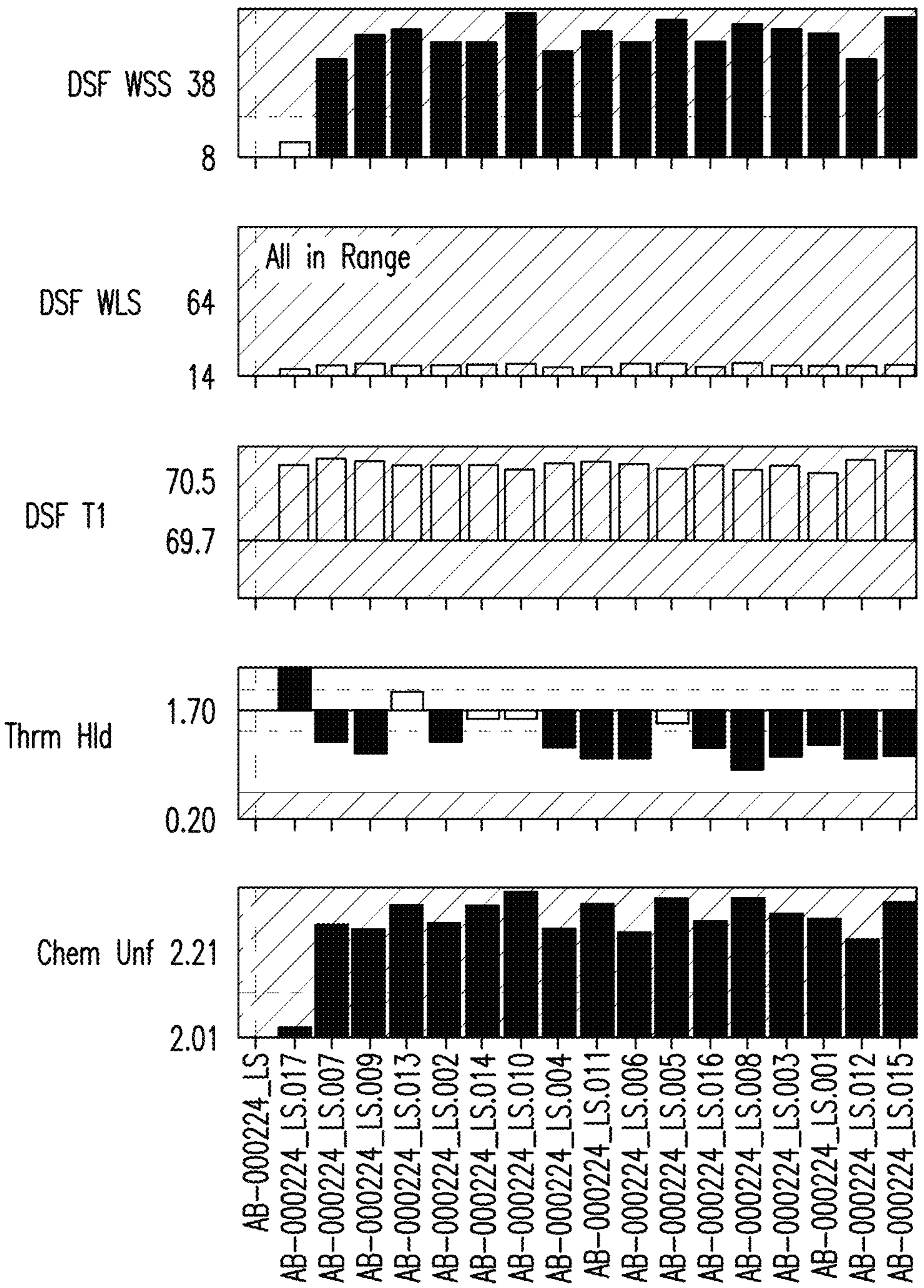
FIG. 12A illustrates the biophysical characterization of AB-000224 and variants thereof.
Figure 12A:
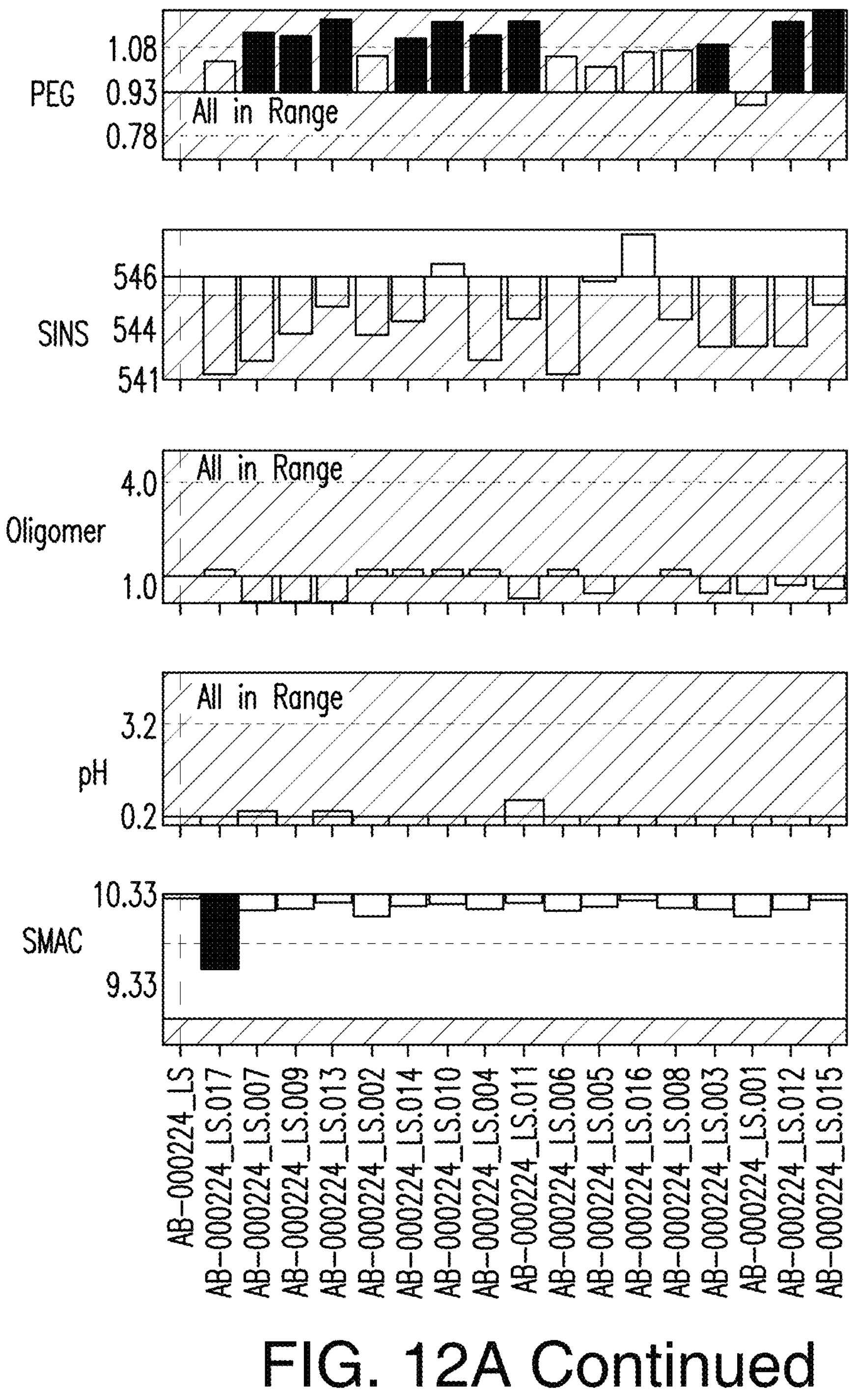
Figure 12A:
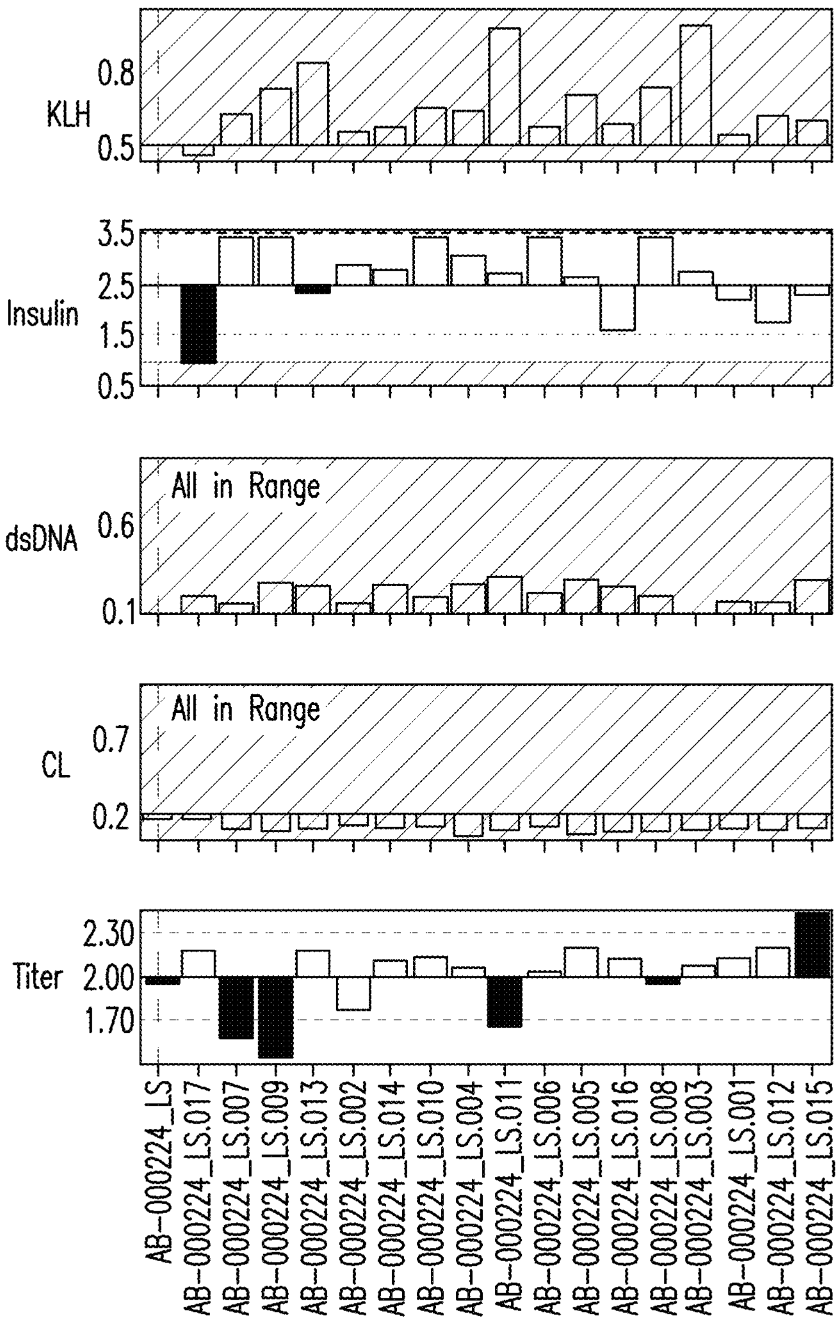
Figure 12B:
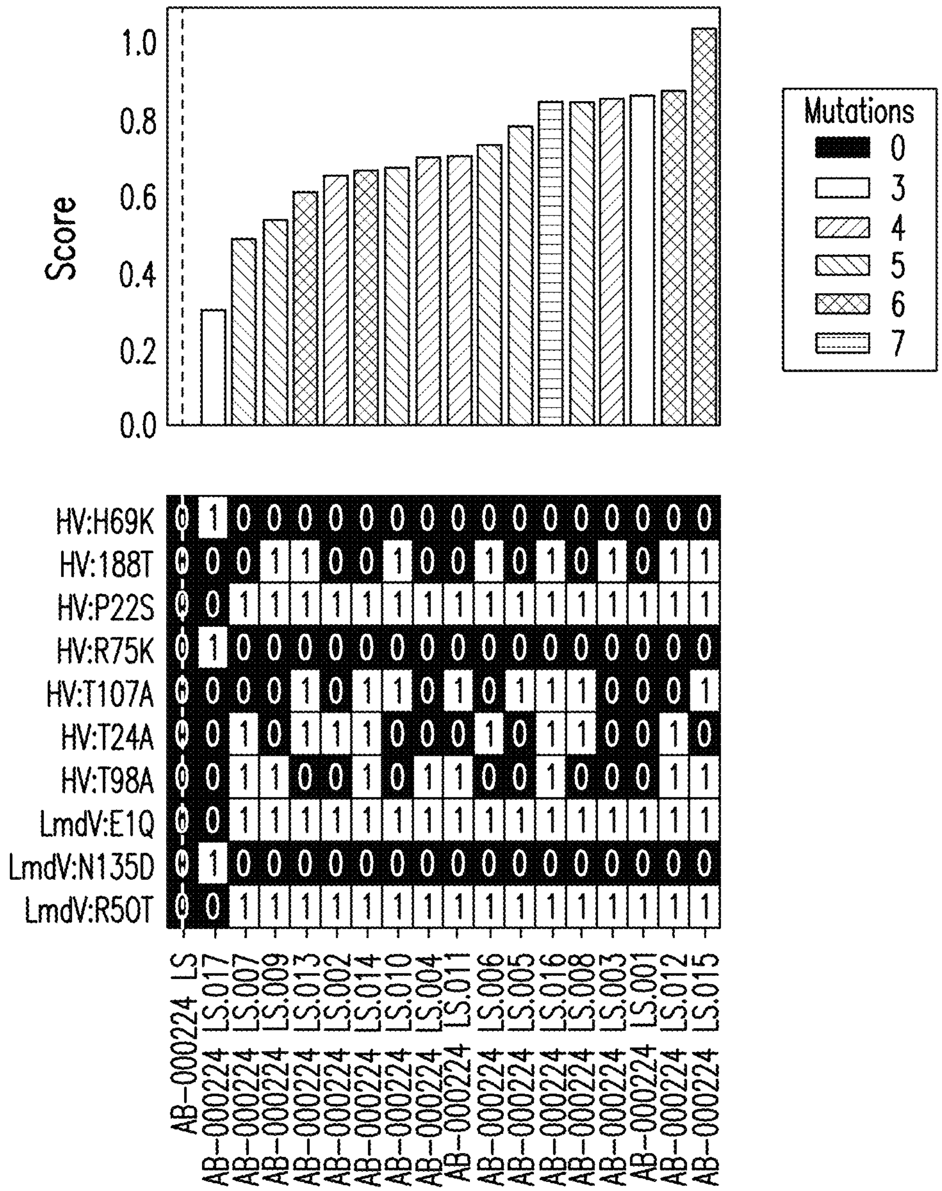
FIG. 12B shows the ranking of the AB-000224 and variants thereof based on all data obtained during biophysical characterization.
Figure 12C:
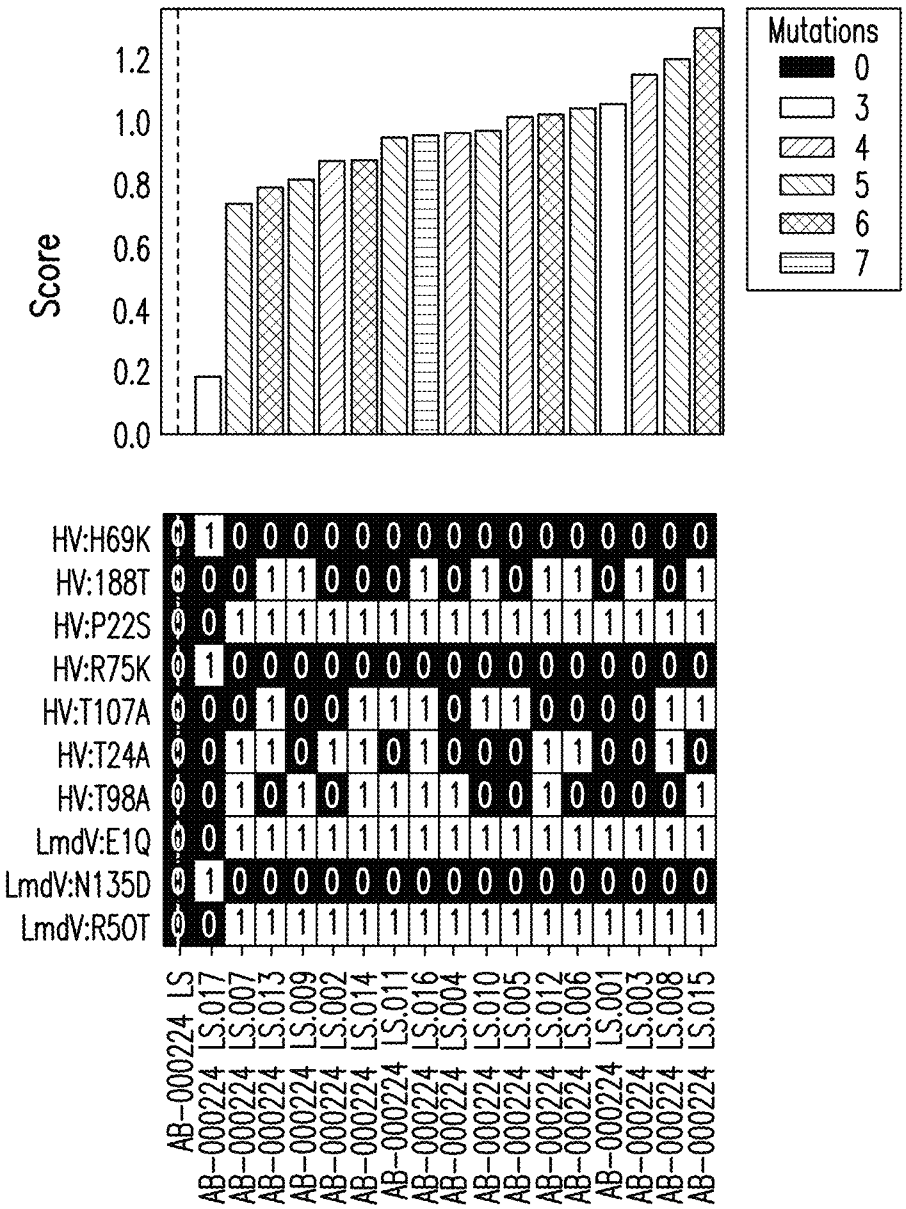
FIG. 12C shows the ranking of the AB-000224 and variants thereof excluding polyreactivity and including titer.

The AB-000224 and variants thereof were ranked based on the different assays and titer results and ranked as described in FIGS. 12B and 12C.

AB-007088 Variants Showed Improved Stability

The harvest yield and titer of the AB-007088 and variants thereof were initially evaluated. The AB-007088 variants showed comparable harvest yield and titer results. AB-007088 and variants thereof were evaluated to determine conformational and colloidal stability as described above for AB-000224 and variants thereof.

The AB-007088.005 variant showed improved thermal stability by the DFS method and a T2 that approached 75° C., while the other variants were similar to the parent AB-007088 with T1 values of approximately 70° C. and no measurable T2. In addition, AB-007088.005 showed a slightly reduced precipitation as compared to the parent AB-007088 and the other variants. When chemical stability was evaluated, AB-007088 and all variants thereof did not show low pH instability (at pH 3.3). Further, AB-007088 and all variants thereof showed stability against chemical unfolding with an inflection point above 2 M guanidine (Gdn). Notably, AB-007088.001 showed improved stability as compared to AB-007088 with an inflection point above 2.3 M guanidine.

AB-007088 and variants thereof were also evaluated for their colloidal stability. When protein-protein interactions were monitored (SINS), all variants showed very low SINS values, indicating absence of protein-protein interactions. In addition, AB-007088 and variants thereof showed comparable retention times on Zenix column. Notably, when PEG solubility was determined, AB-007088 and all variants thereof showed high solubility. Further, while most of the AB-007088 variants did not show any polyreactivity, some variants showed polyreactive signal against insulin (AB-007088.001, AB-007088.003, AB-007088.004).

Figure 13A:
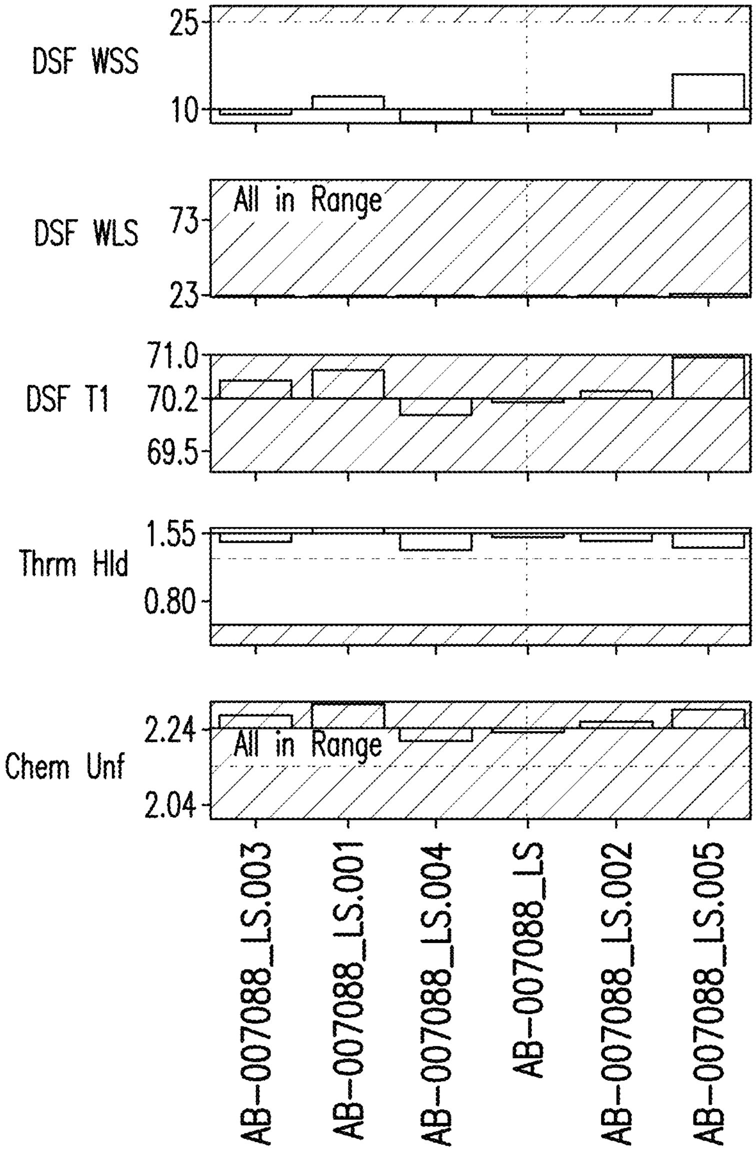
FIG. 13A illustrates the biophysical characterization of AB-007088 and variants thereof.
Figure 13A:
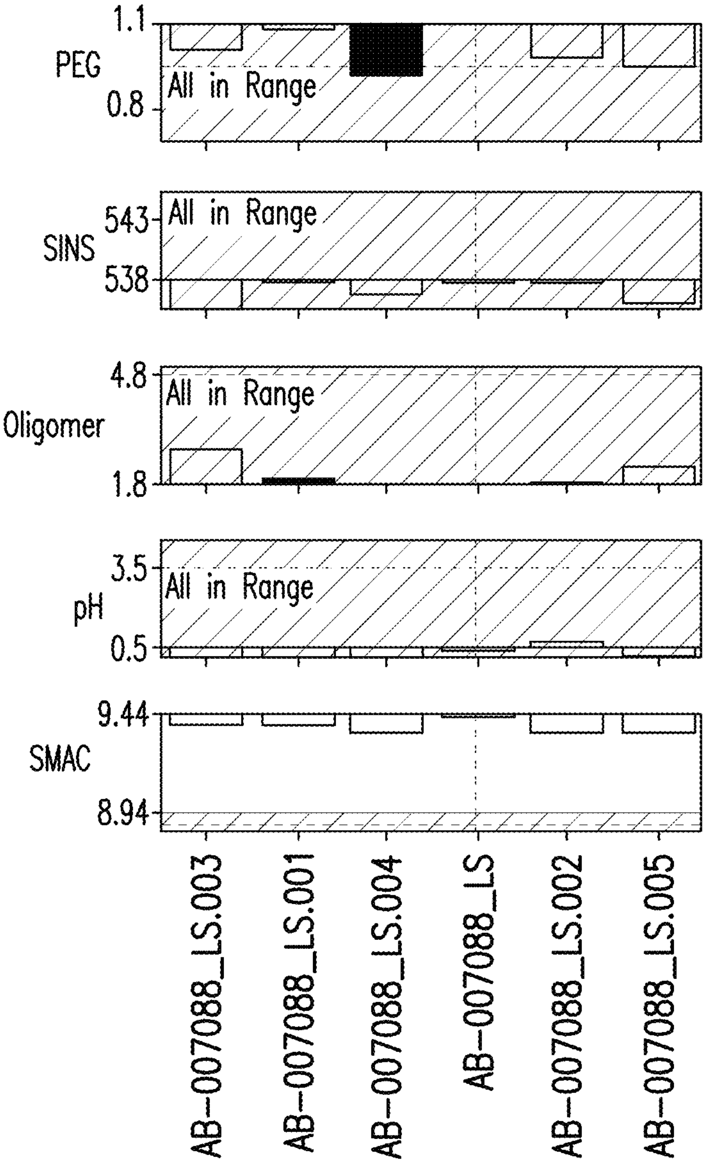
Figure 13A:
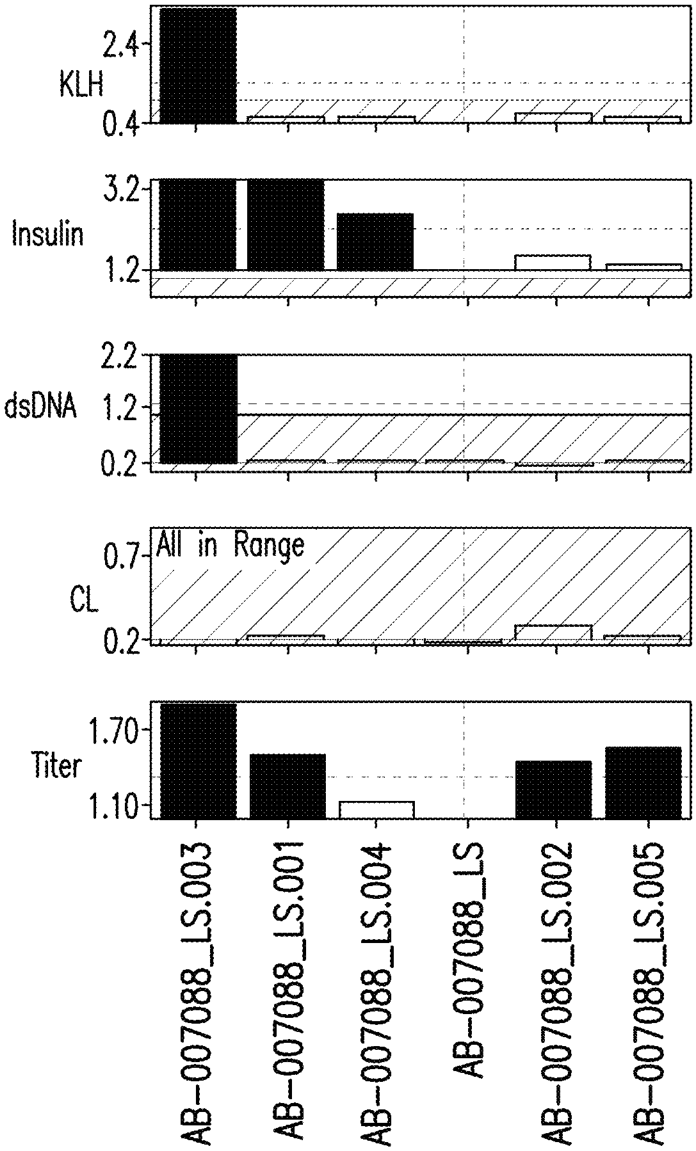
Figure 13B:
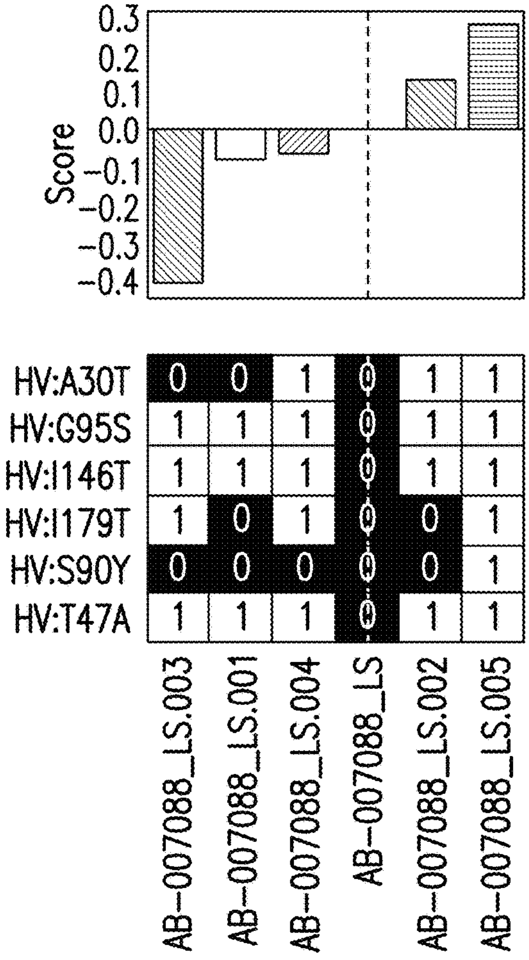
FIG. 13B shows the ranking of the AB-007088 and variants thereof based on all data obtained during biophysical characterization.
Figure 13C:
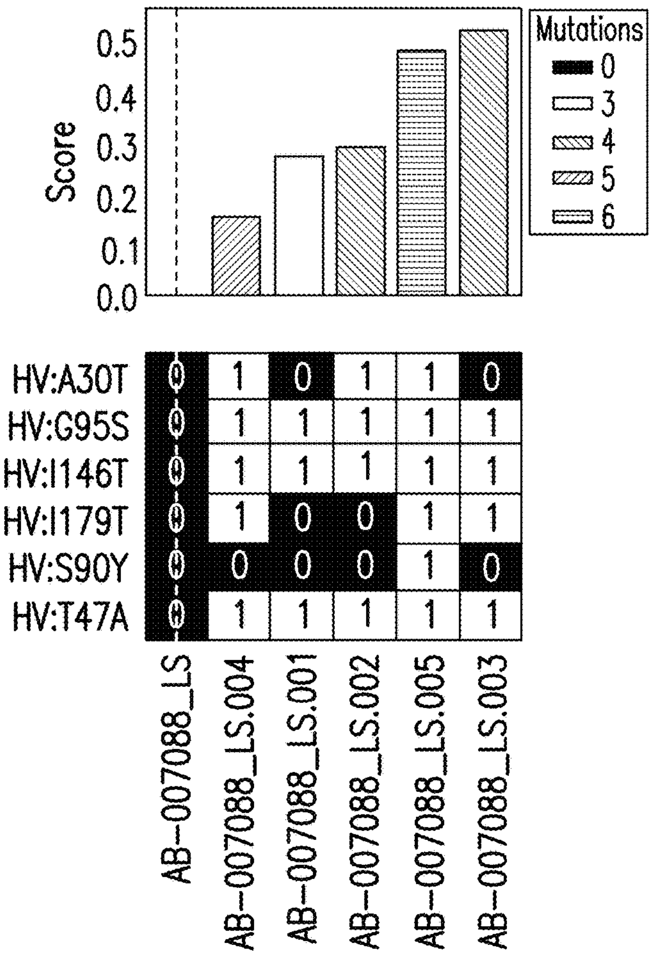
FIG. 13C shows the ranking of the AB-007088 and variants thereof excluding polyreactivity and including titer.

The AB-007088 and variants thereof were ranked based on the different assays and titer results, and ranked as described in FIGS. 13B and 13C.

What is claimed is:

1. A vector comprising a polynucleotide encoding a recombinant anti-circumsporozoite (CSP) antibody comprising a light chain variable region (VL) and a heavy chain variable region (VH), wherein:

a) the light chain variable region comprises a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3; and the heavy chain variable region comprises a CDR1 comprising the amino acid sequence set forth in SEQ ID NO: 4, a CDR2 comprising the amino acid sequence set forth in SEQ ID NO: 5, and a CDR3 comprising the amino acid sequence set forth in SEQ ID NO: 6;

b) the light chain variable region comprises a CDR1 comprising the amino acid sequence set forth in SEQ ID NO: 183, a CDR2 comprising the amino acid sequence set forth in SEQ ID NO: 184, and a CDR3 comprising the amino acid sequence set forth in SEQ ID NO: 185; and the heavy chain variable region comprises a CDR1 comprising the amino acid sequence set forth in SEQ ID NO: 186, a CDR2 comprising the amino acid sequence set forth in SEQ ID NO: 187, and a CDR3 comprising the amino acid sequence set forth in SEQ ID NO: 188; or c) the light chain variable region comprises a CDR1 comprising the amino acid sequence set forth in SEQ ID NO: 205, a CDR2 comprising the amino acid sequence set forth in SEQ ID NO: 206, and a CDR3 comprising the amino acid sequence set forth in SEQ ID NO: 207; and the heavy chain variable region comprises a CDR1 comprising the amino acid sequence set forth in SEQ ID NO: 208, a CDR2 comprising the amino acid sequence set forth in SEQ ID NO: 209, and a CDR3 comprising the amino acid sequence set forth in SEQ ID NO: 210.

2. The vector of claim 1, wherein the light chain variable region (VL) comprises:

a) the amino acid sequence set forth in SEQ ID NO: 23;
b) the amino acid sequence set forth in SEQ ID NO: 33;
c) the amino acid sequence set forth in SEQ ID NO: 43;
d) the amino acid sequence set forth in SEQ ID NO: 53;
e) the amino acid sequence set forth in SEQ ID NO: 63;
f) the amino acid sequence set forth in SEQ ID NO: 73;
g) the amino acid sequence set forth in SEQ ID NO: 83;
h) the amino acid sequence set forth in SEQ ID NO: 93;
i) the amino acid sequence set forth in SEQ ID NO: 103;
j) the amino acid sequence set forth in SEQ ID NO: 113;
k) the amino acid sequence set forth in SEQ ID NO: 123;
l) the amino acid sequence set forth in SEQ ID NO: 133;
m) the amino acid sequence set forth in SEQ ID NO: 143;
n) the amino acid sequence set forth in SEQ ID NO: 153;
o) the amino acid sequence set forth in SEQ ID NO: 163;
p) the amino acid sequence set forth in SEQ ID NO: 173;
q) the amino acid sequence set forth in SEQ ID NO: 195;
r) the amino acid sequence set forth in SEQ ID NO: 227;
s) the amino acid sequence set forth in SEQ ID NO: 237;
t) the amino acid sequence set forth in SEQ ID NO: 247;
u) the amino acid sequence set forth in SEQ ID NO: 257; or
v) the amino acid sequence set forth in SEQ ID NO: 267.

3. The vector of claim 1, wherein the heavy chain variable region (VH) comprises:

a) the amino acid sequence set forth in SEQ ID NO: 24;
b) the amino acid sequence set forth in SEQ ID NO: 34;
c) the amino acid sequence set forth in SEQ ID NO: 44;
d) the amino acid sequence set forth in SEQ ID NO: 54;
e) the amino acid sequence set forth in SEQ ID NO: 64;
f) the amino acid sequence set forth in SEQ ID NO: 74;
g) the amino acid sequence set forth in SEQ ID NO: 84;
h) the amino acid sequence set forth in SEQ ID NO: 94;
i) the amino acid sequence set forth in SEQ ID NO: 104;
j) the amino acid sequence set forth in SEQ ID NO: 114;
k) the amino acid sequence set forth in SEQ ID NO: 124;
l) the amino acid sequence set forth in SEQ ID NO: 134;
m) the amino acid sequence set forth in SEQ ID NO: 144;
n) the amino acid sequence set forth in SEQ ID NO: 154;
o) the amino acid sequence set forth in SEQ ID NO: 164;
p) the amino acid sequence set forth in SEQ ID NO: 174;
q) the amino acid sequence set forth in SEQ ID NO: 196;
r) the amino acid sequence set forth in SEQ ID NO: 228;
s) the amino acid sequence set forth in SEQ ID NO: 238;
t) the amino acid sequence set forth in SEQ ID NO: 248;
u) the amino acid sequence set forth in SEQ ID NO: 258; or
v) the amino acid sequence set forth in SEQ ID NO: 268.

4. The vector of claim 1, wherein:

a) the VL comprises the amino acid sequence set forth in SEQ ID NO: 23, and the VH comprises the amino acid sequence set forth in SEQ ID NO: 24;
b) the VL comprises the amino acid sequence set forth in SEQ ID NO: 33, and the VH comprises the amino acid sequence set forth in SEQ ID NO: 34;
c) the VL comprises the amino acid sequence set forth in SEQ ID NO: 43, and the VH comprises the amino acid sequence set forth in SEQ ID NO: 44;
d) the VL comprises the amino acid sequence set forth in SEQ ID NO: 53, and the VH comprises the amino acid sequence set forth in SEQ ID NO: 54;
e) the VL comprises the amino acid sequence set forth in SEQ ID NO: 63, and the VH comprises the amino acid sequence set forth in SEQ ID NO: 64;
f) the VL comprises the amino acid sequence set forth in SEQ ID NO: 73, and the VH comprises the amino acid sequence set forth in SEQ ID NO: 74;
g) the VL comprises the amino acid sequence set forth in SEQ ID NO: 83, and the VH comprises the amino acid sequence set forth in SEQ ID NO: 84;
h) the VL comprises the amino acid sequence set forth in SEQ ID NO: 93, and the VH comprises the amino acid sequence set forth in SEQ ID NO: 94;
i) the VL comprises the amino acid sequence set forth in SEQ ID NO: 103, and the VH comprises the amino acid sequence set forth in SEQ ID NO: 104;
j) the VL comprises the amino acid sequence set forth in SEQ ID NO: 113, and the VH comprises the amino acid sequence set forth in SEQ ID NO: 114;
k) the VL comprises the amino acid sequence set forth in SEQ ID NO: 123, and the VH comprises the amino acid sequence set forth in SEQ ID NO: 124;
l) the VL comprises the amino acid sequence set forth in SEQ ID NO: 133, and the VH comprises the amino acid sequence set forth in SEQ ID NO: 134;
m) the VL comprises the amino acid sequence set forth in SEQ ID NO: 143, and the VH comprises the amino acid sequence set forth in SEQ ID NO: 144;
n) the VL comprises the amino acid sequence set forth in SEQ ID NO: 153, and the VH comprises the amino acid sequence set forth in SEQ ID NO: 154;
o) the VL comprises the amino acid sequence set forth in SEQ ID NO: 163, and the VH comprises the amino acid sequence set forth in SEQ ID NO: 164;

p) the VL comprises the amino acid sequence set forth in SEQ ID NO: 173, and the VH comprises the amino acid sequence set forth in SEQ ID NO: 174;
q) the VL comprises the amino acid sequence set forth in SEQ ID NO: 195, and the VH comprises the amino acid sequence set forth in SEQ ID NO: 196;
r) the VL comprises the amino acid sequence set forth in SEQ ID NO: 227, and the VH comprises the amino acid sequence set forth in SEQ ID NO: 228;
s) the VL comprises the amino acid sequence set forth in SEQ ID NO: 237, and the VH comprises the amino acid sequence set forth in SEQ ID NO: 238;
t) the VL comprises the amino acid sequence set forth in SEQ ID NO: 247, and the VH comprises the amino acid sequence set forth in SEQ ID NO: 248;
u) the VL comprises the amino acid sequence set forth in SEQ ID NO: 257, and the VH comprises the amino acid sequence set forth in SEQ ID NO: 258; or
v) the VL comprises the amino acid sequence set forth in SEQ ID NO: 267, and the VH comprises the amino acid sequence set forth in SEQ ID NO: 268.

5. The vector of claim 1, wherein the antibody comprises a light chain (LC) and a heavy chain (HC), wherein the LC comprises:
a) the amino acid sequence set forth in SEQ ID NO: 27;
b) the amino acid sequence set forth in SEQ ID NO: 37;
c) the amino acid sequence set forth in SEQ ID NO: 47;
d) the amino acid sequence set forth in SEQ ID NO: 57;
e) the amino acid sequence set forth in SEQ ID NO: 67;
f) the amino acid sequence set forth in SEQ ID NO: 77;
g) the amino acid sequence set forth in SEQ ID NO: 87;
h) the amino acid sequence set forth in SEQ ID NO: 97;
i) the amino acid sequence set forth in SEQ ID NO: 107;
j) the amino acid sequence set forth in SEQ ID NO: 117;
k) the amino acid sequence set forth in SEQ ID NO: 127;
l) the amino acid sequence set forth in SEQ ID NO: 137;
m) the amino acid sequence set forth in SEQ ID NO: 147;
n) the amino acid sequence set forth in SEQ ID NO: 157;
o) the amino acid sequence set forth in SEQ ID NO: 167;
p) the amino acid sequence set forth in SEQ ID NO: 177;
q) the amino acid sequence set forth in SEQ ID NO: 199;
r) the amino acid sequence set forth in SEQ ID NO: 231;
s) the amino acid sequence set forth in SEQ ID NO: 241;
t) the amino acid sequence set forth in SEQ ID NO: 251;
u) the amino acid sequence set forth in SEQ ID NO: 261; or
v) the amino acid sequence set forth in SEQ ID NO: 271.

6. The vector of claim 1, wherein the antibody comprises a light chain (LC) and a heavy chain (HC), wherein the HC comprises:
a) the amino acid sequence set forth in SEQ ID NO: 28 or SEQ ID NO: 29;
b) the amino acid sequence set forth in SEQ ID NO: 38 or SEQ ID NO: 39;
c) the amino acid sequence set forth in SEQ ID NO: 48 or SEQ ID NO: 49;
d) the amino acid sequence set forth in SEQ ID NO: 58 or SEQ ID NO: 59;
e) the amino acid sequence set forth in SEQ ID NO: 68 or SEQ ID NO: 69;
f) the amino acid sequence set forth in SEQ ID NO: 78 or SEQ ID NO: 79;
g) the amino acid sequence set forth in SEQ ID NO: 88 or SEQ ID NO: 89;
h) the amino acid sequence set forth in SEQ ID NO: 98 or SEQ ID NO: 99;
i) the amino acid sequence set forth in SEQ ID NO: 108 or SEQ ID NO: 109;
j) the amino acid sequence set forth in SEQ ID NO: 118 or SEQ ID NO: 119;
k) the amino acid sequence set forth in SEQ ID NO: 128 or SEQ ID NO: 129;
l) the amino acid sequence set forth in SEQ ID NO: 138 or SEQ ID NO: 139;
m) the amino acid sequence set forth in SEQ ID NO: 148 or SEQ ID NO: 149;
n) the amino acid sequence set forth in SEQ ID NO: 158 or SEQ ID NO: 159;
o) the amino acid sequence set forth in SEQ ID NO: 168 or SEQ ID NO: 169;
p) the amino acid sequence set forth in SEQ ID NO: 178 or SEQ ID NO: 179;
q) the amino acid sequence set forth in SEQ ID NO: 200 or SEQ ID NO: 201;
r) the amino acid sequence set forth in SEQ ID NO: 232 or SEQ ID NO: 233;
s) the amino acid sequence set forth in SEQ ID NO: 242 or SEQ ID NO: 243;
t) the amino acid sequence set forth in SEQ ID NO: 252 or SEQ ID NO: 253;
u) the amino acid sequence set forth in SEQ ID NO: 262 or SEQ ID NO: 263; or
v) the amino acid sequence set forth in SEQ ID NO: 272 or SEQ ID NO: 273.

7. The vector of claim 1, wherein the antibody comprises a light chain (LC) and a heavy chain (HC), wherein:
a) the LC comprises the amino acid sequence set forth in SEQ ID NO: 27, and the HC comprises the amino acid sequence set forth in SEQ ID NO: 28 or SEQ ID NO: 29;
b) the LC comprises the amino acid sequence set forth in SEQ ID NO: 37, and the HC comprises the amino acid sequence set forth in SEQ ID NO: 38 or SEQ ID NO: 39;
c) the LC comprises the amino acid sequence set forth in SEQ ID NO: 47, and the HC comprises the amino acid sequence set forth in SEQ ID NO: 48 or SEQ ID NO: 49;
d) the LC comprises the amino acid sequence set forth in SEQ ID NO: 57, and the HC comprises the amino acid sequence set forth in SEQ ID NO: 58 or SEQ ID NO: 59;
e) the LC comprises the amino acid sequence set forth in SEQ ID NO: 67, and the HC comprises the amino acid sequence set forth in SEQ ID NO: 68 or SEQ ID NO: 69;
f) the LC comprises the amino acid sequence set forth in SEQ ID NO: 77, and the HC comprises the amino acid sequence set forth in SEQ ID NO: 78 or SEQ ID NO: 79;
g) the LC comprises the amino acid sequence set forth in SEQ ID NO: 87, and the HC comprises the amino acid sequence set forth in SEQ ID NO: 88 or SEQ ID NO: 89;
h) the LC comprises the amino acid sequence set forth in SEQ ID NO: 97, and the HC comprises the amino acid sequence set forth in SEQ ID NO: 98 or SEQ ID NO: 99;
i) the LC comprises the amino acid sequence set forth in SEQ ID NO: 107, and the HC comprises the amino acid sequence set forth in SEQ ID NO: 108 or SEQ ID NO: 109;

j) the LC comprises the amino acid sequence set forth in SEQ ID NO: 117, and the HC comprises the amino acid sequence set forth in SEQ ID NO: 118 or SEQ ID NO: 119;

k) the LC comprises the amino acid sequence set forth in SEQ ID NO: 127, and the HC comprises the amino acid sequence set forth in SEQ ID NO: 128 or SEQ ID NO: 129;

l) the LC comprises the amino acid sequence set forth in SEQ ID NO: 137, and the HC comprises the amino acid sequence set forth in SEQ ID NO: 138 or SEQ ID NO: 139;

m) the LC comprises the amino acid sequence set forth in SEQ ID NO: 147, and the HC comprises the amino acid sequence set forth in SEQ ID NO: 148 or SEQ ID NO: 149;

n) the LC comprises the amino acid sequence set forth in SEQ ID NO: 157, and the HC comprises the amino acid sequence set forth in SEQ ID NO: 158 or SEQ ID NO: 159;

o) the LC comprises the amino acid sequence set forth in SEQ ID NO: 167, and the HC comprises the amino acid sequence set forth in SEQ ID NO: 168 or SEQ ID NO: 169;

p) the LC comprises the amino acid sequence set forth in SEQ ID NO: 177, and the HC comprises the amino acid sequence set forth in SEQ ID NO: 178 or SEQ ID NO: 179;

q) the LC comprises the amino acid sequence set forth in SEQ ID NO: 199, and the HC comprises the amino acid sequence set forth in SEQ ID NO: 200 or SEQ ID NO: 201;

r) the LC comprises the amino acid sequence set forth in SEQ ID NO: 231, and the HC comprises the amino acid sequence set forth in SEQ ID NO: 232 or SEQ ID NO: 233;

s) the LC comprises the amino acid sequence set forth in SEQ ID NO: 241, and the HC comprises the amino acid sequence set forth in SEQ ID NO: 242 or SEQ ID NO: 243;

t) the LC comprises the amino acid sequence set forth in SEQ ID NO: 251, and the HC comprises the amino acid sequence set forth in SEQ ID NO: 252 or SEQ ID NO: 253;

u) the LC comprises the amino acid sequence set forth in SEQ ID NO: 261, and the HC comprises the amino acid sequence set forth in SEQ ID NO: 262 or SEQ ID NO: 263; or v) the LC comprises the amino acid sequence set forth in SEQ ID NO: 271, and the HC comprises the amino acid sequence set forth in SEQ ID NO: 272 or SEQ ID NO: 273.

8. The vector of claim 1, wherein the VL comprises the amino acid sequence set forth in SEQ ID NO: 13 and at least one amino acid substitution at position 1 and/or at position 44.

9. The vector of claim 8, wherein the amino acid substitution at position 1 is E1Q and the amino acid substitution at position 44 is R44T.

10. The vector of claim 1, wherein the VH comprises the amino acid sequence set forth in SEQ ID NO: 14 and at least one amino acid substitution at position 21, position 23, position 88, position 98, or a combination thereof.

11. The vector of claim 10, wherein a) the amino acid substitution at position 21 is P21S;

b) the amino acid substitution at position 23 is T23A;

c) the amino acid substitution at position 80 is 180T; and d) the amino acid substitution at position 90 is T90A.

12. The vector of claim 1, wherein the antibody comprises a heavy chain (HC) comprising the amino acid sequence set forth in SEQ ID NO: 18 and at least one amino acid substitution at position 438 and/or at position 444.

13. The vector of claim 12, wherein the amino acid substitution at position 438 is M438L and the amino acid substitution at position 444 is N444S.

14. The vector of claim 1, wherein the VH comprises the amino acid sequence set forth in SEQ ID NO: 218 and at least one amino acid substitution at position 40, position 69, position 80, position 85, position 120, or a combination thereof.

15. The vector of claim 14, wherein a) the amino acid substitution at position 40 is T40A;

b) the amino acid substitution at position 69 is I69T;

c) the amino acid substitution at position 80 is S80Y;

d) the amino acid substitution at position 85 is G85S; and e) the amino acid substitution at position 120 is I120T.

16. The vector of claim 1, wherein the HC comprises the amino acid sequence set forth in SEQ ID NO: 222 and at least one amino acid substitution at position 434 and/or at position 440.

17. The vector of claim 16, wherein the amino acid substitution at position 434 is M434L and the amino acid substitution at position 440 is N440S.

18. The vector of claim 1, wherein the antibody exhibits at a) least 20% reduction in parasite liver load as compared to a reference antibody;

b) at least 20% increase in survival rate as compared to a reference antibody;

c) increased conformational stability as compared to a reference antibody;

d) increased colloidal stability as compared to a reference antibody;

wherein the reference antibody is selected from the group consisting of AB-000317, AB-000224, and AB-007088.

19. The vector of claim 1, wherein the polynucleotide comprises:

a) the nucleotide sequence set forth in SEQ ID NO: 25;

b) the nucleotide sequence set forth in SEQ ID NO: 35;

c) the nucleotide sequence set forth in SEQ ID NO: 45;

d) the nucleotide sequence set forth in SEQ ID NO: 55;

e) the nucleotide sequence set forth in SEQ ID NO: 65;

f) the nucleotide sequence set forth in SEQ ID NO: 75;

g) the nucleotide sequence set forth in SEQ ID NO: 85;

h) the nucleotide sequence set forth in SEQ ID NO: 95;

i) the nucleotide sequence set forth in SEQ ID NO: 105;

j) the nucleotide sequence set forth in SEQ ID NO: 115;

k) the nucleotide sequence set forth in SEQ ID NO: 125;

l) the nucleotide sequence set forth in SEQ ID NO: 135;

m) the nucleotide sequence set forth in SEQ ID NO: 145;

n) the nucleotide sequence set forth in SEQ ID NO: 155;

o) the nucleotide sequence set forth in SEQ ID NO: 165;

p) the nucleotide sequence set forth in SEQ ID NO: 175;

q) the nucleotide sequence set forth in SEQ ID NO: 197;

r) the nucleotide sequence set forth in SEQ ID NO: 229;

s) the nucleotide sequence set forth in SEQ ID NO: 239;

t) the nucleotide sequence set forth in SEQ ID NO: 249;

u) the nucleotide sequence set forth in SEQ ID NO: 259; or v) the nucleotide sequence set forth in SEQ ID NO: 269.

20. The vector of claim 1, wherein the polynucleotide comprises:

a) the nucleotide sequence set forth in SEQ ID NO: 26;

b) the nucleotide sequence set forth in SEQ ID NO: 36;

c) the nucleotide sequence set forth in SEQ ID NO: 46;
d) the nucleotide sequence set forth in SEQ ID NO: 56;
e) the nucleotide sequence set forth in SEQ ID NO: 66;
f) the nucleotide sequence set forth in SEQ ID NO: 76;
g) the nucleotide sequence set forth in SEQ ID NO: 86;
h) the nucleotide sequence set forth in SEQ ID NO: 96;
i) the nucleotide sequence set forth in SEQ ID NO: 106;
j) the nucleotide sequence set forth in SEQ ID NO: 116;
k) the nucleotide sequence set forth in SEQ ID NO: 126;
l) the nucleotide sequence set forth in SEQ ID NO: 136;
m) the nucleotide sequence set forth in SEQ ID NO: 146;
n) the nucleotide sequence set forth in SEQ ID NO: 156;
o) the nucleotide sequence set forth in SEQ ID NO: 166;
p) the nucleotide sequence set forth in SEQ ID NO: 176;
q) the nucleotide sequence set forth in SEQ ID NO: 198;
r) the nucleotide sequence set forth in SEQ ID NO: 230;
s) the nucleotide sequence set forth in SEQ ID NO: 240;
t) the nucleotide sequence set forth in SEQ ID NO: 250;
u) the nucleotide sequence set forth in SEQ ID NO: 260; or
v) the nucleotide sequence set forth in SEQ ID NO: 270.

21. The vector of claim 1, wherein the polynucleotide comprises:

a) the nucleotide sequence set forth in SEQ ID NO: 25 and the nucleotide sequence set forth in SEQ ID NO: 26;
b) the nucleotide sequence set forth in SEQ ID NO: 35 and the nucleotide sequence set forth in SEQ ID NO: 36;
c) the nucleotide sequence set forth in SEQ ID NO: 45 and the nucleotide sequence set forth in SEQ ID NO: 46;
d) the nucleotide sequence set forth in SEQ ID NO: 55 and the nucleotide sequence set forth in SEQ ID NO: 56;
e) the nucleotide sequence set forth in SEQ ID NO: 65 and the nucleotide sequence set forth in SEQ ID NO: 66;
f) the nucleotide sequence set forth in SEQ ID NO: 75 and the nucleotide sequence set forth in SEQ ID NO: 76;
g) the nucleotide sequence set forth in SEQ ID NO: 85 and the nucleotide sequence set forth in SEQ ID NO: 86;
h) the nucleotide sequence set forth in SEQ ID NO: 95 and the nucleotide sequence set forth in SEQ ID NO: 96;
i) the nucleotide sequence set forth in SEQ ID NO: 105 and the nucleotide sequence set forth in SEQ ID NO: 106;
j) the nucleotide sequence set forth in SEQ ID NO: 115 and the nucleotide sequence set forth in SEQ ID NO: 116;
k) the nucleotide sequence set forth in SEQ ID NO: 125 and the nucleotide sequence set forth in SEQ ID NO: 126;
l) the nucleotide sequence set forth in SEQ ID NO: 135 and the nucleotide sequence set forth in SEQ ID NO: 136;
m) the nucleotide sequence set forth in SEQ ID NO: 145 and the nucleotide sequence set forth in SEQ ID NO: 146;
n) the nucleotide sequence set forth in SEQ ID NO: 155 and the nucleotide sequence set forth in SEQ ID NO: 156;
o) the nucleotide sequence set forth in SEQ ID NO: 165 and the nucleotide sequence set forth in SEQ ID NO: 166;
p) the nucleotide sequence set forth in SEQ ID NO: 175 and the nucleotide sequence set forth in SEQ ID NO: 176;
q) the nucleotide sequence set forth in SEQ ID NO: 197 and the nucleotide sequence set forth in SEQ ID NO: 198;
r) the nucleotide sequence set forth in SEQ ID NO: 229 and the nucleotide sequence set forth in SEQ ID NO: 230;
s) the nucleotide sequence set forth in SEQ ID NO: 239 and the nucleotide sequence set forth in SEQ ID NO: 240;
t) the nucleotide sequence set forth in SEQ ID NO: 249 and the nucleotide sequence set forth in SEQ ID NO: 250;
u) the nucleotide sequence set forth in SEQ ID NO: 259 and the nucleotide sequence set forth in SEQ ID NO: 260; or
v) the nucleotide sequence set forth in SEQ ID NO: 269 and the nucleotide sequence set forth in SEQ ID NO: 270.

22. The vector of claim 1, wherein the vector is a plasmid or a viral vector.

23. The vector of claim 22, wherein the viral vector is an adenovirus, an adeno-associated virus, or a retrovirus.

24. A vector comprising a polynucleotide encoding a recombinant anti-circumsporozoite (CSP) antibody comprising a light chain variable region (VL) and a heavy chain variable region (VH), wherein the VL comprises a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3; and the VH comprises a CDR1 comprising the amino acid sequence set forth in SEQ ID NO: 4, a CDR2 comprising the amino acid sequence set forth in SEQ ID NO: 5, and a CDR3 comprising the amino acid sequence set forth in SEQ ID NO: 6.

25. A vector comprising a polynucleotide encoding a recombinant anti-circumsporozoite (CSP) antibody comprising a light chain variable region (VL) comprising the amino acid sequence set forth in SEQ ID NO: 163 and a heavy chain variable region (VH) comprising the amino acid sequence set forth in SEQ ID NO: 164.

26. A vector comprising a polynucleotide encoding a recombinant anti-circumsporozoite (CSP) antibody comprising a light chain (LC) comprising the amino acid sequence set forth in SEQ ID NO: 167 and a heavy chain (HC) comprising the amino acid sequence set forth in SEQ ID NO: 168 or SEQ ID NO: 169.

27. A host cell comprising the vector of any one of claims 1, 4, 7, 21, 24, 25, and 26.

28. A composition comprising the vector of any one of claims 1, 4, 7, 21, 24, 25, and 26.

29. The composition of claim 28, further comprising a pharmaceutically acceptable carrier.

30. A method of preventing and/or treating malaria in a subject in need thereof, comprising administering an effective amount of the vector of any one of claims 1, 4, 7, 21, 24, 25, and 26.

31. The method of claim 30, wherein the subject is a pediatric patient.

32. A method of preventing and/or treating malaria in a subject in need thereof, comprising administering an effective amount of the composition of claim 28.

33. The method of claim 32, wherein the subject is a pediatric patient.

* * * * *